(12) United States Patent
Reuzeau

(10) Patent No.: US 7,956,240 B2
(45) Date of Patent: Jun. 7, 2011

(54) PLANTS HAVING IMPROVED GROWTH CHARACTERISTICS AND METHOD FOR MAKING THE SAME

(75) Inventor: Christophe Reuzeau, La Chapelle Gonaguet (FR)

(73) Assignee: CropDesign N.V., Zwijnaarde (BE)

( * ) Notice: Subject to any disclaimer, the term of this patent is extended or adjusted under 35 U.S.C. 154(b) by 453 days.

(21) Appl. No.: 11/921,545

(22) PCT Filed: Jun. 8, 2006

(86) PCT No.: PCT/EP2006/063017
§ 371 (c)(1),
(2), (4) Date: Dec. 3, 2007

(87) PCT Pub. No.: WO2006/131547
PCT Pub. Date: Dec. 14, 2006

(65) Prior Publication Data
US 2009/0138991 A1 May 28, 2009

Related U.S. Application Data

(60) Provisional application No. 60/690,483, filed on Jun. 15, 2005.

(30) Foreign Application Priority Data

Jun. 8, 2005 (EP) .................................. 05104980

(51) Int. Cl.
*C12N 15/82* (2006.01)
*C07H 21/04* (2006.01)
*A01H 5/00* (2006.01)
*A01H 5/10* (2006.01)
*A01H 1/00* (2006.01)

(52) U.S. Cl. ........ 800/278; 800/290; 800/300; 800/306; 800/312; 800/314; 800/320; 800/320.1; 800/320.2; 800/320.3; 536/23.6; 435/468

(58) Field of Classification Search ........................ None
See application file for complete search history.

(56) References Cited

U.S. PATENT DOCUMENTS

| 5,955,653 | A | * | 9/1999 | Scott et al. ..................... 800/303 |
| 7,192,774 | B2 | * | 3/2007 | Takaiwa et al. ................ 435/468 |
| 2004/0216190 | A1 | | 10/2004 | Kovalic |
| 2006/0150283 | A1 | * | 7/2006 | Alexandrov et al. ......... 800/288 |
| 2006/0265783 | A1 | * | 11/2006 | Schmidt ........................ 800/279 |

FOREIGN PATENT DOCUMENTS

| WO | WO 2004/007712 | * | 1/2004 |
| WO | WO-2004/007712 A2 | | 1/2004 |
| WO | WO-2004/016775 A2 | | 2/2004 |

OTHER PUBLICATIONS

Zhang et al, J Mol Evol, (2006), 63:612-621.*

* cited by examiner

*Primary Examiner* — Eileen B O Hara
(74) *Attorney, Agent, or Firm* — Connolly Bove Lodge & Hutz, LLP

(57) ABSTRACT

The present invention concerns a method for improving the growth characteristics of plants by increasing expression of at least part of a Leucine Rich Repeat Receptor-Like Kinase (RKS11, RKS4 or an orthologue of these). One such method comprises introducing into a plant a nucleic acid encoding at least part of a Leucine Rich Repeat Receptor-Like Kinase (RKS11 or RKS4 or an orthologue thereof). The invention also relates to transgenic plants having introduced therein a nucleic acid or variant thereof encoding at least part of a Leucine Rich Repeat Receptor-Like Kinase (RKS11 or RKS4 or an orthologue thereof), which plants have improved growth characteristics relative to corresponding wild type plants. The present invention also concerns constructs useful in the methods of the invention.

24 Claims, 29 Drawing Sheets

```
               1                                                  50
RKS11          MVVVTKKTMKIQIHLLYSFLFLCFSTLTLSSEPRNPEVEALISIRNNLHD
BX827036       MVVVTKKTMKIQIHLLYSFLFLCFSTLTLSSEPRNPEVEALISIRNNLHD
RKS11trunc     MVVVTKKTMKIQIHLLYSFLFLCFSTLTLSSEPRNPEVEALISIRNNLHD 51                                                 100
RKS11          PHGALNNWDEFSVDPCSWAMITCSPDNLVIGLGAPSQSLSGGLSESIGNL
BX827036       PHGALNNWDEFSVDPCSWAMITCSPDNLVIGLGAPSQSLSGGLSESIGNL
RKS11trunc     PHGALNNWDEFSVDPCSWAMITCSPDNLVIGLGAPSQSPSGGLSESIGNL 101                                                150
RKS11          TNLRQVSLQNNNISGKIPPELGFLPKLQTLDLSNNRFSGDIPVSIDQLSS
BX827036       TNLRQVSLQNNNISGKIPPELGFLPKLQTLDLSNNRFSGDIPVSIDQLSS
RKS11trunc     TNLRQVSLQNNNISGKIPPELGFLPKLQTLDLSNNRFSGDIPVSIDQLSS 151                                                200
RKS11          LQYLRLNNNSLSGPFPASLSQIPHLSFLDLSYNNLSGPVPKFPARTFNVA
BX827036       LQYLRLNNNSLSGPFPASLSQIPHLSFLDLSYNNLSGPVPKFPARTFNVA
RKS11trunc     LQYLRLNNNSLSGPFPASLSQIPHLSFLDLSYNNLSGPVPKFPARTFNVA 201                                                250
RKS11          GNPLICRSNPPEICSGSINASPLSVSLSSSSGRRSNRLAIALSVSLGSVV
BX827036       GNPLICRSNPPEICSGSINASPLSVSLSSSSGRRSNRLAIALSVSLGSVV
RKS11trunc     GNPLICRSNPPEICSGSINASPLSVSLSSSSGRRSNRLAIALSVSLGSVV 251                                                300
RKS11          ILVLALGSFCWYRKKQRRLLILNLNDKQEEGLQGLGNLRSFTFRELHVYT
BX827036       ILVLALGSFCWYRKKQRRLLILNLNDKQEEGLQGLGNLRSFTFRELHVYT
RKS11trunc     ILVLALGSFCWYRKKQRRLLILNLNDKQEEGLQGLGNLRSFTFRELHVYT 301                                                350
RKS11          DGFSSKNILGAGGFGNVYRGKLGDGTMVAVKRLKDINGTSGDSQFRMELE
BX827036       DGFSSKNILGAGGFGNVYRGKLGDGTMVAVKRLKDINGTSGDSQFRMELE
RKS11trunc     DGFSSKNILGAGGFGNVYRGKLEMGQWWQ~~~~~~~~~~~~~~~~~~~~~

351                                                400
RKS11          MISLAVHKNLLRLIGYCATSGERLLVYPYMPNGSVASKLKSKPALDWNMR
BX827036       MISLAVHKNLLRLIGYCATSGERLLVYPYMPNGSVASKLKSKPHWTGT~~
RKS11trunc     ~~~~~~~~~~~~~~~~~~~~~~~~~~~~~~~~~~~~~~~~~~~~~~~~~
```

FIGURE 3

```
              401                                            450
RKS11       KRIAIGAARGLLYLHEQCDPKIIHRDVKAANILLDECFEAVVGDFGLAKL
BX827036    ~~~~~~~~~~~~~~~~~~~~~~~~~~~~~~~~~~~~~~~~~~~~~~~~~
RKS11trunc  ~~~~~~~~~~~~~~~~~~~~~~~~~~~~~~~~~~~~~~~~~~~~~~~~~

451                                            500
RKS11       LNHADSHVTTAVRGTVGHIAPEYLSTGQSSEKTDVFGFGILLLELITGLR
BX827036    ~~~~~~~~~~~~~~~~~~~~~~~~~~~~~~~~~~~~~~~~~~~~~~~~~
RKS11trunc  ~~~~~~~~~~~~~~~~~~~~~~~~~~~~~~~~~~~~~~~~~~~~~~~~~

501                                            550
RKS11       ALEFGKTVSQKGAMLEWVRKLHEEMKVEELLDRELGTNYDKIEVGEMLQV
BX827036    ~~~~~~~~~~~~~~~~~~~~~~~~~~~~~~~~~~~~~~~~~~~~~~~~~
RKS11trunc  ~~~~~~~~~~~~~~~~~~~~~~~~~~~~~~~~~~~~~~~~~~~~~~~~~

551                                            600
RKS11       ALLCTQYLPAHRPKMSEVVLMLEGDGLAERWAASHNHSHFYHANISFKTI
BX827036    ~~~~~~~~~~~~~~~~~~~~~~~~~~~~~~~~~~~~~~~~~~~~~~~~~
RKS11trunc  ~~~~~~~~~~~~~~~~~~~~~~~~~~~~~~~~~~~~~~~~~~~~~~~~~

601                                    648
RKS11       SSLSTTSVSRLDAHCNDPTYQMFGSSAFDDDDDHQPLDSFAMELSGPR
BX827036    ~~~~~~~~~~~~~~~~~~~~~~~~~~~~~~~~~~~~~~~~~~~~~~~
RKS11trunc  ~~~~~~~~~~~~~~~~~~~~~~~~~~~~~~~~~~~~~~~~~~~~~~~
```

FIGURE 3 (continued)

SEQ ID NO: 1, Arabidopsis thaliana RKS11 nucleic acid sequence, start and stop codon in bold

AAAGTAATGCTGTCTCTCTTCTCTTCAAAATTATTGTTAACCTCTCGTAACTAAAATCTTCC
ATGGTAGTAGTAACAAAGAAGACCATGAAGATTCAAATTCATCTCCTTTACTCGTTCTTGTT
CCTCTGTTTCTCTACTCTCACTCTATCTTCTGAGCCCAGAAACCCTGAAGTTGAGGCGTTGA
TAAGTATAAGGAACAATTTGCATGATCCTCATGGAGCTTTGAACAATTGGGACGAGTTTTCA
GTTGATCCTTGTAGCTGGGCTATGATCACTTGCTCTCCCGACAACCTCGTCATTGGACTAGG
AGCGCCGAGCCAGTCTCTCTCGGGAGGTTTATCTGAGTCTATCGGAAATCTCACAAATCTCC
GACAAGTGTCATTGCAAAATAACAACATCTCCGGCAAAATTCCACCGGAGCTCGGTTTTCTA
CCCAAATTACAAACCTTGGATCTTTCCAACAACCGATTCTCCGGTGACATCCCTGTTTCCAT
CGACCAGCTAAGCAGCCTTCAATATCTGAGACTCAACAACAACTCTTTGTCTGGGCCCTTCC
CTGCTTCTTTGTCCCAAATTCCTCACCTCTCCTTCTTGGACTTGTCTTACAACAATCTCAGT
GGCCCTGTTCCTAAATTCCCAGCAAGGACTTTCAACGTTGCTGGTAATCCTTTGATTTGTAG
AAGCAACCCACCTGAGATTTGTTCTGGATCAATCAATGCAAGTCCACTTTCTGTTTCTTTGA
GCTCTTCATCAGGACGCAGGTCTAATAGATTGGCAATAGCTCTTAGTGTAAGCCTTGGCTCT
GTTGTTATACTAGTCCTTGCTCTCGGGTCCTTTTGTTGGTACCGAAAGAAACAAAGAAGGCT
ACTGATCCTTAACTTAAACGATAAACAAGAGGAAGGGCTTCAAGGACTTGGGAATCTAAGAA
GCTTCACATTCAGAGAACTCCATGTTTATACAGATGGTTTCAGTTCCAAGAACATTCTCGGC
GCTGGTGGATTCGGTAATGTGTACAGAGGCAAGCTTGGAGATGGGACAATGGTGGCAGTGAA
ACGGTTGAAGGATATTAATGGAACCTCAGGGGATTCACAGTTTCGTATGGAGCTAGAGATGA
TTAGCTTAGCTGTTCATAAGAATCTGCTTCGGTTAATTGGTTATTGCGCAACTTCTGGTGAA
AGGCTTCTTGTTTACCCTTACATGCCTAATGGAAGCGTCGCCTCTAAGCTTAAATCTAAACC
GGCATTGGACTGGAACATGAGGAAGAGGATAGCAATTGGTGCAGCGAGAGGTTTGTTGTATC
TACATGAGCAATGTGATCCCAAGATCATTCATAGAGATGTAAAGGCAGCTAATATTCTCTTA
GACGAGTGCTTTGAAGCTGTTGTTGGTGACTTTGGACTCGCAAAGCTCCTTAACCATGCGGA
TTCTCATGTCACAACTGCGGTCCGTGGTACGGTTGGCCACATTGCACCTGAATATCTCTCCA
CTGGTCAGTCTTCTGAGAAAACCGATGTGTTTGGGTTCGGTATACTATTGCTCGAGCTCATA
ACCGGACTGAGAGCTCTTGAGTTTGGTAAAACCGTTAGCCAGAAAGGAGCTATGCTTGAATG
GGTGAGGAAATTACATGAAGAGATGAAAGTAGAGGAACTATTGGATCGAGAACTCGGAACTA
ACTACGATAAGATTGAAGTTGGAGAGATGTTGCAAGTGGCTTTGCTATGCACACAATATCTG
CCAGCTCATCGTCCTAAAATGTCTGAAGTTGTTTTGATGCTTGAAGGCGATGGATTAGCCGA
GAGATGGGCTGCTTCGCATAACCATTCACATTTCTACCATGCCAATATCTCTTTCAAGACAA
TCTCTTCTCTGTCTACTACTTCTGTCTCAAGGCTTGACGCACATTGCAÀTGATCCAACTTAT
CAAATGTTTGGATCTTCGGCTTTCGATGATGACGATGATCATCAGCCTTTAGATTCCTTTGC
CATGGAACTATCCGGTCCAAGATAACACAATGAAAGAAGATATCATTTTTACGATGGATCA
AACAATCCAATGAAAAAGCTCTACACTTTTATAATATAGACATGTATATGGTGGTGAAAAT
TGATGAAAAATATCTCTACAGTTTGAGATTATGTGTTCGTTATGTTGATGATGTATATATTA
ACTTTTAATTGTGAGTTTC

FIGURE 4

SEQ ID NO: 2, Arabidopsis thaliana RKS11 deduced protein sequence

MVVVTKKTMKIQIHLLYSFLFLCFSTLTLSSEPRNPEVEALISIRNNLHDPHGALNNWDEFS
VDPCSWAMITCSPDNLVIGLGAPSQSLSGGLSESIGNLTNLRQVSLQNNNISGKIPPELGFL
PKLQTLDLSNNRFSGDIPVSIDQLSSLQYLRLNNNSLSGPFPASLSQIPHLSFLDLSYNNLS
GPVPKFPARTFNVAGNPLICRSNPPEICSGSINASPLSVLSSSSGRRSNRLAIALSVSLGS
VVILVLALGSFCWYRKKQRRLLILNLNDKQEEGLQGLGNLRSFTFRELHVYTDGFSSKNILG
AGGFGNVYRGKLGDGTMVAVKRLKDINGTSGDSQFRMELEMISLAVHKNLLRLIGYCATSGE
RLLVYPYMPNGSVASKLKSKPALDWNMRKRIAIGAARGLLYLHEQCDPKIIHRDVKAANILL
DECFEAVVGDFGLAKLLNHADSHVTTAVRGTVGHIAPEYLSTGQSSEKTDVFGFGILLLELI
TGLRALEFGKTVSQKGAMLEWVRKLHEEMKVEELLDRELGTNYDKIEVGEMLQVALLCTQYL
PAHRPKMSEVVLMLEGDGLAERWAASHNHSHFYHANISFKTISSLSTTSVSRLDAHCNDPTY
QMFGSSAFDDDDDHQPLDSFAMELSGPR

SEQ ID NO: 3, prm06771 forward primer, start codon in bold

GGGGACAAGTTTGTACAAAAAAGCAGGCTTAAACAATGGTAGTAGTAACAAAGAAGACC

SEQ ID NO: 4, prm06772 backward primer, reverse complement of stop codon in bold

GGGGACCACTTTGTACAAGAAAGCTGGGTTTCATTGTGTTATCTTGGACC

SEQ ID NO: 5: "RELHXXTDG" motif

RELHXXTDG

SEQ ID NO: 6: "EGDGLA" motif

EGDGLA

SEQ ID NO: 7: "ELSGPR" motif

ELSGPR

SEQ ID NO: 8: FNV(A/V)GNP(L/M)IC motif

FNV(A/V)GNP(L/M)IC

FIGURE 4 (continued)

SEQ ID NO: 9: RKS11$_{trunc}$, coding sequence in CDS3142 (86-1075)

ATGGTAGTAGTAACAAAGAAGACCATGAAGATTCAAATTCATCTCCTTTACTCGTTCTTGTT
CCTCTGTTTCTCTACTCTCACTCTATCTTCTGAGCCCAGAAACCCTGAAGTTGAGGCGTTGA
TAAGTATAAGGAACAATTTGCATGATCCTCATGGAGCTTTGAACAATTGGGACGAGTTTTCA
GTTGATCCTTGTAGCTGGGCTATGATCACTTGCTCTCCCGACAACCTCGTCATTGGACTAGG
AGCGCCGAGCCAGTCTCCCTCGGGAGGTTTATCTGAGTCTATCGGAAATCTCACAAATCTCC
GACAAGTGTCATTGCAAAATAACAACATCTCCGGCAAAATTCCACCGGAGCTCGGTTTTCTA
CCCAAATTACAAACCTTGGATCTTTCCAACAACCGATTCTCCGGTGACATCCCTGTTTCCAT
CGACCAGCTAAGCAGCCTTCAATATCTGAGACTCAACAACAACTCTTTGTCTGGGCCCTTCC
CTGCTTCTTTGTCCCAAATTCCTCACCTCTCCTTCTTGGACTTGTCTTACAACAATCTCAGT
GGCCCTGTTCCTAAATTCCCAGCAAGGACTTTCAACGTTGCTGGTAATCCTTTGATTTGTAG
AAGCAACCCACCTGAGATTTGTTCTGGATCAATCAATGCAAGTCCACTTTCTGTTTCTTTGA
GCTCTTCATCAGGACGCAGGTCTAATAGATTGGCAATAGCTCTTAGTGTAAGCCTTGGCTCT
GTTGTTATACTAGTCCTTGCTCTCGGGTCCTTTGTTGGTACCGAAAGAAACAAAGAAGGCT
ACTGATCCTTAACTTAAACGATAAACAAGAGGAAGGGCTTCAAGGACTTGGGAATCTAAGAA
GCTTCACATTCAGAGAACTCCATGTTTATACAGATGGTTTCAGTTCCAAGAACATTCTCGGC
GCTGGTGGATTCGGTAATGTGTACAGAGGCAAGCTGGAGATGGGACAATGGTGGCAG

SEQ ID NO: 10: RKS11$_{trunc}$, protein sequence

MVVVTKKTMKIQIHLLYSFLFLCFSTLTLSSEPRNPEVEALISIRNNLHDPHGALNNWDEFS
VDPCSWAMITCSPDNLVIGLGAPSQSPSGGLSESIGNLTNLRQVSLQNNNISGKIPPELGFL
PKLQTLDLSNNRFSGDIPVSIDQLSSLQYLRLNNNSLSGPFPASLSQIPHLSFLDLSYNNLS
GPVPKFPARTFNVAGNPLICRSNPPEICSGSINASPLSVSLSSSSGRRSNRLAIALSVSLGS
VVILVLALGSFCWYRKKQRRLLILNLNDKQEEGLQGLGNLRSFTFRELHVYTDGFSSKNILG
AGGFGNVYRGKLEMGQWWQ

SEQ ID NO: 11, Arabidopsis thaliana RKS4 sequence, complete cds, start and stop codon in bold

TGCTTTCTCTCCTCTCTGTTTTTTCTAGCTTTCTCTCTCACAAAATCAAAACTTTTTTTCTG
TGTTCATTATCATCTCCTTAAATTCATAACAATACACTCTCATAATTCTTCTCTGCGTAGGA
GAGACATTGCAGAAATAAAAGAGTTTTTAATAGACCCAAGAAAAAGAGAAAAAAAGCATTCA
TTTTTTTCTTGCTTTGTTGCTTTGCTTTTGCTTTTCTGTTTCTCTTCTTTTGTGGGCACAAC
AAAACATCAACAAAGTAATGATTTTGTGTTCTTCCTTCTCCTTCTGGTAATCTAATCTAAAG
CTTTTCATGGTGGTGATGAAGTTAATAACAATGAAGATATTCTCTGTTCTGTTACTACTATG
TTTCTTCGTTACTTGTTCTCTCTCTTCTGAACCCAGAAACCCTGAAGTGGAGGCGTTGATAA
ACATAAAGAACGAGTTACATGATCCACATGGTGTTTTCAAAAACTGGGATGAGTTTTCTGTT
GATCCTTGTAGCTGGACTATGATCTCTTGTTCTTCAGACAACCTCGTAATTGGCTTAGGAGC
TCCAAGTCAGTCTCTTTCAGGAACTTATCTGGGTCTATTGGAAATCTCACTAATCTTCGAC
AAGTGTCATTACAGAACAATAACATCTCCGGTAAAATCCCACCGGAGATTTGTTCTCTTCCC
AAATTACAGACTCTGGATTTATCCAATAACCGGTTCTCCGGTGAAATCCCCGGTTCTGTTAA
CCAGCTGAGTAATCTCCAATATCTGAGGTTGAACAACAACTCATTATCTGGGCCCTTTCCTG

```
CTTCTCTGTCTCAAATCCCTCACCTCTCTTTCTTAGACTTGTCTTATAACAATCTCAGAGGT
CCTGTTCCTAAATTTCCTGCAAGGACATTCAATGTTGCTGGGAACCCTTTGATTTGTAAAAA
CAGCCTACCGGAGATTTGTTCAGGATCAATCAGTGCAAGCCCTCTTTCTGTCTCTTTACGTT
CTTCATCAGGACGTAGAACCAACATATTAGCAGTTGCACTTGGTGTAAGCCTTGGCTTTGCT
GTTAGTGTAATCCTCTCTCTCGGGTTCATTTGGTATCGAAAGAAACAAAGACGGTTAACGAT
GCTTCGCATTAGTGACAAGCAAGAGGAAGGGTTACTTGGGTTGGGAAATCTAAGAAGCTTCA
CATTCAGGGAACTTCATGTAGCTACGGATGGTTTTAGTTCCAAGAGTATTCTTGGTGCTGGT
GGGTTTGGTAATGTCTACAGAGGAAAATTCGGGGATGGGACAGTGGTTGCAGTGAAACGATT
GAAAGATGTGAATGGAACCTCCGGGAACTCACAGTTTCGTACTGAGCTTGAGATGATCAGCT
TAGCTGTTCATAGGAATTTGCTTCGGTTAATCGGTTATTGTGCGAGTTCTAGCGAAAGACTT
CTTGTTTACCCTTACATGTCCAATGGCAGCGTCGCCTCTAGGCTCAAAGCTAAGCCAGCGTT
GGACTGGAACACAAGGAAGAAGATAGCGATTGGAGCTGCAAGAGGGTTGTTTATCTACACG
AGCAATGCGATCCCAAGATTATTCACCGAGATGTCAAGGCAGCAAACATTCTCCTAGATGAG
TATTTTGAAGCAGTTGTTGGGGATTTTGGACTAGCAAAGCTACTCAACCACGAGGATTCACA
TGTCACAACCGCGGTTAGAGGAACTGTTGGTCACATTGCACCTGAGTATCTCTCCACCGGTC
AGTCATCTGAGAAACCGATGTCTTTGGGTTCGGTATACTTTTGCTAGAGCTCATCACAGGA
ATGAGAGCTCTCGAGTTTGGCAAGTCTGTTAGCCAGAAAGGAGCTATGCTAGAATGGGTGAG
GAAGCTACACAAGGAAATGAAAGTAGAGGAGCTAGTAGACCGAGAACTGGGGACAACCTACG
ATAGAATAGAAGTTGGAGAGATGCTACAAGTGGCACTGCTCTGCACTCAGTTTCTTCCAGCT
CACAGACCCAAAATGTCTGAAGTAGTTCAGATGCTTGAAGGAGATGGATTAGCTGAGAGATG
GGCTGCTTCACATGACCATTCACATTTCTACCATGCCAACATGTCTTACAGGACTATTACCT
CTACTGATGGCAACAACCAAACCAAACATCTGTTTGGCTCCTCAGGATTTGAAGATGAAGAT
GATAATCAAGCGTTAGATTCATTCGCCATGGAACTATCTGGTCCAAGGTAGTAAATCTTGGA
CACAGAAAGAAACAGATATAATATCCCCATGACTTCAATTTTTGTTTTTGAGATGATATAGA
CATGTAAATGGTTATCAAACCTTTGAAAAAATTGAGATTC
```

SEQ ID NO: 12, Arabidopsis thaliana RKS4, deduced protein sequence

```
MVVMKLITMKIFSVLLLLCFFVTCSLSSEPRNPEVEALINIKNELHDPHGVFKNWDEFSVDP
CSWTMISCSSDNLVIGLGAPSQSLSGTLSGSIGNLTNLRQVSLQNNNISGKIPPEICSLPKL
QTLDLSNNRFSGEIPGSVNQLSNLQYLRLNNNSLSGPFPASLSQIPHLSFLDLSYNNLRGPV
PKFPARTFNVAGNPLICKNSLPEICSGSISASPLSVSLRSSSGRRTNILAVALGVSLGFAVS
VILSLGFIWYRKKQRRLTMLRISDKQEEGLLGLGNLRSFTFRELHVATDGFSSKSILGAGGF
GNVYRGKFGDGTVVAVKRLKDVNGTSGNSQFRTELEMISLAVHRNLLRLIGYCASSSERLLV
YPYMSNGSVASRLKAKPALDWNTRKKIAIGAARGLFYLHEQCDPKIIHRDVKAANILLDEYF
EAVVGDFGLAKLLNHEDSHVTTAVRGTVGHIAPEYLSTGQSSEKTDVFGFGILLLELITGMR
ALEFGKSVSQKGAMLEWVRKLHKEMKVEELVDRELGTTYDRIEVGEMLQVALLCTQFLPAHR
PKMSEVVQMLEGDGLAERWAASHDHSHFYHANMSYRTITSTDGNNQTKHLFGSSGFEDEDDN
QALDSFAMELSGPR
```

FIGURE 4 (continued)

SEQ ID NO: 13, Arabidopsis thaliana RKS11 homologue, natural
truncated form, GenBank BX827036

```
CAAACTCATCTCCTCTGAGAGAGACTGTTTGTTTGAGAAGAAGACGAACGTAAAGACTTGTT
TACTAAACCCGAGATTTCTTTCTTTCTTGTTTTCAAAATAAAAAAGCAGAGATCTCTTCTCC
TTCTTCTTCTTTTTGCTTTGTTTGCTTTTGCTTTCTCTTCTTTTTCTATGTGTGTTTGTGGT
CACTACCCCGAAAGGAAATAAAGTAATGCTGTCTCTCTTCTCTTCAAAATTATTGTTAACCT
CTCGTAACTAAGATGTTCCATGGTAGTAGTAACAAAGAAGACCATGAAGATTCAAATTCATC
TCCTTTACTCGTTCTTGTTCCTCTGTTTCTCTACTCTCACTCTATCTTCTGAGCCCAGAAAC
CCTGAAGTTGAGGCGTTGATAAGTATAAGGAACAATTTGCATGATCCTCATGGAGCTTTGAA
CAATTGGGACGAGTTTTCAGTTGATCCTTGTAGCTGGGCTATGATCACTTGCTCTCCCGACA
ACCTCGTCATTGGACTAGGAGCGCCAAGCCAGTCTCTCTCGGGAGGTTTATCTGAGTCTATC
GGAAATCTCACAAATCTCCGACAAGTGTCATTGCAAAATAACAACATCTCCGGCAAAATTCC
ACCGGAGCTCGGTTTTCTACCCAAATTACAAACCTTGGATCTTTCCAACAACCGATTCTCCG
GTGACATCCCTGTTTCCATCGACCAGCTAAGCAGCCTTCAATATCTGAGACTCAACAACAAC
TCTTTGTCTGGGCCCTTCCCTGCTTCTTTGTCCCAAATTCCTCACCTCTCCTTCTTGGACTT
GTCTTACAACAATCTCAGTGGCCCTGTTCCTAAATTCCCAGCAAGGACTTTCAACGTTGCTG
GTAATCCTTTGATTTGTAGAAGCAACCCACCTGAGATTTGTTCTGGATCAATCAATGCAAGT
CCACTTTCTGTTTCTTTGAGCTCTTCATCAGGACGCAGGTCTAATAGATTGGCAATAGCTCT
TAGTGTAAGCCTTGGCTCTGTTGTTATACTAGTCCTTGCTCTCGGGTCCTTTTGTTGGTACC
GAAAGAAACAAAGAAGGCTACTGATCCTTAACTTAAACGATAAACAAGAGGAAGGGCTTCAA
GGACTTGGGAATCTAAGAAGCTTCACATTCAGAGAACTCCATGTTTATACAGATGGTTTCAG
TTCCAAGAACATTCTCGGCGCTGGTGGATTCGGTAATGTGTACAGAGGCAAGCTTGGAGATG
GGACAATGGTGGCAGTGAAACGGTTGAAGGATATTAATGGAACCTCAGGGGATTCACAGTTT
CGTATGGAGCTAGAGATGATTAGCTTAGCTGTTCATAAGAATCTGCTTCGGTTAATTGGTTA
TTGCGCAACTTCTGGTGAAAGGCTTCTTGTTTACCCTTACATGCCTAATGGAAGCGTCGCCT
CTAAGCTTAAATCTAAACCGCATTGGACTGGAACATGAGGAAGAGGATAGCAATTGGTGCAG
CGAGATGTTTGTTGTATCTACATGAGCAATGTGATCCCAAGATCATTCATAGAGATGTAAAG
GCAGCTAATATTCTCTTAGACGAGTGCTTTGAAGCTGTTGTTGGTGACTTTGCACTCGCAAA
GCTCCTTAACCATGCGGATTCTCATGTAACAACTGCGGTCCGTGGTACGGTTGGCCACATTG
CACCTGAATATCTCTCCACTGGTCAGTCTTCTGAGAAACCGATGTGTTTGGGTTCGGTATA
CTATTGCTCGAGCTCATAACCGTATTTTTGTTCTTGAGTTTGGTAAAACCGTTAGCCAGAA
AGGAGCTATGCTTGAATGGGTGAGGAAATTACATGAAGAGATGAAAGTAGAGGAACTATTGG
ATCGAGAACTCGGAACTAACTACGATAAGATTGAAGTTGGAGAGATGTTGCAAGTGGCTTTG
CTATGCACACAATATCTGCCAGCTCATCGTCCTAAAATGTCTGAAGTTGTTTTGATGCTTGA
AGGCGATGGATTAGCCGAGAGATGGGCTGTCGCATAACCATTCACATTTCTACCATGCCAAT
ATCTCTTTCAAGACAATCTCTTCTCTGTCTACTACTTCTGTCTCAAGGCTTTACGCACATTG
CAATGATCCAACTTATCAAATGTTTGGATCTTCGGCTTTCGATGATGACGATGATCATCAGC
CTTTAGATTCCTTTGCCATGGAACTATCCGGTCCAAGATAACACAATGAAAGAAAGATATGA
TTTTTACGATGGATCAAACAATCCAATGAAAAAGCTCTACACTTCCATAATATACACAT
```

FIGURE 4 (continued)

SEQ ID NO: 14, Arabidopsis thaliana RKS11 homologue, natural truncated form, GenBank BX827036, deduced protein sequence

MVVVTKKTMKIQIHLLYSFLFLCFSTLTLSSEPRNPEVEALISIRNNLHDPHGALNNWDEFS
VDPCSWAMITCSPDNLVIGLGAPSQSLSGGLSESIGNLTNLRQVSLQNNNISGKIPPELGFL
PKLQTLDLSNNRFSGDIPVSIDQLSSLQYLRLNNNSLSGPFPASLSQIPHLSFLDLSYNNLS
GPVPKFPARTFNVAGNPLICRSNPPEICSGSINASPLSVSLSSSSGRRSNRLAIALSVSLGS
VVILVLALGSFCWYRKKQRRLLILNLNDKQEEGLQGLGNLRSFTFRELHVYTDGFSSKNILG
AGGFGNVYRGKLGDGTMVAVKRLKDINGTSGDSQFRMELEMISLAVHKNLLRLIGYCATSGE
RLLVYPYMPNGSVASKLKSKPHWTGT

SEQ ID NO: 15, BAD68256.1, putative brassinosteroid insensitive 1-associated receptor kinase 1 [Oryza sativa (japonica cultivar-group)], truncated form of SEQ ID NO: 16

MRMRWWAAPLAAVLAVILLPSSTATLSPAGINYEVVALMAIKTELQDPYNVLDNWDINSVDP
CSWRMVTCSADGYVSALGLPSQSLSGKLSPGIGNLTRLQSVLLQNNAISGTIPASIGRLGML
QTLDMSDNQITGSIPSSIGDLKNLNYLKLNNNSLSGVLPDSLAAINGLALVDLSFNNLSGPL
PKISSRTFNIVGNPMICGVKSGDNCSSVSMDPLSYPPDDLKTQPQQGIARSHRIAIICGVTV
GSVAFATIIVSMLLWWRHRRNQQIFFDVNDQYDPEVCLGHLKRYAFKELRAATNNFNSKNIL
GEGGYGIVYKGFLRDGAIVAVKRLKDYNAVGGEVQFQTEVEVISLAVHRNLLRLIGFCTTEN
ERLLVYPYMPNGSVASQLRELVNGKPALDWSRRRRMFLGLEFCWLS

SEQ ID NO: 16, BAD68255.1, putative brassinosteroid insensitive 1-associated receptor kinase 1 [Oryza sativa (japonica cultivar-group)], full length form

MRMRWWAAPLAAVLAVILLPSSTATLSPAGINYEVVALMAIKTELQDPYNVLDNWDINSVDP
CSWRMVTCSADGYVSALGLPSQSLSGKLSPGIGNLTRLQSVLLQNNAISGTIPASIGRLGML
QTLDMSDNQITGSIPSSIGDLKNLNYLKLNNNSLSGVLPDSLAAINGLALVDLSFNNLSGPL
PKISSRTFNIVGNPMICGVKSGDNCSSVSMDPLSYPPDDLKTQPQQGIARSHRIAIICGVTV
GSVAFATIIVSMLLWWRHRRNQQIFFDVNDQYDPEVCLGHLKRYAFKELRAATNNFNSKNIL
GEGGYGIVYKGFLRDGAIVAVKRLKDYNAVGGEVQFQTEVEVISLAVHRNLLRLIGFCTTEN
ERLLVYPYMPNGSVASQLRELVNGKPALDWSRRKRIALGTARGLLYLHEQCDPKIIHRDVKA
SNVLLDEYFEAIVGDFGLAKLLDHRESHVTTAVRGTVGHIAPEYLSTGQSSEKTDVFGFGVL
LVELITGQKALDFGRLANQKGGVLDWVKKLHQEKQLSMMVDKDLGSNYDRVELEEMVQVALL
CTQYYPSHRPRMSEVIRMLEGDGLAEKWEASQNVDTPKSVSSELLPPKFMDFAADESSLGLE
AMELSGPR

FIGURE 4 (continued)

SEQ ID NO: 17, rice RKS11 orthologue, coding sequence

```
ATGGCCTCCAACCTCTTCCTCCTCCTCTTCTTCCTCGTCGTCTCCTACGCGCCGTTCCTCGC
CTTCTCCTCCGAGCCCCTCAACCCTGAAGTGGAGGCGCTGATCGCCATCAGGCAGGGCTGG
TCGACCCGCACGGCGTGCTGAACAACTGGGACGAGGACTCCGTCGACCCCTGCAGCTGGGCC
ATGGTCACCTGCTCCGCCCACAACCTCGTCATCGGCCTGGGAGCGCCCAGCCAGGGATTGTC
GGGGACCCTGTCCGGCAGGATCGCCAACCTCACCAATCTTGAACAAGTGCTGCTGCAGAACA
ACAACATCACCGGCCGGCTGCCGCCGGAGCTGGGCGCGCTGCCGAGGCTGCAGACGCTCGAC
CTCTCCAACAACCGCTTCTCCGGCCGCGTCCCCGACACGCTCGGCCGCCTCTCCACCCTCCG
ATACCTGAGGCTAAACAACAACAGCTTGTCCGGGGCGTTCCCGTCGTCGCTGGCCAAGATCC
CACAGCTCTCCTTCCTGGACTTGTCCTACAACAACCTCACTGGCCCTGTTCCTCACTTCCCC
ACAAGAACATTCAACGTCGTGGGCAATCCAATGATATGCGGGAGCAGCAGCGGCAGCCATGC
GGGGAACGCGAACGCAGCGGAGTGCGCCACCGTGGTCGCCCCGGTCACCGTGCCATTCCCGC
TGGACTCCACTCCGAGCAGCAGCAGCAGGGCGGCAGCGGCAGCGGTGGGGAGGTCAAAGGGT
GGAGGAGGCGCCGCGCGGTTGCCGATCGGAGTAGGGACAAGCCTTGGCGCCTCCGCGCTTGT
GCTCCTCGCCGTCTCCTGCTTTCTCTGGAGGCGCAGGCGCCGGCACCGCTGCCTCCTCTCGG
GCCCCTCCTCCGTCCTCGGCATCCTCGAGAAGGGGAGAGACGTGGAGGATGGGGAGGAGGG
GAGGTGATGGCGAGGCTGGGGAACGTGAGGCAGTTCGGGCTGAGGGAGCTGCACGCGGCGAC
GGACGGGTTCAGCGCGAGGAACATACTGGGGAAAGGAGGGTTCGGGGACGTGTACCGGGGGA
GGCTCTCCGACGGCACGGTCGTGGCGGTGAAGCGGCTCAAGGACCCGACCGCGTCCGGGGAG
GCGCAGTTCCGGACGGAGGTGGAGATGATCAGCCTCGCCGTGCACCGCCACCTCCTCCGCCT
CGTCGGCTTCTGCGCCGCGGCCTCCGGCGAGCGCCTCCTCGTCTACCCCTACATGCCCAACG
GCAGCGTCGCCTCCCGCCTTCGAGGGAAGCCGCCGCTGGACTGGCAGACGAGGAAGCGGATC
GCGGTGGGGACGGCGAGGGGATTGCTGTACCTGCACGAGCAGTGCGACCCAAAGATCATCCA
CCGCGACGTGAAGGCCGCGAACGTGCTGCTGGACGAGTGCCACGAGGCCGTCGTCGGCGACT
TCGGGCTCGCCAAGCTGCTCGACCACGGCGACTCCCACGTCACCACGGCGGTGCGCGGCACG
GTGGGGCACATCGCGCCGGAGTACCTCTCCACGGGGCAGTCGTCGGAGAAGACCGACGTGTT
CGGCTTCGGCATCCTGCTGCTCGAGCTCGTCACCGGCCAGCGCGCGCTCGAGGTCGGCAAGG
GCTCCGGCGTCATCCAGCACCAGAAGGGCGTCATGCTCGATTGGGTGAGGAAGGTGCACCAA
GAGAAGCTGCATGACTTGCTAGTGGACCAAGATTTGGGGCCTCACTACGACAGGATAGAGGT
GGCGGAGATGGTGCAGGTGGCGCTGCTCTGCACCCAGTTCCAGCCGTCTCACCGGCCGAGGA
TGTCGGAGGTGGTCCGGATGCTGGAGGGAGACGGGCTCGCCGAGAAATGGAGGCCAACCAC
CGGCCGGCGGCGATGGCGGCGGCGGCGGCGCCCCATGAGCTCGGCTACGACCACCGCAACGA
CTCCAACGGCTCCGTCTTCTTCAACGACTTCCACGACAACGACAGCAGCCTTAGCAGCGACG
AGGTGCGGTCCATCGACATGGTAGAGGAGATGGAGCTGTCAGGGCCAAGGTAG
```

SEQ ID NO: 18, rice RKS11 orthologue, deduced protein sequence

MASNLFLLLFFLVVSYAPFLAFSSEPLNPEVEALIAIRQGLVDPHGVLNNWDEDSVDPCSWA
MVTCSAHNLVIGLGAPSQGLSGTLSGRIANLTNLEQVLLQNNNITGRLPPELGALPRLQTLD
LSNNRFSGRVPDTLGRLSTLRYLRLNNNSLSGAFPSSLAKIPQLSFLDLSYNNLTGPVPHFP
TRTFNVVGNPMICGSSSGSHAGNANAAECATVVAPVTVPFPLDSTPSSSRAAAAAVGRSKG
GGGAARLPIGVGTSLGASALVLLAVSCFLWRRRRRHRCLLSGPSSVLGILEKGRDVEDGGGG
EVMARLGNVRQFGLRELHAATDGFSARNILGKGGFGDVYRGRLSDGTVVAVKRLKDPTASGE

FIGURE 4 (continued)

AQFRTEVEMISLAVHRHLLRLVGFCAAASGERLLVYPYMPNGSVASRLRGKPPLDWQTRKRI
AVGTARGLLYLHEQCDPKIIHRDVKAANVLLDECHEAVVGDFGLAKLLDHGDSHVTTAVRGT
VGHIAPEYLSTGQSSEKTDVFGFGILLLELVTGQRALEVGKGSGVIQHQKGVMLDWVRKVHQ
EKLHDLLVDQDLGPHYDRIEVAEMVQVALLCTQFQPSHRPRMSEVVRMLEGDGLAEKWEANH
RPAAMAAAAPHELGYDHRNDSNGSVFFNDFHDNDSSLSSDEVRSIDMVEEMELSGPR

SEQ ID NO: 19, promoter sequence for embryo and aleurone specific expression

GGTCAGCCAATACATTGATCCGTTGCCAATCATGCAAAGTATTTTGGCTGTGGCCGAGTGCC
GGAATTGATAATTGTGTTCTGACTAAATTAAATGACCAGAAGTCGCTATCTTCCAATGTATC
CGAAACCTGGATTAAACAATCCTGTTCTGTTCTCTAGCCCCTCCTGCATGGCCGGATTGTTT
TTTTGACATGTTTTCTTGACTGAGGCCTGTTTGTTCTAAACTTTTTCTTCAAACTTTTAACT
TTTTCATCACATCAGAACTTTTCTACACATATAAACTTTTAACTTTTCCGTCACATCGTTCC
AATTTCAATCAAACTTTCAATTTTGGCGTGAACTAAACACACCCTGAGTCTTTTATTGCTCC
TCCGTACGGGTTGGCTGGTTGAGAATAGGTATTTTCAGAGAGAAATCTAGATATTGGGAGG
AACTTGGCATGAATGGCCACTATATTTAGAGCAATTCTACGGTCCTTGAGGAGGTACCATGA
GGTACCAAAATTTTAGTGTAAATTTTAGTATCTCATTATAACTAGGTATTATGAGGTACCAA
ATTTACAATAGAAAAATAGTACTTCATGGTACTTTCTTAAGTACCGTAAAATTGCTCCTAT
ATTTAAGGGGATGTTTATATCTATCCATATCCATAATTTGATTTTGATAAGAAAAAATGTGA
GCACACCAAGCATGTCCATGACCTTGCACTCTTGGCTCACTCGTCAACTGTGAAGAACCTCA
AAAATGCTCAATATAGCTACAGGTGCCTGAAAAATAACTTTAAAGTTTTGAACATCGATTT
CACTAAACAACAATTATTATCTCCCTCTGAAAGATGATAGTTTAGAACTCTAGAATCATTGT
CGGCGGAGAAAGTAAATTATTTTCCCCAAATTTCCAGCTATGAAAAAACCCTCACCAAACAC
CATCAAACAAGAGTTCACCAAACCGCCCATGCGGCCATGCTGTCACGCAACGCACCGCATTG
CCTGATGGCCGCTCGATGCATGCATGCTTCCCCGTGCACATATCCGACAGACGCGCCGTGTC
AGCGAGCTCCTCGACCGACCTGTGTAGCCCATGCAAGCATCCACCCCCGCCACGTACACCCC
CTCCTCCTCCCTACGTGTCACCGCTCTCTCCACCTATATATGCCCACCTGGCCCCTCCTC
CCATCTCCACTTCACCCGATCGCTTCTTCTTCTTCTTCGTTGCATTCATCTTGCTAGC

SEQ ID NO: 20, NM_103144.3 Arabidopsis thaliana SERK2 (SOMATIC EMBRYOGENESIS RECEPTOR-LIKE KINASE 2); kinase AT1G34210 (SERK2) mRNA, complete cds ACTTTTGTAGTGACTAGTGAGTAGAGTAGGCTTTTAGAGAGAGAGAGAGAGAGACGGCTGTT
GAAAGATAACCACAGAACACAAAAACTCATTCATTAAGAATGAGAAAGAAAGTCCCAAAAAC
CTTTTTTGCTCTGAAAAAGCAACGCAAAGTTTTGAAAAATCTCACACCTTTTTCACTTCTCT
GTTTGTAGCTGTTACCACTTGTGTTTCCCCTTTGGCATTTTTCTCGGTTGTCATTAATGAGA
GTAAAATCATCATCAAGTGTAAACTTCTCTCTCTCTTTCTCTATCTCTATCTCAAAGCTCTC
AACTTTGGAGAGATCATGGTTTGTGTTTGATTTCTCAAGTTTTTTTTTTTTACCCTCTTGG
AGGATCTGGGAGGAGAAATTTGCTTTTTTTGGTAAATGGGGAGAAAAAGTTTGAAGCTTT
TGGTTTTGTCTGCTTAATCTCACTGCTTCTTCTGTTTAATTCGTTATGGCTTGCCTCTTCTA
ACATGGAAGGTGATGCACTGCACAGTTTGAGAGCTAATCTAGTTGATCCAAATAATGTCTTG
CAAAGCTGGGATCCTACGCTTGTTAATCCGTGTACTTGGTTTCACGTAACGTGTAACAACGA
GAACAGTGTTATAAGAGTCGATCTTGGGAATGCAGACTTGTCTGGTCAGTTGGTTCCTCAGC FIGURE 4 (continued)

```
TAGGTCAGCTCAAGAACTTGCAGTACTTGGAGCTTTATAGTAATAACATAACCGGGCCGGTT
CCAAGCGATCTTGGGAATCTGACAAACTTAGTGAGCTTGGATCTTTACTTGAACAGCTTCAC
TGGTCCAATTCCAGATTCTCTAGGAAAGCTATTCAAGCTTCGCTTTCTTCGGCTCAACAATA
ACAGTCTCACCGGACCAATTCCCATGTCATTGACTAATATCATGACCCTTCAAGTTTTGGAT
CTGTCGAACAACCGATTATCCGGATCTGTTCCTGATAATGGTTCCTTCTCGCTCTTCACTCC
CATCAGTTTTGCTAACAACTTGGATCTATGCGGCCCAGTTACTAGCCGTCCTTGTCCTGGAT
CTCCCCCGTTTTCTCCTCCACCACCTTTTATACCACCTCCCATAGTTCCTACACCAGGTGGG
TATAGTGCTACTGGAGCCATTGCGGGAGGAGTTGCTGCTGGTGCTGCTTTACTATTTGCTGC
CCCTGCTTTAGCTTTTGCTTGGTGGCGTAGAAGAAAACCTCAAGAATTCTTCTTTGATGTTC
CTGCCGAAGAGGACCCTGAGGTTCACTTGGGGCAGCTTAAGCGGTTCTCTCTACGGGAACTT
CAAGTAGCAACTGATAGCTTCAGCAACAAGAACATTTTGGGCCGAGGTGGGTTCGGAAAAGT
CTACAAAGGCCGTCTTGCTGATGGAACACTTGTTGCAGTCAAACGGCTTAAAGAAGAGCGAA
CCCCAGGTGGCGAGCTCCAGTTTCAGACAGAAGTGGAGATGATAAGCATGGCCGTTCACAGA
AATCTCCTCAGGCTACGCGGTTTCTGTATGACCCCTACCGAGAGATTGCTTGTTTATCCTTA
CATGGCTAATGGAAGTGTCGCTTCCTGTTTGAGAGAACGTCCACCATCACAGTTGCCTCTAG
CCTGGTCAATAAGACAGCAAATCGCGCTAGGATCAGCGAGGGGTTTGTCTTATCTTCATGAT
CATTGCGACCCCAAAATTATTCACCGTGATGTGAAAGCTGCTAATATTCTGTTGGACGAGGA
ATTTGAGGCGGTGGTAGGTGATTTCGGGTTAGCTAGACTTATGGACTATAAAGATACTCATG
TCACAACGGCTGTGCGTGGGACTATTGGACACATTGCTCCTGAGTATCTCTCAACTGGAAAA
TCTTCAGAGAAAACTGATGTTTTGGCTACGGGATCATGCTTTTGGAACTGATTACAGGTCA
GAGAGCTTTTGATCTTGCAAGACTGGCGAATGACGATGACGTTATGCTCCTAGATTGGGTGA
AAGGGCTTTTGAAGGAGAAGAAGCTGGAGATGCTTGTGGATCCTGACCTGCAAAGCAATTAC
ACAGAAGCAGAAGTAGAACAGCTCATACAAGTGGCTCTTCTCTGCACACAGAGCTCACCTAT
GGAACGACCTAAGATGTCTGAGGTTGTTCGAATGCTTGAAGGTGACGGTTTAGCGGAGAAAT
GGGACGAGTGGCAGAAAGTGGAAGTTCTCAGGCAAGAAGTGGAGCTCTCTTCTCACCCCACC
TCTGACTGGATCCTTGATTCGACTGATAATCTTCATGCTATGGAGTTGTCTGGTCCAAGATA
AACGACATTGTAATTTGCCTAACAGAAAAGAGAAAGAACAGAGAAATATTAAGAGAATCACT
TCTCTGTATTCTTTATTTCTTTGGTAGAAAAATAATGTAGTCTCTAATCAAATCTTATTCCA
TCTATCAGCATTCTTCATTCATTTCTTGTGAAAACCAAGGCCTTTAAATTAAACATAATCAC
AAACACCAAGTTCTATACATTACATATGTCTTCCACTGGATAAAGAGGAAGAAAAGGCTATT
CCAAAAAACATTTTGAGCTCTTTGTTCCGCAAGAGAAGGAACAGCACAAGTGAAACACACTG
AAAAACACCAAGCTTGCATTATAACATATGCAGGTAAGAATCACGAATCATGGGCGGGTCTT
GTATTGTCTGAGAACGAATGAGAGCCAGATGAGGGATCATGCTTCTGCGATGTGAAGAGATT
AGGGTATGAGTAATAGGGATCATCTTCCATTGAAGGCAGTCTCATTTGCTGATGGTCCTGGT
CAGGGCTGAGTCTGTCAAGTGGTGAAGTCTCTGGCCTTTGGAGCTCTGGCAGATCGCCATAG
CTGCTGACTGATGAGTTCTGATGATCAAACTGCGGTTTCTCCATTGACGGGAATCTATGTGG
TGTAAGATCGTCATAGTTGCTGCCTGATGAGTTCTGATGATCAAACTGCGGTTTCTCCAATG
ACGAGAATCTCTGTGGTGTAAGATCGTCATAGTTGCTGCCTGATGAGTTCTGATGATCAAAC
TGTGGTTTTTCCATTGAATGGAATCTCTGTGGGTAAGATCGCCATAGCTACTGAATGATGA
GTTCTGACGATCAAACTGCGGTTTTTCCATTGAAGAGTGTGTCTGTGGCTGTTGGTTGTTCT
GCTCAGAGTTGAAAAGTGACGAAGTTTCTGCTCTCTGGAGCTCTGTAAGATCTCCGCTACTG
CTGGCCGAAGAATTCTGATGATCAAATTGAAGGTTTCCCATTGAGGGAGCATGGAAAGGGTT
CTCAGACGGACTTTCTGGATACTGATCAGAAGTCTTCCTGGTAAGCTCGTTGATTCTGAGTT
GTGCCAGGCTTGCAGCTGAGCGGGCAGCTGATGCTGCACGTTCTGCTGAGTCAGCAGCAGCT
TGAGCAGCCATTAAGACATCCTGCAAGTCTCCATCGGATATTTTCCTTGGA
```

FIGURE 4 (continued)

SEQ ID NO: 21, NP_174683.1, SERK2 (SOMATIC EMBRYOGENESIS RECEPTOR-LIKE KINASE 2); kinase [Arabidopsis thaliana]

MGRKKFEAFGFVCLISLLLLFNSLWLASSNMEGDALHSLRANLVDPNNVLQSWDPTLVNPCT
WFHVTCNNENSVIRVDLGNADLSGQLVPQLGQLKNLQYLELYSNNITGPVPSDLGNLTNLVS
LDLYLNSFTGPIPDSLGKLFKLRFLRLNNNSLTGPIPMSLTNIMTLQVLDLSNNRLSGSVPD
NGSFSLFTPISFANNLDLCGPVTSRPCPGSPPFSPPPPFIPPPIVPTPGGYSATGAIAGGVA
AGAALLFAAPALAFAWWRRRKPQEFFFDVPAEEDPEVHLGQLKRFSLRELQVATDSFSNKNI
LGRGGFGKVYKGRLADGTLVAVKRLKEERTPGGELQFQTEVEMISMAVHRNLLRLRGFCMTP
TERLLVYPYMANGSVASCLRERPPSQLPLAWSIRQQIALGSARGLSYLHDHCDPKIIHRDVK
AANILLDEEFEAVVGDFGLARLMDYKDTHVTTAVRGTIGHIAPEYLSTGKSSEKTDVFGYGI
MLLELITGQRAFDLARLANDDDVMLLDWVKGLLKEKKLEMLVDPDLQSNYTEAEVEQLIQVA
LLCTQSSPMERPKMSEVVRMLEGDGLAEKWDEWQKVEVLRQEVELSSHPTSDWILDSTDNLH
AMELSGPR

SEQ ID NO: 22, NM_104763.2, Arabidopsis thaliana kinase AT1G60800 mRNA, complete cds

ACCAAAGTCATAAAAATGATATAAAATATAAACCAAGAAGCACTATTAGTATCACTCATCAC
TCAATAGCTTTTTTTTTTTCAGATCTCTAGGAAAATTTCTCAGACTTTCAGAGCATTTTGGT
GCTTTTGTTTTGCTTGGTTTCTCGGGAAAATTCTCTTCACACTTTTAGAGTTTTCTCTCTCT
TCTCTATCTCTTGTCACAGCTCGTTTAGCATTCATTCTCTTAATCGTTTCTTCATTCAAAAA
TTCTCTCTTTCTAAGCTGAGTAACTTGCAAGTCGTCATTTTTCAATTGGGGTCTTCTCCTTT
TTACTTCCTTTGAATTGAAATCACAGAGAAAGAGAGGTTCCATTGCTGGAAATGGATTGCT
CAAATTAGTTTCTGTGTCTAAATAAAGACAGAGAAGAAGAAAAGTAGACAAAAGCTAAGTTT
TTTTTTCAGATATGGGAGAGAGAAAAATGAGTTGGTGGGTTCTTTGAAACTTGTTTTTGTTC
AGACCAAAGTTGATTGCTTTAAGAAGGGATATGGAAGGTGTGAGATTTGTGGTGTGGAGATT
AGGATTTCTGGTTTTTGTATGGTTCTTTGATATCTCTTCTGCTACACTTTCTCCTACTGGTG
TAAACTATGAAGTGACAGCTTTGGTTGCTGTGAAGAATGAATTGAATGATCCGTACAAAGTT
CTTGAGAATTGGGATGTGAATTCAGTTGATCCTTGTAGCTGGAGAATGGTTTCTTGCACTGA
TGGCTATGTCTCTTCACTGGATCTTCCTAGCCAAAGCTTGTCTGGTACATTGTCTCCTAGAA
TCGGAAACCTCACCTATTTACAATCAGTGGTGTTGCAAAACAATGCAATCACTGGTCCAATT
CCGGAAACGATTGGGAGGTTGGAGAAGCTTCAGTCACTTGATCTTTCGAACAATTCATTCAC
CGGGGAGATACCGGCCTCACTTGGAGAACTCAAGAACTTGAATTACTTGCGGTTAAACAATA
ACAGTCTTATAGGAACTTGCCCTGAGTCTCTATCCAAGATTGAGGGACTCACTCTAGTCGAC
ATTTCGTATAACAATCTTAGTGGTTCGCTGCCAAAAGTTTCTGCCAGAACTTTCAAGGTAAT
TGGTAATGCGTTAATCTGTGGCCCAAAAGCTGTTTCAAACTGTTCTGCTGTTCCCGAGCCTC
TCACGCTTCCACAAGATGGTCCAGATGAATCAGGAACTCGTACCAATGGCCATCACGTTGCT
CTTGCATTTGCCGCAAGCTTCAGTGCAGCATTTTTGTTTTCTTTACAAGCGGAATGTTTCT
TTGGTGGAGATATCGCCGTAACAAGCAAATATTTTTGACGTTAATGAACAATATGATCCAG
AAGTGAGTTTAGGGCACTTGAAGAGGTATACATTCAAAGAGCTTAGATCTGCCACCAATCAT
TTCAACTCGAAGAACATTCTCGGAAGAGGCGGATACGGGATTGTGTACAAAGGACACTTAAA
CGATGGAACTTTGGTGGCTGTCAAACGTCTCAAGGACTGTAACATTGCGGGTGGAGAAGTCC
AGTTTCAGACAGAAGTAGAGACTATAAGTTTGGCTCTTCATCGCAATCTCCTCCGGCTCCGC
GGTTTCTGTAGTAGCAACCAGGAGAGAATTTTAGTCTACCCTTACATGCCAAATGGGAGTGT

FIGURE 4 (continued)

```
CGCATCACGCTTAAAAGATAATATCCGTGGAGAGCCAGCATTAGACTGGTCGAGAAGGAAGA
AGATAGCGGTTGGGACAGCGAGAGGACTAGTTTACCTACACGAGCAATGTGACCCGAAGATT
ATACACCGCGATGTGAAAGCAGCTAACATTCTGTTAGATGAGGACTTCGAAGCAGTTGTTGG
TGATTTTGGGTTAGCTAAGCTTCTAGACCATAGAGACTCTCATGTCACAACTGCAGTCCGTG
GAACTGTTGGCCACATTGCACCTGAGTACTTATCCACGGGTCAGTCCTCAGAGAAGACTGAT
GTCTTTGGCTTTGGCATACTTCTCCTTGAGCTCATTACTGGTCAGAAAGCTCTTGATTTTGG
CAGATCCGCACACCAGAAAGGTGTAATGCTTGACTGGGTGAAGAAGCTGCACCAAGAAGGGA
AACTAAAGCAGTTAATAGACAAAGATCTAAATGACAAGTTCGATAGAGTAGAACTCGAAGAA
ATCGTTCAAGTTGCGCTACTCTGCACTCAATTCAATCCATCTCATCGACCGAAAATGTCAGA
AGTTATGAAGATGCTTGAAGGTGACGGTTTGGCTGAGAGATGGGAAGCGACGCAGAACGGTA
CTGGTGAGCATCAGCCACCGCCATTGCCACCGGGGATGGTGAGTTCTTCGCCGCGTGTGAGG
TATTACTCGGATTATATTCAGGAATCGTCTCTTGTAGTAGAAGCCATTGAGCTCTCGGGTCC
TCGATGATTATGACTCACTGTTTTAAAAAATTTCTTTTCTTGGGTTTGTTTTTTATTTGTC
GTTTTATAATGTTGATATAGATGTGAAGTTGAGTGTGTAATTTTTATGTAAAGAAAAAATAT
GAAATGCAAAAGAAAATGTTGATTAGCCTGC
```

SEQ ID NO: 23, NP_176279.1, kinase [Arabidopsis thaliana]

```
MEGVRFVVWRLGFLVFVWFFDISSATLSPTGVNYEVTALVAVKNELNDPYKVLENWDVNSVD
PCSWRMVSCTDGYVSSLDLPSQSLSGTLSPRIGNLTYLQSVVLQNNAITGPIPETIGRLEKL
QSLDLSNNSFTGEIPASLGELKNLNYLRLNNNSLIGTCPESLSKIEGLTLVDISYNNLSGSL
PKVSARTFKVIGNALICGPKAVSNCSAVPEPLTLPQDGPDESGTRTNGHHVALAFAASFSAA
FFVFFTSGMFLWWRYRRNKQIFFDVNEQYDPEVSLGHLKRYTFKELRSATNHFNSKNILGRG
GYGIVYKGHLNDGTLVAVKRLKDCNIAGGEVQFQTEVETISLALHRNLLRLRGFCSSNQERI
LVYPYMPNGSVASRLKDNIRGEPALDWSRRKKIAVGTARGLVYLHEQCDPKIIHRDVKAANI
LLDEDFEAVVGDFGLAKLLDHRDSHVTTAVRGTVGHIAPEYLSTGQSSEKTDVFGFGILLLE
LITGQKALDFGRSAHQKGVMLDWVKKLHQEGKLKQLIDKDLNDKFDRVELEEIVQVALLCTQ
FNPSHRPKMSEVMKMLEGDGLAERWEATQNGTGEHQPPPLPPGMVSSSPRVRYYSDYIQESS
LVVEAIELSGPR
```

SEQ ID NO: 24, NM_105841.3, Arabidopsis thaliana SERK1 (SOMATIC EMBRYOGENESIS RECEPTOR-LIKE KINASE 1); kinase AT1G71830 (SERK1) mRNA, complete cds

```
AACAACACACTAATCATAGTTTCTCTGGCAGGCTTGTTGTTGCGGCTTAATAAAAAGCTCTT
TTGTTATTATTACTTCACGTAGATTTTCCCCAAAAAGCTCTTATTTTTTGTTTAAAAAAAA
AAGTTTCATCTTTATTCAACTTTTGTTTTACAGTGTGTGTGTGAGAGAGAGAGTGTGGTTTG
ATTGAGGAAAGACGACGACGAGAACGCCGGAGAATTAGGATTTTGATTTTATTTTTTACTCT
TTGTTTGTTTTAATGCTAATGGGTTTTTAAAAGGGTTATCGAAAAAATGAGTGAGTTTGTGT
TGAGGTTGTCTCTGTAAAGTGTTAATGGTGGTGATTTTCGGAAGTTAGGGTTTTCTCGGATC
TGAAGAGATCAAATCAAGATTCGAAATTTAGCATTGTTGTTTGAAATGGAGTCGAGTTATGT
GGTGTTTATCTTACTTTCACTGATCTTACTTCCGAATCATTCACTGTGGCTTGCTTCTGCTA
ATTTGGAAGGTGATGCTTTGCATACTTTGAGGGTTACTCTAGTTGATCCAAACAATGTCTTG
CAGAGCTGGGATCCTACGCTAGTGAATCCTTGCACATGGTTCCATGTCACTTGCAACAACGA
GAACAGTGTCATAAGAGTTGATTTGGGGAATGCAGAGTTATCTGGCCATTTAGTTCCAGAGC
```

```
TTGGTGTGCTCAAGAATTTGCAGTATTTGGAGCTTTACAGTAACAACATAACTGGCCCGATT
CCTAGTAATCTTGGAAATCTGACAAACTTAGTGAGTTTGGATCTTTACTTAAACAGCTTCTC
CGGTCCTATTCCGGAATCATTGGGAAAGCTTTCAAAGCTGAGATTTCTCCGGCTTAACAACA
ACAGTCTCACTGGGTCAATTCCTATGTCACTGACCAATATTACTACCCTTCAAGTGTTAGAT
CTATCAAATAACAGACTCTCTGGTTCAGTTCCTGACAATGGCTCCTTCTCACTCTTCACACC
CATCAGTTTTGCTAATAACTTAGACCTATGTGGACCTGTTACAAGTCACCCATGTCCTGGAT
CTCCCCCGTTTTCTCCTCCACCACCTTTTATTCAACCTCCCCCAGTTTCCACCCCGAGTGGG
TATGGTATAACTGGAGCAATAGCTGGTGGAGTTGCTGCAGGTGCTGCTTTGCTCTTTGCTGC
TCCTGCAATAGCCTTTGCTTGGTGGCGACGAAGAAAGCCACTAGATATTTTCTTCGATGTCC
CTGCCGAAGAAGATCCAGAAGTTCATCTGGGACAGCTCAAGAGGTTTTCTTTGCGGGAGCTA
CAAGTGGCGAGTGATGGGTTTAGTAACAAGAACATTTTGGGCAGAGGTGGGTTTGGGAAAGT
CTACAAGGGACGCTTGGCAGACGGAACTCTTGTTGCTGTCAAGAGACTGAAGGAAGAGCGAA
CTCCAGGTGGAGAGCTCCAGTTTCAAACAGAAGTAGAGATGATAAGTATGGCAGTTCATCGA
AACCTGTTGAGATTACGAGGTTTCTGTATGACACCGACCGAGAGATTGCTTGTGTATCCTTA
CATGGCCAATGGAAGTGTTGCTTCGTGTCTCAGAGAGAGGCCACCGTCACAACCTCCGCTTG
ATTGGCCAACGCGGAAGAGAATCGCGCTAGGCTCAGCTCGAGGTTTGTCTTACCTACATGAT
CACTGCGATCCGAAGATCATTCACCGTGACGTAAAAGCAGCAAACATCCTCTTAGACGAAGA
ATTCGAAGCGGTTGTTGGAGATTTCGGGTTGGCAAAGCTAATGGACTATAAAGACACTCACG
TGACAACAGCAGTCCGTGGCACCATCGGTCACATCGCTCCAGAATATCTCTCAACCGGAAAA
TCTTCAGAGAAAACCGACGTTTTCGGATACGGAATCATGCTTCTAGAACTAATCACAGGACA
AAGAGCTTTCGATCTCGCTCGGCTAGCTAACGACGACGACGTCATGTTACTTGACTGGGTGA
AAGGATTGTTGAAGGAGAAGAAGCTAGAGATGTTAGTGGATCCAGATCTTCAAACAAACTAC
GAGGAGAGAGAACTGGAACAAGTGATACAAGTGGCGTTGCTATGCACGCAAGGATCACCAAT
GGAAAGACCAAAGATGTCTGAAGTTGTAAGGATGCTGGAAGGAGATGGGCTTGCGGAGAAAT
GGGACGAATGGCAAAAAGTTGAGATTTTGAGGGAAGAGATTGATTTGAGTCCTAATCCTAAC
TCTGATTGGATTCTTGATTCTACTTACAATTTGCACGCCGTTGAGTTATCTGGTCCAAGGTA
AAAAAAAAAACATAAAATTATTGAACAATAACAAATTTTACAAGGTAGGTAGTTTTTTTAC
CCGTAAGTTTTCGTTTTTTTTAATTGTTAATGTAAAATGAAATCTAGCATTCAAAGATTTGT
GATTTTGTGCTATGGTTCGATTAAAAGGGAAAAAAATTGTAATCTAAAGATTTGTGTAAGAT
TACTGTCTATTGTATGAAGTATGAACTATGAACACAATATATGTACATCCAAAAATACGTTA
AACTAACTCCGCTGTTTTGCTAC
```

SEQ ID NO: 25, NP_177328.1, SERK1 (SOMATIC EMBRYOGENESIS RECEPTOR-LIKE KINASE 1); kinase [Arabidopsis thaliana]

```
MESSYVVFILLSLILLPNHSLWLASANLEGDALHTLRVTLVDPNNVLQSWDPTLVNPCTWFH
VTCNNENSVIRVDLGNAELSGHLVPELGVLKNLQYLELYSNNITGPIPSNLGNLTNLVSLDL
YLNSFSGPIPESLGKLSKLRFLRLNNNSLTGSIPMSLTNITTLQVLDLSNNRLSGSVPDNGS
FSLFTPISFANNLDLCGPVTSHPCPGSPPFSPPPPFIQPPPVSTPSGYGITGAIAGGVAAGA
ALLFAAPAIAFAWWRRRKPLDIFFDVPAEEDPEVHLGQLKRFSLRELQVASDGFSNKNILGR
GGFGKVYKGRLADGTLVAVKRLKEERTPGGELQFQTEVEMISMAVHRNLLRLRGFCMTPTER
LLVYPYMANGSVASCLRERPPSQPPLDWPTRKRIALGSARGLSYLHDHCDPKIIHRDVKAAN
ILLDEEFEAVVGDFGLAKLMDYKDTHVTTAVRGTIGHIAPEYLSTGKSSEKTDVFGYGIMLL
ELITGQRAFDLARLANDDDVMLLDWVKGLLKEKKLEMLVDPDLQTNYEERELEQVIQVALLC
TQGSPMERPKMSEVVRMLEGDGLAEKWDEWQKVEILREEIDLSPNPNSDWILDSTYNLHAVE
LSGPR
```

FIGURE 4 (continued)

SEQ ID NO: 26, NM_126955.3, Arabidopsis thaliana ATSERK4; protein binding / protein kinase/ transmembrane receptor protein serine/threonine kinase AT2G13790 (ATSERK4) mRNA, complete cds

```
TTCGAAACTTGGTCAAATGTCGAATACGCGTTACAAAGAACAAACCTTTCTCTTTATTTCGT
TTGTCTTCGTCAACGGCTGAATCAACCAAATGGTCCCTGGAATTAATAAACCTCTAATAATA
ATGGCTTTGCTTTTACTCTGATGACAAGTTCAAAAATGGAACAAAGATCACTCCTTTGCTTC
CTTTATCTGCTCCTACTATTCAATTTCACTCTCAGAGTCGCTGGAAACGCTGAAGGTGATGC
TTTGACTCAGCTGAAAAACAGTTTGTCATCAGGTGACCCTGCAAACAATGTACTCCAAAGCT
GGGATGCTACTCTTGTTACTCCATGTACTTGGTTTCATGTTACTTGCAATCCTGAGAATAAA
GTTACTCGTGTTGACCTTGGGAATGCAAAACTATCTGGAAAGTTGGTTCCAGAACTTGGTCA
GCTTTTAAACTTGCAGTACTTGGAGCTTTATAGCAATAACATTACAGGGGAGATACCTGAGG
AGCTTGGCGACTTGGTGGAACTAGTAAGCTTGGATCTTTACGCAAACAGCATAAGCGGTCCC
ATCCCTTCGTCTCTTGGCAAACTAGGAAAACTCCGGTTCTTGCGTCTTAACAACAATAGCTT
ATCAGGGGAAATTCCAATGACTTTGACTTCTGTGCAGCTGCAAGTTCTGGATATCTCAAACA
ATCGGCTCAGTGGAGATATTCCTGTTAATGGTTCTTTTTCGCTCTTCACTCCTATCAGTTTT
GCGAATAATAGCTTAACGGATCTTCCCGAACCTCCGCCTACTTCTACCTCTCCTACGCCACC
ACCACCTTCAGGGGGGCAAATGACTGCAGCAATAGCAGGGGGAGTTGCTGCAGGTGCAGCAC
TTCTATTTGCTGTTCCAGCCATTGCGTTTGCTTGGTGGCTCAGAAGAAACCACAGGACCAC
TTTTTTGATGTACCTGCTGAAGAAGACCCAGAGGTTCATTTAGGACAACTCAAAAGGTTTAC
CTTGCGTGAACTGTTAGTTGCTACTGATAACTTTAGCAATAAAAATGTATTGGGTAGAGGTG
GTTTTGGTAAAGTGTATAAAGGACGTTTAGCCGATGGCAATCTAGTGGCTGTCAAAAGGCTA
AAAGAAGAACGTACCAAGGGTGGGGAACTGCAGTTTCAAACCGAAGTTGAGATGATCAGTAT
GGCCGTTCATAGGAACTTGCTTCGGCTTCGTGGCTTTTGCATGACTCCAACTGAAAGATTAC
TTGTTTATCCCTACATGGCTAATGGAAGTGTTGCTTCTTGTTTAAGAGAGCGTCCTGAAGGC
AATCCAGCACTTGATTGGCCAAAAAGAAAGCATATTGCTCTGGGATCAGCAAGGGGCTTGC
GTATTTACATGATCATTGCGACCAAAAAATCATTCACCGGGATGTTAAAGCTGCTAATATAT
TGTTAGATGAAGAGTTTGAAGCTGTTGTTGGAGATTTTGGGCTCGCAAAATTAATGAATTAT
AATGACTCCCATGTGACAACTGCTGTACGCGGTACAATTGGCCATATAGCGCCCGAGTACCT
CTCGACAGGAAATCTTCTGAGAAGACTGATGTTTTTGGGTACGGGGTCATGCTTCTCGAGC
TCATCACTGGACAAAAGGCTTTCGATCTTGCTCGGCTTGCAAATGATGATGATATCATGTTA
CTCGACTGGGTGAAAGAGGTTTTGAAAGAGAAGAAGTTGGAAAGCCTTGTGGATGCAGAACT
CGAAGGAAAGTACGTGGAAACAGAAGTGGAGCAGCTGATACAAATGGCTCTGCTCTGCACTC
AAAGTTCTGCAATGGAACGTCCAAAGATGTCAGAAGTAGTGAGAATGCTGGAAGGAGATGGT
TTAGCTGAGAGATGGGAAGAATGGCAAAAGGAGGAGATGCCAATACATGATTTTAACTATCA
AGCCTATCCTCATGCTGGCACTGACTGGCTCATCCCCTATTCCAATTCCCTTATCGAAAACG
ATTACCCCTCGGGTCCAAGATAACCTTTTAGAAAGGGTCTTTTCTTGTGGGTTCTTCAACAA
GTATATATATAGATTGGTGAAGTTTTAAGATGCAAAAAAAACCCATGCACTTTTGAATATCA
ACTCCTCTATAAGTAGTTTTGTGTCTCTTGACGAATAAAGAATATCATTACTCCACTTGAGC
ATAAAGCAAGATGTTTACCAACCAATAAAGCTTAACAATATTTTTCCGT
```

FIGURE 4 (continued)

SEQ ID NO: 27, NP_178999.2, ATSERK4; protein binding / protein kinase/ transmembrane receptor protein serine/threonine kinase [Arabidopsis thaliana]

MTSSKMEQRSLLCFLYLLLLFNFTLRVAGNAEGDALTQLKNSLSSGDPANNVLQSWDATLVT
PCTWFHVTCNPENKVTRVDLGNAKLSGKLVPELGQLLNLQYLELYSNNITGEIPEELGDLVE
LVSLDLYANSISGPIPSSLGKLGKLRFLRLNNNSLSGEIPMTLTSVQLQVLDISNNRLSGDI
PVNGSFSLFTPISFANNSLTDLPEPPPTSTSPTPPPPSGGQMTAAIAGGVAAGAALLFAVPA
IAFAWWLRRKPQDHFFDVPAEEDPEVHLGQLKRFTLRELLVATDNFSNKNVLGRGGFGKVYK
GRLADGNLVAVKRLKEERTKGGELQFQTEVEMISMAVHRNLLRLRGFCMTPTERLLVYPYMA
NGSVASCLRERPEGNPALDWPKRKHIALGSARGLAYLHDHCDQKIIHRDVKAANILLDEEFE
AVVGDFGLAKLMNYNDSHVTTAVRGTIGHIAPEYLSTGKSSEKTDVFGYGVMLLELITGQKA
FDLARLANDDDIMLLDWVKEVLKEKKLESLVDAELEGKYVETEVEQLIQMALLCTQSSAMER
PKMSEVVRMLEGDGLAERWEEWQKEEMPIHDFNYQAYPHAGTDWLIPYSNSLIENDYPSGPR

SEQ ID NO: 28, NM_126956.3, Arabidopsis thaliana ATSERK5; ATP binding / protein kinase/ transmembrane receptor protein serine/threonine kinase AT2G13800 (ATSERK5) mRNA, complete cds GGAAAATGGAACATGGATCATCCCGTGGCTTTATTTGGCTGATTCTATTTCTCGATTTTGTT
TCCAGAGTCACCGGAAAAACACAAGTTGATGCTCTCATTGCTCTAAGAAGCAGTTTATCATC
AGGTGACCATACAAACAATATACTCCAAAGCTGGAATGCCACTCACGTTACTCCATGTTCAT
GGTTTCATGTTACTTGCAATACTGAAAACAGTGTTACTCGTCTTGACCTGGGGAGTGCTAAT
CTATCTGGAGAACTGGTGCCACAGCTTGCTCAGCTTCCAAATTTGCAGTACTTGGAACTTTT
TAACAATAATATTACTGGGGAGATACCTGAGGAGCTTGGCGACTTGATGGAACTAGTAAGCT
TGGACCTTTTTGCAAACAACATAAGCGGTCCCATCCCTTCCTCTCTTGGCAAACTAGGAAAA
CTCCGCTTCTTGCGTCTTTATAACAACAGCTTATCTGGAGAAATTCCAAGGTCTTTGACTGC
TCTGCCGCTGGATGTTCTTGATATCTCAAACAATCGGCTCAGTGGAGATATTCCTGTTAATG
GTTCCTTTTCGCAGTTCACTTCTATGAGTTTTGCCAATAATAAATTAAGGCCGCGACCTGCA
TCTCCTTCACCATCACCTTCAGGAACGTCTGCAGCAATAGTAGTGGGAGTTGCTGCGGGTGC
AGCACTTCTATTTGCGCTTGCTTGGTGGCTGAGAAGAAAACTGCAGGGTCACTTTCTTGATG
TACCTGCTGAAGAAGACCCAGAGGTTTATTTAGGACAATTTAAAAGGTTCTCCTTGCGTGAA
CTGCTAGTTGCTACAGAGAAATTTAGCAAAAGAAATGTATTGGGCAAAGGACGTTTTGGTAT
ATTGTATAAAGGACGTTTAGCTGATGACACTCTAGTGGCTGTGAAACGGCTAAATGAAGAAC
GTACCAAGGGTGGGGAACTGCAGTTTCAAACCGAAGTTGAGATGATCAGTATGGCCGTTCAT
AGGAACTTGCTTCGGCTTCGTGGCTTTTGCATGACTCCAACTGAAAGATTACTTGTTTATCC
CTACATGGCTAATGGAAGTGTTGCTTCTTGTTAAGAGAGCGTCCTGAAGGCAATCCAGCCC
TTGACTGGCCAAAAAGAAAGCATATTGCTCTGGGATCAGCAAGGGGGCTCGCATATTTACAC
GATCATTGCGACCAAAAGATCATTCACCTGGATGTGAAAGCTGCAAATATACTGTTAGATGA
AGAGTTTGAAGCTGTTGTTGGAGATTTTGGGCTAGCAAAATTAATGAATTATAACGACTCCC
ATGTGACAACTGCTGTACGGGGTACGATTGGCCATATAGCGCCCGAGTACCTCTCGACAGGA
AAATCTTCTGAGAAGACTGATGTTTTTGGGTACGGGGTCATGCTTCTCGAGCTCATCACTGG
ACAAAAGGCTTTCGATCTTGCTCGGCTTGCAAATGATGATATCATGTTACTCGACTGGG
TGAAAGAGGTTTTGAAAGAGAAGAAGTTGGAAAGCCTTGTGGATGCAGAACTCGAAGGAAAG
TACGTGGAAACAGAAGTGGAGCAGCTGATACAAATGGCTCTGCTCTGCACTCAAAGTTCTGC

FIGURE 4 (continued)

```
AATGGAACGTCCAAAGATGTCAGAAGTAGTGAGAATGCTGGAAGGAGATGGTTTAGCTGAGA
GATGGGAAGAATGGCAAAAGGAGGAGATGCCAATACATGATTTTAACTATCAAGCCTATCCT
CATGCTGGCACTGACTGGCTCATCCCCTATTCCAATTCCCTTATCGAAAACGATTACCCCTC
GGGGCCAAGATAACCTTTTAGAAAGGGTCATTTCTTGTGGGTTCTTCAACAAGTATATATAT
AGGTAGTGAAGTTGTAAGAAGCAAAACCCCACATTCACCTTTGAATATCACTACTCTATAAT
ACTAATCATATCTACTATACTTTCTCTCCACTTCCATTAAGCAATAAAAACTATTCTTAAAT
C
```

SEQ ID NO: 29, NP_179000.3, ATSERK5; ATP binding / protein kinase/ transmembrane receptor protein serine/threonine kinase [Arabidopsis thaliana]

```
MEHGSSRGFIWLILFLDFVSRVTGKTQVDALIALRSSLSSGDHTNNILQSWNATHVTPCSWF
HVTCNTENSVTRLDLGSANLSGELVPQLAQLPNLQYLELFNNNITGEIPEELGDLMELVSLD
LFANNISGPIPSSLGKLGKLRFLRLYNNSLSGEIPRSLTALPLDVLDISNNRLSGDIPVNGS
FSQFTSMSFANNKLRPRPASPSPSPSGTSAAIVVGVAAGAALLFALAWWLRRKLQGHFLDVP
AEEDPEVYLGQFKRFSLRELLVATEKFSKRNVLGKGRFGILYKGRLADDTLVAVKRLNEERT
KGGELQFQTEVEMISMAVHRNLLRLRGFCMTPTERLLVYPYMANGSVASCLRERPEGNPALD
WPKRKHIALGSARGLAYLHDHCDQKIIHLDVKAANILLDEEFEAVVGDFGLAKLMNYNDSHV
TTAVRGTIGHIAPEYLSTGKSSEKTDVFGYGVMLLELITGQKAFDLARLANDDDIMLLDWVK
EVLKEKKLESLVDAELEGKYVETEVEQLIQMALLCTQSSAMERPKMSEVVRMLEGDGLAERW
EEWQKEEMPIHDFNYQAYPHAGTDWLIPYSNSLIENDYPSGPR
```

SEQ ID NO: 30, NM_202631.1, Arabidopsis thaliana ATP binding / protein kinase/ protein serine/threonine kinase/ protein-tyrosine kinase AT3G25560 transcript variant AT3G25560.2 mRNA, complete cds

```
TTTTCTTAAAAACCTCCAAACAAAGAATCGAAAAAAGAATATTTCTTATACAAAAGAAATA
AACCTCAAACTCTGCACCTTAGAGATTAATACTCTCAAGAAAAACAAGTTTTGATTCGGACA
AAGATGTTGCAAGGAAGAAGAGAAGCAAAAAGAGTTATGCTTTGTTCTCTTCAACTTTCTT
CTTCTTCTTTATCTGTTTTCTTTCTTCTTCTGCAGAACTCACAGACAAAGGTGTTAACT
TTGAAGTTGTTGCCTTAATAGGAATCAAAAGCTCACTGACTGATCCTCATGGAGTTCTAATG
AATTGGGATGACACAGCAGTTGATCCATGTAGCTGGAACATGATCACTTGTTCTGATGGTTT
TGTCATAAGGCTAGAAGCTCCAAGCCAAAACTTATCAGGAACTCTTTCATCAAGTATTGGAA
ATTTAACAAATCTTCAAACTGTGTTATTGCAGAACAATTACATAACAGGAAACATCCCTCAT
GAGATTGGGAAATTGATGAAACTCAAAACACTTGATCTCTCTACCAATAACTTCACTGGTCA
AATCCCATTCACTCTTTCTTACTCCAAAAATCTTCAGTACTTCAGGAGGGTTAATAATAACA
GCCTGACAGGAACAATTCCTAGCTCATTGGCAAACATGACCCAACTCACTTTTTTGGATTTG
TCGTATAATAACTTGAGTGGACCAGTTCCAAGATCACTTGCCAAAACATTCAATGTTATGGG
CAATTCTCAGATTTGTCCAACAGGAACTGAGAAGACTGTAATGGGACTCAGCCTAAGCCAA
TGTCAATCACCTTGAACAGTTCTCAAAATAAATCATCTGATGGAGGAACTAAAAACCGGAAA
ATCGCGGTAGTCTTCGGTGTAAGCTTGACATGTGTTTGCTTGTTGATCATTGGCTTTGGTTT
TCTTCTTTGGTGGAGAAGAAGACATAACAAACAAGTATTATTCTTTGACATTAATGAGCAAA
ACAAGGAAGAAATGTGTCTAGGGAATCTAAGGAGGTTTAATTTCAAAGAACTTCAATCCGCA
```

ACTAGTAACTTCAGCAGCAAGAATCTGGTCGGAAAAGGAGGGTTTGGAAATGTGTATAAGG
TTGTCTTCATGATGGAAGTATCATCGCGGTGAAGAGATTAAAGGATATAAACAATGGTGGTG
GAGAGGTTCAGTTTCAGACAGAGCTTGAAATGATAAGCCTTGCCGTCCACCGGAATCTCCTC
CGCTTATACGGTTTCTGTACTACTTCCTCTGAACGGCTTCTCGTTTATCCTTACATGTCCAA
TGGCAGTGTCGCTTCTCGTCTCAAAGCTAAACCGGTATTGGATTGGGGCACAAGAAAGCGAA
TAGCATTAGGAGCAGGAAGAGGGTTGCTGTATTTGCATGAGCAATGTGATCCAAAGATCATT
CACCGTGATGTCAAAGCTGCGAACATACTTCTTGACGATTACTTTGAAGCTGTTGTCGGAGA
TTTCGGGTTGGCTAAGCTTTTGGATCATGAGGAGTCGCATGTGACAACCGCCGTGAGAGGAA
CAGTGGGTCACATTGCACCTGAGTATCTCTCAACAGGACAATCTTCTGAGAAGACAGATGTG
TTCGGTTTCGGGATTCTTCTTCTCGAATTGATTACTGGATTGAGAGCTCTTGAATTCGGAAA
AGCAGCAAACCAAAGAGGAGCGATACTTGATTGGGTAAAGAAACTACAACAAGAGAAGAAGC
TAGAACAGATAGTAGACAAGGATTTGAAGAGCAACTACGATAGAATAGAAGTGGAAGAAATG
GTTCAAGTGGCTTTGCTTTGTACACAGTATCTTCCCATTCACCGTCCTAAGATGTCTGAAGT
TGTGAGAATGCTTGAAGGCGATGGTCTTGTTGAGAAATGGGAAGCTTCTTCTCAGAGAGCAG
AAACCAATAGAAGTTACAGTAAACCTAACGAGTTTTCTTCCTCTGAACGTTATTCGGATCTT
ACAGATGATTCCTCGGTGCTGGTTCAAGCCATGGAGTTATCAGGTCCAAGATGACAAGAGAA
ACTATATGAATGGCTTTGGGTTTGTAAAAAACATATATAAGATTGTGTATTTGTTGTATGC
TGTGATCTTGTACAGGTTTTGGTATCAGAAAGACATATTCTCATGCTTTATCCCATGATTAG
GAGGAGGTGGAATCACCGCCTCCATTTCGTAGAAACG

SEQ ID NO: 31, NP_974360.1, ATP binding / protein kinase/ protein serine/threonine kinase/ protein-tyrosine kinase [Arabidopsis thaliana]

MLQGRREAKKSYALFSSTFFFFFICFLSSSSAELTDKGVNFEVVALIGIKSSLTDPHGVLMN
WDDTAVDPCSWNMITCSDGFVIRLEAPSQNLSGTLSSSIGNLTNLQTVLLQNNYITGNIPHE
IGKLMKLKTLDLSTNNFTGQIPFTLSYSKNLQYFRRVNNNSLTGTIPSSLANMTQLTFLDLS
YNNLSGPVPRSLAKTFNVMGNSQICPTGTEKDCNGTQPKPMSITLNSSQNKSSDGGTKNRKI
AVVFGVSLTCVCLLIIGFGFLLWWRRRHNKQVLFFDINEQNKEEMCLGNLRRFNFKELQSAT
SNFSSKNLVGKGGFGNVYKGCLHDGSIIAVKRLKDINNGGGEVQFQTELEMISLAVHRNLLR
LYGFCTTSSERLLVYPYMSNGSVASRLKAKPVLDWGTRKRIALGAGRGLLYLHEQCDPKIIH
RDVKAANILLDDYFEAVVGDFGLAKLLDHEESHVTTAVRGTVGHIAPEYLSTGQSSEKTDVF
GFGILLLELITGLRALEFGKAANQRGAILDWVKKLQQEKKLEQIVDKDLKSNYDRIEVEEMV
QVALLCTQYLPIHRPKMSEVVRMLEGDGLVEKWEASSQRAETNRSYSKPNEFSSSERYSDLT
DDSSVLVQAMELSGPR

SEQ ID NO: 32, NM_119497.3, Arabidopsis thaliana BAK1 (BRI1-ASSOCIATED RECEPTOR KINASE); kinase AT4G33430 (BAK1) mRNA, complete cds

AATAATTAAAATTCGTCTTCCTTCCTTGCTCTCGGCGATAACTTGGTTTCTCTCCTCTCTCT
CATCTCTCTTTGTTTCGACCCTTTTTAGTATATTTCCAGGAAATATCTTCTTCCTCCTTTC
GTTTTCTCTATCTCAGTTTTCTCTCTTCTCAGCATTAAGTAGTCAACGGTCAGCGATCTCGG
CGTTCCTTCTAATCGGAAAAGTCTAGCTTCAGTTTCTTTTTTTTTGCTTTTTTGGTTTCCG
CGATTAATCGATTTGGGTATTTTGATTTTCTCTTCAAATTAAGTCAACGGGTGGATACGCGT

FIGURE 4 (continued)

```
TGAGAGGGCTTTTCTCGTATTCTGCTTCTAATTTCATCATCTTGGTATTACCTTGTGTGGGT
GGTAGCTTAATCGAAGGATTCGAGATCCCTTTTATCAGGGGTTTTAACAATGATGGATTTTC
TCTGATGAGGGATAGTTCTAGGGTTTGTTTTTAATCTCTTGAGGATAAAATGGAACGAAGAT
TAATGATCCCTTGCTTCTTTTGGTTGATTCTCGTTTTGGATTTGGTTCTCAGAGTCTCGGGC
AACGCCGAAGGTGATGCTCTAAGTGCACTGAAAAACAGTTTAGCCGACCCTAATAAGGTGCT
TCAAAGTTGGGATGCTACTCTTGTTACTCCATGTACATGGTTTCATGTTACTTGCAATAGCG
ACAATAGTGTTACACGTGTTGACCTTGGGAATGCAAATCTATCTGGACAGCTCGTAATGCAA
CTTGGTCAGCTTCCAAACTTGCAGTACTTGGAGCTTTATAGCAATAACATTACTGGGACAAT
CCCAGAACAGCTTGGAAATCTGACGGAATTGGTGAGCTTGGATCTTTACTTGAACAATTTAA
GCGGGCCTATTCCATCAACTCTCGGCCGACTTAAGAAACTCCGTTTCTTGCGTCTTAATAAC
AATAGCTTATCTGGAGAAATTCCAAGGTCTTTGACTGCTGTCCTGACGCTACAAGTTCTGGA
TCTCTCAAACAATCCTCTCACCGGAGATATTCCTGTTAATGGTTCCTTTTCACTTTTCACTC
CAATCAGTTTTGCCAACACCAAGTTGACTCCCCTTCCTGCATCTCCACCGCCTCCTATCTCT
CCTACACCGCCATCACCTGCAGGGAGTAATAGAATTACTGGAGCGATTGCGGGAGGAGTTGC
TGCAGGTGCTGCACTTCTATTTGCTGTTCCGGCCATTGCACTAGCTTGGTGGCGAAGGAAAA
AGCCGCAGGACCACTTCTTTGATGTACCAGCTGAAGAGGACCCAGAAGTTCATTTAGGACAA
CTGAAGAGGTTTTCATTGCGTGAACTACAAGTTGCTTCGGATAATTTTAGCAACAAGAACAT
ATTGGGTAGAGGTGGTTTTGGTAAAGTTTATAAAGGACGGTTAGCTGATGGTACTTTAGTGG
CCGTTAAAAGGCTAAAAGAGGAGCGCACCCAAGGTGGCGAACTGCAGTTCCAGACAGAGGTT
GAGATGATTAGTATGGCGGTTCACAGAAACTTGCTTCGGCTTCGTGGATTTTGCATGACTCC
AACCGAAAGATTGCTTGTTTATCCCTACATGGCTAATGGAAGTGTTGCCTCCTGTTTAAGAG
AACGTCCCGAGTCCCAGCCACCACTTGATTGGCCAAAGAGACAGCGTATTGCGTTGGGATCT
GCAAGAGGGCTTGCGTATTTACATGATCATTGCGACCCAAAGATTATTCATCGAGATGTGAA
AGCTGCAAATATTTTGTTGGATGAAGAGTTTGAAGCCGTGGTTGGGGATTTTGGACTTGCAA
AACTCATGGACTACAAAGACACACATGTGACAACCGCAGTGCGTGGGACAATTGGTCATATA
GCCCCTGAGTACCTTTCCACTGGAAAATCATCAGAGAAACCGATGTCTTTGGGTATGGAGT
CATGCTTCTTGAGCTTATCACTGGACAAAGGGCTTTTGATCTTGCTCGCCTCGCGAATGATG
ATGATGTCATGTTACTAGACTGGGTGAAAGGGTTGTTAAAAGAGAAGAAATTGGAAGCACTA
GTAGATGTTGATCTTCAGGGTAATTACAAAGACGAAGAAGTGGAGCAGCTAATCCAAGTGGC
TTTACTCTGCACTCAGAGTTCACCAATGGAAAGACCCAAAATGTCTGAAGTTGTAAGAATGC
TTGAAGGAGATGGTTTAGCTGAGAGATGGGAAGAGTGGCAAAAGGAGGAAATGTTCAGACAA
GATTTCAACTACCCAACCCACCATCCAGCCGTGTCTGGCTGGATCATTGGCGATTCCACTTC
CCAGATCGAAAACGAATACCCCTCGGGTCCAAGATAAGATTCGAAACACGAATGTTTTTTCT
GTATTTTGTTTTTCTCTGTATTTATTGAGGGTTTTAGCTTCTGCTGCTCCATATTATTGGTT
CTTAAGTGAATACATGAGGATCAGATTGGGTTTGTAAGTGTTATATGATGAAAAGGATTTG
AATGTTGTTGAAAGCTAAAACCCAAACATGTCTTAAGCTCACCACTTGAGGATTGTTGCGCA
CTTGATTCACAAATATGTATCCCATCAATTATTCTTT
```

FIGURE 4 (continued)

SEQ ID NO: 33, NP_567920.1, BAK1 (BRI1-ASSOCIATED RECEPTOR KINASE); kinase [Arabidopsis thaliana]

MERRLMIPCFFWLILVLDLVLRVSGNAEGDALSALKNSLADPNKVLQSWDATLVTPCTWFHV
TCNSDNSVTRVDLGNANLSGQLVMQLGQLPNLQYLELYSNNITGTIPEQLGNLTELVSLDLY
LNNLSGPIPSTLGRLKKLRFLRLNNNSLSGEIPRSLTAVLTLQVLDLSNNPLTGDIPVNGSF
SLFTPISFANTKLTPLPASPPPPISPTPPSPAGSNRITGAIAGGVAAGAALLFAVPAIALAW
WRRKKPQDHFFDVPAEEDPEVHLGQLKRFSLRELQVASDNFSNKNILGRGGFGKVYKGRLAD
GTLVAVKRLKEERTQGGELQFQTEVEMISMAVHRNLLRLRGFCMTPTERLLVYPYMANGSVA
SCLRERPESQPPLDWPKRQRIALGSARGLAYLHDHCDPKIIHRDVKAANILLDEEFEAVVGD
FGLAKLMDYKDTHVTTAVRGTIGHIAPEYLSTGKSSEKTDVFGYGVMLLELITGQRAFDLAR
LANDDDVMLLDWVKGLLKEKKLEALVDVDLQGNYKDEEVEQLIQVALLCTQSSPMERPKMSE
VVRMLEGDGLAERWEEWQKEEMFRQDFNYPTHHPAVSGWIIGDSTSQIENEYPSGPR

SEQ ID NO: 34, NM_121067.3, Arabidopsis thaliana kinase AT5G10290 mRNA, complete cds GAGAGTGATAATTGCGAAATTGCCAAAAAACGCAAAGTCTACCACTAGACAAGAAAATCGAA
GCTTTTCACTTTCTCTTTTTTCTGTTTTGTTGTCTTTGGTTCTACTCTCCGCACTGAATCTT
TCGATCAGCGATAATTGTTTCCTTCTTTTGGGATTTTCTCCTTGGATGGAACCAGCTCAATT
AATGAGATGAGATGAGAATGTTCAGCTTGCAGAAGATGGCTATGGCTTTTACTCTCTTGTTT
TTTGCCTGTTTATGCTCATTTGTGTCTCCAGATGCTCAAGGGGATGCACTGTTTGCGTTGAG
GATCTCCTTACGTGCATTACCGAATCAGCTAAGTGACTGGAATCAGAACCAAGTTAATCCTT
GCACTTGGTCCCAAGTTATTTGTGATGACAAAAACTTTGTCACTTCTCTTACATTGTCAGAT
ATGAACTTCTCGGGAACCTTGTCTTCAAGAGTAGGAATCCTAGAAAATCTCAAGACTCTTAC
TTTAAAGGGAAATGGAATTACGGGTGAAATACCAGAAGACTTTGGAAATCTGACTAGCTTGA
CTAGTTTGGATTTGGAGGACAATCAGCTAACTGGTCGTATACCATCCACTATCGGTAATCTC
AAGAAACTTCAGTTCTTGACCTTGAGTAGGAACAAACTTAATGGGACTATTCCGGAGTCACT
CACTGGTCTTCCAAACCTGTTAAACCTGCTGCTTGATTCCAATAGTCTCAGTGGTCAGATTC
CTCAAAGTCTGTTTGAGATCCCAAAATATAATTTCACGTCAAACAACTTGAATTGTGGCGGT
CGTCAACCTCACCCTTGTGTATCCGCGGTTGCCCATTCAGGTGATTCAAGCAAGCCTAAAAC
TGGCATTATTGCTGGAGTTGTTGCTGGAGTTACAGTTGTTCTCTTTGGAATCTTGTTGTTTC
TGTTCTGCAAGGATAGGCATAAAGGATATAGACGTGATGTGTTTGTGGATGTTGCAGGTGAA
GTGGACAGGAGAATTGCATTTGGACAGTTGAAAAGGTTTGCATGGAGAGAGCTCCAGTTAGC
GACAGATAACTTCAGCGAAAAGAATGTACTTGGTCAAGGAGGCTTTGGGAAAGTTTACAAAG
GAGTGCTTCCGGATAACACCAAAGTTGCTGTGAAGAGATTGACGGATTTCGAAAGTCCTGGT
GGAGATGCTGCTTTCCAAAGGGAAGTAGAGATGATAAGTGTAGCTGTTCATAGGAATCTACT
CCGTCTTATCGGGTTCTGCACCACACAAACAGAACGCCTTTTGGTTTATCCCTTCATGCAGA
ATCTAAGTCTTGCACATCGTCTGAGAGAGATCAAAGCAGGCGACCCGGTTCTAGATTGGGAG
ACGAGGAAACGGATTGCCTTAGGAGCAGCGCGTGGTTTTGAGTATCTTCATGAACATTGCAA
TCCGAAGATCATACATCGTGATGTGAAAGCAGCTAATGTGTTACTAGATGAAGATTTTGAAG
CAGTGGTTGGTGATTTTGGTTTAGCCAAGCTAGTAGATGTTAGAAGGACTAATGTGACTACT
CAAGTTCGAGGAACAATGGGTCACATTGCACCAGAATATTTATCAACAGGGAAATCATCAGA
GAGAACCGATGTTTTCGGGTATGGAATTATGCTTCTTGAGCTTGTTACAGGACAACGCGCAA
TAGACTTTTCACGTTTGGAGGAAGAAGATGATGTCTTGTTACTTGACCACGTGAAGAAACTG FIGURE 4 (continued)

GAAAGAGAGAAGAGATTAGGAGCAATCGTAGATAAGAATTTGGATGGAGAGTATATAAAAGA
AGAAGTAGAGATGATGATACAAGTGGCTTTGCTTTGTACACAAGGTTCACCAGAAGACCGAC
CAGTGATGTCTGAAGTTGTGAGGATGTTAGAAGGAGAAGGGCTTGCGGAGAGATGGGAAGAG
TGGCAAAACGTGGAAGTCACGAGACGTCATGAGTTTGAACGGTTGCAGAGGAGATTTGATTG
GGGTGAAGATTCTATGCATAACCAAGATGCCATTGAATTATCTGGTGGAAGATGACCAAAAA
CATCAAACCTTGAGTTTACTGTAAAGTTGCCAACTTCACTTTTTTGTTTTGTTCTTCGGTGA
AGAAGTAAAATCAGTTGTATAAATCTTGTTTTTGTTTCATGATGTATCTTTTGACTTTAATA
AATTCTGTGAATGAAAAGAACTATGATGTTTTGTTG

SEQ ID NO: 35, NP_196591.2| kinase [Arabidopsis thaliana]

MRMFSLQKMAMAFTLLFFACLCSFVSPDAQGDALFALRISLRALPNQLSDWNQNQVNPCTWS
QVICDDKNFVTSLTLSDMNFSGTLSSRVGILENLKTLTLKGNGITGEIPEDFGNLTSLTSLD
LEDNQLTGRIPSTIGNLKKLQFLTLSRNKLNGTIPESLTGLPNLLNLLLDSNSLSGQIPQSL
FEIPKYNFTSNNLNCGGRQPHPCVSAVAHSGDSSKPKTGIIAGVVAGVTVVLFGILLFLFCK
DRHKGYRRDVFVDVAGEVDRRIAFGQLKRFAWRELQLATDNFSEKNVLGQGGFGKVYKGVLP
DNTKVAVKRLTDFESPGGDAAFQREVEMISVAVHRNLLRLIGFCTTQTERLLVYPFMQNLSL
AHRLREIKAGDPVLDWETRKRIALGAARGFEYLHEHCNPKIIHRDVKAANVLLDEDFEAVVG
DFGLAKLVDVRRTNVTTQVRGTMGHIAPEYLSTGKSSERTDVFGYGIMLLELVTGQRAIDFS
RLEEEDDVLLLDHVKKLEREKRLGAIVDKNLDGEYIKEEVEMMIQVALLCTQGSPEDRPVMS
EVVRMLEGEGLAERWEEWQNVEVTRRHEFERLQRRFDWGEDSMHNQDAIELSGGR

SEQ ID NO: 36, NM_121605.2| Arabidopsis thaliana kinase AT5G16000 mRNA, complete cds

ATAGAGATTTGGTTTTTTGATTCTTCCAATCTCACTCTCTCTGTCTTTCTCTCTCCATCAAA
TACCAAATTATCTGGAAGCTGAGTACATCTTGTTTTCTGCTCATTCCTCTGTTTCAACAATG
GAGAGTACTATTGTTATGATGATGATGATAACAAGATCTTTCTTTTGCTTCTTGGGATTTTT
ATGCCTTCTCTGCTCTTCTGTTCACGGATTGCTTTCTCCTAAAGGTGTTAACTTTGAAGTGC
AAGCTTTGATGGACATAAAAGCTTCATTACATGATCCTCATGGTGTTCTTGATAACTGGGAT
AGAGATGCTGTTGATCCTTGTAGTTGGACAATGGTCACTTGTTCTTCTGAAAACTTTGTCAT
TGGCTTAGGCACACCAAGTCAGAATTTATCTGGTACACTATCTCCAAGCATTACCAACTTAA
CAAATCTTCGGATTGTGCTGTTGCAGAACAACAACATAAAAGGAAAAATTCCTGCTGAGATT
GGTCGGCTTACGAGGCTTGAGACTCTTGATCTTTCTGATAATTTCTTCCACGGTGAAATTCC
TTTTTCAGTAGGCTATCTACAAAGCCTGCAATATCTGAGGCTTAACAACAATTCTCTCTCTG
GAGTGTTTCCTCTGTCACTATCTAATATGACTCAACTTGCCTTTCTTGATTATCATACAAC
AATCTTAGTGGTCCTGTTCCAAGATTTGCTGCAAAGACGTTTAGCATCGTTGGGAACCCGCT
GATATGTCCAACGGGTACCGAACCAGACTGCAATGGAACAACATTGATACCTATGTCTATGA
ACTTGAATCAAACTGGAGTTCCTTTATACGCCGGTGGATCGAGGAATCACAAAATGGCAATC
GCTGTTGGATCCAGCGTTGGGACTGTATCATTAATCTTCATTGCTGTTGGTTTGTTTCTCTG
GTGGAGACAAAGACATAACCAAAACACATTCTTTGATGTTAAAGATGGGAATCATCATGAGG
AAGTTTCACTTGGAAACCTGAGGAGATTTGGTTTCAGGGAGCTTCAGATTGCGACCAATAAC
TTCAGCAGTAAGAACTTATTGGGGAAAGGTGGCTATGGAAATGTATACAAAGGAATACTTGG
AGATAGTACAGTGGTTGCAGTGAAAAGGCTTAAAGATGGAGGAGCATTGGGAGGAGAGATTC
AGTTTCAGACAGAAGTTGAAATGATCAGTTTAGCTGTTCATCGAAATCTCTTAAGACTCTAC

FIGURE 4 (continued)

GGTTTCTGCATCACACAAACTGAGAAGCTTCTAGTTTATCCTTATATGTCTAATGGAAGCGT
TGCATCTCGAATGAAAGCAAAACCTGTTCTTGACTGGAGCATAAGGAAGAGGATAGCCATAG
GAGCTGCAAGAGGGCTTGTGTATCTCCATGAGCAATGTGATCCGAAGATTATCCACCGCGAT
GTCAAAGCAGCGAATATACTTCTTGATGACTACTGTGAAGCTGTGGTTGGCGATTTTGGTTT
AGCTAAACTCTTGGATCATCAAGATTCTCATGTGACAACCGCGGTTAGAGGCACGGTGGGTC
ACATTGCTCCAGAGTATCTCTCAACTGGTCAATCCTCTGAGAAAACAGATGTTTTTGGCTTC
GGGATTCTTCTTCTTGAGCTTGTAACCGGACAAGAGCTTTTGAGTTTGGTAAAGCGGCTAA
CCAGAAAGGTGTGATGCTTGATTGGGTTAAAAAGATTCATCAAGAGAAGAAACTTGAGCTAC
TTGTGGATAAAGAGTTGTTGAAGAAGAAGAGCTACGATGAGATTGAGTTAGACGAAATGGTA
AGAGTAGCTTTGTTGTGCACACAGTACCTGCCAGGACATAGACCAAAAATGTCTGAAGTTGT
TCGAATGCTGGAAGGAGATGGACTTGCAGAGAAATGGGAAGCTTCTCAAAGATCAGACAGTG
TTTCAAAATGTAGCAACAGGATAAATGAATTGATGTCATCTTCAGACAGATACTCTGATCTT
ACCGATGACTCTAGTTTACTTGTGCAAGCAATGGAGCTCTCTGGTCCTAGATGAAATCTATA
CATGAATCTGAAGAAGAAGAAGAACATGCATCTGTTTCTTGAATCAAGAGGGATTCTTGTTT
TTTTGTATAATAGAGAGGTTTTTGGAGGGAAATGTTGTGTCTCTGTAACTGTATAGGCTTG
TTGTGTAAGAAGTTATTACTGCACTTAGGGTTAATTCAAAGTTCTTTACATAAAAAATGATT
AGTTGCGTTGAATAGAGGGAACACTTTGGGAGATTTCATGTGTGAAATTTGGGAATTCATGT
TTGAGAATGAAATTTATCTTATTATTGGA

SEQ ID NO: 37, NP_197104.1, kinase [Arabidopsis thaliana]

MESTIVMMMMITRSFFCFLGFLCLLCSSVHGLLSPKGVNFEVQALMDIKASLHDPHGVLDNW
DRDAVDPCSWTMVTCSSENFVIGLGTPSQNLSGTLSPSITNLTNLRIVLLQNNNIKGKIPAE
IGRLTRLETLDLSDNFFHGEIPFSVGYLQSLQYLRLNNNSLSGVFPLSLSNMTQLAFLDLSY
NNLSGPVPRFAAKTFSIVGNPLICPTGTEPDCNGTTLIPMSMNLNQTGVPLYAGGSRNHKMA
IAVGSSVGTVSLIFIAVGLFLWWRQRHNQNTFFDVKDGNHHEEVSLGNLRRFGFRELQIATN
NFSSKNLLGKGGYGNVYKGILGDSTVVAVKRLKDGGALGGEIQFQTEVEMISLAVHRNLLRL
YGFCITQTEKLLVYPYMSNGSVASRMKAKPVLDWSIRKRIAIGAARGLVYLHEQCDPKIIHR
DVKAANILLDDYCEAVVGDFGLAKLLDHQDSHVTTAVRGTVGHIAPEYLSTGQSSEKTDVFG
FGILLLELVTGQRAFEFGKAANQKGVMLDWVKKIHQEKKLELLVDKELLKKKSYDEIELDEM
VRVALLCTQYLPGHRPKMSEVVRMLEGDGLAEKWEASQRSDSVSKCSNRINELMSSSDRYSD
LTDDSSLLVQAMELSGPR

SEQ ID NO: 38, NM_123946.2, Arabidopsis thaliana ATP binding / kinase/ protein serine/threonine kinase AT5G45780 mRNA, complete cds

ATGGAGATTTCTTTGATGAAGTTTCTGTTTTTAGGAATCTGGGTTTATTATTACTCTGTTCT
TGACTCTGTTTCTGCCATGGATAGTCTTTTATCTCCCAAGGGTGTTAACTATGAAGTGGCTG
CGTTAATGTCAGTGAAGAACAAGATGAAAGATGAGAAAGAGGTTTTGTCTGGTTGGGATATT
AACTCTGTTGATCCTTGTACTTGGAACATGGTTGGTTGTTCTTCTGAAGGTTTTGTGGTTTC
TCTAGAGATGGCTAGTAAAGGATTATCAGGGATACTATCTACTAGTATTGGGGAATTAACTC
ATCTTCATACTTTGTTACTTCAGAATAATCAGTTAACTGGTCCGATTCCTTCTGAGTTAGGC
CAACTCTCTGAGCTTGAAACGCTTGATTTATCGGGGAATCGGTTTAGTGGTGAAATCCCAGC
TTCTTTAGGGTTCTTAACTCACTTAAACTACTTGCGGCTTAGCAGGAATCTTTTATCTGGGC

FIGURE 4 (continued)

```
AAGTCCCTCACCTCGTCGCTGGCCTCTCAGGTCTTTCTTTCTTGGATCTATCTTTCAACAAT
CTAAGCGGACCAACTCCGAATATATCAGCAAAAGATTACAGGATTGTAGGAAATGCATTTCT
TTGTGGTCCAGCTTCCCAAGAGCTTTGCTCAGATGCTACACCTGTGAGAAATGCGACGGGTT
TGTCTGAAAAGGACAATAGCAAACATCACAGCTTAGTGCTCTCTTTTGCATTTGGCATTGTT
GTTGCCTTTATCATCTCCCTAATGTTTCTCTTCTTCTGGGTGCTTTGGCATCGATCACGTCT
CTCAAGATCACACGTGCAGCAAGACTACGAATTTGAAATCGGCCATCTGAAAAGGTTCAGTT
TTCGCGAAATACAAACCGCAACAAGCAATTTTAGTCCAAAGAACATTTTGGGACAAGGAGGG
TTTGGGATGGTTTATAAAGGGTATCTCCCAAATGGAACTGTGGTGGCAGTTAAAAGATTGAA
AGATCCGATTTATACAGGAGAAGTTCAGTTTCAAACCGAAGTAGAGATGATTGGCTTAGCTG
TTCACCGTAACCTTTTACGCCTCTTTGGATTCTGTATGACCCCGGAAGAGAGAATGCTTGTG
TATCCGTACATGCCAAATGGAAGCGTAGCTGATCGTCTGAGAGACAATTATGGAGAAAAGCC
GTCTCTAGATTGGAATCGGAGGATAAGCATTGCACTCGGCGCAGCTCGAGGACTTGTTTACT
TGCACGAGCAATGCAATCCAAAGATTATTCACAGAGACGTCAAAGCTGCAAATATTCTACTT
GATGAGAGCTTTGAAGCAATAGTTGGCGATTTTGGTCTAGCAAAGCTTTTAGACCAGAGAGA
TTCACATGTCACTACCGCAGTCCGAGGAACCATTGGACACATCGCTCCCGAGTACCTTTCCA
CTGGACAGTCCTCAGAGAAAACCGATGTTTTCGGATTCGGAGTACTAATCCTTGAACTCATA
ACAGGTCATAAGATGATTGATCAAGGCAATGGTCAAGTTCGAAAAGGAATGATATTGAGCTG
GGTAAGGACATTGAAAGCAGAGAAGAGATTTGCAGAGATGGTGGACAGAGATTTGAAGGGAG
AGTTTGATGATTTGGTGTTGGAGGAAGTAGTGGAATTGGCTTTGCTTTGTACACAGCCACAT
CCGAATCTAAGACCGAGGATGTCTCAAGTGTTGAAGGTACTAGAAGGTTTAGTGGAACAGTG
TGAAGGAGGGTATGAAGCTAGAGCTCCAAGTGTCTCTAGGAACTACAGTAATGGTCATGAAG
AGCAGTCCTTTATTATTGAAGCCATTGAGCTCTCTGGACCACGATGA
```

SEQ ID NO: 39, NP_199390.2, ATP binding / kinase/ protein serine/threonine kinase [Arabidopsis thaliana]

```
MEISLMKFLFLGIWVYYYSVLDSVSAMDSLLSPKGVNYEVAALMSVKNKMKDEKEVLSGWDI
NSVDPCTWNMVGCSSEGFVVSLEMASKGLSGILSTSIGELTHLHTLLLQNNQLTGPIPSELG
QLSELETLDLSGNRFSGEIPASLGFLTHLNYLRLSRNLLSGQVPHLVAGLSGLSFLDLSFNN
LSGPTPNISAKDYRIVGNAFLCGPASQELCSDATPVRNATGLSEKDNSKHHSLVLSFAFGIV
VAFIISLMFLFFWVLWHRSRLSRSHVQQDYEFEIGHLKRFSFREIQTATSNFSPKNILGQGG
FGMVYKGYLPNGTVVAVKRLKDPIYTGEVQFQTEVEMIGLAVHRNLLRLFGFCMTPEERMLV
YPYMPNGSVADRLRDNYGEKPSLDWNRRISIALGAARGLVYLHEQCNPKIIHRDVKAANILL
DESFEAIVGDFGLAKLLDQRDSHVTTAVRGTIGHIAPEYLSTGQSSEKTDVFGFGVLILELI
TGHKMIDQGNGQVRKGMILSWVRTLKAEKRFAEMVDRDLKGEFDDLVLEEVVELALLCTQPH
PNLRPRMSQVLKVLEGLVEQCEGGYEARAPSVSRNYSNGHEEQSFIIEAIELSGPR
```

SEQ ID NO: 40, NM_125766.2, Arabidopsis thaliana ATP binding / protein kinase/ protein serine/threonine kinase/ protein-tyrosine kinase AT5G63710 mRNA, complete cds

```
CATTTCTCTCTTCAACCCCATGTTTTCGTTCTCTTCCGTTTAGAGTGTTTTCAGCTCCTCTA
TGGCTCACTCGGGGAACGGTGAAAGTTTCCATGATCCTCTTCGAGGATTCATTCAAAGAAAT
TGCTTTAGATGGAACAATCAGAAATTGATCTTACAATGTTTCATGGCCTTAGCTTTTGTGGG
AATCACTTCGTCAACAACTCAACCAGATATCGAAGGAGGAGCTCTGTTGCAGCTCAGAGATT
CGCTTAATGATTCGAGCAATCGTCTAAAATGGACACGCGATTTTGTGAGCCCTTGCTATAGT
```

FIGURE 4 (continued)

```
TGGTCTTATGTTACCTGCAGAGGCCAGAGTGTTGTGGCTCTAAATCTTGCCTCGAGTGGATT
CACAGGAACACTCTCTCCAGCTATTACAAAACTGAAGTTCTTGGTTACCTTAGAGTTACAGA
ACAATAGTTTATCTGGTGCCTTACCAGATTCTCTTGGGAACATGGTTAATCTACAGACTTTA
AACCTATCAGTGAATAGTTTCAGCGGATCGATACCAGCGAGCTGGAGTCAGCTCTCGAATCT
AAAGCACTTGGATCTCTCATCCAATAATTTAACAGGAAGCATCCCAACACAATTCTTCTCAA
TCCCAACATTCGATTTTTCAGGAACTCAGCTTATATGCGGTAAAAGTTTGAATCAGCCTTGT
TCTTCAAGTTCTCGTCTTCCAGTCACATCCTCCAAGAAAAAGCTGAGAGACATTACTTTGAC
TGCAAGTTGTGTTGCTTCTATAATCTTATTCCTTGGAGCAATGGTTATGTATCATCACCATC
GCGTCCGCAGAACCAAATACGACATCTTTTTTGATGTAGCTGGGGAAGATGACAGGAAGATT
TCCTTTGGACAACTAAAACGATTCTCTTTACGTGAAATCCAGCTCGCAACAGATAGTTTCAA
CGAGAGCAATTTGATAGGACAAGGAGGATTTGGTAAAGTATACAGAGGTTTGCTTCCAGACA
AAACAAAAGTTGCAGTGAAACGCCTTGCGGATTACTTCAGTCCTGGAGGAGAAGCTGCTTTC
CAAAGAGAGATTCAGCTCATAAGCGTTGCGGTTCATAAAAATCTCTTACGCCTTATTGGCTT
CTGCACAACTTCCTCTGAGAGAATCCTTGTTTATCCATACATGGAAAATCTTAGTGTTGCAT
ATCGACTAAGAGATTTGAAAGCGGGAGAGGAAGGATTAGACTGGCCAACAAGGAAGCGTGTA
GCTTTTGGTTCAGCTCACGGTTTAGAGTATCTACACGAACATTGTAACCCGAAGATCATACA
CCGCGATCTCAAGGCTGCAAACATACTTTTAGACAACAATTTTGAGCCAGTTCTTGGAGATT
TCGGTTTAGCTAAGCTTGTGGACACATCTCTGACTCATGTCACAACTCAAGTCCGAGGCACA
ATGGGTCACATTGCGCCAGAGTATCTCTGCACAGGAAAATCATCTGAAAAACCGATGTTTT
TGGTTACGGTATAACGCTTCTTGAGCTTGTTACTGGTCAGCGCGCAATCGATTTTTCACGCT
TGGAAGAAGAGGAAAATATTCTCTTGCTTGATCATATAAAGAAGTTGCTTAGAGAACAGAGA
CTTAGAGACATTGTTGATAGCAATTTGACTACATATGACTCCAAAGAAGTTGAAACAATCGT
TCAAGTGGCTCTTCTCTGCACACAAGGCTCACCAGAAGATAGACCAGCGATGTCTGAAGTGG
TCAAAATGCTTCAAGGGACTGGTGGTTTGGCTGAGAAATGGACTGAATGGGAACAACTTGAA
GAAGTTAGGAACAAAGAAGCATTGTTGCTTCCGACTTTACCGGCTACTTGGGATGAAGAAGA
AACCACCGTTGATCAAGAATCTATCCGATTATCGACAGCAAGATGAAGAAGAAACAGAGAGA
GAAAGATATCTATGAAAACAAACTTGCATTACAGAAGATAAACTTAGAAAGTATTTTAAGCT
GCTAATTGTATTGAACCAGGTGGGGAAAACGAAGCAAACACACAACGTTGATTTGTGTAATA
GATGATATGATATACATAACTAGTTGTGTTTTGTATATATATGAATTTGGTTATTTTCGT
```

SEQ ID NO: 41, NP_568977.1, ATP binding / protein kinase/ protein serine/threonine kinase/ protein-tyrosine kinase [Arabidopsis thaliana]

```
MAHSGNGESFHDPLRGFIQRNCFRWNNQKLILQCFMALAFVGITSSTTQPDIEGGALLQLRD
SLNDSSNRLKWTRDFVSPCYSWSYVTCRGQSVVALNLASSGFTGTLSPAITKLKFLVTLELQ
NNSLSGALPDSLGNMVNLQTLNLSVNSFSGSIPASWSQLSNLKHLDLSSNNLTGSIPTQFFS
IPTFDFSGTQLICGKSLNQPCSSSSRLPVTSSKKKLRDITLTASCVASIILFLGAMVMYHHH
RVRRTKYDIFFDVAGEDDRKISFGQLKRFSLREIQLATDSFNESNLIGQGGFGKVYRGLLPD
KTKVAVKRLADYFSPGGEAAFQREIQLISVAVHKNLLRLIGFCTTSSERILVYPYMENLSVA
YRLRDLKAGEEGLDWPTRKRVAFGSAHGLEYLHEHCNPKIIHRDLKAANILLDNNFEPVLGD
FGLAKLVDTSLTHVTTQVRGTMGHIAPEYLCTGKSSEKTDVFGYGITLLELVTGQRAIDFSR
LEEEENILLLDHIKKLLREQRLRDIVDSNLTTYDSKEVETIVQVALLCTQGSPEDRPAMSEV
VKMLQGTGGLAEKWTEWEQLEEVRNKEALLLPTLPATWDEEETTVDQESIRLSTAR
```

FIGURE 4 (continued)

SEQ ID NO: 42, NM_125922.1, Arabidopsis thaliana kinase AT5G65240 mRNA, complete cds

ATGGCTCTGCTTATTATCACTGCCTTAGTTTTTAGTAGTTTATGGTCATCTGTGTCACCAGA
TGCTCAAGGGGATGCATTATTTGCGTTGAGGAGCTCGTTACGTGCATCTCCTGAACAGCTTA
GTGATTGGAACCAGAATCAAGTCGATCCTTGTACTTGGTCTCAAGTTATTTGTGATGACAAG
AAACATGTTACTTCTGTAACCTTGTCTTACATGAACTTCTCCTCGGGAACACTGTCTTCAGG
AATAGGAATCTTGACAACTCTCAAGACTCTTACATTGAAGGGAATGGAATAATGGGTGGAA
TACCAGAATCCATTGGAAATCTGTCTAGCTTGACCAGCTTAGATTTGGAGGATAATCACTTA
ACTGATCGCATTCCATCCACTCTCGGTAATCTCAAGAATCTACAGTTCTTGACCTTGAGTAG
GAATAACCTTAATGGTTCTATCCCGGATTCACTTACAGGTCTATCAAAACTGATAAATATTC
TGCTCGACTCAAATAATCTCAGTGGTGAGATTCCTCAGAGTTTATTCAAAATCCCAAAATAC
AATTTCACAGCAAACAACTTGAGCTGTGGTGGCACTTTCCCGCAACCTTGTGTAACCGAGTC
CAGTCCTTCAGGTGATTCAAGCAGTAGAAAAACTGGAATCATCGCTGGAGTTGTTAGCGGAA
TAGCGGTTATTCTACTAGGATTCTTCTTCTTTTTCTTCTGCAAGGATAAACATAAAGGATAT
AAACGAGACGTATTTGTGGATGTTGCAGGAACGAACTTTAAAAAAGGTTTGATTTCAGGTGA
AGTGGACAGAAGGATTGCTTTTGGACAGTTGAGAAGATTTGCATGGAGAGAGCTTCAGTTGG
CTACAGATGAGTTCAGTGAAAAGAATGTTCTCGGACAAGGAGGCTTTGGGAAAGTTTACAAA
GGATTGCTTTCGGATGGCACCAAAGTCGCTGTAAAAAGATTGACTGATTTTGAACGTCCAGG
AGGAGATGAAGCTTTCCAGAGAGAAGTTGAGATGATAAGTGTAGCTGTTCATAGGAATCTGC
TTCGCCTTATCGGCTTTTGTACAACACAAACTGAACGACTTTTGGTGTATCCTTTCATGCAG
AATCTAAGTGTTGCATATTGCTTAAGAGAGATTAAACCCGGGGATCCAGTTCTGGATTGGTT
CAGGAGGAAACAGATTGCGTTAGGTGCAGCACGAGGACTCGAATATCTTCATGAACATTGCA
ACCCGAAGATCATACACAGAGATGTGAAAGCTGCAAATGTGTTACTAGATGAAGACTTTGAA
GCAGTGGTTGGTGATTTTGGTTTAGCCAAGTTGGTAGATGTTAGAAGGACTAATGTAACCAC
TCAGGTCCGAGGAACAATGGGTCATATTGCACCAGAATGTATATCCACAGGGAAATCGTCAG
AGAAAACCGATGTTTTCGGGTACGGAATTATGCTTCTGGAGCTTGTAACTGGACAAAGAGCA
ATTGATTTCTCGCGGTTAGAGGAAGAAGATGATGTCTTATTGCTAGACCATGTGAAGAAACT
GGAAAGAGAGAAGAGATTAGAAGACATAGTAGATAAGAAGCTTGATGAGGATTATATAAAGG
AAGAAGTTGAAATGATGATACAAGTAGCTCTGCTATGCACACAAGCAGCACCGGAAGAACGA
CCAGCGATGTCGGAAGTAGTAAGAATGCTAGAAGGAGAAGGGCTTGCAGAGAGATGGGAAGA
GTGGCAGAATCTTGAAGTGACGAGACAAGAAGAGTTTCAGAGGTTGCAGAGGAGATTTGATT
GGGGTGAAGATTCCATTAATAATCAAGATGCTATTGAATTATCTGGTGGAAGATAG

SEQ ID NO: 43, NP_201327.1, kinase [Arabidopsis thaliana]

MALLIITALVFSSLWSSVSPDAQGDALFALRSSLRASPEQLSDWNQNQVDPCTWSQVICDDK
KHVTSVTLSYMNFSSGTLSSGIGILTTLKTLTLKGNGIMGGIPESIGNLSSLTSLDLEDNHL
TDRIPSTLGNLKNLQFLTLSRNNLNGSIPDSLTGLSKLINILLDSNNLSGEIPQSLFKIPKY
NFTANNLSCGGTFPQPCVTESSPSGDSSSRKTGIIAGVVSGIAVILLGFFFFFFCKDKHKGY
KRDVFVDVAGTNFKKGLISGEVDRRIAFGQLRRFAWRELQLATDEFSEKNVLGQGGFGKVYK
GLLSDGTKVAVKRLTDFERPGGDEAFQREVEMISVAVHRNLLRLIGFCTTQTERLLVYPFMQ
NLSVAYCLREIKPGDPVLDWFRRKQIALGAARGLEYLHEHCNPKIIHRDVKAANVLLDEDFE
AVVGDFGLAKLVDVRRTNVTTQVRGTMGHIAPECISTGKSSEKTDVFGYGIMLLELVTGQRA
IDFSRLEEEDDVLLLDHVKKLEREKRLEDIVDKKLDEDYIKEEVEMMIQVALLCTQAAPEER
PAMSEVVRMLEGEGLAERWEEWQNLEVTRQEEFQRLQRRFDWGEDSINNQDAIELSGGR

FIGURE 4 (continued)

SEQ ID NO: 44, NM_114242.2, Arabidopsis thaliana protein binding AT3G43740 transcript variant AT3G43740.1 mRNA, complete cds

GGCGAAAACCATGGTGGCGCAAAACAGTCGGCGGGAGCTTCTAGCAGCTTCCCTGATCCTAA
CTTTAGCTCTAATTCGTCTAACGGAAGCAAACTCCGAAGGGGACGCTCTTCACGCGCTTCGC
CGGAGCTTATCAGATCCAGACAATGTTGTTCAGAGTTGGGATCCAACTCTTGTTAATCCTTG
TACTTGGTTTCATGTCACTTGTAATCAACACCATCAAGTCACTCGTCTGGATTTGGGGAATT
CAAACTTATCTGGACATCTAGTACCTGAACTTGGGAAGCTTGAACATTTACAATATCTTGAA
CTCTACAAAAACGAGATTCAAGGAACTATACCTTCTGAGCTTGGAAATCTGAAGAGTCTAAT
CAGTTTGGATCTGTACAACAACAATCTCACCGGGAAAATCCCATCTTCTTTGGGAAAATTGA
AGTCACTTGTTTTTTTGCGGCTTAACGAAAACCGATTGACCGGTCCTATTCCTAGAGAACTC
ACAGTTATTTCAAGCCTTAAAGTTGTTGATGTCTCAGGGAATGATTTGTGTGGAACAATTCC
AGTAGAAGGACCTTTTGAACACATTCCTATGCAAACTTTGAGAACAACCTGAGATTGGAGG
GACCAGAACTACTAGGTCTTGCGAGCTATGACACCAATTGCACTTAAAAAGAAGTTGAAGAA
CCTATAAAGAAGAATGTTAGGTGACCTTGTAAGAACTCTGTACCAAGTGTTTGTAAATCTAT
ATAGAGCCTTGTTTCATGTTATATATGAAAGCTTTGAGAGACAGTAACTTGCAATGTATTGG
TATTGGTAGAAAAAGTTGAAATGAGAATTGCTTTGTAA

SEQ ID NO: 45, NP_189960.2, protein binding [Arabidopsis thaliana]

MVAQNSRRELLAASLILTLALIRLTEANSEGDALHALRRSLSDPDNVVQSWDPTLVNPCTWF
HVTCNQHHQVTRLDLGNSNLSGHLVPELGKLEHLQYLELYKNEIQGTIPSELGNLKSLISLD
LYNNNLTGKIPSSLGKLKSLVFLRLNENRLTGPIPRELTVISSLKVVDVSGNDLCGTIPVEG
PFEHIPMQNFENNLRLEGPELLGLASYDTNCT

SEQ ID NO: 46, NM_122117.2, Arabidopsis thaliana protein binding AT5G21090 mRNA, complete cds

ACCAATCGCATAATCGATTTCTTCCAACTTCAATAAAGGGGAACCAACGTAACCCTAATTTT
GCTTTCTCCTCTTTGTTCAGAAAATTTTCCCTTTACTCTCAAATTCCTTTTCGATTTCCCTC
TCTTAAACCTCCGAAAGCTCACATGGCGTCTCGAAACTATCGGTGGGAGCTCTTCGCAGCTT
CGTTAACCCTAACCTTAGCTTTGATTCACCTGGTCGAAGCAAACTCCGAAGGAGATGCTCTC
TACGCTCTTCGCCGGAGTTTGACAGATCCAGACCATGTCCTCCAGAGCTGGGATCCAACTCT
TGTTAATCCTTGTACCTGGTTCCATGTCACCTGTAACCAAGACAACCGCGTCACTCGTGTGG
ATTTGGGAAATTCAAACCTCTCTGGACATCTTGCGCCTGAGCTTGGGAAGCTTGAACATTTA
CAGTATCTAGAGCTCTACAAAACAACATCCAAGGAACTATACCTTCCGAACTTGGAAATCT
GAAGAATCTCATCAGCTTGGATCTGTACAACAACAATCTTACAGGGATAGTTCCCACTTCTT
TGGGAAAATTGAAGTCTCTGGTCTTTTTACGGCTTAATGACAACCGATTGACCGGTCCAATC
CCTAGAGCACTCACGGCAATCCCAAGCCTTAAAGTTGTTGACGTCTCAAGCAATGATTTGTG
TGGAACAATCCCAACAAACGGACCCTTTGCTCACATTCCTTTACAGAACTTTGAGAACAACC
CGAGATTGGAGGGACCGGAATTACTCGGTCTTGCAAGCTACGACACTAACTGCACCTGAAAC
AACTGGCAAAACCTGAAAATGAAGAATTGGGGGGTGACCTTGTAAGAACACTTCACCACTTT
ATCAAATATCACATCTATTATGTAATAAGTATATATATGTAGTAAAAACAAAAAAAAATGAAG

FIGURE 4 (continued)

AATCGAATCGGTAATATCATCTGGTCTCAATTGAGAACTTCGAGGTCTGTATGTAAAATTTC
TAAATGCGATTTTCGCTTACTGTAATGTTCGGTTGTGGGATTCTGAGAAGTAACATTTGTAT
TGGTATGGTATCAAGTTGTTCTGCCTTGTCTGCATTTAACACTTGTGTTTTAGATCTGTTAT
ATAAAGCCAAAAAAGGTTTTGTGTGATTTGGTACTATC

SEQ ID NO: 47, NP_197608.1, protein binding [Arabidopsis thaliana]

MASRNYRWELFAASLTLTLALIHLVEANSEGDALYALRRSLTDPDHVLQSWDPTLVNPCTWF
HVTCNQDNRVTRVDLGNSNLSGHLAPELGKLEHLQYLELYKNNIQGTIPSELGNLKNLISLD
LYNNNLTGIVPTSLGKLKSLVFLRLNDNRLTGPIPRALTAIPSLKVVDVSSNDLCGTIPTNG
PFAHIPLQNFENNPRLEGPELLGLASYDTNCT

SEQ ID NO: 48, Arabidopsis thaliana, RKS11 splice variant, coding sequence

ATGAAGATTCAAATTCATCTCCTTTACTCGTTCTTGTTCCTCTGTTTCTCTACTCTCACT
CTATCTTCTGAGCCCAGAAACCCTGAAGTTGAGGCGTTGATAAGTATAAGGAACAATTTG
CATGATCCTCATGGAGCTTTGAACAATTGGGACGAGTTTTCAGTTGATCCTTGTAGCTGG
GCTATGATCACTTGCTCTCCCGACAACCTCGTCATTGGACTAGGAGCGCCGAGCCAGTCT
CTCTCGGGAGGTTTATCTGAGTCTATCGGAAATCTCACAAATCTCCGACAAGTGTCATTG
CAAAATAACAACATCTCCGGCAAAATTCCACCGGAGCTCGGTTTTCTACCCAAATTACAA
ACCTTGGATCTTTCCAACAACCGATTCTCCGGTGACATCCCTGTTTCCATCGACCAGCTA
AGCAGCCTTCAATATCTGGACTTGTCTTACAACAATCTCAGTGGCCCTGTTCCTAAATTC
CCAGCAAGGACTTTCAACGTTGCTGGTAATCCTTTGATTTGTAGAAGCAACCCACCTGAG
ATTTGTTCTGGATCAATCAATGCAAGTCCACTTTCTGTTTCTTTGAGCTCTTCATCAGCA
GATAAACAAGAGGAAGGGCTTCAAGGACTTGGGAATCTAAGAAGCTTCACATTCAGAGAA
CTCCATGTTTATACAGATGGTTTCAGTTCCAAGAACATTCTCGGCGCTGGTGGATTCGGT
AATGTGTACAGAGGCAAGCTTGGAGATGGGACAATGGTGGCAGTGAAACGGTTGAAGGAT
ATTAATGGAACCTCAGGGGATTCACAGTTTCGTATGGAGCTAGAGATGATTAGCTTAGCT
GTTCATAAGAATCTGCTTCGGTTAATTGGTTATTGCGCAACTTCTGGTGAAAGGCTTCTT
GTTTACCCTTACATGCCTAATGGAAGCGTCGCCTCTAAGCTTAAATCTAAACCGGCATTG
GACTGGAACATGAGGAAGAGGATAGCAATTGGTGCAGCGAGAGGTTTGTTGTATCTACAT
GAGCAATGTGATCCCAAGATCATTCATAGAGATGTAAAGGCAGCTAATATTCTCTTAGAC
GAGTGCTTTGAAGCTGTTGTTGGTGACTTTGGACTCGCAAAGCTCCTTAACCATGCGGAT
TCTCATGTCACAACTGCGGTCCGTGGTACGGTTGGCCACATTGCACCTGAATATCTCTCC
ACTGGTCAGTCTTCTGAGAAAACCGATGTGTTTGGGTTCGGTATACTATTGCTCGAGCTC
ATAACCGGACTGAGAGCTCTTGAGTTTGGTAAAACCGTTAGCCAGAAAGGAGCTATGCTT
GAATGGGTGAGGAAATTACATGAAGAGATGAAAGTAGAGGAACTATTGGATCGAGAACTC
GGAACTAACTACGATAAGATTGAAGTTGGAGAGATGTTGCAAGTGGCTTTGCTATGCACA
CAATATCTGCCAGCTCATCGTCCTAAAATGTCTGAAGTTGTTTTGATGCTTGAAGGCGAT
GGATTAGCCGAGAGATGGGCTGCTTCGCATAACCATTCACATTTCTACCATGCCAATATC
TCTTTCAAGACAATCTCTTCTCTGTCTACTACTTCTGTCTCAAGGCTTGACGCACATTGC
AATGATCCAACTTATCAAATGTTTGGATCTTCGGCTTTCGATGATGACGATGATCATCAG
CCTTTAGATTCCTTTGCCATGGAACTATCCGGTCCAAGATAA

FIGURE 4 (continued)

SEQ ID NO: 49, Arabidopsis thaliana, RKS11 splice variant, deduced protein sequence

MKIQIHLLYSFLFLCFSTLTLSSEPRNPEVEALISIRNNLHDPHGALNNWDEFSVDPCSW
AMITCSPDNLVIGLGAPSQSLSGGLSESIGNLTNLRQVSLQNNNISGKIPPELGFLPKLQ
TLDLSNNRFSGDIPVSIDQLSSLQYLDLSYNNLSGPVPKFPARTFNVAGNPLICRSNPPE
ICSGSINASPLSVSLSSSSADKQEEGLQGLGNLRSFTFRELHVYTDGFSSKNILGAGGFG
NVYRGKLGDGTMVAVKRLKDINGTSGDSQFRMELEMISLAVHKNLLRLIGYCATSGERLL
VYPYMPNGSVASKLKSKPALDWNMRKRIAIGAARGLLYLHEQCDPKIIHRDVKAANILLD
ECFEAVVGDFGLAKLLNHADSHVTTAVRGTVGHIAPEYLSTGQSSEKTDVFGFGILLLEL
ITGLRALEFGKTVSQKGAMLEWVRKLHEEMKVEELLDRELGTNYDKIEVGEMLQVALLCT
QYLPAHRPKMSEVVLMLEGDGLAERWAASHNHSHFYHANISFKTISSLSTTSVSRLDAHC
NDPTYQMFGSSAFDDDDDHQPLDSFAMELSGPR

SEQ ID NO: 50, Oryza promoter PRO0058

TCTCTTCTGAAGCTGAAGCCCTGCGAAATAGGCCTTTAAACGCTTTAAGGTTACTGGATGAT
CATATCGGCGTAAGACCGGTTTAAACATGGTTTCGCTTTGTGAATCCAATGTGAGTCACGAC
GTGACACATGGCACGTCCTTGGAGCTTTAGACATATCGAATCTGAGCACTGGAGTGGCCGAG
TGGGTGAGCGGCCAAATCCGTTTTAGACAGATCGCACTGACACGATGTTGATCATTGATACT
AATACCATTTTATCAAGCAGTAGTGTTGAAAAAAAAACTTATGTTCTCTTCAACTGTGAGAT
TTCATCCCGTTTCAAGATGAACAAGCCATGCATGTGAGATGTGAACAGAAGGCAGAAGACAG
TGGAAAGACAGGACAAATAAGTGAAGAGGGATCAAATCAATGGGCCTGACGGTTTCTGAAAG
TTGACATGGAAATCGCCGGTGATCACCGGTTTATACGTTATTTAAATCTGCGATTTCCACTT
TCGTTTGCTTTCGGGGTTCCAATTTGAGTCACGCACATATTCTTCATCGTGCTTTGGATCTC
AGCACCGTAGTAACTTTTGGACAAATTGCATTCGCCGACACTAATAACATGTTCTTTTATG
CTGCTTTACATATACTGCTTATCCACACCCAATCCCATGTTCATATATTATGAGATGGAGGG
AGTAAACTTTGTTAACAGCAACATTTTTTATATTAAAGCATCAACTAATTAAAGCACAAGAT
ACGCATGTTATCTCAATAAATCTTCCAGTGCATGTATAAAGAAGATGTCGCCGCTAACTTAG
ATAATTTTGTGACTTTTATCCTGGCCGGCATAATTAATTCTTCCGGAAATTAAAAGCTAGT
TTTTCCATATTCATCAGTACAGACAAGACAGCATAGTAAGCGAAGCATACCTGACGTGTTAG
CTCATTGTAACTCGATCTGGAACACTCGATGCTAGATACAGACAGACACTCCTCGTGATGAA
CGTTAGCATTTAGCAACATACGGTGATAAAGCAGCTGGGGATCGATCCATCCATCCATCGTC
TTTACACGTACTTACCTTGCTAACCGCACTGTCGACTCTTGCATGTTTGCATGTAATCCAAA
TGGACCCCACGTGGAACATGCTCACAGTGCTTTGCAGCTGCTTTCCAAAATGCTTTCTTTCA
CTTCTTCCATTCCTCTGTCCACAAAAAAGTAGTGTGTTCTTGAGCCTATATAAGAGAGGGT
CACACGCTCCAGTCGACTCACCATCGATCCATCTGACGGTTAGTTCCAAGGGAAAGAAGAA

FIGURE 4 (continued)

PLANTS HAVING IMPROVED GROWTH CHARACTERISTICS AND METHOD FOR MAKING THE SAME

RELATED APPLICATIONS

This application is a national stage application (under 35 U.S.C. 371) of PCT/EP2006/063017 filed Jun. 8, 2006, which claims benefit of European application 05104980.7 filed Jun. 8, 2005 and U. S. Provisional Application 60/690,483 filed Jun. 15, 2005.

The present invention relates generally to the field of molecular biology and concerns a method for modifying plant growth characteristics. More specifically, the present invention concerns a method for improving plant growth characteristics, in particular yield, by increasing expression in a plant of at least part of a Leucine Rich Repeat Receptor-Like Kinase (RKS11 or RKS4 or an orthologue thereof). The present invention also concerns plants having increased expression of at least part of a Leucine Rich Repeat Receptor-Like Kinase (RKS11 or RKS4 or an orthologue thereof), which plants have improved growth characteristics relative to corresponding wild type plants. The invention also provides constructs useful in the methods of the invention.

The ever-increasing world population and the dwindling supply of arable land available for agriculture fuel research towards improving the efficiency of agriculture. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic components (including undesirable traits) that may not always result in the desirable trait being passed on from parent plants. Advances in molecular biology have allowed mankind to modify the germplasm of animals and plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits.

A trait of particular economic interest is yield, and in the case of many plants seed yield. Yield is normally defined as the measurable produce of economic value from a crop. This may be defined in terms of quantity and/or quality. Yield is directly dependent on several factors, for example, the number and size of the organs, plant architecture (for example, the number of branches), seed production and more. Root development, nutrient uptake and stress tolerance may also be important factors in determining yield. Optimizing one of the above-mentioned factors may therefore contribute to increasing crop yield. Plant seeds are an important source of human and animal nutrition. Crops such as, corn, rice, wheat, canola and soy bean account for over half of the total human caloric intake, whether through direct consumption of the seeds themselves or through consumption of meat products raised on processed seeds. They are also a source of sugars, oils and many kinds of metabolites used in industrial processes. Seeds contain an embryo, the source of new shoots and roots after germination, and an endosperm, the source of nutrients for embryo growth, during germination and early growth of seedlings. The development of a seed involves many genes, and requires the transfer of metabolites from roots, leaves and stems into the growing seed. The endosperm, in particular, assimilates the metabolic precursors of carbohydrates, oils and proteins and synthesizes them into storage macromolecules to fill out the grain. The ability to increase plant seed yield, whether through seed number, seed biomass, seed development, seed filling, or any other seed-related trait would have many applications in agriculture, and even many non-agricultural uses such as in the biotechnological production of substances such as pharmaceuticals, antibodies or vaccines.

Receptor like kinases (RLKs) are involved in transmission of extracellular signals into the cell. The RLK proteins have a modular structure, starting from the N-terminus with a secretion signal that gets processed, an extracellular domain, a single transmembrane domain and a cytoplasmic kinase domain. Receptor like kinases are postulated to form homodimers or heterodimers of two related kinases, similar as for animal receptor kinases (Torii, Curr. Opin. Plant Biol. 3, 361-367, 2000). Animal receptor-like kinases mostly have tyrosine kinase activity, whereas plant RLKs all have Ser/Thr kinase specificity, or may sometimes have a dual specificity. In animals, most of the RLKs act as growth factor receptors, whereas plant receptor like kinases may function in various processes, including development, hormone perception or pathogen responses. An overview of developmental functions of plant receptor like kinases such as meristem development, pollen-pistil interactions, hormone signalling, gametophyte development, cell morphogenesis and differentiation, organ shape, organ abscission and somatic embryogenesis is given by Becraft (Annu. Rev. Cell Dev. Biol., 18, 163-192, 2002).

Alternatively, receptor-like kinases may be grouped according to the structure of their extracellular domain (Shiu and Bleecker, Proc. Natl. Acad. Sci. USA 98, 10763-10768, 2001). The largest group was that of the Leucine Rich Repeat (LRR) containing RLKs; which may be split up in 13 subgroups (LRR I to LRR XIII) based on the organisation of the LRR domains in the extracellular part of the RLK. The LRR units may be present in varying numbers and may be arranged in continuous or interrupted repeats.

RKS (Receptor Kinase SERK-like) proteins have a modular structure that corresponds to the LRR II subfamily of the LRR-RLK. The domain organisation is, from N-terminus to C-terminus: a signal sequence, a number of leucine zipper motifs, a conserved pair of cysteines, 4 or 5 LRR domains followed by another conserved pair of cysteines, a transmembrane domain and the intracellular kinase domain. The *Arabidopsis* RKS genes form a gene family of 14 members, and are related to SERK (Somatic Embryogenesis Receptor Kinase). SERK was first characterised in carrot (Schmidt et al., Development 124, 2049-2069, 1997) and is specifically expressed in embryogenic cells. SERK homologues were also found in other plant species (*Arabidopsis* (Hecht et al., Plant Physiol. 127, 803-816, 2001) or *Helianthus*, and in monocotyledonous plants such as maize or *Dactylis glomerata* (Somleva et al., Plant Cell Rep. 19, 718-726, 2000)). Overexpression of SERK in *Arabidopsis* increased the embryogenic potential of *Arabidopsis* cultures, confirming the postulated function of increasing embryogenic competence. In *Arabidopsis*, AtSERK1 is only expressed in developing ovules (in particular in the embryo sac), and after fertilization in the endosperm and embryo, up to the heart stage. Transgenic plants with constitutive expression of AtSERK1 were reported to have no altered plant phenotype (Hecht et al., 2001). The characterisation of *Medicago truncatula* MtSERK1 suggests that, at least in legumes, SERK may play a broader role in development than embryogenesis alone (Nolan et al. Plant Physiol. 133, 218-230, 2003).

WO 2004/007712 describes and characterises a number of *Arabidopsis* RKS genes. It was postulated that modification of expression of the RKS genes would cause a modification of the brassinosteroid-signalling pathway. The data show that, depending on the specific RKS gene and the kind of expression (up- or downregulation of expression compared to wild type), results in various phenotypes. For example, RKS4 and RKS 10 are reported to stimulate cell division. Overexpression of the RKS4 gene resulted in increased cell division and an altered plant phenotype, whereas modulation of RKS10 did change the cell number, but not plant or organ size. Overexpression of RKS10 also caused the formation of many generative meristems that did not end up in normally developed flowers. Both overexpression and downregulated expression of RKS10 had a strong negative effect on pollen formation. Root length was negatively affected by overexpressing RKS10, while initiation and outgrowth of lateral roots was promoted. The same effects on root growth may be obtained by suppressing RKS1 expression. Also overexpression of the RKS3, RKS4 or RKS6 genes had positive effects on root length. Increased apical shoot meristem formation and outgrowth was obtained by overexpressing RKS0 but also by downregulating expression of RKS3, RKS4, RKS8 or RKS10. RKS4 overexpression was reported to result in larger seed size, but did not result in higher seed yield; no functional analysis was made of the RKS11 gene. In this disclosure however, only full length RKS proteins were studied.

It is known in the art that expression of truncated receptor like kinases typically result in loss-of-function phenotypes. For example, Shpak et al. (Plant Cell 15, 1095-1110, 2003) describe a truncated ERECTA protein (a LRR-RLK of the LRR XIII subfamily) that lacks the cytoplasmic kinase domain. ERECTA regulates organ shape and inflorescence architecture. Transgenic plants expressing the truncated ERECTA protein had compact inflorescences and short blunt siliques; this phenotype is characteristic for loss-of-function erecta mutant plants. CLAVATA, another LRR-RLK but classified in subfamily XI, controls shoot and floral meristems in plants. Two mutants of clavata1, clv1-6 and clv1-7, lack the entire kinase domain, yet the mutant phenotype is rather mild compared to other mutations within the kinase domain (Clark et al. Cell 89, 575-585, 1997; Torii, 2000).

It has now surprisingly been found that increasing expression of at least part of a Leucine Rich Repeat Receptor-Like Kinase (LRR-RLK) of subfamily II (preferably RKS11 or RKS4 or an orthologue of these) gives plants having improved growth characteristics relative to control plants.

Therefore, the invention provides a method for improving the growth characteristics of a plant, comprising increasing expression of a subfamily II LRR-RLK (preferably RKS11 or RKS4 or an orthologue thereof), or of a part thereof (which parts are hereafter named LRR-II-RLP, for subfamily II Leucine Rich Repeat Receptor-Like Proteins); provided that the improved growth characteristics do not encompass increased seed size upon increased expression of RKS4 (SEQ ID NO: 12).

The choice of suitable control plants is a routine part of an experimental set-up and may include corresponding wild type plants or corresponding plants without the gene of interest. The control plant is typically of the same plant species or even of the same variety as the plant to be compared. The control plant may also be a nullizygote of the plant to be compared. A "control plant" as used herein refers not only to whole plants, but also to plant parts, including seeds and seed parts.

A preferred method for increasing expression of a nucleic acid encoding a subfamily II LRR-RLK or an LRR-II-RLP is by introducing and expressing in a plant an isolated nucleic acid encoding a subfamily II LRR-RLK or an LRR-II-RLP.

The nucleic acid to be introduced into a plant (and therefore useful in performing the methods of the invention) is any nucleic acid encoding a subfamily II LRR-RLK, but preferably RKS11 or RKS4 or an orthologue of one of these, more preferably the nucleic acid encodes the type of LRR-II-RLP which is described below.

The term "RKS11" or "RKS11 polypeptide" as used herein refers to the polypeptide as represented by SEQ ID NO: 2. The term "RKS4" or "RKS4 polypeptide" as used herein refers to the polypeptide as represented by SEQ ID NO: 12. Both the RKS11 and RKS4 polypeptide comprise the following domains (from N-terminus to C-terminus): (i) a signal sequence, (ii) a Leucine zipper motif with 3 Leu residues separated from each other by 6 other amino acids, (iii) a motif with 2 conserved Cysteine residues, (iv) 4 Leucine Rich Repeat units of each approximately 23 amino acid residues, (v) a domain enriched in serine and proline residues, (vi) a single transmembrane domain, and (vii) a kinase domain, flanked at both sides by a domain of unknown function.

The term "domain" means a set of amino acids conserved at specific positions along an alignment of sequences (performed as described below) of evolutionarily related proteins. While amino acids at other positions can vary between homologues, amino acids that are highly conserved at specific positions indicate amino acids that are essential in the structure, the stability, or the activity of a protein. Because they are identified by their high degree of conservation in aligned sequences of a family of protein homologues, they can be used as identifiers to determine if a polypeptide with a newly determined sequence belongs to a previously identified polypeptide family.

The signal peptide of RKS11 is predicted to be 31 amino acids long. The motif with the conserved cysteine residues in RKS11 is described in Diévart & Clark (2003), the Cys residues are located at positions 66 and 73 in SEQ ID NO: 2. The LRR domains are tandemly placed, from amino acid 102 to 196. In addition, the RKS11 protein comprises a stretch of amino acids is found that consists for 34% of proline and serine between the fourth LRR domain and the TM region. The transmembrane (TM) region is predicted to span amino acids 240 to 262. The kinase domain corresponds to both the Pfam PF00069 and the Pfam PF07714 type of kinase domains, which may be an indication for dual specificity activity and comprises amino acids 303 to 572. The N-terminal extremity of the kinase catalytic domain comprises a glycine-rich stretch of residues in the vicinity of a lysine residue, which has been shown to be involved in ATP binding. The central part of the kinase catalytic domain has a conserved Aspartic acid residue, which is important for the kinase activity of the RKS11 protein. Between the transmembrane domain and the kinase domain, a domain with unknown function is found (RELH-domain), characterised by the presence of a "RELHXXTDG" motif (SEQ ID NO: 5). The X may represent any amino acid, preferably the first X is a hydrophobic non-polar amino acid, more preferably a Valine or Alanine. C-terminal of the kinase domain, another domain of unknown function is found (EGD-domain), starting with a "EGDGLA" motif (SEQ ID NO: 6) and ending with a "ELSGPR" motif (SEQ ID NO: 7)

RKS4 (SEQ ID NO: 12) is a paralogue of RKS11, and is highly homologous to RKS11. By aligning the sequences of the RKS11 and RKS4 proteins, the corresponding Leu zipper motif, the conserved cysteine residues, the LRR, transmembrane and kinase domains in RKS4 may easily be identified. RKS11 and RKS4 furthermore share a FNVAGNPLIC motif (SEQ ID NO: 8) and the last 20 amino acids of both proteins comprise 7 Asp or Glu residues. RKS4 and RKS11 differ from each other for example in the Leu zipper motif; the RKS11 protein comprises 3 Leu residues in the zipper motif, whereas RKS4 has 2 Leu residues. Furthermore, the motifs with the conserved cysteines differ in two residues between both proteins.

The term "LRR-II-RLP" as used herein encompasses truncated forms of Leucine-rich repeat receptor-like kinases (LRR-RLK) belonging to the subfamily II (as defined for *Arabidopsis* in Shiu and Bleeker, 2001, or listed in Diévart and Clark, Curr. Opin. Plant Biol. 6, 507-516, 2003), wherein the truncations are located in the kinase domain. The term "LRR-II-RLP" also encompasses subfamily II LRR-RLK kinases that are mutated in the kinase domain, which mutants have at least reduced kinase activity compared to the wild type protein, but preferably lack kinase activity. Since the extracellular domains of subfamily II LRR-RLKs are very similar in structure, any subfamily II LRR-RLK may be useful in the methods of the present invention; preferably, such LRR-RLK is RKS11 (At4g30520) or RKS4 (At2g23950) from *Arabidopsis*, or an orthologue of one of these; more preferably, the LRR-RLK is the *Arabidopsis* RKS11 as represented by SEQ ID NO: 2. The term LRR-II-RLP furthermore encompasses truncated forms of subfamily II LRR-RLK kinases that exist in nature, and in which no active kinase domain is present. Examples of such natural truncated receptor-like kinases are SEQ ID NO: 14 (GenBank accession BX827036, a truncated homologue of RKS11), or the rice sequence of SEQ ID NO: 15 (BAD68256), which is a truncated version of SEQ ID NO: 16 (BAD68255). Preferably, the LRR-II-RLP protein useful in the methods of the present invention is a truncated form of a subfamily II Leucine-rich repeat receptor-like kinases (LRR-RLK), with a deletion in the C-terminal half of the protein that at least reduces, preferably substantially inactivates the kinase activity of the receptor kinase, but more preferably with a deletion that consists of substantially the complete kinase domain. Furthermore preferably, the LRR-II-RLP protein is a truncated form of RKS11 or RKS4 or of an orthologue thereof; most preferably, the LRR-II-RLP is RKS11$_{trunc}$ as represented by SEQ ID NO: 10 or the sequence represented by SEQ ID NO: 14.

The subfamily II of LRR-RLK proteins not only encompasses the *Arabidopsis* proteins listed in Diévart and Clark (2003), but also homologues thereof, provided that these homologues fall within the subfamily II of LRR-RLK as defined by Shiu and Bleeker (2001). Preferred homologues are orthologues and paralogues of RKS11 (SEQ ID NO: 2) and RKS4 (SEQ ID NO: 12).

Paralogues are genes within the same species that have originated through duplication of an ancestral gene and orthologues are genes from different organisms that have originated through speciation. Orthologues and paralogues may easily be found by performing a so-called reciprocal blast search. This may be done by a first BLAST involving submitting a query sequence (for example, SEQ ID NO: 1 or SEQ ID NO: 2) for a BLAST search against any sequence database, such as the publicly available NCBI database. BLASTN or TBLASTX (using standard default values) may be used when starting from a nucleotide sequence and BLASTP or TBLASTN (using standard default values) may be used when starting from a protein sequence. The BLAST results may optionally be filtered. The full-length sequences of either the filtered results or non-filtered results are then submitted to a second BLAST search (BLAST back) against sequences from the organism from which the query sequence is derived (where the query sequence is SEQ ID NO: 1 or SEQ ID NO: 2 the second BLAST would therefore be against *Arabidopsis* sequences). The results of the first and second BLAST searches are then compared. A paralogue is identified if a high-ranking hit from the first blast is from the same species as from which the query sequence is derived, a BLAST back then ideally results in the query sequence as highest hit; an orthologue is identified if a high-ranking hit in the first BLAST is not from the same species as from which the query sequence is derived and preferably results upon BLAST back in the query sequence among the highest hits. Preferred orthologues are orthologues of RKS11 (SEQ ID NO: 2), RKS4 (SEQ ID NO: 12) or of the truncated form of RKS11 (SEQ ID NO: 10). High-ranking hits are those having a low E-value. The lower the E-value, the more significant the score (or in other words the lower the chance that the hit was found by chance). Computation of the E-value is well known in the art. In the case of large families, ClustalW may be used, followed by a neighbour joining tree, to help visualize clustering of related genes and to identify orthologues and paralogues. In addition to E-values, comparisons are also scored by percentage identity. Percentage identity refers to the number of identical nucleotides (or amino acids) between the two compared nucleic acid (or polypeptide) sequences over a particular length.

Orthologues of RKS11 or RKS4 receptor-like kinases preferably comprise a signal peptide, the Leu zipper motif and the motif with two conserved cysteine residues, the LRR domain consisting of four LRR repeats, a transmembrane domain and preferably also a kinase domain corresponding to the Pfam PF00069 and/or the Pfam PF07714 type of kinase domains as defined in the Pfam database. The prediction of signal peptide sequences and transmembrane domains is known in the art, and the LRR and kinase domains defined above are highly conserved. Also the conserved cysteine residues and the Leucine zipper motif may be readily identified by comparison with the SEQ ID NO: 2 or SEQ ID NO: 12, thereby allowing a person skilled in the art to readily identify orthologous sequences falling within the definition above. Preferably, the orthologues useful in the present invention have at least 59% sequence identity to SEQ ID NO: 2 when compared using the Needleman and Wunsch algorithm with a gap-opening penalty of 11 and a gap-extension penalty of 1. Furthermore, the orthologues useful in the present invention preferably comprise a domain enriched in Serine and/or Proline between the last LRR domain and the transmembrane domain (corresponding to amino acids 197 to 240 in SEQ ID NO: 2), which Ser/Pro enriched-domain comprises at least 23% Serine and/or Proline residues and comprises a FNV(A/V)GNP(UM)IC motif (SEQ ID NO: 8). Further preferably, the domain of unknown function located N-terminal of the kinase domain comprises the RELHXXTDG motif as defined above. Furthermore preferably, the orthologues useful in the present invention comprise an EGD domain that is at least 60 amino acids long.

An example of a plant-derived polypeptide falling under the definition of an "RKS11 or an orthologue thereof" is represented by SEQ ID NO: 18 (*Oryza sativa*, GenBank accession BAD10034).

The Table below shows the percentage sequence identity and similarity of polypeptide sequences homologous to RKS11 compared to the amino acid sequence represented by SEQ ID NO: 2, based on overall global sequence alignment. The percentage identity and similarity was calculated using the Needleman and Wunsch algorithm with a gap-opening penalty of 11 and a gap-extension penalty of 1.

TABLE 1

| Homology of RKS4 and RKS11 protein sequences with SEQ ID NO: 2 based on overall global sequence alignment | | |
|---|---|---|
| RKS homologue | SEQ ID NO: | % identity/% similarity |
| Arabidopsis RKS4 | SEQ ID NO: 12 | 82.4/89.7 |
| Oryza sativa RKS11 | SEQ ID NO: 18 | 59.9/71.7 |

According to a preferred feature of the invention, the orthologue has at least 59% sequence identity to the amino acid sequence represented by SEQ ID NO: 2. Whether a polypeptide has at least 59% identity to the amino acid represented by SEQ ID NO: 2 may readily be established by sequence alignment. Methods for the alignment of sequences for comparison are well known in the art, such methods include GAP, BESTFIT, BLAST, FASTA and TFASTA. GAP uses the algorithm of Needleman and Wunsch (J. Mol. Biol. 48: 443-453, 1970) to find the alignment of two complete sequences that maximises the number of matches and minimises the number of gaps. The BLAST algorithm calculates percent sequence identity and performs a statistical analysis of the similarity between the two sequences. The software for performing BLAST analysis is publicly available through the National Centre for Biotechnology Information. An RKS 11 polypeptide or an orthologue thereof having at least 59% identity to the amino acid represented by SEQ ID NO: 2 may readily be identified by aligning a query sequence (preferably a protein sequence (full length or the mature form without secretion signal sequence)) with known RKS11 orthologous protein sequences. Also for an RKS4 polypeptide, the sequence identity may be established by aligning a query sequence with known RKS4 orthologous protein sequences. Such homologues may readily be identified using, for example, the ClustalW multiple sequence alignment algorithm (version 1.83) available at clustalw.genome.jp/sit-bin/nph-ClustalW, with the default pairwise alignment parameters, and a scoring method in percentage. Minor manual editing may be performed to optimise alignment between conserved motifs, as would be apparent to a person skilled in the art. However, when searching for suitable LRR-II-RLP proteins or for identifying suitable subfamily II LRR-RLKs for generating such LRR-II-RLPs, it is preferred that only the extracellular domain of the protein (i.e. N-terminal of the transmembrane domain) be used for determining the sequence homology. Preferred homologues are those with the highest sequence identity to SEQ ID NO: 10.

Suitable mutants that fall in the scope of LRR-II-RLPs encompass those mutants in which the kinase activity is reduced (compared to the wild type protein) or completely inactivated. It is well known in the art how to introduce mutations such that the transphosphorylation or autophosphorylation is inhibited. Lack of transphosphorylation or autophosphorylation results in unstable protein complexes such that ligands cannot bind and no signalling is possible. For example, mutations may be introduced in or around the active site of the kinase domain for reducing or inhibiting kinase activity, other mutations may also be of use, for example in the ATP binding site whereby ATP binding is prevented, or in case of autophosphorylation, by altering the amino acids that normally get phosphorylated.

To determine the kinase activity of receptor like kinases, several assays are available and known in the art (for example Current Protocols in Molecular Biology, Volumes 1 and 2, Ausubel et al. (1994), Current Protocols). In brief, a kinase assay generally involves (1) bringing the kinase protein into contact with a substrate polypeptide containing the target site to be phosphorylated; (2) allowing phosphorylation of the target site in an appropriate kinase buffer under appropriate conditions; (3) separating phosphorylated products from non-phosphorylated substrate after a suitable reaction period. The presence or absence of kinase activity is determined by the presence or absence of a phosphorylated target. In addition, quantitative measurements can be performed. Purified receptor like kinase, or cell extracts containing or enriched in the receptor like kinase could be used as source for the kinase protein. Alternatively, the approach of Zhao et al. (Plant Mol. Biol. 26, 791-803, 1994) could be used, where the cytoplasmic domain of a rice receptor like kinase was expressed in Escherichia coli and assayed for kinase activity. As a substrate, small peptides are particularly well suited. The peptide must comprise one or more serine, threonine or tyrosine residues in a phosphorylation site motif. A compilation of phosphorylation sites can be found in Biochimica et Biophysica Acta 1314, 191-225, (1996). In addition, the peptide substrates may advantageously have a net positive charge to facilitate binding to phosphocellulose filters, (allowing to separate the phosphorylated from non-phosphorylated peptides and to detect the phosphorylated peptides). If a phosphorylation site motif is not known, a general tyrosine kinase substrate can be used. For example, "Src-related peptide" (RRLIEDAEYAARG) is a substrate for many receptor and non-receptor tyrosine kinases). To determine the kinetic parameters for phosphorylation of the synthetic peptide, a range of peptide concentrations is required. For initial reactions, a peptide concentration of 0.7-1.5 mM could be used. For each kinase enzyme, it is important to determine the optimal buffer, ionic strength, and pH for activity. A standard 5× Kinase Buffer generally contains 5 mg/ml BSA (Bovine Serum Albumin preventing kinase adsorption to the assay tube), 150 mM Tris-Cl (pH 7.5), 100 mM $MgCl_2$. Divalent cations are required for most tyrosine kinases, although some tyrosine kinases (for example, insulin-, IGF-1-, and PDGF receptor kinases) require $MnCl_2$ instead of $MgCl_2$ (or in addition to $MgCl_2$). The optimal concentrations of divalent cations must be determined empirically for each protein kinase. A commonly used donor for the phosphoryl group is radio-labelled [gamma-$^{32}$P]ATP (normally at 0.2 mM final concentration). The amount of $^{32}$P incorporated in the peptides may be determined by measuring activity on the nitrocellulose dry pads in a scintillation counter.

Furthermore, the activity of an LRR-II-RLP polypeptide may be assayed by expressing the LRR-II-RLP polypeptide under control of a rice seed-specific promoter in rice plants, and in particular in the rice variety Nipponbare, which results in plants with increased yield compared to corresponding control plants. This increase in yield may for example be measured as one or more of an increase in number of filled seeds, in total weight of seeds, in harvest index and/or increased levels of amino acids in seeds.

Mutants (and also homologues) of a protein encompass peptides, oligopeptides, polypeptides, proteins and enzymes having amino acid substitutions, deletions and/or insertions relative to the unmodified protein in question and (in case of homologues, but also for certain mutants) having similar biological and functional activity as the unmodified protein from which they are derived. To produce such homologues, amino acids of the protein may be replaced by other amino acids having similar properties (such as similar hydrophobicity, hydrophilicity, antigenicity, propensity to form or break α-helical structures or β-sheet structures). Conservative substitution tables are well known in the art (see for example Creighton (1984) Proteins. W.H. Freeman and Company and Table 2).

TABLE 2

Examples of conserved amino acid substitutions

| Residue | Conservative Substitutions |
|---|---|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

A mutant may be in the form of a "substitutional variant" of a protein, i.e. where at least one residue in an amino acid sequence has been removed and a different residue inserted in its place. Amino acid substitutions are typically of single residues, but may be clustered depending upon functional constraints placed upon the polypeptide; insertions will usually be of the order of about 1 to 10 amino acid residues. Preferably, amino acid substitutions comprise conservative amino acid substitutions, unless an alteration of functional or structural properties of the protein is intended.

A mutant may also be in the form of an "insertional variant" of a protein, i.e. where one or more amino acid residues are introduced into a predetermined site in a protein. Insertions may comprise amino-terminal and/or carboxy-terminal fusions as well as intra-sequence insertions of single or multiple amino acids. Generally, insertions within the amino acid sequence will be smaller than amino- or carboxy-terminal fusions, of the order of about 1 to 10 residues. Examples of amino- or carboxy-terminal fusion proteins or peptides include the binding domain or activation domain of a transcriptional activator as used in the yeast two-hybrid system, phage coat proteins, (histidine)$_6$-tag, glutathione S-transferase-tag, protein A, maltose-binding protein, dihydrofolate reductase, Tag-100 epitope, c-myc epitope, FLAG®-epitope, lacZ, CMP (calmodulin-binding peptide), HA epitope, protein C epitope and VSV epitope. In particular, useful LRR-II-RLP polypeptides may be created by inserting one or more Leucine Rich Repeat domain(s) in the extracellular domain, or by fusing a transmembrane domain at the C-terminus of naturally occurring proteins that resemble the extracellular domain of subfamily II LRR-RLKs, preferably of RKS11, RKS4 or orthologues thereof (such as the proteins encoded in At3g43740 (SEQ ID NO: 44) or At5g21090 (SEQ ID NO: 46)).

Mutants in the form of "deletion variants" of a protein are characterised by the removal of one or more amino acids from a protein. Preferred deletion mutants are those in which part of the kinase domain is deleted, such that the remaining part has at least reduced transphosphorylation or autophosphorylation activity, preferably complete loss of activity. More preferred mutants are those in which substantially all of the kinase domain is deleted. Furthermore preferred mutants are those which, upon alignment with SEQ ID NO: 10, lack substantially the same part of the kinase domain. Most preferably, the mutant is RKS11$_{trunc}$ as represented by SEQ ID NO: 10.

Amino acid variants of a protein may readily be made using peptide synthetic techniques well known in the art, such as solid phase peptide synthesis and the like, or by recombinant DNA manipulations. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other step-directed mutagenesis protocols. All these techniques may be used for generating a LRR-II-RLP suitable for the methods of the present invention.

The RKS11 or RKS4 polypeptide may be a derivative of SEQ ID NO: 2, respectively SEQ ID NO: 12. "Derivatives" include peptides, oligopeptides, polypeptides which may, compared to the amino acid sequence of the naturally-occurring form of the protein, such as the one presented in SEQ ID NO: 2 or SEQ ID NO: 12, comprise substitutions of amino acids with non-naturally occurring amino acid residues, or additions of non-naturally occurring amino acid residues. Derivatives of SEQ ID NO: 10, SEQ ID NO: 14 and SEQ ID NO: 18 are further examples which may be suitable for generating an LRR-II-RLP useful in the methods of the invention.

"Derivatives" of a protein also encompass peptides, oligopeptides, polypeptides which may comprise naturally occurring altered (glycosylated, acylated, ubiquinated, prenylated, phosphorylated, myristoylated, sulphated etc) or non-naturally altered amino acid residues compared to the amino acid sequence of a naturally-occurring form of the polypeptide. A derivative may also comprise one or more non-amino acid substituents or additions compared to the amino acid sequence from which it is derived, for example a reporter molecule or other ligand, covalently or noncovalently bound to the amino acid sequence, such as a reporter molecule which is bound to facilitate its detection, and non-naturally occurring amino acid residues relative to the amino acid sequence of a naturally-occurring protein.

It is to be understood that sequences falling under the definition of "RKS11 polypeptide or orthologue thereof" or "RKS4 polypeptide or orthologue thereof" are not to be limited to the sequences represented by SEQ ID NO: 2, SEQ ID NO: 12 and SEQ ID NO: 18, but that any polypeptide meeting the criteria of comprising (i) a signal sequence, (ii) a Leucine zipper motif with 2 or 3 Leu residues separated from each other by 6 other amino acids, (iii) a motif with 2 conserved cysteine residues, (iv) 4 Leucine Rich Repeat units of each approximately 23 amino acid residues, (v) a domain enriched in serine and proline residues, (vi) a single transmembrane domain, and (vii) a kinase domain, flanked at both sides by a domain of unknown function (RELH- and EGD-domains); and furthermore being orthologues of RKS11 as represented by SEQ ID NO: 2 may be suitable for generating a LRR-II-RLP protein useful in the methods of the invention.

The LRR-II-RLP protein of SEQ ID NO: 10 was previously unknown. The present invention therefore provides a novel isolated LRR-II-RLP protein selected from the group consisting of:
  a) a polypeptide without kinase activity comprising (i) a signal sequence, (ii) a Leucine zipper motif with 2 or 3 Leu residues separated from each other by 6 other amino acids, (iii) a motif with 2 conserved cysteine residues, (iv) 4 Leucine Rich Repeat units of each approximately 23 amino acid residues, (v) a domain enriched in serine and proline residues, (vi) a single transmembrane domain, and (vii) part or the whole of a RELH-domain;
b) a subfamily II Leucine Rich Repeat Receptor Like Kinase lacking substantially the whole kinase domain;
c) a polypeptide as given in SEQ ID NO: 10;
d) a polypeptide with an amino acid sequence which has at least 90% sequence identity, preferably 95%, 96%, 97%, 98% or 99% sequence identity to any one or more of the amino acid sequence as given in SEQ ID NO 10, provided that the LRR-II-RLP protein is not the protein as represented by SEQ ID NO: 14.

The sequence represented by SEQ ID NO: 9 was hitherto unknown as a LRR-II-RLP encoding nucleic acid. There is therefore also provided an isolated nucleic acid selected from the group consisting:
 i) a nucleic acid sequence represented by SEQ ID NO: 9, or the complement strand thereof;
 ii) a nucleic acid sequence encoding an amino acid sequence represented by SEQ ID NO: 10;
 iii) a nucleic acid sequence capable of hybridising under stringent conditions with a nucleic acid sequence of (i) or (ii) above, which hybridising sequence encodes a LRR-II-RLP protein;
 iv) a nucleic acid encoding a protein as defined above in (a) to (d);
 v) a portion of a nucleic acid sequence according to any of (i) to (iii) above, which portion encodes a LRR-II-RLP protein, provided that the LRR-II-RLP encoding nucleic acid is not as represented by SEQ ID NO: 13 or does not encode the protein of SEQ ID NO: 14.

The nucleic acid encoding an RKS11 polypeptide, an RKS4 polypeptide or an orthologue thereof, and suitable for generating a LRR-II-RLP protein useful in the methods of the invention, may be any natural or synthetic nucleic acid. An RKS11 polypeptide or an orthologue thereof as defined hereinabove is one that is encoded by an RKS11 nucleic acid/gene. Therefore the term "RKS11 nucleic acid/gene" as defined herein is any nucleic acid/gene encoding RKS11 polypeptide or an orthologue thereof as defined hereinabove. Examples of RKS11 nucleic acids include those represented by SEQ ID NO: 1 and SEQ ID NO: 17. RKS11 nucleic acids/genes and variants thereof may be suitable for generating a nucleic acid encoding an LRR-II-RLP protein useful in practising the methods of the invention. Variant RKS11 nucleic acid/genes include portions of an RKS11 nucleic acid/gene and/or nucleic acids capable of hybridising with an RKS11 nucleic acid/gene, on the condition that these hybridising sequences encode all or part of RKS11 or of orthologues thereof.

An RKS4 polypeptide or an orthologue thereof as defined hereinabove is one that is encoded by an RKS4 nucleic acid/gene. Therefore the term "RKS4 nucleic acid/gene" as defined herein is any nucleic acid/gene encoding RKS4 polypeptide, such as SEQ ID NO: 11, or an orthologue thereof as defined hereinabove. RKS4 nucleic acids/genes and variants thereof may be suitable in practising the methods of the invention. Variant RKS4 nucleic acid/genes include portions of an RKS4 nucleic acid/gene and/or nucleic acids capable of hybridising with an RKS4 nucleic acid/gene, on the condition that these hybridising sequences encode all or part of RKS4 or orthologues thereof.

The term portion as defined herein refers to a piece of DNA comprising at least enough nucleotides to encode a protein comprising (i) a signal sequence, (ii) a Leucine zipper motif with 2 or 3 Leu residues separated from each other by 6 other amino acids, (iii) a motif with 2 conserved cysteine residues, (iv) 4 Leucine Rich Repeat units of each approximately 23 amino acid residues, (v) a domain enriched in serine and proline residues, (vi) a single transmembrane domain, and (vii) part or the whole of a RELH-domain, which portion is derived from RKS11, RKS4 or an orthologue thereof. A portion may be prepared, for example, by making one or more deletions to an RKS11 or RKS4 nucleic acid. The portions may be used in isolated form or they may be fused to other coding (or non coding) sequences in order to, for example, produce a protein that combines several activities. When fused to other coding sequences, the resulting polypeptide produced upon translation could be bigger than that predicted for the RKS11 or RKS4 fragment. Preferably, the functional portion is a portion of a nucleic acid as represented by any one of SEQ ID NO: 1, SEQ ID NO: 11 and SEQ ID NO: 17.

Another variant RKS11 or RKS4 nucleic acid/gene is a nucleic acid capable of hybridising under reduced stringency conditions, preferably under stringent conditions, with an RKS11 nucleic acid/gene or RKS4 nucleic acid/gene respectively as hereinbefore defined, which hybridising sequence encodes a polypeptide comprising: (i) a signal sequence, (ii) a Leucine zipper motif with 2 or 3 Leu residues separated from each other by 6 other amino acids, (iii) a motif with 2 conserved cysteine residues, (iv) 4 Leucine Rich Repeat units of each approximately 23 amino acid residues, (v) a domain enriched in serine and proline residues, (vi) a single transmembrane domain, and (vii) part or the whole of a RELH-domain, and which hybridising sequences encode all or part of RKS11 or RKS4, or of an orthologue thereof. Preferably, the hybridising sequence is one that is capable of hybridising to a nucleic acid as represented by any one of SEQ ID NO: 1, SEQ ID NO: 11 and SEQ ID NO: 17, or to a portion of any of the aforementioned sequences as defined hereinabove.

The term "hybridisation" as defined herein is a process wherein substantially homologous complementary nucleotide sequences anneal to each other. The hybridisation process can occur entirely in solution, i.e. both complementary nucleic acids are in solution. The hybridisation process can also occur with one of the complementary nucleic acids immobilised to a matrix such as magnetic beads, Sepharose beads or any other resin. The hybridisation process can furthermore occur with one of the complementary nucleic acids immobilised to a solid support such as a nitro-cellulose or nylon membrane or immobilised by e.g. photolithography to, for example, a siliceous glass support (the latter known as nucleic acid arrays or micro-arrays or as nucleic acid chips). In order to allow hybridisation to occur, the nucleic acid molecules are generally thermally or chemically denatured to melt a double strand into two single strands and/or to remove hairpins or other secondary structures from single stranded nucleic acids.

The term "stringency" refers to the conditions under which a hybridisation takes place. The stringency of hybridisation is influenced by conditions such as temperature, salt concentration, ionic strength and hybridisation buffer composition. Generally, low stringency conditions are selected to be about 30° C. lower than the thermal melting point ($T_m$) for the specific sequence at a defined ionic strength and pH. Medium stringency conditions are when the temperature is 20° C. below $T_m$, and high stringency conditions are when the temperature is 10° C. below $T_m$. High stringency hybridisation conditions are typically used for isolating hybridising sequences that have high sequence similarity to the target nucleic acid sequence. However, nucleic acids may deviate in sequence and still encode a substantially identical polypeptide, due to the degeneracy of the genetic code. Therefore medium stringency hybridisation conditions may sometimes be needed to identify such nucleic acid molecules.

The $T_m$ is the temperature under defined ionic strength and pH, at which 50% of the target sequence hybridises to a perfectly matched probe. The $T_m$ is dependent upon the solution conditions and the base composition and length of the probe. For example, longer sequences hybridise specifically at higher temperatures. The maximum rate of hybridisation is obtained from about 16° C. up to 32° C. below $T_m$. The presence of monovalent cations in the hybridisation solution reduce the electrostatic repulsion between the two nucleic acid strands thereby promoting hybrid formation; this effect is visible for sodium concentrations of up to 0.4M (for higher concentrations, this effect may be ignored). Formamide reduces the melting temperature of DNA-DNA and DNA-RNA duplexes with 0.6 to 0.7° C. for each percent formamide, and addition of 50% formamide allows hybridisation to be performed at 30 to 45° C., though the rate of hybridisation will be lowered. Base pair mismatches reduce the hybridisation rate and the thermal stability of the duplexes. On average and for large probes, the $T_m$ decreases about 1° C. per % base mismatch. The $T_m$ may be calculated using the following equations, depending on the types of hybrids:

1)—DNA-DNA hybrids (Meinkoth and Wahl, Anal. Biochem., 138: 267-284, 1984):

$$T_m = 81.5° C. + 16.6 \times \log_{10}[Na+]^a + 0.41 \times \%[G/C^b] - 500 \times [L^c]^{-1} - 0.61 \times \% \text{ formamide}$$

2)—DNA-RNA or RNA-RNA hybrids:

$$T_m = 79.8 + 18.5(\log_{10}[Na+]^a) + 0.58(\% G/C^b) + 11.8(\% G/C^b)^2 - 820/L^c$$

3)—oligo-DNA or oligo-RNA$^d$ hybrids:
For <20 nucleotides: T m=2 ($I_n$)
For 20-35 nucleotides: T=22+1.46 ($I_n$)

$^a$ or for other monovalent cation, but only accurate in the 0.01-0.4 M range.
$^b$ only accurate for % GC in the 30% to 75% range.
$^c$ L=length of duplex in base pairs.
$^d$ Oligo, oligonucleotide; $I_n$, effective length of primer=2× (no. of G/C)+(no. of A/T).

Non-specific binding may be controlled using any one of a number of known techniques such as, for example, blocking the membrane with protein containing solutions, additions of heterologous RNA, DNA, and SDS to the hybridisation buffer, and treatment with Rnase. For non-homologous probes, a series of hybridizations may be performed by varying one of (i) progressively lowering the annealing temperature (for example from 68° C. to 42° C.) or (ii) progressively lowering the formamide concentration (for example from 50% to 0%). The skilled artisan is aware of various parameters which may be altered during hybridisation and which will either maintain or change the stringency conditions.

Besides the hybridisation conditions, specificity of hybridisation typically also depends on the function of post-hybridisation washes. To remove background resulting from non-specific hybridisation, samples are washed with dilute salt solutions. Critical factors of such washes include the ionic strength and temperature of the final wash solution: the lower the salt concentration and the higher the wash temperature, the higher the stringency of the wash. Wash conditions are typically performed at or below hybridisation stringency. A positive hybridisation gives a signal that is at least twice of that of the background. Generally, suitable stringent conditions for nucleic acid hybridisation assays or gene amplification detection procedures are as set forth above. More or less stringent conditions may also be selected. The skilled artisan is aware of various parameters which may be altered during washing and which will either maintain or change the stringency conditions.

For example, typical high stringency hybridisation conditions for DNA hybrids longer than 50 nucleotides encompass hybridisation at 65° C. in 1×SSC or at 42° C. in 1×SSC and 50% formamide, followed by washing at 65° C. in 0.3×SSC. Examples of medium stringency hybridisation conditions for DNA hybrids longer than 50 nucleotides encompass hybridisation at 50° C. in 4×SSC or at 40° C. in 6×SSC and 50% formamide, followed by washing at 50° C. in 2×SSC. The length of the hybrid is the anticipated length for the hybridising nucleic acid. When nucleic acids of known sequence are hybridised, the hybrid length may be determined by aligning the sequences and identifying the conserved regions described herein. 1×SSC is 0.15M NaCl and 15 mM sodium citrate; the hybridisations and washes may additionally include 5×Denhardt's reagent, 0.5-1.0% SDS, 100 μg/ml denatured, fragmented salmon sperm DNA, 0.5% sodium pyrophosphate.

For the purposes of defining the level of stringency, reference can conveniently be made to Sambrook et al. (2001) Molecular Cloning: a laboratory manual, 3rd Edition Cold Spring Harbor Laboratory Press, CSH, New York, or to Current Protocols in Molecular Biology, John Wiley & Sons, N.Y. (1989 and yearly updates).

The RKS11 or RKS4 nucleic acid or variant thereof may be derived from any natural or artificial source. The nucleic acid/gene or variant thereof may be isolated from a microbial source, such as bacteria, yeast or fungi, or from a plant, algae or animal (including human) source. This nucleic acid may be modified from its native form in composition and/or genomic environment through deliberate human manipulation, in particular for generating a suitable LRR-II-RLP. The nucleic acid is preferably of plant origin, whether from the same plant species (for example to the one in which it is to be introduced) or whether from a different plant species. The nucleic acid may be isolated from a dicotyledonous species, preferably from the family Brassicaceae, further preferably from *Arabidopsis thaliana*. More preferably, the RKS11 nucleic acid isolated from *Arabidopsis thaliana* is represented by SEQ ID NO: 1 and the RKS11 amino acid sequence is as represented by SEQ ID NO: 2. Furthermore preferably, the RKS4 nucleic acid isolated from *Arabidopsis thaliana* is represented by SEQ ID NO: 11 and the RKS4 amino acid sequence is as represented by SEQ ID NO: 12.

The RKS11 or RKS4 polypeptide or homologue thereof may be encoded by an alternative splice variant of an RKS11 or RKS4 nucleic acid/gene. The term "alternative splice variant" as used herein encompasses variants of a nucleic acid sequence in which selected introns and/or exons have been excised, replaced or added. Such variants will be ones in which the biological activity of the protein is retained, which may be achieved by selectively retaining functional segments of the protein. Such splice variants may be found in nature or may be manmade. Methods for making such splice variants are known in the art. Preferred splice variants are splice variants of the RKS11 nucleic acid represented by SEQ ID NO: 1 and SEQ ID NO: 17; and preferred splice variants of RKS4 are splice variants of the sequence represented by SEQ ID NO: 11. An example of a splice variant of SEQ ID NO: 1 is the sequence represented by SEQ ID NO: 48. Further preferred are splice variants encoding a polypeptide comprising: (i) a signal sequence, (ii) a Leucine zipper motif with 2 or 3 Leu residues separated from each other by 6 other amino acids, (iii) a motif with 2 conserved cysteine residues, (iv) 4 Leucine Rich Repeat units of each approximately 23 amino acid residues, (v) a domain enriched in serine and proline residues, (vi) a single transmembrane domain, and (vii) a kinase domain, flanked at both sides by a domain of unknown function (RELH- and EGD-domains), which splice variants may be used for generating a suitable LRR-II-RLP protein.

The homologue may also be encoded by an allelic variant of a nucleic acid encoding RKS11, RKS4 or an orthologue thereof, preferably an allelic variant of the nucleic acid represented by SEQ ID NO: 1, SEQ ID NO: 11 and SEQ ID NO: 17. Further preferably, the polypeptide encoded by the allelic variant comprises: (i) a signal sequence, (ii) a Leucine zipper motif with 2 or 3 Leu residues separated from each other by 6 other amino acids, (iii) a motif with 2 conserved cysteine residues, (iv) 4 Leucine Rich Repeat units of each approximately 23 amino acid residues, (v) a domain enriched in serine and proline residues, (vi) a single transmembrane domain, and (vii) a kinase domain, flanked at both sides by a domain of unknown function (RELH- and EGD-domains). Allelic variants exist in nature and encompassed within the methods of the present invention is the use of these natural alleles for generating a suitable LRR-II-RLP protein. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms.

Advantageously, performance of the methods according to the present invention results in plants having a variety of improved growth characteristics, especially increased yield, particularly seed yield.

"Increased yield" as defined herein is taken to mean an increase in biomass (weight) of one or more parts of a plant, which may include aboveground (harvestable) parts and/or (harvestable) parts below ground.

In particular, such harvestable parts are seeds, and performance of the methods of the invention results in plants having increased seed yield relative to the seed yield of suitable control plants.

Increased seed yield may manifest itself as one or more of the following: a) an increase in seed biomass (total seed weight) which may be on an individual seed basis and/or per plant and/or per hectare or acre; b) increased number of flowers per plant; c) increased number of (filled) seeds; d) increased seed filling rate (which is expressed as the ratio between the number of filled seeds divided by the total number of seeds; e) increased harvest index, which is expressed as a ratio of the yield of harvestable parts, such as seeds, divided by the total biomass; and f) increased thousand kernel weight (TKW), which is extrapolated from the number of filled seeds counted and their total weight. An increased TKW may result from an increased seed size and/or seed weight, and may also result from an increase in embryo and/or endosperm size.

An increase in seed yield may also be manifested as an increase in seed size and/or seed volume. It should be noted however that the term "increased seed yield" does not encompass increased seed size when RKS4 (SEQ ID NO: 12) is overexpressed. Furthermore, an increase in seed yield may also manifest itself as an increase in seed area and/or seed length and/or seed width and/or seed perimeter. Increased seed yield also encompasses improved composition of amino acids and/or other metabolites in seeds, preferably increased levels of amino acids. Increased yield may also result in modified architecture, or may occur because of modified architecture.

Taking corn as an example, a yield increase may be manifested as one or more of the following: increase in the number of plants per hectare or acre, an increase in the number of ears per plant, an increase in the number of rows, number of kernels per row, kernel weight, thousand kernel weight, ear length/diameter, increase in the seed filling rate (which is the number of filled seeds divided by the total number of seeds and multiplied by 100), among others. Taking rice as an example, a yield increase may manifest itself as an increase in one or more of the following: number of plants per hectare or acre, number of panicles per plant, number of spikelets per panicle, number of flowers (florets) per panicle (which is expressed as a ratio of the number of filled seeds over the number of primary panicles), increase in the seed filling rate (which is the number of filled seeds divided by the total number of seeds and multiplied by 100), increase in thousand kernel weight, among others.

Since the transgenic plants according to the present invention have increased yield, it is likely that these plants exhibit an increased growth rate (during at least part of their life cycle), relative to the growth rate of corresponding wild type plants at a corresponding stage in their life cycle. The increased growth rate may be specific to one or more parts of a plant (including seeds), or may be throughout substantially the whole plant. A plant having an increased growth rate may even exhibit early flowering. The increase in growth rate may take place at one or more stages in the life cycle of a plant or during substantially the whole plant life cycle. Increased growth rate during the early stages in the life cycle of a plant may reflect enhanced vigour (increased seedling vigor at emergence). The increase in growth rate may alter the harvest cycle of a plant allowing plants to be sown later and/or harvested sooner than would otherwise be possible. If the growth rate is sufficiently increased, it may allow for the further sowing of seeds of the same plant species (for example sowing and harvesting of rice plants followed by sowing and harvesting of further rice plants all within one conventional growing period). Similarly, if the growth rate is sufficiently increased, it may allow for the further sowing of seeds of different plants species (for example the sowing and harvesting of rice plants followed by, for example, the sowing and optional harvesting of soy bean, potato or any other suitable plant). Harvesting additional times from the same rootstock in the case of some crop plants may also be possible. Altering the harvest cycle of a plant may lead to an increase in annual biomass production per acre (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves, such parameters may be: T-Mid (the time taken for plants to reach 50% of their maximal size) and T-90 (time taken for plants to reach 90% of their maximal size), amongst others.

The term "metabolites" refers to intermediate substances, preferably such of low molecular weight, which occur during anabolism and catabolism in a plant or a plant cell, in other words, a substance produced or consumed during metabolism, such as amino acids. The term "improved composition" of metabolites refers to desired changes in concentration of these metabolites. Depending on the type of metabolite, the change may be an increase or decrease in concentration. Preferably, the change in metabolite concentration/level is measured relative to suitable control plants. Preferred metabolites in the present invention are amino acids, in particular one or more of tryptophane, phenylalanine, tyrosine, isoleucine, valine. Metabolite levels may be improved substantially throughout the whole plant or in certain plant parts, organs, tissues or cells. In a preferred embodiment, the metabolite levels are improved in seeds.

According to a preferred feature of the present invention, performance of the methods of the invention gives plants having an increased growth rate relative to control plants, particularly during the early stages of plant development (typically three weeks post germination) leading to early vigour. Therefore, according to the present invention, there is provided a method for increasing the growth rate of plants, which method comprises increasing expression in a plant of a nucleic acid encoding a LRR-II-RLP protein. The present invention therefore also provides a method for obtaining plants having early vigour relative to control plants, which method comprises modulating, preferably increasing, expression in a plant of a nucleic acid encoding a LRR-II-RLP protein.

The methods of the invention are advantageously applicable to any plant.

The term "plant" as used herein encompasses whole plants, ancestors and progeny of the plants and plant parts, including seeds, shoots, stems, leaves, roots (including tubers), flowers, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising *Acer* spp., *Actinidia* spp., *Abelmoschus* spp., *Agropyron* spp., *Allium* spp., *Amaranthus* spp., *Ananas comosus, Annona* spp., *Apium graveolens, Arabidopsis thaliana, Arachis* spp, *Artocarpus* spp., *Asparagus officinalis, Avena sativa, Averrhoa carambola, Benincasa hispida, Bertholletia excelsea, Beta vulgaris, Brassica* spp., *Cadaba farinosa, Camellia sinensis, Canna indica, Capsicum* spp., *Carex elata, Carica papaya, Carissa macrocarpa, Carya* spp., *Carthamus tinctorius, Castanea* spp., *Cichorium endivia, Cinnamomum* spp., *Citrullus lanatus, Cftrus* spp., *Cocos* spp., *Coffea* spp., *Colocasia esculenta, Cola* spp., *Coriandrum sativum, Corylus* spp., *Crataegus* spp., *Crocus sativus, Cucurbita* spp., *Cucumis* spp., *Cynara* spp., *Daucus carota, Desmodium* spp., *Dimocarpus longan, Dioscorea* spp., *Diospyros* spp., *Echinochloa* spp., *Eleusine coracana, Eriobotrya japonica, Eugenia uniflora, Fagopyrum* spp., *Fagus* spp., *Ficus carica, Fortunella* spp., *Fragaria* spp., *Ginkgo biloba, Glycine* spp., *Gossypium hirsutum, Helianthus* spp., *Hemerocallis fulva, Hibiscus* spp., *Hordeum* spp., *Ipomoea batatas, Juglans* spp., *Lactuca sativa, Lathyrus* spp., *Lens culinaris, Linum usitatissimum, Litchi chinensis, Lotus* spp., *Luffa acutangula, Lupinus* spp., *Luzula sytvatica, Macrotyloma* spp., *Malus* spp., *Malpighia semarginata, Mammea americana, Mangifera indica, Manihot* spp., *Manilkara zapota, Medicago sativa, Melilotus* spp., *Mentha* spp., *Momordica* spp., *Morus nigra, Musa* spp., *Nicotiana* spp., *Olea* spp., *Opuntia* spp., *Omithopus* spp., *Oryza* spp., *Panicum* sp., *Passiflora edulis, Pastinaca sativa, Persea* spp., *Petroselinum ctispum, Phaseolus* spp., *Phoenix* spp., *Physalis* spp., *Pinus* spp., *Pistacia vera, Pisum* spp., *Poa* spp., *Populus* spp., *Prosopis* spp., *Prunus* spp., *Psidium* spp., *Punica granatum, Pyrus communis, Quercus* spp., *Raphanus sativus, Rheum rhabarbarum, Ribes* spp., *Rubus* spp., *Saccharum* spp., *Sambucus* spp., *Secale cereale, Sesamum* spp., *Sinapis* sp., *Solanum* spp., *Sorghum bicolor, Spinacia* spp., *Syzygium* spp., *Tamarindus indica, Theobmma cacao, Trifolium* spp., *Triticosecale rimpaui, Triticum* spp., *Tropaeolum minus, Tropaeolum majus, Vaccinium* spp., *Vicia* spp., *Vigna* spp., *Viola odorata, Vitis* spp., *Zea mays, Zizania palustris, Ziziphus* spp., amongst others. According to a preferred embodiment of the present invention, the plant is a crop plant such as soybean, sunflower, canola, alfalfa, rapeseed, cotton, tomato, potato or tobacco. Further preferably, the plant is a monocotyledonous plant, such as sugar cane. More preferably the plant is a cereal, such as rice, maize, wheat, barley, millet, rye, sorghum or oats.

According to a preferred embodiment of the present invention, the plant is a crop plant. Examples of crop plants include soybean, sunflower, canola, alfalfa, rapeseed, cotton, tomato, potato and tobacco. Further preferably, the plant is a monocotyledonous plant. Examples of monocotyledonous plants include sugarcane. More preferably the plant is a cereal. Examples of cereals include rice, maize, wheat, barley, millet, rye, sorghum and oats.

The activity of an LRR-II-RLP protein may be increased by increasing levels of the polypeptide. Alternatively, activity may also be increased when there is no change in levels of the LRR-II-RLP polypeptide, or even when there is a reduction in levels of the LRR-II-RLP polypeptide. This may occur when the intrinsic properties of the polypeptide are altered, for example, by making mutant versions that are more active than the wild type polypeptide.

The activity of the LRR-II-RLP polypeptide useful in the methods of the present invention may be increased by introducing a genetic modification (preferably in the locus of an RKS11 gene, an RKS4 gene or in the locus of a gene encoding a natural truncated form of RKS11 or of RKS4). The locus of a gene as defined herein is taken to mean a genomic region, which includes the gene of interest and 10 kb up- or downstream of the coding region.

The genetic modification may be introduced, for example, by any one (or more) of the following methods: TDNA activation, TILLING, site-directed mutagenesis, transposon mutagenesis, directed evolution and homologous recombination or by introducing and expressing in a plant cell of a nucleic acid encoding an LRR-II-RLP polypeptide. Following introduction of the genetic modification, there follows a step of selecting for increased activity of the LRR-II-RLP polypeptide, which increase in activity gives plants having improved growth characteristics.

T-DNA activation tagging (Hayashi et al. Science (1992) 1350-1353) involves insertion of T-DNA usually containing a promoter (may also be a translation enhancer or an intron), in the genomic region of the gene of interest or 10 kb up- or down stream of the coding region of a gene in a configuration such that the promoter directs expression of the targeted gene. Typically, regulation of expression of the targeted gene by its natural promoter is disrupted and the gene falls under the control of the newly introduced promoter. The promoter is typically embedded in a T-DNA. This T-DNA is randomly inserted into the plant genome, for example, through *Agrobacterium* infection and leads to overexpression of genes near to the inserted T-DNA. The resulting transgenic plants show dominant phenotypes due to overexpression of genes close to the introduced promoter. The promoter to be introduced may be any promoter capable of directing expression of a gene in the desired organism, in this case a plant. For example, constitutive, tissue-preferred, cell type-preferred and inducible promoters are all suitable for use in T-DNA activation.

A genetic modification may also be introduced in the locus of an RKS11 or RKS4 gene or in the locus of a natural LRR-II-RLP, using the technique of TILLING (Targeted Induced Local Lesions IN Genomes). This is a mutagenesis technology useful to generate and/or identify, and to eventually isolate mutagenised variants of an RKS11 or RKS4 nucleic acid capable of exhibiting LRR-II-RLP activity respectively (i.e. the effect of increasing yield of the transgenic plant when compared to corresponding wild type plants, wherein increased yield comprises at least one of: total weight of seeds, number of filled seeds and harvest index). TILLING also allows selection of plants carrying such mutant variants. These mutant variants may even exhibit higher LRR-II-RLP activity than that exhibited by the gene in its natural form. TILLING combines high-density mutagenesis with high-throughput screening methods. The steps typically followed in TILLING are: (a) EMS mutagenesis (Redei and Koncz, 1992; Feldmann et al., 1994; Lightner and Caspar, 1998); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (g) sequencing of the mutant PCR product. Methods for TILLING are well known in the art (McCallum Nat Biotechnol. 2000 April; 18(4):455-7, reviewed by Stemple 2004 (TILLING-a high-throughput harvest for functional genomics. Nat Rev Genet. 2004 February; 5(2):145-50)).

Site directed mutagenesis may be used to generate variants of RKS11 or RKS4 nucleic acids or portions thereof (such as those encoding LRR-II-RLP proteins). Several methods are available to achieve site directed mutagenesis; the most common being PCR based methods (Current Protocols in Molecular Biology. Wiley Eds.).

Transposon mutagenesis is a mutagenesis technique based on the insertion of transposons in genes, which frequently results in truncation or in gene-knockout. The technique has been used for several plant species, including rice (Greco et al., Plant Physiol, 125, 1175-1177, 2001), corn (McCarty et al., Plant J. 44, 52-61, 2005) and *Arabidopsis* (Parinov and Sundaresan, Curr. Opin. Biotechnol. 11, 157-161, 2000).

Domain shuffling or directed evolution may be used to generate variants of RKS11 or RKS4 nucleic acids or portions thereof or of nucleic acids encoding LRR-II-RLP proteins having an increased LRR-II-RLP activity. Directed evolution consists of iterations of DNA shuffling followed by appropriate screening and/or selection (Castle et al., (2004) Science 304(5674): 1151-4; U.S. Pat. Nos. 5,811,238 and 6,395,547).

TDNA activation, TILLING, site-directed mutagenesis, transposon mutagenesis and directed evolution are examples of technologies that enable the generation of novel alleles and variants of RKS11, RKS4 or nucleic acids encoding LRR-II-RLP proteins.

Homologous recombination allows introduction in a genome of a selected nucleic acid at a defined selected position. Homologous recombination is a standard technology used routinely in biological sciences for lower organisms such as yeast or the moss *Physcomitrella*. Methods for performing homologous recombination in plants have been described not only for model plants (Offringa et al. Extrachromosomal homologous recombination and gene targeting in plant cells after *Agrobacterium*-mediated transformation. 1990 EMBO J. 1990 October; 9(10):3077-84) but also for crop plants, for example rice (Terada R, Urawa H, Inagaki Y, Tsugane K, Iida S. Efficient gene targeting by homologous recombination in rice. Nat Biotechnol. 2002. Iida and Terada: A tale of two integrations, transgene and T-DNA: gene targeting by homologous recombination in rice. Curr Opin Biotechnol. 2004 April; 15(2):1328). The nucleic acid to be targeted (which may be an RKS11 or RKS4 nucleic acid or a variant thereof as hereinbefore defined) need not be targeted to the locus of an RKS11 or RKS4 gene respectively, but may be introduced in, for example, regions of high expression. The nucleic acid to be targeted may be an improved allele used to replace the endogenous gene or may be introduced in addition to the endogenous gene.

According to a preferred embodiment of the invention, plant growth characteristics may be improved by introducing and expressing in a plant a nucleic acid encoding an LRR-II-RLP protein. Preferably, the LRR-II-RLP protein is derived from *Arabidopsis* RKS11 or RKS4 or from an orthologue thereof as described above, more preferably, the LRR-II-RLP protein is a truncation of *Arabidopsis* RKS11 or RKS4 or of an orthologue thereof as described above, most preferably, the LRR-II-RLP protein is as represented by SEQ ID NO: 10 or SEQ ID NO: 14.

According to a preferred aspect of the present invention, enhanced or increased expression of the LRR-II-RLP encoding nucleic acid is envisaged. Methods for obtaining enhanced or increased expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of an RKS11 or RKS4 nucleic acid or of a variant thereof. For example, endogenous promoters may be altered in vivo by mutation, deletion, and/or substitution (see, Kmiec, U.S. Pat. No. 5,565,350; Zarling et al., PCT/US93/03868), or isolated promoters may be introduced into a plant cell in the proper orientation and distance from a gene of the present invention so as to control the expression of the gene.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold, Buchman and Berg, Mol. Cell biol. 8:4395-4405 (1988); Callis et al., Genes Dev. 1:1183-1200 (1987). Such intron enhancement of gene expression is typically greatest when placed near the 5' end of the transcription unit. Use of the maize introns Adh1-S intron 1, 2, and 6, the Bronze-1 intron are known in the art. See generally, The Maize Handbook, Chapter 116, Freeling and Walbot, Eds., Springer, N.Y. (1994).

Other control sequences (besides promoter, enhancer, silencer, intron sequences, 3' UTR and/or 5' UTR regions) may be protein and/or RNA stabilizing elements.

The invention also provides genetic constructs and vectors to facilitate introduction and/or expression of the nucleotide sequences useful in the methods according to the invention.

Therefore, there is provided a gene construct comprising:

(i) an LRR-II-RLP encoding nucleic acid;
(ii) one or more control sequences capable of driving expression of the nucleic acid sequence of (i); and optionally
(iii) a transcription termination sequence.

Constructs useful in the methods according to the present invention may be constructed using recombinant DNA technology well known to persons skilled in the art. The gene constructs may be inserted into vectors, which may be commercially available, suitable for transforming into plants and suitable for expression of the gene of interest in the transformed cells.

Plants are transformed with a vector comprising the sequence of interest (i.e., an LRR-II-RLP encoding nucleic acid). The sequence of interest is operably linked to one or more control sequences (at least to a promoter). The terms "regulatory element", "control sequence" and "promoter" are all used interchangeably herein and are to be taken in a broad context to refer to regulatory nucleic acid sequences capable of effecting expression of the sequences to which they are ligated. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative which confers, activates or enhances expression of a nucleic acid molecule in a cell, tissue or organ. The term "operably linked" as used herein refers to a functional linkage between the promoter sequence and the gene of interest, such that the promoter sequence is able to initiate transcription of the gene of interest.

Advantageously, any type of promoter may be used to drive expression of the nucleic acid sequence. The term "promoter" refers to a nucleic acid control sequence located upstream from the transcriptional start of a gene and which is involved in recognising and binding of RNA polymerase and other proteins, thereby directing transcription of an operably linked nucleic acid. The promoter may be a constitutive promoter, which refers to a promoter that is transcriptionally active during most, but not necessarily all, phases of its growth and development and under most environmental conditions, in at least one cell, tissue or organ. Alternatively, the promoter may be an inducible promoter, i.e. having induced or increased transcription initiation in response to a chemical, environmental or physical stimulus. An example of an inducible promoter is a stress-inducible promoter, i.e. a promoter activated when a plant is exposed to various stress conditions, or a pathogen-induced promoter. Additionally or alternatively, the promoter may be a tissue-specific promoter, i.e. one that is capable of preferentially initiating transcription in certain tissues, such as the leaves, roots, seed tissue etc; or may be a ubiquitous promoter, which is active in substantially all tissues or cells of an organism, or the promoter may be developmentally regulated, thereby being active during certain developmental stages or in parts of the plant that undergo developmental changes. Promoters able to initiate transcription in certain tissues only are referred to herein as "tissue-specific", similarly, promoters able to initiate transcription in certain cells only are referred to herein as "cell-specific".

Preferably, the LRR-II-RLP encoding nucleic acid is operably linked to a seed-specific promoter. A seed-specific promoter is transcriptionally active predominantly in seed tissue, but not necessarily exclusively in seed tissue (in cases of leaky expression). The seed-specific promoter may be active during seed development and/or during germination. Seed-specific promoters are well known in the art. Preferably, the seed-specific promoter is the promoter represented by SEQ ID NO: 19 or a promoter of similar strength and/or with a similar expression pattern, such as PRO0058 from WO 2004/070039. Similar strength and/or similar expression pattern may be analysed, for example, by coupling the promoters to a reporter gene and checking the function of the reporter gene in tissues of the plant. One well-known reporter gene is beta-glucuronidase and the calorimetric GUS stain used to visualize beta-glucuronidase activity in plant tissue. It should be clear that the applicability of the present invention is not restricted to the LRR-II-RLP encoding nucleic acid represented by SEQ ID NO: 10, nor to SEQ ID NO: 14, nor is the applicability of the invention restricted to expression of an LRR-II-RLP encoding nucleic acid when driven by a seed-specific promoter. Examples of other seed-specific promoters which may also be used to drive expression of a LRR-II-RLP encoding nucleic acid are shown in Table 3 below.

TABLE 3

Examples of seed-specific promoters

| Gene source | Expression pattern | Reference |
|---|---|---|
| seed-specific genes | seed | Simon et al., Plant Mol. Biol. 5: 191, 1985; Scofield et al., J. Biol. Chem. 262: 12202, 1987.; Baszczynski et al., Plant Mol. Biol. 14: 633, 1990. |
| Brazil Nut albumin | seed | Pearson et al., Plant Mol. Biol. 18: 235-245, 1992. |
| legumin | seed | Ellis et al., Plant Mol. Biol. 10: 203-214, 1988. |
| glutelin (rice) | seed | Takaiwa et al., Mol. Gen. Genet. 208: 15-22, 1986; Takaiwa et al., FEBS Letts. 221: 43-47, 1987. |
| zein | seed | Matzke et al Plant Mol Biol, 14(3): 323-32 1990 |
| napA | seed | Stalberg et al, Planta 199: 515-519, 1996. |
| wheat LMW and HMW | endosperm | Mol Gen Genet 216: 81-90, 1989; NAR |

TABLE 3-continued

Examples of seed-specific promoters

| Gene source | Expression pattern | Reference |
|---|---|---|
| glutenin-1 | | 17: 461-2, 1989 |
| wheat SPA | seed | Albani et al, Plant Cell, 9: 171-184, 1997 |
| wheat a, b, g-gliadins | endosperm | EMBO J. 3: 1409-15, 1984 |
| barley ltr1 promoter | endosperm | |
| barley B1, C, D, hordein | endosperm | Theor Appl Gen 98: 1253-62, 1999; Plant J 4: 343-55, 1993; Mol Gen Genet 250: 750-60, 1996 |
| barley DOF | endosperm | Mena et al, The Plant Journal, 116(1): 53-62, 1998 |
| blz2 | endosperm | EP99106056.7 |
| synthetic promoter | endosperm | Vicente-Carbajosa et al., Plant J. 13: 629-640, 1998. |
| rice prolamin NRP33 | endosperm | Wu et al, Plant Cell Physiology 39(8) 885-889, 1998 |
| rice a-globulin Glb-1 | endosperm | Wu et al, Plant Cell Physiology 39(8) 885-889, 1998 |
| rice OSH1 | embryo | Sato et al, Proc. Natl. Acad. Sci. USA, 93: 8117-8122, 1996 |
| rice a-globulin REB/OHP-1 | endosperm | Nakase et al. Plant Mol. Biol. 33: 513-522, 1997 |
| rice ADP-glucose PP | endosperm | Trans Res 6: 157-68, 1997 |
| maize ESR gene family | endosperm | Plant J 12: 235-46, 1997 |
| sorgum g-kafirin | endosperm | PMB 32: 1029-35, 1996 |
| KNOX | embryo | Postma-Haarsma et al, Plant Mol. Biol. 39: 257-71, 1999 |
| rice oleosin | embryo and aleurone | Wu et al, J. Biochem. 123: 386, 1998 |
| sunflower oleosin | seed (embryo and dry seed) | Cummins et al., Plant Mol. Biol. 19: 873-876, 1992 |
| PRO0117, putative rice 40S ribosomal protein | weak in endosperm | WO 2004/070039 |
| PRO0136, rice alanine aminotransferase | weak in endosperm | |
| PRO0147, trypsin inhibitor ITR1 (barley) | weak in endosperm | |
| PRO0151, rice WSI18 | embryo + stress | WO 2004/070039 |
| PRO0175, rice RAB21 | embryo + stress | WO 2004/070039 |
| PRO0058 | seed | WO 2004/070039 |

Optionally, one or more terminator sequences may also be used in the construct introduced into a plant. The term "terminator" encompasses a control sequence which is a DNA sequence at the end of a transcriptional unit which signals 3' processing and polyadenylation of a primary transcript and termination of transcription. Additional regulatory elements may include transcriptional as well as translational enhancers. Those skilled in the art will be aware of terminator and enhancer sequences which may be suitable for use in performing the invention. Such sequences would be known or may readily be obtained by a person skilled in the art.

The genetic constructs of the invention may further include an origin of replication sequence which is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

The genetic construct may optionally comprise a selectable marker gene. As used herein, the term "selectable marker gene" includes any gene which confers a phenotype on a cell in which it is expressed to facilitate the identification and/or selection of cells which are transfected or transformed with a nucleic acid construct of the invention. Suitable markers may be selected from markers that confer antibiotic or herbicide resistance, that introduce a new metabolic trait or that allow visual selection. Examples of selectable marker genes include genes conferring resistance to antibiotics (such as nptII that phosphorylates neomycin and kanamycin, or hpt, phosphorylating hygromycin), to herbicides (for example bar which provides resistance to Basta; aroA or gox providing resistance against glyphosate), or genes that provide a metabolic trait (such as manA that allows plants to use mannose as sole carbon source). Visual marker genes result in the formation of colour (for example β-glucuronidase, GUS), luminescence (such as luciferase) or fluorescence (Green Fluorescent Protein, GFP, and derivatives thereof).

The present invention also encompasses plants obtainable by the methods according to the present invention. The present invention therefore provides plants obtainable by the method according to the present invention, which plants have introduced therein an LRR-II-RLP encoding nucleic acid.

The invention also provides a method for the production of transgenic plants having improved growth characteristics, comprising introduction and expression in a plant cell of an LRR-II-RLP encoding nucleic acid.

More specifically, the present invention provides a method for the production of transgenic plants having improved growth characteristics, which method comprises:
  (i) introducing and expressing in a plant cell an LRR-II-RLP encoding nucleic acid; and
  (ii) cultivating the plant cell under conditions promoting plant growth and development.

The nucleic acid may be introduced directly into a plant cell or into the plant itself (including introduction into a tissue, organ or any other part of a plant). According to a preferred feature of the present invention, the nucleic acid is preferably introduced into a plant by transformation.

The term "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

Transformation of plant species is now a fairly routine technique. Advantageously, any of several transformation methods may be used to introduce the gene of interest into a suitable ancestor cell. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., 1882, Nature 296, 72-74; Negrutiu I. et al., June 1987, Plant Mol. Biol. 8, 363-373); electroporation of protoplasts (Shillito R. D. et al., 1985 Bio/Technol 3, 1099-1102); microinjection into plant material (Crossway A. et al., 1986, Mol. Gen Genet 202, 179-185); DNA or RNA-coated particle bombardment (Klein T. M. et al., 1987, Nature 327, 70) infection with (non-integrative) viruses and the like. Transgenic rice plants expressing an LRR-II-RLP encoding nucleic acid/gene are preferably produced via Agrobacterium-mediated transformation using any of the well known methods for rice transformation, such as described in any of the following: published European patent application EP 1198985 A1, Aldemita and Hodges (Planta, 199, 612-617, 1996); Chan et al. (Plant Mol. Biol. 22 (3) 491-506, 1993); Hiei et al. (Plant J. 6 (2) 271-282, 1994), which disclosures are incorporated by reference herein as if fully set forth. In the case of corn transformation, the preferred method is as described in either Ishida et al. (Nat. Biotechnol. 1996 June; 14(6): 745-50) or Frame et al. (Plant Physiol. 2002 May; 129(1): 13-22), which disclosures are incorporated by reference herein as if fully set forth.

Generally after transformation, plant cells or cell groupings are selected for the presence of one or more markers which are encoded by plant-expressible genes co-transferred with the gene of interest, following which the transformed material is regenerated into a whole plant.

Following DNA transfer and regeneration, putatively transformed plants may be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced in the parent by the methods according to the invention. The invention also includes host cells containing an isolated nucleic acid encoding an LRR-II-RLP protein. Preferred host cells according to the invention are plant cells.

The invention also extends to harvestable parts of a plant such as, but not limited to, seeds, leaves, fruits, flowers, stem cultures, rhizomes, tubers and bulbs. The invention further relates to products derived directly from a harvestable part of such a plant, such products including dry pellets or powders, oil, fat and fatty acids, starch or proteins.

The present invention also encompasses use of LRR-II-RLP encoding nucleic acids.

One such use relates to improving the growth characteristics of plants, in particular in improving yield, especially seed yield. The seed yield may include one or more of the following: increased number of filled seeds, increased seed weight (total weight of seeds), harvest index, improved metabolite composition, among others.

LRR-II-RLP encoding nucleic acids, or the LRR-II-RLP polypeptides may find use in breeding programmes in which a DNA marker is identified which may be genetically linked to an LRR-II-RLP encoding gene. The LRR-II-RLP encoding nucleic acids/genes, or the LRR-II-RLP polypeptide may be used to define a molecular marker. This DNA or protein marker may then be used in breeding programs to select plants having altered growth characteristics. The LRR-II-RLP encoding gene or variant thereof may, for example, be a nucleic acid as represented by SEQ ID NO: 9 and SEQ ID NO: 13.

Allelic variants of an LRR-II-RLP encoding nucleic acid/gene may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called "natural" origin caused unintentionally. Identification of allelic variants then takes place by, for example, PCR. This is followed by a selection step for selection of superior allelic variants of the sequence in question and which give improved growth characteristics in a plant. Selection is typically carried out by monitoring growth performance of plants containing different allelic variants of the sequence in question, for example, different allelic variants of any one of SEQ ID NO: 9 and SEQ ID NO: 13. Growth performance may be monitored in a greenhouse or in the field. Further optional steps include crossing plants, in which the superior allelic variant was identified, with another plant. This could be used, for example, to make a combination of interesting phenotypic features.

An LRR-II-RLP encoding nucleic acid may also be used as probes for genetically and physically mapping the genes that they are a part of, and as markers for traits linked to those genes. Such information may be useful in plant breeding in order to develop lines with desired phenotypes. Such use of LRR-II-RLP encoding nucleic acids requires only a nucleic acid sequence of at least 15 nucleotides in length. The LRR-II-RLP encoding nucleic acids may be used as restriction fragment length polymorphism (RFLP) markers. Southern blots of restriction-digested plant genomic DNA may be probed with the LRR-II-RLP encoding nucleic acids. The resulting banding patterns may then be subjected to genetic analyses using computer programs such as MapMaker (Lander et al. (1987) Genomics 1:174-181) in order to construct a genetic map. In addition, the nucleic acids may be used to probe Southern blots containing restriction endonuclease-treated genomic DNAs of a set of individuals representing parent and progeny of a defined genetic cross. Segregation of the DNA polymorphisms is noted and used to calculate the position of the LRR-II-RLP encoding nucleic acid or of a variant thereof in the genetic map previously obtained using this population (Botstein et al. (1980) Am. J. Hum. Genet. 32:314-331).

The production and use of plant gene-derived probes for use in genetic mapping is described in Bernatzky and Tanksley (1986) Plant Mol. Biol. Reporter 4:37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid probes may also be used for physical mapping (i.e. placement of sequences on physical maps; see Hoheisel et al. In: Non-mammalian Genomic Analysis: A Practical Guide, Academic press 1996, pp. 319-346, and references cited therein).

In another embodiment, the nucleic acid probes may be used in direct fluorescence in situ hybridization (FISH) mapping (Trask (1991) Trends Genet. 7:149-154). Although current methods of FISH mapping favour use of large clones (several to several hundred kb; see Laan et al. (1995) Genome Res. 5:13-20), improvements in sensitivity may allow performance of FISH mapping using shorter probes.

A variety of nucleic acid amplification-based methods for genetic and physical mapping may be carried out using the nucleic acids. Examples include allele-specific amplification (Kazazian (1989) J. Lab. Clin. Med 11:95-96), polymorphism of PCR-amplified fragments (CAPS; Sheffield et al. (1993) Genomics 16:325-332), allele-specific ligation (Landegren et al. (1988) Science 241:1077-1080), nucleotide extension reactions (Sokolov (1990) Nucleic Acid Res. 18:3671), Radiation Hybrid Mapping (Walter et al. (1997) Nat. Genet. 7:22-28) and Happy Mapping (Dear and Cook (1989) Nucleic Acid Res. 17:6795-6807). For these methods, the sequence of a nucleic acid is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

The methods according to the present invention result in plants having improved growth characteristics, as described hereinbefore. These advantageous growth characteristics may also be combined with other economically advantageous traits, such as further yield-enhancing traits, tolerance to various stresses, traits modifying various architectural features and/or biochemical and/or physiological features.

DESCRIPTION OF FIGURES

The present invention will now be described with reference to the following figures in which:

FIG. 3 represents a multiple alignment of the full length RKS11 RLK (SEQ ID NO: 2), the truncated version used in the examples section (RKS11$_{trunc}$, SEQ ID NO: 10) and a natural form of an LRR-II-RLP protein (SEQ ID NO: 14, Genbank BX827036). The alignment demonstrates that some sequence variability is allowable in the C-terminus of LRR-II-RLP proteins.

FIG. 4 details examples of sequences useful in performing the methods according to the present invention.

EXAMPLES

Figure 1:
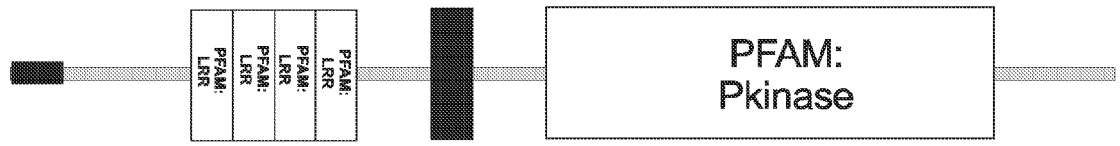
FIG. 1 gives a graphical overview of domains in common between the RKS11 and RKS4 receptor kinase proteins. At the N-terminus, the signal sequence is indicated; furthermore the four LRR domains, the transmembrane domain and the kinase domain are shown.

The present invention will now be described with reference to the following examples, which are by way of illustration alone.

DNA manipulation: unless otherwise stated, recombinant DNA techniques are performed according to standard protocols such as those described in Sambrook (Molecular Cloning: a laboratory manual, 3rd Edition Cold Spring Harbor Laboratory Press, CSH, New York, 2001) or in Volumes 1 and 2 of Ausubel et al. (1994), Current Protocols in Molecular Biology, Current Protocols. Standard materials and methods for plant molecular work are described in Plant Molecular Biology Labfax (1993) by R. D. D. Croy, published by BIOS Scientific Publications Ltd (UK) and Blackwell Scientific Publications (UK).

Example 1

Identification of Sequences Related to the Nucleic Acid Sequence Used in the Methods of the Invention Sequences (full length cDNA, ESTs or genomic) related to the nucleic acid sequence used in the methods of the present invention were identified amongst those maintained in the Entrez Nucleotides database at the National Center for Biotechnology Information (NCBI)(ncbi.nlm.nih.gov) using database sequence search tools, such as the Basic Local Alignment Tool (BLAST) (Altschul et al. (1990) J. Mol. Biol. 215:403-410; and Altschul et al. (1997) Nucleic Acids Res. 25:3389-3402). The program is used to find regions of local similarity between sequences by comparing nucleic acid or polypeptide sequences to sequence databases and by calculating the statistical significance of matches. For example, the polypeptide encoded by the nucleic acid of the present invention was used for the TBLASTN algorithm, with default settings and the filter to ignore low complexity sequences set off. The output of the analysis was viewed by pairwise comparison, and ranked according to the probability score (E-value), where the score reflect the probability that a particular alignment occurs by chance (the lower the E-value, the more significant the hit). In addition to E-values, comparisons were also scored by percentage identity. Percentage identity refers to the number of identical nucleotides (or amino acids) between the two compared nucleic acid (or polypeptide) sequences over a particular length. In some instances, the default parameters may be adjusted to modify the stringency of the search. For example the E-value may be increased to show less stringent matches. This way, short nearly exact matches may be identified. Table 1 above provides a few nucleic acid sequences related to the nucleic acid sequence used in the methods of the present invention. Table 4 below gives an overview of subfamily II LRR-RLK sequences in *Arabidopsis*, which may easily be identified using the sequence of the extracellular domain as a query.

TABLE 4

| Common name | "chromosomal location" | SEQ ID NO nucleic acid/protein |
|---|---|---|
| RKS8 | At1g34210 | 20/21 |
| RKS1 | At1g60800 | 22/23 |
| RKS0 | At1g71830 | 24/25 |
| RKS13 | At2g13790 | 26/27 |
| RKS12 | At2g13800 | 28/29 |
| RKS4 | At2g23950 | 11/12 |
| RKS14 | At3g25560 | 30/31 |
| RKS11 | At4g30520 | 1/2 |
| RKS10 | At4g33430 | 32/33 |
| RKS6 | At5g10290 | 34/35 |
| RKS7 | At5g16000 | 36/37 |
| RKS5 | At5g45780 | 38/39 |
| RKS3 | At5g63710 | 40/41 |
| RKS2 | At5g65240 | 42/43 |

Example 2

Gene Cloning

The *Arabidopsis* RKS11 (internal code CDS3142, SEQ ID NO: 1) was amplified by PCR using as template an *Arabidopsis thaliana* seedling CDNA library (Invitrogen, Paisley, UK). After reverse transcription of RNA extracted from seedlings, the cDNAs were cloned into pCMV Sport 6.0. Average insert size of the bank was 1.5 kb, and the original number of clones was $1.59 \times 10^7$ cfu. Original titer was determined to be $9.6 \times 10^5$ cfu/ml, and after a first amplification of $6 \times 10^{11}$ cfu/ml. After plasmid extraction, 200 ng of template was used in a 50 µl PCR mix. Primers Prm06771 (SEQ ID NO 3, sense) and Prm06772 (SEQ ID NO 4, reverse complementary), which include the AttB sites for Gateway recombination, were used for PCR amplification of the RKS11 coding sequence. PCR was performed using Hifi Taq DNA polymerase in standard conditions. A PCR fragment of 2020 bp (with the attB sites) for RKS11 was amplified and purified also using standard methods. The first step of the Gateway procedure, the BP reaction, was then performed, during which the PCR fragment recombines in vivo with the pDONR201 plasmid to produce, according to the Gateway® terminology, the "entry done" p424. Plasmid pDONR201 was purchased from Invitrogen, as part of the Gateway® technology.

Example 3

Vector Construction and Rice Transformation

The entry done p424 was subsequently used in an LR reaction with p0831, a destination vector used for *Oryza sativa* transformation. This vector contained as functional elements within the T-DNA borders: a plant selectable marker; a visual marker expression cassette; and a Gateway cassette intended for LR in vivo recombination with the sequence of interest already cloned in the entry done. A rice promoter for embryo and aleurone specific expression (SEQ ID NO: 19) was located upstream of this Gateway cassette.

Figure 2:
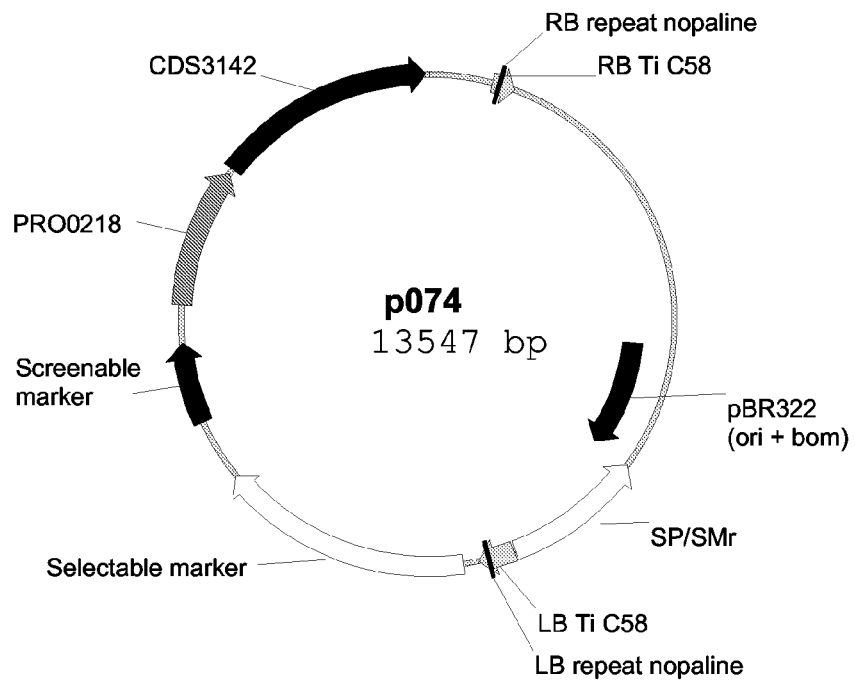
FIG. 2 shows the binary vector for transformation and expression in *Oryza sativa* of the *Arabidopsis thaliana* RKS11$_{trunc}$ coding sequence (internal reference CDS3142, p074, FIG. 2*a*) under the control of a rice aleurone and embryo specific promoter (internal reference PRO0218, SEQ ID NO: 19).

After the LR recombination step, the resulting expression vectors p074 (FIG. 2) was transformed into the *Agrobacterium* strain LBA4404 and subsequently to *Oryza sativa* plants. Transformed rice plants were allowed to grow and were then examined for the parameters described in Example 4.

Example 4

Evaluation of Transformants: Growth Measurements

Approximately 15 to 20 independent T0 transformants were generated. The primary transformants were transferred from tissue culture chambers to a greenhouse for growing and harvest of T1 seed. Five events of which the T1 progeny segregated 3:1 for presence/absence of the transgene were retained. For each of these events, 10 T1 seedlings containing the transgene (hetero- and homo-zygotes), and 10 T1 seedlings lacking the transgene (nullizygotes), were selected by visual marker screening. The selected T1 plants were transferred to a greenhouse. Each plant received a unique barcode label to link unambiguously the phenotyping data to the corresponding plant. The selected T1 plants were grown on soil in 10 cm diameter pots under the following environmental settings: photoperiod=11.5 h, daylight intensity=30,000 lux or more, daytime temperature=28° C., night time temperature=22° C., relative humidity=60-70%. Transgenic plants and the corresponding nullizygotes were grown side-by-side at random positions. From the stage of sowing until the stage of maturity the plants were passed several times through a digital imaging cabinet. At each time point digital images (2048×1536 pixels, 16 million colours) were taken of each plant from at least 6 different angles.

The mature primary panicles were harvested, bagged, barcode-labelled and then dried for three days in the oven at 37° C. The panicles were then threshed and all the seeds collected. The filled husks were separated from the empty ones using an air-blowing device. After separation, both seed lots were then counted using a commercially available counting machine. The empty husks were discarded. The filled husks were weighed on an analytical balance and the cross-sectional area of the seeds was measured using digital imaging. This procedure resulted in the set of seed-related parameters described below.

These parameters were derived in an automated way from the digital images using image analysis software and were analysed statistically. A two factor ANOVA (analyses of variance) corrected for the unbalanced design was used as statistical model for the overall evaluation of plant phenotypic characteristics. An F-test was carried out on all the parameters measured of all the plants of all the events transformed with that gene. The F-test was carried out to check for an effect of the gene over all the transformation events and to verify for an overall effect of the gene, also named herein "global gene effect". If the value of the F test shows that the data are significant, than it is concluded that there is a "gene" effect, meaning that not only presence or the position of the gene is causing the effect. The threshold for significance for a true global gene effect is set at 5% probability level for the F test.

To check for an effect of the genes within an event, i.e., for a line-specific effect, a t-test was performed within each event using data sets from the transgenic plants and the corresponding null plants. "Null plants" or "null segregants" or "nullizygotes" are the plants treated in the same way as the transgenic plant, but from which the transgene has segregated. Null plants can also be described as the homozygous negative transformed plants. The threshold for significance for the t-test is set at 10% probability level. The results for some events can be above or below this threshold. This is based on the hypothesis that a gene might only have an effect in certain positions in the genome, and that the occurrence of this position-dependent effect is not uncommon. This kind of gene effect is also named herein a "line effect of the gene". The p-value is obtained by comparing the t-value to the t-distribution or alternatively, by comparing the F-value to the F-distribution. The p-value then gives the probability that the null hypothesis (i.e., that there is no effect of the transgene) is correct.

The data obtained for RKS11 in the first experiment were confirmed in a second experiment with T2 plants. Four lines that had the correct expression pattern were selected for further analysis. Seed batches from the positive plants (both hetero- and homozygotes) in T1, were screened by monitoring marker expression. For each chosen event, the heterozygote seed batches were then retained for T2 evaluation. Within each seed batch an equal number of positive and negative plants were grown in the greenhouse for evaluation.

A total number of 120 RKS11 transformed plants were evaluated in the T2 generation, that is 30 plants per event of which 15 positives for the transgene, and 15 negatives.

Because two experiments with overlapping events have been carried out, a combined analysis was performed. This is useful to check consistency of the effects over the two experiments, and if this is the case, to accumulate evidence from both experiments in order to increase confidence in the conclusion. The method used was a mixed-model approach that takes into account the multilevel structure of the data (i.e. experiment-event-segregants). P-values are obtained by comparing likelihood ratio test to chi square distributions.

Example 5

Evaluation of RKS11 Transformants: Measurement of Yield-Related Parameters

Upon analysis of the seeds as described above, the inventors found that plants transformed with the RKS11 gene construct had a higher seed yield, expressed as number of filled seeds, total weight of seeds and harvest index, compared to plants lacking the RKS11 transgene. The number of filled seeds was determined by counting the number of filled husks that remained after the separation step. The total seed weight per plant was measured by weighing all filled husks harvested from a plant. The harvest index in the present invention is defined as the ratio between the total seed yield and the above ground area ($mm^2$), multiplied by a factor $10^6$.

The results obtained for plants in the T1 generation are summarised in Table 5:

TABLE 5

|  | % difference | p-value |
|---|---|---|
| Nr filled seeds | +29 | 0.0194 |
| Total weight seeds | +28 | 0.0248 |
| Harvest Index | +27 | 0.0181 |

These positive results were again obtained in the T2 generation. In Table 6, data show the overall % increases for the number of filled seeds, total weight of seeds and harvest index, calculated from the data of the individual lines of the T2 generation, and the respective p-values. These T2 data were re-evaluated in a combined analysis with the results for the T1 generation, and the obtained p-values show that the observed effects were significant.

TABLE 6

|  | T2 generation | | Combined analysis |
|---|---|---|---|
|  | % difference | p-value | p-value |
| Nr filled seeds | +17 | 0.0408 | 0.0033 |
| Total weight seeds | +16 | 0.0698 | 0.0017 |
| Harvest Index | +18 | 0.0081 | 0.0004 |

Similarly, increased seed yield was obtained in rice transformed with a construct comprising CDS3142 (SEQ ID NO: 1) under control of PRO0058 (SEQ ID NO: 50).

Example 6

Metabolic Analysis of Transformed Plants

Plants transformed with RKS11 (as described in Example 2) were grown in the greenhouse as described in Example 4. The modified composition in accordance with the invention, with respect to various metabolites, was determined by the following procedure.

a) Homogenization of the Samples

Ten to thirty rice kernels were transferred into plastic tubes (Eppendorf, Safe-Lock, 2 mL) and homogenized with a stainless steel ball in a ball-mill (Retsch) under cooling with liquid nitrogen.

b) Lyophilization

During the experiment, care was taken that the samples either remained in a deep-frozen state (below −40° C.) or were freed from water by lyophilization of the homogenized material until the first contact with solvents. The samples were transferred in a pre-cooled (−40° C.) freeze dryer. The initial temperature during the main drying phase was −35° C. and the pressure was 0.120 mbar. During the process of drying, the parameters were altered, following a pressure and temperature program. The final temperature after 12 hours was +30° C. and the final pressure was 0.001 to 0.004 mbar. Upon switching off the vacuum pump and the refrigerating machine, the system was flushed with air (dried via a drying tube) or argon.

c) Extraction

Immediately after the lyophilization apparatus had been flushed, the tubes with the lyophilized plant material were tightly sealed to protect the material from air humidity. For the extraction, a portion of 50 mg dried homogenized plant material was weighed in glass fibre extraction thimbles and transferred into 5 ml extraction cartridges of the ASE device (Accelerated Solvent Extractor ASE 200 with Solvent Controller and AutoASE software (DIONEX)). The 24 sample positions of an ASE device (Accelerated Solvent Extractor ASE 200 with Solvent Controller and AutoASE software (DIONEX)) were filled with plant samples, including some samples for quality control testing.

Polar substances were extracted with approximately 10 ml of methanol/water (80/20, v/v) at 70° C. and a pressure of 140 bar, 5 minutes heating-up phase, 1 minute static extraction. The more lipophilic substances were extracted with approximately 10 ml of methanol/dichloromethane (40/60, v/v) at 70° C. and a pressure of 140 bar, 5 minute heating-up phase, 1 minute static extraction. The two solvent mixtures were pooled into the same glass tubes (centrifuge tubes, 50 ml, equipped with screw cap and pierceable septum for the ASE (DIONEX)). The solution was supplemented with commercially available internal standards, such as ribitol, L-glycine-2,2-$d_2$, L alanine-2,3,3,3-$d_4$, methionine-$d_3$, Arginine_($^{13}$C), Tryptophan-$d_5$, α-methylglucopyranoside methyl nonadecanoate, methyl undecanoate, methyl tridecanoate, methyl pentadecanoate and methyl nonacosanoate. The total extract was mixed with 8 ml of water. The solid residue of the plant sample and the extraction sleeve were discarded. The extract was shaken and then centrifuged for 5 to 10 minutes at minimally 1400 g in order to accelerate phase separation. 1 ml of the supernatant methanol/water phase ("polar phase", colorless) was removed for gas chromatographic (GC) analysis, and 1 ml was removed for liquid chromatographic (LC) analysis. The remainder of the methanol/water phase was discarded. Similarly, 0.75 ml of the organic phase ("lipid phase", dark green) was removed for the further GC analysis and 0.75 ml was removed for LC analysis. All these samples were evaporated to dryness using the IR Dancer infrared vacuum evaporator (Hettich). The maximum temperature during the evaporation process did not exceed 40° C. Pressure in the apparatus was 10 mbar or lower.

d) Processing the Lipid and Polar Phase for LC/MS or LC/MS/MS Analysis

The lipid extract and polar extract, which had been evaporated to dryness, were taken up in mobile phase for LC analysis.

e) LC-MS Analysis

The LC part was carried out on a commercially available LC/MS system from Agilent Technologies, USA. From the polar extracts 10 µl were injected into the system at a flow rate of 200 µl/min. The separation column (Reversed Phase C18) was maintained at 15° C. during chromatography. For lipid extracts, 5 µl were injected into the system at a flow rate of 200 µl/min. The separation column (Reversed Phase C18) was maintained at 30° C. HPLC was performed with gradient elution. The mass spectrometric analysis was performed on a Applied Biosystems API 4000 triple quadrupole instrument with turbo ion spray source. For polar extracts, the instrument measured in negative ion mode in fullscan mode from 100-1000 amu; whereas for the lipid extracts the instrument measured in positive ion mode in fullscan mode from 100-1000 amu.

f) Derivatization of the Lipid Phase for the GC/MS Analysis

A mixture of 140 µl of chloroform, 37 µl of hydrochloric acid (37% by weight HCl in water), 320 µl of methanol and 20 µl of toluene was added to the evaporated extract for the transmethanolysis. The vessel was sealed tightly and heated for 2 hours at 100° C., while shaking. The solution was subsequently evaporated until the residue was dried completely. The methoximation of the carbonyl groups was carried out by reaction with methoxyamine hydrochloride (5 mg/ml in pyridine, 100 ml for 1.5 hours at 60° C.) in a tightly sealed vessel. 20 µl of a solution of odd-numbered, straight-chain fatty acids (solution of each 0.3 mg/mL of fatty acids from 7 to 25 carbon atoms and each 0.6 mg/mL of fatty acids with 27, 29 and 31 carbon atoms in 3/7 (v/v) pyridine/toluene) were added as time standards. Finally, the derivatization with 100 µl of N methyl-N-(trimethylsilyl)-2,2,2-trifluoroacetamide (MSTFA) was carried out for 30 minutes at 60° C., again in the tightly sealed vessel. The final volume before injection into the GC was 220 µl.

g) Derivatization of the Polar Phase for the GC/MS Analysis

The methoximation of the carbonyl groups was carried out by reaction with methoxyamine hydrochloride (5 mg/ml in pyridine, 50 ml for 1.5 hours at 60° C.) in a tightly sealed vessel. 10 µl of a solution of odd-numbered, straight-chain fatty acids (solution of each 0.3 mg/mL of fatty acids from 7 to 25 carbon atoms and each 0.6 mg/mL of fatty acids with 27, 29 and 31 carbon atoms in 3/7 (v/v) pyridine/toluene) were added as time standards. Finally, the derivatization with 50 µl of N methyl-N-(trimethylsilyl)-2,2,2-trifluoroacetamide (MSTFA) was carried out for 30 minutes at 60° C., again in the tightly sealed vessel. The final volume before injection into the GC was 110 µl.

h) GC-MS Analysis

The GC-MS system consisted of an Agilent 6890 GC coupled to an Agilent 5973 MSD. The autosamplers were CompiPal or GCPal from CTC. For the analysis commercially available capillary separation columns (30 m×0.25 mm×0.25 µm) with different poly-methyl-siloxane stationary phases containing 0% up to 35% of aromatic moieties were used, depending on the sample material and the fractions from the phase separation step to be analysed (for example: DB-1 ms, HP-5 ms, DB-XLB, DB-35 ms, Agilent Technologies). Up to 1 µL of the final volume was injected splitless and with an oven temperature gradient from 70° C. to 340° C. with different heating rates depending on the sample material and fraction from the phase separation step, in order to achieve a sufficient chromatographic separation and number of scans within each analyte peak. Usual GC-MS standard conditions, for example constant flow with nominal 1 to 1.7 ml/min. and helium as the mobile phase gas were used. Ionisation was done by electron impact with 70 eV, scanning within a m/z range from 15 to 600 with scan rates from 2.5 to 3 scans/sec and standard tune conditions.

i) Analysis of the Various Plant Samples

The samples were measured in individual series of 20 plant samples each. In the experiments each series contained at least 3 replicates per transgenic line plus at least 3 plants of the respective null-segregant line as controls. The peak areas for each analyte were adjusted for the dry weight established for the plant (normalized area). Ratio values were calculated by further normalization to the control. In the experiments ratio values were calculated by dividing the normalized area by the mean of the corresponding data of the control group in the same series. The values obtained are referred to as ratio-_by_control. They are comparable among series and indicate how much the analyte concentration in the transgenic plant differs from the control group, which are the plants of the respective null-segregant lines in a given series. Appropriate controls were done at forehand to prove that the vector and transformation procedure itself had no significant influence on the metabolic composition of the plants.

The results of the different plant analyses can be seen from the following table 7:

TABLE 7

Results of the analysis of seeds from RKS11

| Metabolite | min_ratio | max_ratio | Method |
|---|---|---|---|
| Tryptophane | 1.61163522 | 1.855345912 | LC |
| Phenylalanine | 1.558558559 | 2.207207207 | LC |
| Tyrosine | 1.342697685 | 1.574832386 | GC |
| Isoleucine | 1.567605011 | 1.788026211 | GC |
| Valine | 1.384151826 | 1.667510183 | GC |

Column 1 shows the metabolite analyzed. Columns 2 and 3 show the minimum and maximum ratio, from which the range of increase of the analyzed metabolite as found in independent experiments between the transgenic plants and their wild type respective null-segregant control lines may be derived. Column 4 indicates the analytical method.

The invention claimed is:

1. A method for improving plant growth characteristics, comprising increasing expression in a plant of a nucleic acid encoding a subfamily II Leucine Rich Repeat Receptor-Like Protein (LRR-II-RLP) and selecting for plants having improved growth characteristics, wherein said improved plant growth characteristics are increased yield or increased seed yield, relative to corresponding wild type plants, and wherein the nucleic acid encodes an RKS11 having a mutated inactive kinase domain or a truncated RKS11 with no active kinase domain.

2. The method according to claim 1, wherein said increased expression is effected by introducing a genetic modification in the locus of a gene encoding RKS11 or in the locus of a gene encoding RKS4 or in the locus of a gene encoding an LRR-II-RLP protein.

3. The method according to claim 2, wherein said genetic modification is effected by one or more of: site-directed mutagenesis, transposon mutagenesis, directed evolution, homologous recombination, TILLING and T-DNA activation.

4. A method for improving plant growth characteristics, comprising introducing and expressing in a plant an isolated LRR-II-RLP encoding nucleic acid, wherein said isolated LRR-II-RLP encoding nucleic acid encodes an RKS11 having a mutated inactive kinase domain or a truncated RKS11 with no active kinase domain.

5. The method according to claim 4, wherein said improved plant growth characteristics are increased yield or increased seed yield, relative to corresponding wild type plants.

6. The method according to claim 4, wherein said isolated LRR-II-RLP encoding nucleic acid is overexpressed in the plant.

7. The method according to claim 4, wherein said isolated LRR-II-RLP encoding nucleic acid is of plant origin, from a dicotyledonous plant, from the family Brassicaceae, or from Arabidopsis thaliana.

8. The method according to claim 4, wherein said isolated LRR-II-RLP encoding nucleic acid encodes a polypeptide comprising the sequence of SEQ ID NO: 10 or SEQ ID NO: 14.

9. The method according to claim 4, wherein said isolated LRR-II-RLP encoding nucleic acid is operably linked to a seed-specific promoter.

10. The method according to claim 9, wherein said seed-specific promoter comprises the sequence of SEQ ID NO: 19.

11. The method according to claim 1, wherein said increased seed yield is selected from any one or more of (i) increased seed weight, (ii) increased number of (filled) seeds, (iii) increased harvest index, and (iv) improved metabolite composition.

12. A plant obtained by the method according to claim 1.

13. A construct comprising:
  i. an LRR-II-RLP encoding nucleic acid;
  ii. one or more control sequences capable of driving expression of the LRR-II-RLP encoding nucleic acid of (i); and
  iii. a transcription termination sequence,
  wherein the LRR-II-RLP encoding nucleic acid encodes an RKS11 having a mutated inactive kinase domain or a truncated RKS11 with no active kinase domain.

14. The construct according to claim 13, wherein said one or more control sequences is a seed-specific promoter.

15. The construct according to claim 14, wherein said seed-specific promoter comprises the sequence of SEQ ID NO: 19.

16. A plant transformed with the construct according to claim 13.

17. A method for the production of a transgenic plant having modified growth characteristics comprising increased yield or increased seed yield relative to corresponding wild type plants, wherein the method comprises:
  i. introducing and expressing in a plant cell an LRR-II-RLP encoding nucleic acid; and
  ii. cultivating the plant cell under conditions promoting plant growth and development,
  wherein the LRR-II-RLP encoding nucleic acid encodes an RKS11 having a mutated inactive kinase domain or a truncated RKS11 with no active kinase domain.

18. A transgenic plant having improved growth characteristics or increased yield, relative to corresponding wild type plants, resulting from introduction and expression of an LRR-II-RLP encoding nucleic acid in said plant, wherein the LRR-II-RLP encoding nucleic acid encodes an RKS11 having a mutated inactive kinase domain or a truncated RKS11 with no active kinase domain.

19. The plant according to claim 12, wherein said plant is a crop plant, a monocotyledonous plant, or a cereal.

20. Harvestable parts of the plant according to claim 12.

21. The harvestable parts according to claim 20, wherein said harvestable parts are seeds.

22. The transgenic plant according to claim 18, wherein said increased yield is increased seed yield selected from one or more of the following: increased number of (filled) seeds, increased seed weight, increased harvest index, and improved metabolite composition.

23. An isolated nucleic acid selected from the group consisting of:
i. a nucleic acid sequence of SEQ ID NO: 9, or the complement strand thereof;
ii. a nucleic acid sequence encoding the amino acid sequence of SEQ ID NO: 10;
iii. a nucleic acid sequence capable of hybridising under stringent conditions with the nucleic acid sequence of (i) or (ii) above, wherein the stringent conditions comprise hybridization at 65° C. in 1× sodium chloride/sodium citrate (1×SSC) or at 42° C. in 1×SSC and 50% formamide, followed by washing at 65° C. in 0.3×SSC, and wherein the nucleic acid sequence encodes a an RKS11 having a mutated inactive kinase domain or a truncated RKS11 with no active kinase domain;
iv. a nucleic acid encoding a protein selected from the group consisting of:
a) a polypeptide without kinase activity comprising (i) a signal sequence, (ii) a Leucine zipper motif with 2 or 3 Leu residues separated from each other by 6 other amino acids, (iii) a motif with 2 conserved cysteine residues, (iv) 4 Leucine Rich Repeat units of each approximately 23 amino acid residues, (v) a domain enriched in serine and proline residues, (vi) a single transmembrane domain, and (vii) part or the whole of a RELH-domain;
b) a subfamily II Leucine Rich Repeat Receptor-Like Kinase lacking substantially the whole kinase domain; and
c) a polypeptide with an amino acid sequence which has at least 90% sequence identity to the amino acid sequence of SEQ ID NO 10, and
v. a portion of a nucleic acid sequence according to any of (i) to (iii) above, which portion encodes a LRR-II-RLP protein,
provided that the isolated nucleic acid is not the sequence of SEQ ID NO: 13 or does not encode the protein of SEQ ID NO: 14.

24. The plant according to claim 12, wherein said plant is soybean, sunflower, canola, alfalfa, rapeseed, cotton, sugar cane, rice, maize, wheat, barley, millet, rye, oats, or sorghum.

* * * * *

SEQUENCE LISTING

<160> NUMBER OF SEQ ID NOS: 50

<210> SEQ ID NO 1
<211> LENGTH: 2189
<212> TYPE: DNA
<213> ORGANISM: Arabidopsis thaliana

<400> SEQUENCE: 1

```
aaagtaatgc tgtctctctt ctcttcaaaa ttattgttaa cctctcgtaa ctaaaatctt      60
ccatggtagt agtaacaaag aagaccatga agattcaaat tcatctcctt tactcgttct     120
tgttcctctg tttctctact ctcactctat cttctgagcc cagaaaccct gaagttgagg     180
cgttgataag tataaggaac aatttgcatg atcctcatgg agctttgaac aattgggacg     240
agttttcagt tgatccttgt agctgggcta tgatcacttg ctctcccgac aacctcgtca     300
ttggactagg agcgccgagc cagtctctct cgggaggttt atctgagtct atcggaaatc     360
tcacaaatct ccgacaagtg tcattgcaaa ataacaacat ctccggcaaa attccaccgg     420
agctcggttt tctacccaaa ttacaaacct tggatctttc caacaaccga ttctccggtg     480
acatccctgt ttccatcgac cagctaagca gccttcaata tctgagactc aacaacaact     540
ctttgtctgg gcccttccct gcttctttgt cccaaattcc tcacctctcc ttcttggact     600
tgtcttacaa caatctcagt ggccctgttc ctaaattccc agcaaggact ttcaacgttg     660
ctggtaatcc tttgatttgt agaagcaacc cacctgagat ttgttctgga tcaatcaatg     720
caagtccact ttctgtttct ttgagctctt catcaggacg caggtctaat agattggcaa     780
tagctcttag tgtaagcctt ggctctgttg ttatactagt ccttgctctc gggtcctttt     840
gttggtaccg aaagaaacaa agaaggctac tgatccttaa cttaaacgat aaacaagagg     900
aagggcttca aggacttggg aatctaagaa gcttcacatt cagagaactc catgtttata     960
cagatggttt cagttccaag aacattctcg gcgctggtgg attcggtaat gtgtacagag    1020
gcaagcttgg agatgggaca atggtggcag tgaaacggtt gaaggatatt aatggaacct    1080
cagggattc acagtttcgt atggagctag agatgattag cttagctgtt cataagaatc    1140
tgcttcggtt aattggttat tgcgcaactt ctggtgaaag gcttcttgtt taccttaca    1200
tgcctaatgg aagcgtcgcc tctaagctta atctaaacc ggcattggac tggaacatga    1260
ggaagaggat agcaattggt gcagcgagag gtttgttgta tctacatgag caatgtgatc    1320
ccaagatcat tcatagagat gtaaaggcag ctaatattct cttagacgag tgctttgaag    1380
ctgttgttgg tgactttgga ctcgcaaagc tccttaacca tgcggattct catgtcacaa    1440
ctgcggtccg tggtacggtt ggccacattg cacctgaata tctctccact ggtcagtctt    1500
ctgagaaaac cgatgtgttt gggttcggta ctattgct cgagctcata accggactga    1560
gagctcttga gtttggtaaa accgttagcc agaaaggagc tatgcttgaa tgggtgagga    1620
aattacatga agagatgaaa gtagaggaac tattggatcg agaactcgga actaactacg    1680
```

```
ataagattga agttggagag atgttgcaag tggctttgct atgcacacaa tatctgccag    1740
ctcatcgtcc taaaatgtct gaagttgttt tgatgcttga aggcgatgga ttagccgaga    1800
gatgggctgc ttcgcataac cattcacatt tctaccatgc caatatctct ttcaagacaa    1860
tctcttctct gtctactact tctgtctcaa ggcttgacgc acattgcaat gatccaactt    1920
atcaaatgtt tggatcttcg gctttcgatg atgacgatga tcatcagcct ttagattcct    1980
ttgccatgga actatccggt ccaagataac acaatgaaag aaagatatca tttttacgat    2040
ggatcaaaca atccaatgaa aaaagctcta cacttttata atatagacat gtatatggtg    2100
gtgaaaattg atgaaaaata tctctacagt ttgagattat gtgttcgtta tgttgatgat    2160
gtatatatta acttttaatt gtgagtttc                                      2189
```

<210> SEQ ID NO 2
<211> LENGTH: 648
<212> TYPE: PRT
<213> ORGANISM: Arabidopsis thaliana

<400> SEQUENCE: 2

```
Met Val Val Thr Lys Lys Thr Met Lys Ile Gln Ile His Leu Leu
1               5                   10                  15

Tyr Ser Phe Leu Phe Leu Cys Phe Ser Thr Leu Thr Leu Ser Ser Glu
            20                  25                  30

Pro Arg Asn Pro Glu Val Glu Ala Leu Ile Ser Ile Arg Asn Asn Leu
        35                  40                  45

His Asp Pro His Gly Ala Leu Asn Asn Trp Asp Glu Phe Ser Val Asp
    50                  55                  60

Pro Cys Ser Trp Ala Met Ile Thr Cys Ser Pro Asp Asn Leu Val Ile
65                  70                  75                  80

Gly Leu Gly Ala Pro Ser Gln Ser Leu Ser Gly Gly Leu Ser Glu Ser
                85                  90                  95

Ile Gly Asn Leu Thr Asn Leu Arg Gln Val Ser Leu Gln Asn Asn Asn
            100                 105                 110

Ile Ser Gly Lys Ile Pro Pro Glu Leu Gly Phe Leu Pro Lys Leu Gln
        115                 120                 125

Thr Leu Asp Leu Ser Asn Asn Arg Phe Ser Gly Asp Ile Pro Val Ser
    130                 135                 140

Ile Asp Gln Leu Ser Ser Leu Gln Tyr Leu Arg Leu Asn Asn Asn Ser
145                 150                 155                 160

Leu Ser Gly Pro Phe Pro Ala Ser Leu Ser Gln Ile Pro His Leu Ser
                165                 170                 175

Phe Leu Asp Leu Ser Tyr Asn Asn Leu Ser Gly Pro Val Pro Lys Phe
            180                 185                 190

Pro Ala Arg Thr Phe Asn Val Ala Gly Asn Pro Leu Ile Cys Arg Ser
        195                 200                 205

Asn Pro Pro Glu Ile Cys Ser Gly Ser Ile Asn Ala Ser Pro Leu Ser
    210                 215                 220

Val Ser Leu Ser Ser Ser Gly Arg Arg Ser Asn Arg Leu Ala Ile
225                 230                 235                 240

Ala Leu Ser Val Ser Leu Gly Ser Val Val Ile Leu Val Leu Ala Leu
                245                 250                 255

Gly Ser Phe Cys Trp Tyr Arg Lys Lys Gln Arg Arg Leu Leu Ile Leu
            260                 265                 270

Asn Leu Asn Asp Lys Gln Glu Glu Gly Leu Gln Gly Leu Gly Asn Leu
        275                 280                 285
```

```
Arg Ser Phe Thr Phe Arg Glu Leu His Val Tyr Thr Asp Gly Phe Ser
    290                 295                 300
Ser Lys Asn Ile Leu Gly Ala Gly Gly Phe Gly Asn Val Tyr Arg Gly
305                 310                 315                 320
Lys Leu Gly Asp Gly Thr Met Val Ala Val Lys Arg Leu Lys Asp Ile
                325                 330                 335
Asn Gly Thr Ser Gly Asp Ser Gln Phe Arg Met Glu Leu Glu Met Ile
            340                 345                 350
Ser Leu Ala Val His Lys Asn Leu Leu Arg Leu Ile Gly Tyr Cys Ala
        355                 360                 365
Thr Ser Gly Glu Arg Leu Leu Val Tyr Pro Tyr Met Pro Asn Gly Ser
    370                 375                 380
Val Ala Ser Lys Leu Lys Ser Lys Pro Ala Leu Asp Trp Asn Met Arg
385                 390                 395                 400
Lys Arg Ile Ala Ile Gly Ala Ala Arg Gly Leu Leu Tyr Leu His Glu
                405                 410                 415
Gln Cys Asp Pro Lys Ile Ile His Arg Asp Val Lys Ala Ala Asn Ile
            420                 425                 430
Leu Leu Asp Glu Cys Phe Glu Ala Val Val Gly Asp Phe Gly Leu Ala
        435                 440                 445
Lys Leu Leu Asn His Ala Asp Ser His Val Thr Thr Ala Val Arg Gly
    450                 455                 460
Thr Val Gly His Ile Ala Pro Glu Tyr Leu Ser Thr Gly Gln Ser Ser
465                 470                 475                 480
Glu Lys Thr Asp Val Phe Gly Phe Gly Ile Leu Leu Glu Leu Ile
                485                 490                 495
Thr Gly Leu Arg Ala Leu Glu Phe Gly Lys Thr Val Ser Gln Lys Gly
            500                 505                 510
Ala Met Leu Glu Trp Val Arg Lys Leu His Glu Glu Met Lys Val Glu
    515                 520                 525
Glu Leu Leu Asp Arg Glu Leu Gly Thr Asn Tyr Asp Lys Ile Glu Val
530                 535                 540
Gly Glu Met Leu Gln Val Ala Leu Leu Cys Thr Gln Tyr Leu Pro Ala
545                 550                 555                 560
His Arg Pro Lys Met Ser Glu Val Val Leu Met Leu Glu Gly Asp Gly
                565                 570                 575
Leu Ala Glu Arg Trp Ala Ala Ser His Asn His Ser His Phe Tyr His
            580                 585                 590
Ala Asn Ile Ser Phe Lys Thr Ile Ser Ser Leu Ser Thr Thr Ser Val
        595                 600                 605
Ser Arg Leu Asp Ala His Cys Asn Asp Pro Thr Tyr Gln Met Phe Gly
    610                 615                 620
Ser Ser Ala Phe Asp Asp Asp Asp His Gln Pro Leu Asp Ser Phe
625                 630                 635                 640
Ala Met Glu Leu Ser Gly Pro Arg
                645

<210> SEQ ID NO 3
<211> LENGTH: 59
<212> TYPE: DNA
<213> ORGANISM: Artificial sequence
<220> FEATURE:
<223> OTHER INFORMATION: primer: prm06771

<400> SEQUENCE: 3
ggggacaagt ttgtacaaaa aagcaggctt aaacaatggt agtagtaaca agaagacc      59
```

<210> SEQ ID NO 4
<211> LENGTH: 50
<212> TYPE: DNA
<213> ORGANISM: Artificial sequence
<220> FEATURE:
<223> OTHER INFORMATION: primer: prm06772

<400> SEQUENCE: 4
ggggaccact ttgtacaaga aagctgggtt tcattgtgtt atcttggacc            50

<210> SEQ ID NO 5
<211> LENGTH: 9
<212> TYPE: PRT
<213> ORGANISM: Artificial sequence
<220> FEATURE:
<223> OTHER INFORMATION: "RELHXXTDG" motif
<220> FEATURE:
<221> NAME/KEY: misc_feature
<222> LOCATION: (5)..(6)
<223> OTHER INFORMATION: Xaa can be any naturally occurring amino acid

<400> SEQUENCE: 5

Arg Glu Leu His Xaa Xaa Thr Asp Gly
1               5

<210> SEQ ID NO 6
<211> LENGTH: 6
<212> TYPE: PRT
<213> ORGANISM: Artificial sequence
<220> FEATURE:
<223> OTHER INFORMATION: "EGDGLA" motif

<400> SEQUENCE: 6

Glu Gly Asp Gly Leu Ala
1               5

<210> SEQ ID NO 7
<211> LENGTH: 6
<212> TYPE: PRT
<213> ORGANISM: Artificial sequence
<220> FEATURE:
<223> OTHER INFORMATION: "ELSGPR" motif

<400> SEQUENCE: 7

Glu Leu Ser Gly Pro Arg
1               5

<210> SEQ ID NO 8
<211> LENGTH: 10
<212> TYPE: PRT
<213> ORGANISM: Artificial sequence
<220> FEATURE:
<223> OTHER INFORMATION: FNV(A/V)GNP(L/M)IC motif
<220> FEATURE:
<221> NAME/KEY: MISC_FEATURE
<222> LOCATION: (4)..(4)
<223> OTHER INFORMATION: Xaa can be Ala or Val
<220> FEATURE:
<221> NAME/KEY: MISC_FEATURE
<222> LOCATION: (8)..(8)
<223> OTHER INFORMATION: Xaa can be Leu or Met

<400> SEQUENCE: 8

Phe Asn Val Xaa Gly Asn Pro Xaa Ile Cys
1               5                   10

<210> SEQ ID NO 9
<211> LENGTH: 987

<212> TYPE: DNA
<213> ORGANISM: Arabidopsis thaliana

<400> SEQUENCE: 9

```
atggtagtag taacaaagaa gaccatgaag attcaaattc atctccttta ctcgttcttg      60
ttcctctgtt tctctactct cactctatct tctgagccca gaaaccctga agttgaggcg    120
ttgataagta taaggaacaa tttgcatgat cctcatggag ctttgaacaa tgggacgag     180
ttttcagttg atccttgtag ctgggctatg atcacttgct ctcccgacaa cctcgtcatt    240
ggactaggag cgccgagcca gtctccctcg ggaggtttat ctgagtctat cggaaatctc    300
acaaatctcc gacaagtgtc attgcaaaat aacaacatct ccggcaaaat tccaccggag    360
ctcggttttc tacccaaatt acaaaccttg gatctttcca acaaccgatt ctccggtgac    420
atccctgttt ccatcgacca gctaagcagc cttcaatatc tgagactcaa caacaactct    480
ttgtctgggc ccttccctgc ttctttgtcc caaattcctc acctctcctt cttggacttg    540
tcttacaaca atctcagtgg ccctgttcct aaattcccag caaggacttt caacgttgct    600
ggtaatcctt tgatttgtag aagcaaccca cctgagattt gttctggatc aatcaatgca    660
agtccacttt ctgtttcttt gagctcttca tcaggacgca ggtctaatag attggcaata    720
gctcttagtg taagccttgg ctctgttgtt atactagtcc ttgctctcgg gtccttttgt    780
tggtaccgaa agaaacaaag aaggctactg atccttaact taaacgataa acaagaggaa    840
gggcttcaag gacttgggaa tctaagaagc ttcacattca gagaactcca tgtttataca    900
gatggtttca gttccaagaa cattctcggc gctggtggat cggtaatgt gtacagaggc    960
aagctggaga tgggacaatg gtggcag                                         987
```

<210> SEQ ID NO 10
<211> LENGTH: 329
<212> TYPE: PRT
<213> ORGANISM: Arabidopsis thaliana

<400> SEQUENCE: 10

```
Met Val Val Val Thr Lys Lys Thr Met Lys Ile Gln Ile His Leu Leu
1               5                   10                  15

Tyr Ser Phe Leu Phe Leu Cys Phe Ser Thr Leu Thr Leu Ser Ser Glu
            20                  25                  30

Pro Arg Asn Pro Glu Val Glu Ala Leu Ile Ser Ile Arg Asn Asn Leu
        35                  40                  45

His Asp Pro His Gly Ala Leu Asn Asn Trp Asp Glu Phe Ser Val Asp
    50                  55                  60

Pro Cys Ser Trp Ala Met Ile Thr Cys Ser Pro Asp Asn Leu Val Ile
65                  70                  75                  80

Gly Leu Gly Ala Pro Ser Gln Ser Pro Ser Gly Gly Leu Ser Glu Ser
                85                  90                  95

Ile Gly Asn Leu Thr Asn Leu Arg Gln Val Ser Leu Gln Asn Asn Asn
            100                 105                 110

Ile Ser Gly Lys Ile Pro Pro Glu Leu Gly Phe Leu Pro Lys Leu Gln
        115                 120                 125

Thr Leu Asp Leu Ser Asn Asn Arg Phe Ser Gly Asp Ile Pro Val Ser
    130                 135                 140

Ile Asp Gln Leu Ser Ser Leu Gln Tyr Leu Arg Leu Asn Asn Asn Ser
145                 150                 155                 160

Leu Ser Gly Pro Phe Pro Ala Ser Leu Ser Gln Ile Pro His Leu Ser
                165                 170                 175
```

```
Phe Leu Asp Leu Ser Tyr Asn Asn Leu Ser Gly Pro Val Pro Lys Phe
            180                 185                 190
Pro Ala Arg Thr Phe Asn Val Ala Gly Asn Pro Leu Ile Cys Arg Ser
        195                 200                 205
Asn Pro Pro Glu Ile Cys Ser Gly Ser Ile Asn Ala Ser Pro Leu Ser
    210                 215                 220
Val Ser Leu Ser Ser Ser Gly Arg Arg Ser Asn Arg Leu Ala Ile
225                 230                 235                 240
Ala Leu Ser Val Ser Leu Gly Ser Val Val Ile Leu Val Leu Ala Leu
                245                 250                 255
Gly Ser Phe Cys Trp Tyr Arg Lys Lys Gln Arg Leu Leu Ile Leu
            260                 265                 270
Asn Leu Asn Asp Lys Gln Glu Glu Gly Leu Gln Gly Leu Gly Asn Leu
        275                 280                 285
Arg Ser Phe Thr Phe Arg Glu Leu His Val Tyr Thr Asp Gly Phe Ser
    290                 295                 300
Ser Lys Asn Ile Leu Gly Ala Gly Gly Phe Gly Asn Val Tyr Arg Gly
305                 310                 315                 320
Lys Leu Glu Met Gly Gln Trp Trp Gln
                325

<210> SEQ ID NO 11
<211> LENGTH: 2334
<212> TYPE: DNA
<213> ORGANISM: Arabidopsis thaliana

<400> SEQUENCE: 11
tgctttctct cctctctgtt ttttctagct ttctctctca caaaatcaaa acttttttc      60 tgtgttcatt atcatctcct taaattcata acaatacact ctcataattc ttctctgcgt    120
aggagagaca ttgcagaaat aaaagagttt ttaatagacc caagaaaaag agaaaaaaag    180
cattcatttt tttcttgctt tgttgctttg cttttgcttt tctgtttctc ttcttttgtg    240
ggcacaacaa aacatcaaca aagtaatgat tttgtgttct tccttctcct tctggtaatc    300
taatctaaag cttttcatgg tggtgatgaa gttaataaca atgaagatat tctctgttct    360
gttactacta tgtttcttcg ttacttgttc tctctcttct gaacccagaa accctgaagt    420
ggaggcgttg ataaacataa agaacgagtt acatgatcca catggtgttt tcaaaaactg    480
ggatgagttt tctgttgatc cttgtagctg gactatgatc tcttgttctt cagacaacct    540
cgtaattggc ttaggagctc caagtcagtc tctttcagga actttatctg ggtctattgg    600
aaatctcact aatcttcgac aagtgtcatt acagaacaat aacatctccg gtaaaatccc    660
accggagatt tgttctcttc ccaaattaca gactctggat ttatccaata accggttctc    720
cggtgaaatc cccggttctg ttaaccagct gagtaatctc caatatctga ggttgaacaa    780
caactcatta tctgggccct ttcctgcttc tctgtctcaa atccctcacc tctctttctt    840
agacttgtct tataacaatc tcagaggtcc tgttcctaaa tttcctgcaa ggacattcaa    900
tgttgctggg aacccttga tttgtaaaaa cagcctaccg agatttgtt caggatcaat     960 cagtgcaagc cctctttctg tctctttacg ttcttcatca ggacgtagaa ccaacatatt   1020
agcagttgca cttggtgtaa gccttggctt tgctgttagt gtaatcctct ctctcgggtt   1080
catttggtat cgaaagaaac aaagacggtt aacgatgctt cgcattagtg acaagcaaga   1140
ggaagggtta cttgggttgg gaatctcaag aagcttcaca ttcagggaac ttcatgtagc   1200
tacggatggt tttagttcca agagtattct tggtgctggt gggtttggta atgtctacag   1260
```

-continued

| | |
|---|---|
| aggaaaattc gggatggga cagtggttgc agtgaaacga ttgaaagatg tgaatggaac | 1320 |
| ctccgggaac tcacagtttc gtactgagct tgagatgatc agcttagctg ttcataggaa | 1380 |
| tttgcttcgg ttaatcggtt attgtgcgag ttctagcgaa agacttcttg tttaccctta | 1440 |
| catgtccaat ggcagcgtcg cctctaggct caaagctaag ccagcgttgg actggaacac | 1500 |
| aaggaagaag atagcgattg gagctgcaag agggttgttt tatctacacg agcaatgcga | 1560 |
| tcccaagatt attcaccgag atgtcaaggc agcaaacatt ctcctagatg agtatttga | 1620 |
| agcagttgtt ggggattttg gactagcaaa gctactcaac cacgaggatt cacatgtcac | 1680 |
| aaccgcggtt agaggaactg ttggtcacat tgcacctgag tatctctcca ccggtcagtc | 1740 |
| atctgagaaa accgatgtct ttgggttcgg tatacttttg ctagagctca tcacaggaat | 1800 |
| gagagctctc gagtttggca agtctgttag ccagaaagga gctatgctag aatgggtgag | 1860 |
| gaagctacac aaggaaatga agtagagga gctagtagac cgagaactgg ggacaaccta | 1920 |
| cgatagaata gaagttggag agatgctaca agtggcactg ctctgcactc agtttcttcc | 1980 |
| agctcacaga cccaaaatgt ctgaagtagt tcagatgctt gaaggagatg gattagctga | 2040 |
| gagatgggct gcttcacatg accattcaca tttctaccat gccaacatgt cttacaggac | 2100 |
| tattacctct actgatggca acaaccaaac caaacatctg tttggctcct caggatttga | 2160 |
| agatgaagat gataatcaag cgttagattc attcgccatg gaactatctg gtccaaggta | 2220 |
| gtaaatcttg gacacagaaa gaaacagata taatatcccc atgacttcaa tttttgtttt | 2280 |
| tgagatgata tagacatgta aatggttatc aaacctttga aaaaattgag attc | 2334 |

<210> SEQ ID NO 12
<211> LENGTH: 634
<212> TYPE: PRT
<213> ORGANISM: Arabidopsis thaliana

<400> SEQUENCE: 12

```
Met Val Val Met Lys Leu Ile Thr Met Lys Ile Phe Ser Val Leu Leu
1               5                  10                  15

Leu Leu Cys Phe Phe Val Thr Cys Ser Leu Ser Ser Glu Pro Arg Asn
            20                  25                  30

Pro Glu Val Glu Ala Leu Ile Asn Ile Lys Asn Glu Leu His Asp Pro
        35                  40                  45

His Gly Val Phe Lys Asn Trp Asp Glu Phe Ser Val Asp Pro Cys Ser
    50                  55                  60

Trp Thr Met Ile Ser Cys Ser Ser Asp Asn Leu Val Ile Gly Leu Gly
65                  70                  75                  80

Ala Pro Ser Gln Ser Leu Ser Gly Thr Leu Ser Gly Ser Ile Gly Asn
                85                  90                  95

Leu Thr Asn Leu Arg Gln Val Ser Leu Gln Asn Asn Asn Ile Ser Gly
            100                 105                 110

Lys Ile Pro Pro Glu Ile Cys Ser Leu Pro Lys Leu Gln Thr Leu Asp
        115                 120                 125

Leu Ser Asn Asn Arg Phe Ser Gly Glu Ile Pro Gly Ser Val Asn Gln
    130                 135                 140

Leu Ser Asn Leu Gln Tyr Leu Arg Leu Asn Asn Asn Ser Leu Ser Gly
145                 150                 155                 160

Pro Phe Pro Ala Ser Leu Ser Gln Ile Pro His Leu Ser Phe Leu Asp
                165                 170                 175

Leu Ser Tyr Asn Asn Leu Arg Gly Pro Val Pro Lys Phe Pro Ala Arg
            180                 185                 190
```

```
Thr Phe Asn Val Ala Gly Asn Pro Leu Ile Cys Lys Asn Ser Leu Pro
            195                 200                 205

Glu Ile Cys Ser Gly Ser Ile Ser Ala Ser Pro Leu Ser Val Ser Leu
210                 215                 220

Arg Ser Ser Gly Arg Arg Thr Asn Ile Leu Ala Val Ala Leu Gly
225                 230                 235                 240

Val Ser Leu Gly Phe Ala Val Ser Val Ile Leu Ser Leu Gly Phe Ile
                245                 250                 255

Trp Tyr Arg Lys Lys Gln Arg Arg Leu Thr Met Leu Arg Ile Ser Asp
            260                 265                 270

Lys Gln Glu Glu Gly Leu Leu Gly Leu Gly Asn Leu Arg Ser Phe Thr
            275                 280                 285

Phe Arg Glu Leu His Val Ala Thr Asp Gly Phe Ser Ser Lys Ser Ile
290                 295                 300

Leu Gly Ala Gly Gly Phe Gly Asn Val Tyr Arg Gly Lys Phe Gly Asp
305                 310                 315                 320

Gly Thr Val Val Ala Val Lys Arg Leu Lys Asp Val Asn Gly Thr Ser
                325                 330                 335

Gly Asn Ser Gln Phe Arg Thr Glu Leu Glu Met Ile Ser Leu Ala Val
            340                 345                 350

His Arg Asn Leu Leu Arg Leu Ile Gly Tyr Cys Ala Ser Ser Ser Glu
            355                 360                 365

Arg Leu Leu Val Tyr Pro Tyr Met Ser Asn Gly Ser Val Ala Ser Arg
370                 375                 380

Leu Lys Ala Lys Pro Ala Leu Asp Trp Asn Thr Arg Lys Lys Ile Ala
385                 390                 395                 400

Ile Gly Ala Ala Arg Gly Leu Phe Tyr Leu His Glu Gln Cys Asp Pro
                405                 410                 415

Lys Ile Ile His Arg Asp Val Lys Ala Ala Asn Ile Leu Leu Asp Glu
            420                 425                 430

Tyr Phe Glu Ala Val Val Gly Asp Phe Gly Leu Ala Lys Leu Leu Asn
            435                 440                 445

His Glu Asp Ser His Val Thr Thr Ala Val Arg Gly Thr Val Gly His
450                 455                 460

Ile Ala Pro Glu Tyr Leu Ser Thr Gly Gln Ser Ser Glu Lys Thr Asp
465                 470                 475                 480

Val Phe Gly Phe Gly Ile Leu Leu Leu Glu Leu Ile Thr Gly Met Arg
                485                 490                 495

Ala Leu Glu Phe Gly Lys Ser Val Ser Gln Lys Gly Ala Met Leu Glu
            500                 505                 510

Trp Val Arg Lys Leu His Lys Glu Met Lys Val Glu Glu Leu Val Asp
            515                 520                 525

Arg Glu Leu Gly Thr Thr Tyr Asp Arg Ile Glu Val Gly Glu Met Leu
530                 535                 540

Gln Val Ala Leu Leu Cys Thr Gln Phe Leu Pro Ala His Arg Pro Lys
545                 550                 555                 560

Met Ser Glu Val Val Gln Met Leu Glu Gly Asp Gly Leu Ala Glu Arg
                565                 570                 575

Trp Ala Ala Ser His Asp His Ser His Phe Tyr His Ala Asn Met Ser
            580                 585                 590

Tyr Arg Thr Ile Thr Ser Thr Asp Gly Asn Asn Gln Thr Lys His Leu
            595                 600                 605

Phe Gly Ser Ser Gly Phe Glu Asp Glu Asp Asn Gln Ala Leu Asp
610                 615                 620
```

Ser Phe Ala Met Glu Leu Ser Gly Pro Arg
625                 630

<210> SEQ ID NO 13
<211> LENGTH: 2292
<212> TYPE: DNA
<213> ORGANISM: Arabidopsis thaliana

<400> SEQUENCE: 13

| | | | | | |
|---|---|---|---|---|---|
| caaactcatc | tcctctgaga | gagactgttt | gtttgagaag | aagacgaacg | taaagacttg | 60 |
| tttactaaac | ccgagatttc | tttcttttctt | gttttcaaaa | taaaaaagca | gagatctctt | 120 |
| ctccttcttc | ttcttttttgc | tttgtttgct | tttgctttct | cttctttttc | tatgtgtgtt | 180 |
| tgtggtcact | accccgaaag | gaaataaagt | aatgctgtct | ctcttctctt | caaaattatt | 240 |
| gttaacctct | cgtaactaag | atgttccatg | gtagtagtaa | caaagaagac | catgaagatt | 300 |
| caaattcatc | tcctttactc | gttcttgttc | ctctgtttct | ctactctcac | tctatcttct | 360 |
| gagcccagaa | accctgaagt | tgaggcgttg | ataagtataa | ggaacaattt | gcatgatcct | 420 |
| catggagctt | tgaacaattg | ggacgagttt | tcagttgatc | cttgtagctg | ggctatgatc | 480 |
| acttgctctc | ccgacaacct | cgtcattgga | ctaggagcgc | caagccagtc | tctctcggga | 540 |
| ggtttatctg | agtctatcgg | aaatctcaca | aatctccgac | aagtgtcatt | gcaaaataac | 600 |
| aacatctccg | gcaaaattcc | accggagctc | ggttttctac | ccaaattaca | aaccttggat | 660 |
| ctttccaaca | accgattctc | cggtgacatc | cctgtttcca | tcgaccagct | aagcagcctt | 720 |
| caatatctga | gactcaacaa | caactctttg | tctgggccct | tccctgcttc | tttgtcccaa | 780 |
| attcctcacc | tctccttctt | ggacttgtct | tacaacaatc | tcagtggccc | tgttcctaaa | 840 |
| ttcccagcaa | ggactttcaa | cgttgctggt | aatcctttga | tttgtagaag | caacccacct | 900 |
| gagatttgtt | ctggatcaat | caatgcaagt | ccacttttctg | tttctttgag | ctcttcatca | 960 |
| ggacgcaggt | ctaatagatt | ggcaatagct | cttagtgtaa | gccttggctc | tgttgttata | 1020 |
| ctagtccttg | ctctcgggtc | cttttgttgg | taccgaaaga | aacaaagaag | gctactgatc | 1080 |
| cttaacttaa | acgataaaca | agaggaaggg | cttcaaggac | ttgggaatct | aagaagcttc | 1140 |
| acattcagag | aactccatgt | ttatacagat | ggtttcagtt | ccaagaacat | tctcggcgct | 1200 |
| ggtggattcg | gtaatgtgta | cagaggcaag | cttggagatg | ggacaatggt | ggcagtgaaa | 1260 |
| cggttgaagg | atattaatgg | aacctcaggg | gattcacagt | ttcgtatgga | gctagagatg | 1320 |
| attagcttag | ctgttcataa | gaatctgctt | cggttaattg | gttattgcgc | aacttctggt | 1380 |
| gaaaggcttc | ttgtttaccc | ttacatgcct | aatggaagcg | tcgcctctaa | gcttaaatct | 1440 |
| aaaccgcatt | ggactggaac | atgaggaaga | ggatagcaat | tggtgcagcg | agatgttgt | 1500 |
| tgtatctaca | tgagcaatgt | gatcccaaga | tcattcatag | agatgtaaag | gcagctaata | 1560 |
| ttctcttaga | cgagtgcttt | gaagctgttg | ttggtgactt | tgcactcgca | aagctcctta | 1620 |
| accatgcgga | ttctcatgta | acaactgcgg | tccgtggtac | ggttggccac | attgcacctg | 1680 |
| aatatctctc | cactggtcag | tcttctgaga | aaaccgatgt | gtttgggttc | ggtatactat | 1740 |
| tgctcgagct | cataaccgta | tttttttgttc | ttgagtttgg | taaaaccgtt | agccagaaag | 1800 |
| gagctatgct | tgaatgggtg | aggaaattac | atgaagagat | gaaagtagag | gaactattgg | 1860 |
| atcgagaact | cggaactaac | tacgataaga | ttgaagttgg | agagatgttg | caagtggctt | 1920 |
| tgctatgcac | acaatatctg | ccagctcatc | gtcctaaaat | gtctgaagtt | gttttgatgc | 1980 |
| ttgaaggcga | tggattagcc | gagagatggg | ctgtcgcata | accattcaca | tttctaccat | 2040 |

```
gccaatatct ctttcaagac aatctcttct ctgtctacta cttctgtctc aaggctttac    2100
gcacattgca atgatccaac ttatcaaatg tttggatctt cggctttcga tgatgacgat    2160
gatcatcagc ctttagattc ctttgccatg gaactatccg gtccaagata acacaatgaa    2220
agaaagatat gatttttacg atggatcaaa caatccaatg aaaaaagctc tacacttcca    2280
taatatacac at                                                        2292
```

<210> SEQ ID NO 14
<211> LENGTH: 398
<212> TYPE: PRT
<213> ORGANISM: Arabidopsis thaliana

<400> SEQUENCE: 14

```
Met Val Val Thr Lys Lys Thr Met Lys Ile Gln Ile His Leu Leu
1               5                   10                  15

Tyr Ser Phe Leu Phe Leu Cys Phe Ser Thr Leu Thr Leu Ser Ser Glu
                20                  25                  30

Pro Arg Asn Pro Glu Val Glu Ala Leu Ile Ser Ile Arg Asn Asn Leu
            35                  40                  45

His Asp Pro His Gly Ala Leu Asn Asn Trp Asp Glu Phe Ser Val Asp
50                  55                  60

Pro Cys Ser Trp Ala Met Ile Thr Cys Ser Pro Asp Asn Leu Val Ile
65                  70                  75                  80

Gly Leu Gly Ala Pro Ser Gln Ser Leu Ser Gly Leu Ser Glu Ser
                85                  90                  95

Ile Gly Asn Leu Thr Asn Leu Arg Gln Val Ser Leu Gln Asn Asn Asn
            100                 105                 110

Ile Ser Gly Lys Ile Pro Pro Glu Leu Gly Phe Leu Pro Lys Leu Gln
        115                 120                 125

Thr Leu Asp Leu Ser Asn Asn Arg Phe Ser Gly Asp Ile Pro Val Ser
    130                 135                 140

Ile Asp Gln Leu Ser Ser Leu Gln Tyr Leu Arg Leu Asn Asn Asn Ser
145                 150                 155                 160

Leu Ser Gly Pro Phe Pro Ala Ser Leu Ser Gln Ile Pro His Leu Ser
                165                 170                 175

Phe Leu Asp Leu Ser Tyr Asn Asn Leu Ser Gly Pro Val Pro Lys Phe
            180                 185                 190

Pro Ala Arg Thr Phe Asn Val Ala Gly Asn Pro Leu Ile Cys Arg Ser
        195                 200                 205

Asn Pro Pro Glu Ile Cys Ser Gly Ser Ile Asn Ala Ser Pro Leu Ser
    210                 215                 220

Val Ser Leu Ser Ser Ser Gly Arg Arg Ser Asn Arg Leu Ala Ile
225                 230                 235                 240

Ala Leu Ser Val Ser Leu Gly Ser Val Val Ile Leu Val Leu Ala Leu
                245                 250                 255

Gly Ser Phe Cys Trp Tyr Arg Lys Lys Gln Arg Arg Leu Leu Ile Leu
            260                 265                 270

Asn Leu Asn Asp Lys Gln Glu Glu Gly Leu Gln Gly Leu Gly Asn Leu
        275                 280                 285

Arg Ser Phe Thr Phe Arg Glu Leu His Val Tyr Thr Asp Gly Phe Ser
    290                 295                 300

Ser Lys Asn Ile Leu Gly Ala Gly Gly Phe Gly Asn Val Tyr Arg Gly
305                 310                 315                 320

Lys Leu Gly Asp Gly Thr Met Val Ala Val Lys Arg Leu Lys Asp Ile
                325                 330                 335
```

```
Asn Gly Thr Ser Gly Asp Ser Gln Phe Arg Met Glu Leu Glu Met Ile
            340                 345                 350

Ser Leu Ala Val His Lys Asn Leu Leu Arg Leu Ile Gly Tyr Cys Ala
            355                 360                 365

Thr Ser Gly Glu Arg Leu Leu Val Tyr Pro Tyr Met Pro Asn Gly Ser
370                 375                 380

Val Ala Ser Lys Leu Lys Ser Lys Pro His Trp Thr Gly Thr
385                 390                 395

<210> SEQ ID NO 15
<211> LENGTH: 418
<212> TYPE: PRT
<213> ORGANISM: Oryza sativa

<400> SEQUENCE: 15

Met Arg Met Arg Trp Ala Ala Pro Leu Ala Ala Val Leu Ala Val
1               5                   10                  15

Ile Leu Leu Pro Ser Ser Thr Ala Thr Leu Ser Pro Ala Gly Ile Asn
                20                  25                  30

Tyr Glu Val Val Ala Leu Met Ala Ile Lys Thr Glu Leu Gln Asp Pro
            35                  40                  45

Tyr Asn Val Leu Asp Asn Trp Asp Ile Asn Ser Val Asp Pro Cys Ser
        50                  55                  60

Trp Arg Met Val Thr Cys Ser Ala Asp Gly Tyr Val Ser Ala Leu Gly
65                  70                  75                  80

Leu Pro Ser Gln Ser Leu Ser Gly Lys Leu Ser Pro Gly Ile Gly Asn
                85                  90                  95

Leu Thr Arg Leu Gln Ser Val Leu Leu Gln Asn Asn Ala Ile Ser Gly
            100                 105                 110

Thr Ile Pro Ala Ser Ile Gly Arg Leu Gly Met Leu Gln Thr Leu Asp
        115                 120                 125

Met Ser Asp Asn Gln Ile Thr Gly Ser Ile Pro Ser Ser Ile Gly Asp
130                 135                 140

Leu Lys Asn Leu Asn Tyr Leu Lys Leu Asn Asn Asn Ser Leu Ser Gly
145                 150                 155                 160

Val Leu Pro Asp Ser Leu Ala Ala Ile Asn Gly Leu Ala Leu Val Asp
                165                 170                 175

Leu Ser Phe Asn Asn Leu Ser Gly Pro Leu Pro Lys Ile Ser Ser Arg
            180                 185                 190

Thr Phe Asn Ile Val Gly Asn Pro Met Ile Cys Gly Val Lys Ser Gly
        195                 200                 205

Asp Asn Cys Ser Ser Val Ser Met Asp Pro Leu Ser Tyr Pro Pro Asp
210                 215                 220

Asp Leu Lys Thr Gln Pro Gln Gln Gly Ile Ala Arg Ser His Arg Ile
225                 230                 235                 240

Ala Ile Ile Cys Gly Val Thr Val Gly Ser Val Ala Phe Ala Thr Ile
                245                 250                 255

Ile Val Ser Met Leu Leu Trp Trp Arg His Arg Arg Asn Gln Gln Ile
            260                 265                 270

Phe Phe Asp Val Asn Asp Gln Tyr Asp Pro Glu Val Cys Leu Gly His
        275                 280                 285

Leu Lys Arg Tyr Ala Phe Lys Glu Leu Arg Ala Ala Thr Asn Asn Phe
290                 295                 300

Asn Ser Lys Asn Ile Leu Gly Glu Gly Gly Tyr Gly Ile Val Tyr Lys
305                 310                 315                 320
```

```
Gly Phe Leu Arg Asp Gly Ala Ile Val Ala Val Lys Arg Leu Lys Asp
            325                 330                 335

Tyr Asn Ala Val Gly Gly Glu Val Gln Phe Gln Thr Glu Val Glu Val
            340                 345                 350

Ile Ser Leu Ala Val His Arg Asn Leu Leu Arg Leu Ile Gly Phe Cys
            355                 360                 365

Thr Thr Glu Asn Glu Arg Leu Leu Val Tyr Pro Tyr Met Pro Asn Gly
        370                 375                 380

Ser Val Ala Ser Gln Leu Arg Glu Leu Val Asn Gly Lys Pro Ala Leu
385                 390                 395                 400

Asp Trp Ser Arg Arg Arg Met Phe Leu Gly Leu Glu Phe Cys Trp
                405                 410                 415

Leu Ser
```

<210> SEQ ID NO 16
<211> LENGTH: 628
<212> TYPE: PRT
<213> ORGANISM: Oryza sativa

<400> SEQUENCE: 16

```
Met Arg Met Arg Trp Ala Ala Pro Leu Ala Ala Val Leu Ala Val
1               5                   10                  15

Ile Leu Leu Pro Ser Ser Thr Ala Thr Leu Ser Pro Ala Gly Ile Asn
            20                  25                  30

Tyr Glu Val Val Ala Leu Met Ala Ile Lys Thr Glu Leu Gln Asp Pro
        35                  40                  45

Tyr Asn Val Leu Asp Asn Trp Asp Ile Asn Ser Val Asp Pro Cys Ser
    50                  55                  60

Trp Arg Met Val Thr Cys Ser Ala Asp Gly Tyr Val Ser Ala Leu Gly
65                  70                  75                  80

Leu Pro Ser Gln Ser Leu Ser Gly Lys Leu Ser Pro Gly Ile Gly Asn
                85                  90                  95

Leu Thr Arg Leu Gln Ser Val Leu Leu Gln Asn Asn Ala Ile Ser Gly
            100                 105                 110

Thr Ile Pro Ala Ser Ile Gly Arg Leu Gly Met Leu Gln Thr Leu Asp
        115                 120                 125

Met Ser Asp Asn Gln Ile Thr Gly Ser Ile Pro Ser Ser Ile Gly Asp
    130                 135                 140

Leu Lys Asn Leu Asn Tyr Leu Lys Leu Asn Asn Ser Leu Ser Gly
145                 150                 155                 160

Val Leu Pro Asp Ser Leu Ala Ala Ile Asn Gly Leu Ala Leu Val Asp
                165                 170                 175

Leu Ser Phe Asn Asn Leu Ser Gly Pro Leu Pro Lys Ile Ser Ser Arg
            180                 185                 190

Thr Phe Asn Ile Val Gly Asn Pro Met Ile Cys Gly Val Lys Ser Gly
        195                 200                 205

Asp Asn Cys Ser Ser Val Ser Met Asp Pro Leu Ser Tyr Pro Pro Asp
    210                 215                 220

Asp Leu Lys Thr Gln Pro Gln Gln Gly Ile Ala Arg Ser His Arg Ile
225                 230                 235                 240

Ala Ile Ile Cys Gly Val Thr Val Gly Ser Val Ala Phe Ala Thr Ile
                245                 250                 255

Ile Val Ser Met Leu Leu Trp Arg His Arg Arg Asn Gln Gln Ile
            260                 265                 270
```

```
Phe Phe Asp Val Asn Asp Gln Tyr Asp Pro Glu Val Cys Leu Gly His
        275                 280                 285

Leu Lys Arg Tyr Ala Phe Lys Glu Leu Arg Ala Ala Thr Asn Asn Phe
290                 295                 300

Asn Ser Lys Asn Ile Leu Gly Glu Gly Tyr Gly Ile Val Tyr Lys
305                 310                 315                 320

Gly Phe Leu Arg Asp Gly Ala Ile Val Ala Val Lys Arg Leu Lys Asp
                325                 330                 335

Tyr Asn Ala Val Gly Gly Glu Val Gln Phe Gln Thr Glu Val Glu Val
            340                 345                 350

Ile Ser Leu Ala Val His Arg Asn Leu Leu Arg Leu Ile Gly Phe Cys
        355                 360                 365

Thr Thr Glu Asn Glu Arg Leu Leu Val Tyr Pro Tyr Met Pro Asn Gly
    370                 375                 380

Ser Val Ala Ser Gln Leu Arg Glu Leu Val Asn Gly Lys Pro Ala Leu
385                 390                 395                 400

Asp Trp Ser Arg Arg Lys Arg Ile Ala Leu Gly Thr Ala Arg Gly Leu
                405                 410                 415

Leu Tyr Leu His Glu Gln Cys Asp Pro Lys Ile Ile His Arg Asp Val
            420                 425                 430

Lys Ala Ser Asn Val Leu Leu Asp Glu Tyr Phe Glu Ala Ile Val Gly
        435                 440                 445

Asp Phe Gly Leu Ala Lys Leu Leu Asp His Arg Glu Ser His Val Thr
    450                 455                 460

Thr Ala Val Arg Gly Thr Val Gly His Ile Ala Pro Glu Tyr Leu Ser
465                 470                 475                 480

Thr Gly Gln Ser Ser Glu Lys Thr Asp Val Phe Gly Phe Gly Val Leu
                485                 490                 495

Leu Val Glu Leu Ile Thr Gly Gln Lys Ala Leu Asp Phe Gly Arg Leu
            500                 505                 510

Ala Asn Gln Lys Gly Gly Val Leu Asp Trp Val Lys Lys Leu His Gln
        515                 520                 525

Glu Lys Gln Leu Ser Met Met Val Asp Lys Asp Leu Gly Ser Asn Tyr
    530                 535                 540

Asp Arg Val Glu Leu Glu Glu Met Val Gln Val Ala Leu Leu Cys Thr
545                 550                 555                 560

Gln Tyr Tyr Pro Ser His Arg Pro Arg Met Ser Glu Val Ile Arg Met
                565                 570                 575

Leu Glu Gly Asp Gly Leu Ala Glu Lys Trp Glu Ala Ser Gln Asn Val
            580                 585                 590

Asp Thr Pro Lys Ser Val Ser Ser Glu Leu Leu Pro Pro Lys Phe Met
        595                 600                 605

Asp Phe Ala Ala Asp Glu Ser Ser Leu Gly Leu Glu Ala Met Glu Leu
    610                 615                 620

Ser Gly Pro Arg
625

<210> SEQ ID NO 17
<211> LENGTH: 2037
<212> TYPE: DNA
<213> ORGANISM: Oryza sativa

<400> SEQUENCE: 17
atggcctcca acctcttcct cctcctcttc ttcctcgtcg tctcctacgc gccgttcctc      60
gccttctcct ccgagcccct caaccctgaa gtggaggcgc tgatcgccat caggcagggg     120
```

| | | | | |
|---|---|---|---|---|
| ctggtcgacc | cgcacggcgt | gctgaacaac | tgggacgagg | actccgtcga | cccctgcagc | 180 |
| tgggccatgg | tcacctgctc | cgcccacaac | ctcgtcatcg | gctgggagc | gcccagccag | 240 |
| ggattgtcgg | ggaccctgtc | cggcaggatc | gccaacctca | ccaatcttga | acaagtgctg | 300 |
| ctgcagaaca | caacatcac | cggccggctg | ccgccggagc | tgggcgcgct | gccgaggctg | 360 |
| cagacgctcg | acctctccaa | caaccgcttc | tccggccgcg | tccccgacac | gctcggccgc | 420 |
| ctctccaccc | tccgatacct | gaggctaaac | aacaacagct | tgtccggggc | gttcccgtcg | 480 |
| tcgctggcca | agatcccaca | gctctccttc | ctggacttgt | cctacaacaa | cctcactggc | 540 |
| cctgttcctc | acttccccac | aagaacattc | aacgtcgtgg | gcaatccaat | gatatgcggg | 600 |
| agcagcagcg | gcagccatgc | ggggaacgcg | aacgcagcgg | agtgcgccac | cgtggtcgcc | 660 |
| ccggtcaccg | tgccattccc | gctggactcc | actccgagca | gcagcagcag | ggcggcagcg | 720 |
| gcagcggtgg | ggaggtcaaa | gggtggagga | ggcgccgcgc | ggttgccgat | cggagtaggg | 780 |
| acaagccttg | gcgcctccgc | gcttgtgctc | ctcgccgtct | cctgctttct | ctggaggcgc | 840 |
| aggcgccggc | accgctgcct | cctctcgggc | ccctcctccg | tcctcggcat | cctcgagaag | 900 |
| gggagagacg | tggaggatgg | ggaggagggg | gaggtgatgg | cgaggctggg | gaacgtgagg | 960 |
| cagttcgggc | tgagggagct | gcacgcggcg | acggacgggt | tcagcgcgag | gaacatactg | 1020 |
| gggaaaggag | ggttcgggga | cgtgtaccgg | gggaggctct | ccgacggcac | ggtcgtggcg | 1080 |
| gtgaagcggc | tcaaggaccc | gaccgcgtcc | ggggaggcgc | agttccggac | ggaggtggag | 1140 |
| atgatcagcc | tcgccgtgca | ccgccacctc | ctccgcctcg | tcggcttctg | cgccgcggcc | 1200 |
| tccggcgagc | gcctcctcgt | ctaccccttac | atgcccaacg | gcagcgtcgc | ctcccgcctt | 1260 |
| cgagggaagc | cgccgctgga | ctggcagacg | aggaagcgga | tcgcggtggg | gacggcgagg | 1320 |
| ggattgctgt | acctgcacga | gcagtgcgac | ccaaagatca | tccaccgcga | cgtgaaggcc | 1380 |
| gcgaacgtgc | tgctggacga | gtgccacgag | gccgtcgtcg | gcgacttcgg | gctcgccaag | 1440 |
| ctgctcgacc | acggcgactc | ccacgtcacc | acggcggtgc | gcggcacggt | ggggcacatc | 1500 |
| gcgccggagt | acctctccac | ggggcagtcg | tcggagaaga | ccgacgtgtt | cggcttcggc | 1560 |
| atcctgctgc | tcgagctcgt | caccggccag | cgcgcgctcg | aggtcggcaa | gggctccggc | 1620 |
| gtcatccagc | accagaaggg | cgtcatgctc | gattgggtga | ggaaggtgca | ccaagagaag | 1680 |
| ctgcatgact | tgctagtgga | ccaagatttg | gggcctcact | acgacaggat | agaggtggcg | 1740 |
| gagatggtgc | aggtggcgct | gctctgcacc | cagttccagc | cgtctcaccg | gccgaggatg | 1800 |
| tcggaggtgg | tccggatgct | ggagggagac | gggctcgccg | agaaatggga | ggccaaccac | 1860 |
| cggccggcgg | cgatggcggc | ggcggcggcg | ccccatgagc | tcggctacga | ccaccgcaac | 1920 |
| gactccaacg | gctccgtctt | cttcaacgac | ttccacgaca | cgacagcag | ccttagcagc | 1980 |
| gacgaggtgc | ggtccatcga | catggtagag | gagatggagc | tgtcagggcc | aaggtag | 2037 |

<210> SEQ ID NO 18
<211> LENGTH: 678
<212> TYPE: PRT
<213> ORGANISM: Oryza sativa

<400> SEQUENCE: 18

Met Ala Ser Asn Leu Phe Leu Leu Leu Phe Phe Leu Val Val Ser Tyr
1               5                   10                  15

Ala Pro Phe Leu Ala Phe Ser Ser Glu Pro Leu Asn Pro Glu Val Glu
            20                  25                  30

Ala Leu Ile Ala Ile Arg Gln Gly Leu Val Asp Pro His Gly Val Leu

```
                    35                  40                  45
Asn Asn Trp Asp Glu Asp Ser Val Asp Pro Cys Ser Trp Ala Met Val
 50                  55                  60
Thr Cys Ser Ala His Asn Leu Val Ile Gly Leu Gly Ala Pro Ser Gln
 65                  70                  75                  80
Gly Leu Ser Gly Thr Leu Ser Gly Arg Ile Ala Asn Leu Thr Asn Leu
                     85                  90                  95
Glu Gln Val Leu Leu Gln Asn Asn Ile Thr Gly Arg Leu Pro Pro
                100                 105                 110
Glu Leu Gly Ala Leu Pro Arg Leu Gln Thr Leu Asp Leu Ser Asn Asn
                115                 120                 125
Arg Phe Ser Gly Arg Val Pro Asp Thr Leu Gly Arg Leu Ser Thr Leu
                130                 135                 140
Arg Tyr Leu Arg Leu Asn Asn Ser Leu Ser Gly Ala Phe Pro Ser
145                 150                 155                 160
Ser Leu Ala Lys Ile Pro Gln Leu Ser Phe Leu Asp Leu Ser Tyr Asn
                165                 170                 175
Asn Leu Thr Gly Pro Val Pro His Phe Pro Thr Arg Thr Phe Asn Val
                180                 185                 190
Val Gly Asn Pro Met Ile Cys Gly Ser Ser Gly Ser His Ala Gly
                195                 200                 205
Asn Ala Asn Ala Ala Glu Cys Ala Thr Val Val Ala Pro Val Thr Val
210                 215                 220
Pro Phe Pro Leu Asp Ser Thr Pro Ser Ser Ser Arg Ala Ala Ala
225                 230                 235                 240
Ala Ala Val Gly Arg Ser Lys Gly Gly Gly Ala Ala Arg Leu Pro
                245                 250                 255
Ile Gly Val Gly Thr Ser Leu Gly Ala Ser Ala Leu Val Leu Leu Ala
                260                 265                 270
Val Ser Cys Phe Leu Trp Arg Arg Arg Arg His Arg Cys Leu Leu
                275                 280                 285
Ser Gly Pro Ser Ser Val Leu Gly Ile Leu Glu Lys Gly Arg Asp Val
                290                 295                 300
Glu Asp Gly Gly Gly Glu Val Met Ala Arg Leu Gly Asn Val Arg
305                 310                 315                 320
Gln Phe Gly Leu Arg Glu Leu His Ala Ala Thr Asp Gly Phe Ser Ala
                325                 330                 335
Arg Asn Ile Leu Gly Lys Gly Gly Phe Gly Asp Val Tyr Arg Gly Arg
                340                 345                 350
Leu Ser Asp Gly Thr Val Val Ala Val Lys Arg Leu Lys Asp Pro Thr
                355                 360                 365
Ala Ser Gly Glu Ala Gln Phe Arg Thr Glu Val Glu Met Ile Ser Leu
370                 375                 380
Ala Val His Arg His Leu Leu Arg Leu Val Gly Phe Cys Ala Ala Ala
385                 390                 395                 400
Ser Gly Glu Arg Leu Leu Val Tyr Pro Tyr Met Pro Asn Gly Ser Val
                405                 410                 415
Ala Ser Arg Leu Arg Gly Lys Pro Pro Leu Asp Trp Gln Thr Arg Lys
                420                 425                 430
Arg Ile Ala Val Gly Thr Ala Arg Gly Leu Leu Tyr Leu His Glu Gln
                435                 440                 445
Cys Asp Pro Lys Ile Ile His Arg Asp Val Lys Ala Ala Asn Val Leu
450                 455                 460
```

```
Leu Asp Glu Cys His Glu Ala Val Val Gly Asp Phe Gly Leu Ala Lys
465                 470                 475                 480

Leu Leu Asp His Gly Asp Ser His Val Thr Thr Ala Val Arg Gly Thr
            485                 490                 495

Val Gly His Ile Ala Pro Glu Tyr Leu Ser Thr Gly Gln Ser Ser Glu
        500                 505                 510

Lys Thr Asp Val Phe Gly Phe Gly Ile Leu Leu Leu Glu Leu Val Thr
    515                 520                 525

Gly Gln Arg Ala Leu Glu Val Gly Lys Gly Ser Gly Val Ile Gln His
530                 535                 540

Gln Lys Gly Val Met Leu Asp Trp Val Arg Lys Val His Gln Glu Lys
545                 550                 555                 560

Leu His Asp Leu Leu Val Asp Gln Asp Leu Gly Pro His Tyr Asp Arg
            565                 570                 575

Ile Glu Val Ala Glu Met Val Gln Val Ala Leu Leu Cys Thr Gln Phe
        580                 585                 590

Gln Pro Ser His Arg Pro Arg Met Ser Glu Val Val Arg Met Leu Glu
    595                 600                 605

Gly Asp Gly Leu Ala Glu Lys Trp Glu Ala Asn His Arg Pro Ala Ala
610                 615                 620

Met Ala Ala Ala Ala Pro His Glu Leu Gly Tyr Asp His Arg Asn
625                 630                 635                 640

Asp Ser Asn Gly Ser Val Phe Phe Asn Asp Phe His Asp Asn Asp Ser
            645                 650                 655

Ser Leu Ser Ser Asp Glu Val Arg Ser Ile Asp Met Val Glu Glu Met
        660                 665                 670

Glu Leu Ser Gly Pro Arg
    675

<210> SEQ ID NO 19
<211> LENGTH: 1236
<212> TYPE: DNA
<213> ORGANISM: Oryza sativa

<400> SEQUENCE: 19
ggtcagccaa tacattgatc cgttgccaat catgcaaagt attttggctg tggccgagtg      60
ccggaattga taattgtgtt ctgactaaat taaatgacca gaagtcgcta tcttccaatg     120
tatccgaaac ctggattaaa caatcctgtt ctgttctcta gcccctcctg catggccgga     180
ttgttttttt gacatgtttt cttgactgag gcctgtttgt tctaaacttt ttcttcaaac     240
ttttaacttt ttcatcacat cagaactttt ctacacatat aaactttta cttttccgtc     300 acatcgttcc aatttcaatc aaactttcaa ttttggcgtg aactaaacac accctgagtc     360
ttttattgct cctccgtacg ggttggctgg ttgagaatag gtattttcag agagaaaatc     420
tagatattgg gaggaacttg gcatgaatgg ccactatatt tagagcaatt ctacggtcct     480
tgaggaggta ccatgaggta ccaaaatttt agtgtaaatt ttagtatctc attataacta     540
ggtattatga ggtaccaaat ttacaataga aaaatagta cttcatggta ctttcttaag     600
taccgtaaaa ttgctcctat atttaagggg atgtttatat ctatccatat ccataatttg     660
attttgataa gaaaaaatgt gagcacacca agcatgtcca tgaccttgca ctcttggctc     720
actcgtcaac tgtgaagaac ctcaaaaatg ctcaatatag ctacaggtgc ctgaaaaaat     780
aactttaaag ttttgaacat cgatttcact aaacaacaat tattatctcc ctctgaaaga     840
tgatagttta gaactctaga atcattgtcg gcggagaaag taaattattt tccccaaatt     900
```

-continued

| | |
|---|---|
| tccagctatg aaaaaaccct caccaaacac catcaaacaa gagttcacca aaccgcccat | 960 |
| gcggccatgc tgtcacgcaa cgcaccgcat tgcctgatgg ccgctcgatg catgcatgct | 1020 |
| tccccgtgca catatccgac agacgcgccg tgtcagcgag ctcctcgacc gacctgtgta | 1080 |
| gcccatgcaa gcatccaccc ccgccacgta cacccccctcc tcctccctac gtgtcaccgc | 1140 |
| tctctccacc tatatatgcc cacctggccc ctctcctccc atctccactt cacccgatcg | 1200 |
| cttcttcttc ttcttcgttg cattcatctt gctagc | 1236 |

<210> SEQ ID NO 20
<211> LENGTH: 3461
<212> TYPE: DNA
<213> ORGANISM: Arabidopsis thaliana

<400> SEQUENCE: 20

| | |
|---|---|
| acttttgtag tgactagtga gtagagtagg cttttagaga gagagagaga gagacggctg | 60 |
| ttgaaagata accacagaac acaaaaactc attcattaag aatgagaaag aaagtcccaa | 120 |
| aaacctttt tgctctgaaa aagcaacgca aagttttgaa aaatctcaca ccttttttcac | 180 |
| ttctctgttt gtagctgtta ccacttgtgt ttcccctttg gcattttttct cggttgtcat | 240 |
| taatgagagt aaaatcatca tcaagtgtaa acttctctct ctctttctct atctctatct | 300 |
| caaagctctc aactttggag agatcatggt ttgtgtttga tttctcaagt ttttttttttt | 360 |
| ttaccctctt ggaggatctg ggaggagaaa tttgcttttt tttggtaaat ggggagaaaa | 420 |
| aagtttgaag cttttggttt tgtctgctta atctcactgc ttcttctgtt taattcgtta | 480 |
| tggcttgcct cttctaacat ggaaggtgat gcactgcaca gtttgagagc taatctagtt | 540 |
| gatccaaata atgtcttgca aagctgggat cctacgcttg ttaatccgtg tacttggttt | 600 |
| cacgtaacgt gtaacaacga gaacagtgtt ataagagtcg atcttgggaa tgcagacttg | 660 |
| tctggtcagt tggttcctca gctaggtcag ctcaagaact tgcagtactt ggagctttat | 720 |
| agtaataaca taaccgggcc ggttccaagc gatcttggga atctgacaaa cttagtgagc | 780 |
| ttggatcttt acttgaacag cttcactggt ccaattccag attctctagg aaagctattc | 840 |
| aagcttcgct ttcttcggct caacaataac agtctcaccg gaccaattcc catgtcattg | 900 |
| actaatatca tgacccttca agttttggat ctgtcgaaca accgattatc cggatctgtt | 960 |
| cctgataatg gttccttctc gctcttcact cccatcagtt ttgctaacaa cttggatcta | 1020 |
| tgcggcccag ttactagccg tccttgtcct ggatctcccc cgtttttctcc tccaccacct | 1080 |
| tttataccac ctcccatagt tcctacacca ggtgggtata gtgctactgg agccattgcg | 1140 |
| ggaggagttg ctgctggtgc tgctttacta tttgctgccc ctgctttagc ttttgcttgg | 1200 |
| tggcgtagaa gaaaacctca agaattcttc tttgatgttc ctgccgaaga ggaccctgag | 1260 |
| gttcacttgg ggcagcttaa gcggttctct ctacgggaac ttcaagtagc aactgatagc | 1320 |
| ttcagcaaca agaacatttt gggccgaggt gggttcggaa aagtctacaa aggccgtctt | 1380 |
| gctgatggaa cacttgttgc agtcaaacgg cttaaagaag agcgaacccc aggtggcgag | 1440 |
| ctccagtttc agacagaagt ggagatgata agcatggccg ttcacagaaa tctcctcagg | 1500 |
| ctacgcggtt tctgtatgac ccctaccgag agattgcttg tttatcctta catggctaat | 1560 |
| ggaagtgtcg cttcctgttt gagagaacgt ccaccatcac agttgcctct agcctggtca | 1620 |
| ataagacagc aaatcgcgct aggatcagcg aggggtttgt cttatcttca tgatcattgc | 1680 |
| gaccccaaaa ttattcaccg tgatgtgaaa gctgctaata ttctgttgga cgaggaattt | 1740 |
| gaggcggtgg taggtgattt cgggttagct agacttatgg actataaaga tactcatgtc | 1800 |

-continued

```
acaacggctg tgcgtgggac tattggacac attgctcctg agtatctctc aactggaaaa   1860
tcttcagaga aaactgatgt ttttggctac gggatcatgc ttttggaact gattacaggt   1920
cagagagctt ttgatcttgc aagactggcg aatgacgatg acgttatgct cctagattgg   1980
gtgaaagggc ttttgaagga gaagaagctg agatgcttg tggatcctga cctgcaaagc    2040
aattacacag aagcagaagt agaacagctc atacaagtgg ctcttctctg cacacagagc   2100
tcacctatgg aacgacctaa gatgtctgag gttgttcgaa tgcttgaagg tgacggttta   2160
gcggagaaat gggacgagtg gcagaaagtg gaagttctca ggcaagaagt ggagctctct   2220
tctcacccca cctctgactg gatccttgat tcgactgata atcttcatgc tatggagttg   2280
tctggtccaa gataaacgac attgtaattt gcctaacaga aagagaaag aacagagaaa    2340
tattaagaga atcacttctc tgtattcttt atttctttgg tagaaaaata atgtagtctc   2400
taatcaaatc ttattccatc tatcagcatt cttcattcat ttcttgtgaa aaccaaggcc   2460
tttaaattaa acataatcac aaacaccaag ttctatacat tacatatgtc ttccactgga   2520
taaagaggaa gaaaaggcta ttccaaaaaa catttttgagc tctttgttcc gcaagagaag   2580
gaacagcaca agtgaaacac actgaaaaac accaagcttg cattataaca tatgcaggta   2640
agaatcacga atcatgggcg ggtcttgtat tgtctgagaa cgaatgagag ccagatgagg   2700
gatcatgctt ctgcgatgtg aagagattag ggtatgagta atagggatca tcttccattg   2760
aaggcagtct catttgctga tggtcctggt cagggctgag tctgtcaagt ggtgaagtct   2820
ctggcctttg gagctctggc agatcgccat agctgctgac tgatgagttc tgatgatcaa   2880
actgcggttt ctccattgac gggaatctat gtggtgtaag atcgtcatag ttgctgcctg   2940
atgagttctg atgatcaaac tgcggttttct ccaatgacga gaatctctgt ggtgtaagat   3000
cgtcatagtt gctgcctgat gagttctgat gatcaaactg tggttttttcc attgaatgga   3060
atctctgtgg ggtaagatcg ccatagctac tgaatgatga gttctgacga tcaaactgcg   3120
gttttttccat tgaagagtgt gtctgtggct gttggttgtt ctgctcagag ttgaaaagtg   3180
acgaagtttc tgctctctgg agctctgtaa gatctccgct actgctggcc gaagaattct   3240
gatgatcaaa ttgaaggttt cccattgagg gagcatggaa agggttctca gacggacttt   3300
ctggatactg atcagaagtc ttcctggtaa gctcgttgat tctgagttgt gccaggcttg   3360
cagctgagcg ggcagctgat gctgcacgtt ctgctgagtc agcagcagct tgagcagcca   3420
ttaagacatc ctgcaagtct ccatcggata tttccttgg a                        3461
```

<210> SEQ ID NO 21
<211> LENGTH: 628
<212> TYPE: PRT
<213> ORGANISM: Arabidopsis thaliana

<400> SEQUENCE: 21

Met Gly Arg Lys Lys Phe Glu Ala Phe Gly Phe Val Cys Leu Ile Ser
1               5                   10                  15

Leu Leu Leu Leu Phe Asn Ser Leu Trp Leu Ala Ser Ser Asn Met Glu
            20                  25                  30

Gly Asp Ala Leu His Ser Leu Arg Ala Asn Leu Val Asp Pro Asn Asn
        35                  40                  45

Val Leu Gln Ser Trp Asp Pro Thr Leu Val Asn Pro Cys Thr Trp Phe
    50                  55                  60

His Val Thr Cys Asn Asn Glu Asn Ser Val Ile Arg Val Asp Leu Gly
65                  70                  75                  80

Asn Ala Asp Leu Ser Gly Gln Leu Val Pro Gln Leu Gly Gln Leu Lys

```
                       85                  90                  95
Asn Leu Gln Tyr Leu Glu Leu Tyr Ser Asn Asn Ile Thr Gly Pro Val
            100                 105                 110

Pro Ser Asp Leu Gly Asn Leu Thr Asn Leu Val Ser Leu Asp Leu Tyr
        115                 120                 125

Leu Asn Ser Phe Thr Gly Pro Ile Pro Asp Ser Leu Gly Lys Leu Phe
    130                 135                 140

Lys Leu Arg Phe Leu Arg Leu Asn Asn Ser Leu Thr Gly Pro Ile
145                 150                 155                 160

Pro Met Ser Leu Thr Asn Ile Met Thr Leu Gln Val Leu Asp Leu Ser
                165                 170                 175

Asn Asn Arg Leu Ser Gly Ser Val Pro Asp Asn Gly Ser Phe Ser Leu
            180                 185                 190

Phe Thr Pro Ile Ser Phe Ala Asn Asn Leu Asp Leu Cys Gly Pro Val
        195                 200                 205

Thr Ser Arg Pro Cys Pro Gly Ser Pro Pro Phe Ser Pro Pro Pro
    210                 215                 220

Phe Ile Pro Pro Pro Ile Val Pro Thr Pro Gly Gly Tyr Ser Ala Thr
225                 230                 235                 240

Gly Ala Ile Ala Gly Gly Val Ala Ala Gly Ala Ala Leu Leu Phe Ala
                245                 250                 255

Ala Pro Ala Leu Ala Phe Ala Trp Trp Arg Arg Lys Pro Gln Glu
            260                 265                 270

Phe Phe Phe Asp Val Pro Ala Glu Glu Asp Pro Glu Val His Leu Gly
        275                 280                 285

Gln Leu Lys Arg Phe Ser Leu Arg Glu Leu Gln Val Ala Thr Asp Ser
    290                 295                 300

Phe Ser Asn Lys Asn Ile Leu Gly Arg Gly Gly Phe Gly Lys Val Tyr
305                 310                 315                 320

Lys Gly Arg Leu Ala Asp Gly Thr Leu Val Ala Val Lys Arg Leu Lys
                325                 330                 335

Glu Glu Arg Thr Pro Gly Gly Glu Leu Gln Phe Gln Thr Glu Val Glu
            340                 345                 350

Met Ile Ser Met Ala Val His Arg Asn Leu Leu Arg Leu Arg Gly Phe
        355                 360                 365

Cys Met Thr Pro Thr Glu Arg Leu Leu Val Tyr Pro Tyr Met Ala Asn
    370                 375                 380

Gly Ser Val Ala Ser Cys Leu Arg Glu Arg Pro Pro Ser Gln Leu Pro
385                 390                 395                 400

Leu Ala Trp Ser Ile Arg Gln Gln Ile Ala Leu Gly Ser Ala Arg Gly
                405                 410                 415

Leu Ser Tyr Leu His Asp His Cys Asp Pro Lys Ile Ile His Arg Asp
            420                 425                 430

Val Lys Ala Ala Asn Ile Leu Leu Asp Glu Glu Phe Glu Ala Val Val
        435                 440                 445

Gly Asp Phe Gly Leu Ala Arg Leu Met Asp Tyr Lys Asp Thr His Val
    450                 455                 460

Thr Thr Ala Val Arg Gly Thr Ile Gly His Ile Ala Pro Glu Tyr Leu
465                 470                 475                 480

Ser Thr Gly Lys Ser Ser Glu Lys Thr Asp Val Phe Gly Tyr Gly Ile
                485                 490                 495

Met Leu Leu Glu Leu Ile Thr Gly Gln Arg Ala Phe Asp Leu Ala Arg
            500                 505                 510
```

```
Leu Ala Asn Asp Asp Val Met Leu Leu Asp Trp Val Lys Gly Leu
        515                 520                 525
Leu Lys Glu Lys Lys Leu Glu Met Leu Val Asp Pro Asp Leu Gln Ser
    530                 535                 540
Asn Tyr Thr Glu Ala Glu Val Glu Gln Leu Ile Gln Val Ala Leu Leu
545                 550                 555                 560
Cys Thr Gln Ser Ser Pro Met Glu Arg Pro Lys Met Ser Glu Val Val
                565                 570                 575
Arg Met Leu Glu Gly Asp Gly Leu Ala Glu Lys Trp Asp Glu Trp Gln
            580                 585                 590
Lys Val Glu Val Leu Arg Gln Glu Val Glu Leu Ser Ser His Pro Thr
        595                 600                 605
Ser Asp Trp Ile Leu Asp Ser Thr Asp Asn Leu His Ala Met Glu Leu
    610                 615                 620
Ser Gly Pro Arg
625

<210> SEQ ID NO 22
<211> LENGTH: 2573
<212> TYPE: DNA
<213> ORGANISM: Arabidopsis thaliana

<400> SEQUENCE: 22
accaaagtca taaaaatgat ataaaatata aaccaagaag cactattagt atcactcatc      60
actcaatagc tttttttttt tcagatctct aggaaaattt ctcagacttt cagagcattt     120
tggtgctttt gttttgcttg gtttctcggg aaaattctct tcacactttt agagttttct     180
ctctcttctc tatctcttgt cacagctcgt ttagcattca ttctcttaat cgtttcttca     240
ttcaaaaatt ctctctttct aagctgagta acttgcaagt cgtcattttt caattggggt     300
cttctccttt ttacttcctt tgaattgaaa tcacagagaa agagaggttc cattgctgga     360
aaatggattg ctcaaattag tttctgtgtc taaataaaga cagagaagaa gaaaagtaga     420
caaaagctaa gtttttttt cagatatggg agagagaaaa atgagttggt gggttctttg      480
aaacttgttt ttgttcagac caaagttgat tgctttaaga agggatatgg aaggtgtgag     540
atttgtggtg tggagattag gatttctggt ttttgtatgg ttctttgata tctcttctgc     600
tacactttct cctactggtg taaactatga agtgacagct ttggttgctg tgaagaatga     660
attgaatgat ccgtacaaag ttcttgagaa ttgggatgtg aattcagttg atccttgtag     720
ctggagaatg gtttcttgca ctgatggcta tgtctcttca ctggatcttc ctagccaaag     780
cttgtctggt acattgtctc ctagaatcgg aaacctcacc tatttacaat cagtggtgtt     840
gcaaaacaat gcaatcactg gtccaattcc ggaaacgatt gggaggttgg agaagcttca     900
gtcacttgat ctttcgaaca attcattcac cggggagata ccggcctcac ttggagaact     960
caagaacttg aattacttgc ggttaaacaa taacagtctt ataggaactt gccctgagtc    1020
tctatccaag attgagggac tcactctagt cgacatttcg tataacaatc ttagtggttc    1080
gctgccaaaa gttctgcca gaactttcaa ggtaattggt aatgcgttaa tctgtggccc     1140
aaaagctgtt tcaaactgtt ctgctgttcc cgagcctctc acgcttccac aagatggtcc    1200
agatgaatca ggaactcgta ccaatggcca tcacgttgct cttgcatttg ccgcaagctt    1260
cagtgcagca ttttttgttt tctttacaag cggaatgttt ctttggtgga gatatcgccg    1320
taacaagcaa atatttttg acgttaatga acaatatgat ccagaagtga gtttagggca    1380
cttgaagagg tatacattca aagagcttag atctgccacc aatcatttca actcgaagaa    1440
```

-continued

```
cattctcgga agaggcggat acgggattgt gtacaaagga cacttaaacg atggaacttt    1500
ggtggctgtc aaacgtctca aggactgtaa cattgcgggt ggagaagtcc agtttcagac    1560
agaagtagag actataagtt tggctcttca tcgcaatctc ctccggctcc gcggtttctg    1620
tagtagcaac caggagagaa ttttagtcta cccttacatg ccaaatggga gtgtcgcatc    1680
acgcttaaaa gataatatcc gtggagagcc agcattagac tggtcgagaa ggaagaagat    1740
agcggttggg acagcgagag gactagttta cctacacgag caatgtgacc cgaagattat    1800
acaccgcgat gtgaaagcag ctaacattct gttagatgag gacttcgaag cagttgttgg    1860
tgattttggg ttagctaagc ttctagacca tagagactct catgtcacaa ctgcagtccg    1920
tggaactgtt ggccacattg cacctgagta cttatccacg ggtcagtcct cagagaagac    1980
tgatgtcttt ggctttggca tacttctcct tgagctcatt actggtcaga agctcttga    2040 ttttggcaga tccgcacacc agaaaggtgt aatgcttgac tgggtgaaga agctgcacca    2100
agaagggaaa ctaaagcagt taatagacaa agatctaaat gacaagttcg atagagtaga    2160
actcgaagaa atcgttcaag ttgcgctact ctgcactcaa ttcaatccat ctcatcgacc    2220
gaaaatgtca gaagttatga agatgcttga aggtgacggt ttggctgaga gatgggaagc    2280
gacgcagaac ggtactggtg agcatcagcc accgccattg ccaccgggga tggtgagttc    2340
ttcgccgcgt gtgaggtatt actcggatta tattcaggaa tcgtctcttg tagtagaagc    2400
cattgagctc tcgggtcctc gatgattatg actcactgtt tttaaaaaat ttcttttctt    2460
gggtttgttt tttatttgtc gttttataat gttgatatag atgtgaagtt gagtgtgtaa    2520
tttttatgta aagaaaaaat atgaaatgca aaagaaaatg ttgattagcc tgc           2573
```

<210> SEQ ID NO 23
<211> LENGTH: 632
<212> TYPE: PRT
<213> ORGANISM: Arabidopsis thaliana

<400> SEQUENCE: 23

```
Met Glu Gly Val Arg Phe Val Val Trp Arg Leu Gly Phe Leu Val Phe
1               5                   10                  15

Val Trp Phe Phe Asp Ile Ser Ser Ala Thr Leu Ser Pro Thr Gly Val
                20                  25                  30

Asn Tyr Glu Val Thr Ala Leu Val Ala Val Lys Asn Glu Leu Asn Asp
            35                  40                  45

Pro Tyr Lys Val Leu Glu Asn Trp Asp Val Asn Ser Val Asp Pro Cys
        50                  55                  60

Ser Trp Arg Met Val Ser Cys Thr Asp Gly Tyr Val Ser Ser Leu Asp
65                  70                  75                  80

Leu Pro Ser Gln Ser Leu Ser Gly Thr Leu Ser Pro Arg Ile Gly Asn
                85                  90                  95

Leu Thr Tyr Leu Gln Ser Val Val Leu Gln Asn Asn Ala Ile Thr Gly
            100                 105                 110

Pro Ile Pro Glu Thr Ile Gly Arg Leu Glu Lys Leu Gln Ser Leu Asp
        115                 120                 125

Leu Ser Asn Asn Ser Phe Thr Gly Glu Ile Pro Ala Ser Leu Gly Glu
    130                 135                 140

Leu Lys Asn Leu Asn Tyr Leu Arg Leu Asn Asn Ser Leu Ile Gly
145                 150                 155                 160

Thr Cys Pro Glu Ser Leu Ser Lys Ile Glu Gly Leu Thr Leu Val Asp
                165                 170                 175

Ile Ser Tyr Asn Asn Leu Ser Gly Ser Leu Pro Lys Val Ser Ala Arg
```

```
                   180                 185                 190
Thr Phe Lys Val Ile Gly Asn Ala Leu Ile Cys Gly Pro Lys Ala Val
            195                 200                 205

Ser Asn Cys Ser Ala Val Pro Glu Pro Leu Thr Leu Pro Gln Asp Gly
    210                 215                 220

Pro Asp Glu Ser Gly Thr Arg Thr Asn Gly His His Val Ala Leu Ala
225                 230                 235                 240

Phe Ala Ala Ser Phe Ser Ala Ala Phe Phe Val Phe Phe Thr Ser Gly
                245                 250                 255

Met Phe Leu Trp Trp Arg Tyr Arg Arg Asn Lys Gln Ile Phe Phe Asp
            260                 265                 270

Val Asn Glu Gln Tyr Asp Pro Glu Val Ser Leu Gly His Leu Lys Arg
    275                 280                 285

Tyr Thr Phe Lys Glu Leu Arg Ser Ala Thr Asn His Phe Asn Ser Lys
    290                 295                 300

Asn Ile Leu Gly Arg Gly Gly Tyr Gly Ile Val Tyr Lys Gly His Leu
305                 310                 315                 320

Asn Asp Gly Thr Leu Val Ala Val Lys Arg Leu Lys Asp Cys Asn Ile
                325                 330                 335

Ala Gly Gly Glu Val Gln Phe Gln Thr Glu Val Glu Thr Ile Ser Leu
            340                 345                 350

Ala Leu His Arg Asn Leu Leu Arg Leu Arg Gly Phe Cys Ser Ser Asn
            355                 360                 365

Gln Glu Arg Ile Leu Val Tyr Pro Tyr Met Pro Asn Gly Ser Val Ala
    370                 375                 380

Ser Arg Leu Lys Asp Asn Ile Arg Gly Glu Pro Ala Leu Asp Trp Ser
385                 390                 395                 400

Arg Arg Lys Lys Ile Ala Val Gly Thr Ala Arg Gly Leu Val Tyr Leu
                405                 410                 415

His Glu Gln Cys Asp Pro Lys Ile Ile His Arg Asp Val Lys Ala Ala
            420                 425                 430

Asn Ile Leu Leu Asp Glu Asp Phe Glu Ala Val Val Gly Asp Phe Gly
            435                 440                 445

Leu Ala Lys Leu Leu Asp His Arg Asp Ser His Val Thr Thr Ala Val
    450                 455                 460

Arg Gly Thr Val Gly His Ile Ala Pro Glu Tyr Leu Ser Thr Gly Gln
465                 470                 475                 480

Ser Ser Glu Lys Thr Asp Val Phe Gly Phe Gly Ile Leu Leu Leu Glu
                485                 490                 495

Leu Ile Thr Gly Gln Lys Ala Leu Asp Phe Gly Arg Ser Ala His Gln
            500                 505                 510

Lys Gly Val Met Leu Asp Trp Val Lys Lys Leu His Gln Glu Gly Lys
    515                 520                 525

Leu Lys Gln Leu Ile Asp Lys Asp Leu Asn Asp Lys Phe Asp Arg Val
    530                 535                 540

Glu Leu Glu Glu Ile Val Gln Val Ala Leu Leu Cys Thr Gln Phe Asn
545                 550                 555                 560

Pro Ser His Arg Pro Lys Met Ser Glu Val Met Lys Met Leu Glu Gly
                565                 570                 575

Asp Gly Leu Ala Glu Arg Trp Glu Ala Thr Gln Asn Gly Thr Gly Glu
            580                 585                 590

His Gln Pro Pro Leu Pro Pro Gly Met Val Ser Ser Pro Arg
    595                 600                 605
```

Val Arg Tyr Tyr Ser Asp Tyr Ile Gln Glu Ser Ser Leu Val Val Glu
    610                 615                 620

Ala Ile Glu Leu Ser Gly Pro Arg
625                 630

<210> SEQ ID NO 24
<211> LENGTH: 2565
<212> TYPE: DNA
<213> ORGANISM: Arabidopsis thaliana

<400> SEQUENCE: 24

| | | | | | |
|---|---|---|---|---|---|
| aacaacacac | taatcatagt | ttctctggca | ggcttgttgt | tgcggcttaa | taaaaagctc | 60 |
| ttttgttatt | attacttcac | gtagattttc | cccaaaaagc | tcttattttt | ttgtttaaaa | 120 |
| aaaaaagttt | catctttatt | caacttttgt | tttacagtgt | gtgtgtgaga | gagagagtgt | 180 |
| ggtttgattg | aggaaagacg | acgacgagaa | cgccggagaa | ttaggatttt | gattttattt | 240 |
| tttactcttt | gtttgtttta | atgctaatgg | gttttttaaa | gggttatcga | aaaaatgagt | 300 |
| gagtttgtgt | tgaggttgtc | tctgtaaagt | gttaatggtg | gtgattttcg | gaagttaggg | 360 |
| ttttctcgga | tctgaagaga | tcaaatcaag | attcgaaatt | tagcattgtt | gtttgaaatg | 420 |
| gagtcgagtt | atgtggtgtt | tatcttactt | tcactgatct | tacttccgaa | tcattcactg | 480 |
| tggcttgctt | ctgctaattt | ggaaggtgat | gctttgcata | ctttgagggt | tactctagtt | 540 |
| gatccaaaca | atgtcttgca | gagctgggat | cctacgctag | tgaatccttg | cacatggttc | 600 |
| catgtcactt | gcaacaacga | gaacagtgtc | ataagagttg | atttggggaa | tgcagagtta | 660 |
| tctggccatt | tagttccaga | gcttggtgtg | ctcaagaatt | tgcagtattt | ggagctttac | 720 |
| agtaacaaca | taactggccc | gattcctagt | aatcttggaa | atctgacaaa | cttagtgagt | 780 |
| ttggatcttt | acttaaacag | cttctccggt | cctattccgg | aatcattggg | aaagctttca | 840 |
| aagctgagat | tctcccggct | taacaacaac | agtctcactg | ggtcaattcc | tatgtcactg | 900 |
| accaatatta | ctacccttca | agtgttagat | ctatcaaata | acagactctc | tggttcagtt | 960 |
| cctgacaatg | gctccttctc | actcttcaca | cccatcagtt | ttgctaataa | cttagaccta | 1020 |
| tgtggacctg | ttacaagtca | cccatgtcct | ggatctcccc | cgttttctcc | tccaccacct | 1080 |
| tttattcaac | ctcccccagt | ttccaccccg | agtgggtatg | gtataactgg | agcaatagct | 1140 |
| ggtggagttg | ctgcaggtgc | tgctttgctc | tttgctgctc | ctgcaatagc | ctttgcttgg | 1200 |
| tggcgacgaa | gaaagccact | agatattttc | ttcgatgtcc | ctgccgaaga | agatccagaa | 1260 |
| gttcatctgg | gacagctcaa | gaggttttct | ttgcgggagc | tacaagtggc | gagtgatggg | 1320 |
| tttagtaaca | agaacatttt | gggcagaggt | gggtttggga | agtctacaa | gggacgcttg | 1380 |
| gcagacggaa | ctcttgttgc | tgtcaagaga | ctgaaggaag | agcgaactcc | aggtggagag | 1440 |
| ctccagtttc | aaacagaagt | agagatgata | agtatggcag | ttcatcgaaa | cctgttgaga | 1500 |
| ttacgaggtt | tctgtatgac | accgaccgag | agattgcttg | tgtatcctta | catggccaat | 1560 |
| ggaagtgttg | cttcgtgtct | cagagagagg | ccaccgtcac | aacctccgct | tgattggcca | 1620 |
| acgcggaaga | gaatcgcgct | aggctcagct | cgaggtttgt | cttacctaca | tgatcactgc | 1680 |
| gatccgaaga | tcattcaccg | tgacgtaaaa | gcagcaaaca | tcctcttaga | cgaagaattc | 1740 |
| gaagcggttg | ttggagattt | cgggttggca | agctaatgg | actataaaga | cactcacgtg | 1800 |
| acaacagcag | tccgtggcac | catcggtcac | atcgctccag | aatatctctc | aaccggaaaa | 1860 |
| tcttcagaga | aaaccgacgt | tttcggatac | ggaatcatgt | ttctagaact | aatcacagga | 1920 |
| caaagagctt | tcgatctcgc | tcggctagct | aacgacgacg | acgtcatgtt | acttgactgg | 1980 |

-continued

```
gtgaaaggat tgttgaagga gaagaagcta gagatgttag tggatccaga tcttcaaaca    2040
aactacgagg agagagaact ggaacaagtg atacaagtgg cgttgctatg cacgcaagga    2100
tcaccaatgg aaagaccaaa gatgtctgaa gttgtaagga tgctggaagg agatgggctt    2160
gcggagaaat gggacgaatg gcaaaaagtt gagattttga gggaagagat tgatttgagt    2220
cctaatccta actctgattg gattcttgat tctacttaca atttgcacgc cgttgagtta    2280
tctggtccaa ggtaaaaaaa aaaacataa aattattgaa caataacaaa ttttacaagg    2340
taggtagttt ttttacccgt aagttttcgt tttttttaat tgttaatgta aaatgaaatc    2400
tagcattcaa agatttgtga ttttgtgcta tggttcgatt aaaagggaaa aaaattgtaa    2460
tctaaagatt tgtgtaagat tactgtctat tgtatgaagt atgaactatg aacacaatat    2520
atgtacatcc aaaatacgt taaactaact ccgctgtttt gctac                    2565
```

<210> SEQ ID NO 25
<211> LENGTH: 625
<212> TYPE: PRT
<213> ORGANISM: Arabidopsis thaliana

<400> SEQUENCE: 25

```
Met Glu Ser Ser Tyr Val Val Phe Ile Leu Leu Ser Leu Ile Leu Leu
1               5                   10                  15

Pro Asn His Ser Leu Trp Leu Ala Ser Ala Asn Leu Glu Gly Asp Ala
            20                  25                  30

Leu His Thr Leu Arg Val Thr Leu Val Asp Pro Asn Asn Val Leu Gln
        35                  40                  45

Ser Trp Asp Pro Thr Leu Val Asn Pro Cys Thr Trp Phe His Val Thr
    50                  55                  60

Cys Asn Asn Glu Asn Ser Val Ile Arg Val Asp Leu Gly Asn Ala Glu
65                  70                  75                  80

Leu Ser Gly His Leu Val Pro Glu Leu Gly Val Leu Lys Asn Leu Gln
                85                  90                  95

Tyr Leu Glu Leu Tyr Ser Asn Asn Ile Thr Gly Pro Ile Pro Ser Asn
            100                 105                 110

Leu Gly Asn Leu Thr Asn Leu Val Ser Leu Asp Leu Tyr Leu Asn Ser
        115                 120                 125

Phe Ser Gly Pro Ile Pro Glu Ser Leu Gly Lys Leu Ser Lys Leu Arg
    130                 135                 140

Phe Leu Arg Leu Asn Asn Asn Ser Leu Thr Gly Ser Ile Pro Met Ser
145                 150                 155                 160

Leu Thr Asn Ile Thr Thr Leu Gln Val Leu Asp Leu Ser Asn Asn Arg
                165                 170                 175

Leu Ser Gly Ser Val Pro Asp Asn Gly Ser Phe Ser Leu Phe Thr Pro
            180                 185                 190

Ile Ser Phe Ala Asn Asn Leu Asp Leu Cys Gly Pro Val Thr Ser His
        195                 200                 205

Pro Cys Pro Gly Ser Pro Pro Phe Ser Pro Pro Pro Phe Ile Gln
    210                 215                 220

Pro Pro Pro Val Ser Thr Pro Ser Gly Tyr Gly Ile Thr Gly Ala Ile
225                 230                 235                 240

Ala Gly Gly Val Ala Ala Gly Ala Ala Leu Leu Phe Ala Ala Pro Ala
                245                 250                 255

Ile Ala Phe Ala Trp Trp Arg Arg Arg Lys Pro Leu Asp Ile Phe Phe
            260                 265                 270

Asp Val Pro Ala Glu Glu Asp Pro Glu Val His Leu Gly Gln Leu Lys
```

```
                275                 280                 285
Arg Phe Ser Leu Arg Glu Leu Gln Val Ala Ser Asp Gly Phe Ser Asn
290                 295                 300
Lys Asn Ile Leu Gly Arg Gly Phe Gly Lys Val Tyr Lys Gly Arg
305                 310                 315                 320
Leu Ala Asp Gly Thr Leu Val Ala Val Lys Arg Leu Lys Glu Glu Arg
                325                 330                 335
Thr Pro Gly Gly Glu Leu Gln Phe Gln Thr Glu Val Glu Met Ile Ser
                340                 345                 350
Met Ala Val His Arg Asn Leu Leu Arg Leu Arg Gly Phe Cys Met Thr
                355                 360                 365
Pro Thr Glu Arg Leu Leu Val Tyr Pro Tyr Met Ala Asn Gly Ser Val
                370                 375                 380
Ala Ser Cys Leu Arg Glu Arg Pro Pro Ser Gln Pro Pro Leu Asp Trp
385                 390                 395                 400
Pro Thr Arg Lys Arg Ile Ala Leu Gly Ser Ala Arg Gly Leu Ser Tyr
                405                 410                 415
Leu His Asp His Cys Asp Pro Lys Ile Ile His Arg Asp Val Lys Ala
                420                 425                 430
Ala Asn Ile Leu Leu Asp Glu Glu Phe Glu Ala Val Val Gly Asp Phe
                435                 440                 445
Gly Leu Ala Lys Leu Met Asp Tyr Lys Asp Thr His Val Thr Thr Ala
450                 455                 460
Val Arg Gly Thr Ile Gly His Ile Ala Pro Glu Tyr Leu Ser Thr Gly
465                 470                 475                 480
Lys Ser Ser Glu Lys Thr Asp Val Phe Gly Tyr Gly Ile Met Leu Leu
                485                 490                 495
Glu Leu Ile Thr Gly Gln Arg Ala Phe Asp Leu Ala Arg Leu Ala Asn
                500                 505                 510
Asp Asp Asp Val Met Leu Leu Asp Trp Val Lys Gly Leu Leu Lys Glu
                515                 520                 525
Lys Lys Leu Glu Met Leu Val Asp Pro Asp Leu Gln Thr Asn Tyr Glu
                530                 535                 540
Glu Arg Glu Leu Glu Gln Val Ile Gln Val Ala Leu Leu Cys Thr Gln
545                 550                 555                 560
Gly Ser Pro Met Glu Arg Pro Lys Met Ser Glu Val Val Arg Met Leu
                565                 570                 575
Glu Gly Asp Gly Leu Ala Glu Lys Trp Asp Glu Trp Gln Lys Val Glu
                580                 585                 590
Ile Leu Arg Glu Glu Ile Asp Leu Ser Pro Asn Pro Asn Ser Asp Trp
                595                 600                 605
Ile Leu Asp Ser Thr Tyr Asn Leu His Ala Val Glu Leu Ser Gly Pro
                610                 615                 620
Arg
625

<210> SEQ ID NO 26
<211> LENGTH: 2219
<212> TYPE: DNA
<213> ORGANISM: Arabidopsis thaliana

<400> SEQUENCE: 26
ttcgaaactt ggtcaaatgt cgaatacgcg ttacaaagaa caaacctttc tctttatttc    60
gtttgtcttc gtcaacggct gaatcaacca aatggtccct ggaattaata aacctctaat   120
```

-continued

| | |
|---|---|
| aataatggct tgcttttac tctgatgaca agttcaaaaa tggaacaaag atcactcctt | 180 |
| tgcttccttt atctgctcct actattcaat ttcactctca gagtcgctgg aaacgctgaa | 240 |
| ggtgatgctt tgactcagct gaaaaacagt ttgtcatcag gtgaccctgc aaacaatgta | 300 |
| ctccaaagct gggatgctac tcttgttact ccatgtactt ggtttcatgt tacttgcaat | 360 |
| cctgagaata aagttactcg tgttgacctt gggaatgcaa aactatctgg aaagttggtt | 420 |
| ccagaacttg gtcagctttt aaacttgcag tacttggagc tttatagcaa taacattaca | 480 |
| ggggagatac ctgaggagct tggcgacttg gtggaactag taagcttgga tctttacgca | 540 |
| aacagcataa gcggtcccat cccttcgtct cttggcaaac taggaaaact ccggttcttg | 600 |
| cgtcttaaca caatagctt atcaggggaa attccaatga ctttgacttc tgtgcagctg | 660 |
| caagttctgg atatctcaaa caatcggctc agtggagata ttcctgttaa tggttctttt | 720 |
| tcgctcttca ctcctatcag ttttgcgaat aatagcttaa cggatcttcc cgaacctccg | 780 |
| cctacttcta cctctcctac gccaccacca ccttcagggg ggcaaatgac tgcagcaata | 840 |
| gcaggggag ttgctgcagg tgcagcactt ctatttgctg ttccagccat tgcgtttgct | 900 |
| tggtggctca agagaaaacc acaggaccac tttttttgatg tacctgctga agaagaccca | 960 |
| gaggttcatt taggacaact caaaaggttt accttgcgtg aactgttagt tgctactgat | 1020 |
| aactttagca ataaaaatgt attgggtaga ggtggtttg gtaaagtgta taaaggacgt | 1080 |
| ttagccgatg gcaatctagt ggctgtcaaa aggctaaaag aagaacgtac caagggtggg | 1140 |
| gaactgcagt ttcaaaccga agttgagatg atcagtatgg ccgttcatag gaacttgctt | 1200 |
| cggcttcgtg gcttttgcat gactccaact gaaagattac ttgtttatcc ctacatggct | 1260 |
| aatggaagtg ttgcttcttg tttaagagag cgtcctgaag gcaatccagc acttgattgg | 1320 |
| ccaaaaagaa agcatattgc tctgggatca gcaaggggc ttgcgtattt acatgatcat | 1380 |
| tgcgaccaaa aaatcattca ccgggatgtt aaagctgcta atatattgtt agatgaagag | 1440 |
| tttgaagctg ttgttggaga ttttgggctc gcaaaattaa tgaattataa tgactcccat | 1500 |
| gtgacaactg ctgtacgcgg tacaattggc catatagcgc ccgagtacct ctcgacagga | 1560 |
| aaatcttctg agaagactga tgtttttggg tacggggtca tgcttctcga gctcatcact | 1620 |
| ggacaaaagg ctttcgatct tgctcggctt gcaaatgatg atgatatcat gttactcgac | 1680 |
| tgggtgaaag aggttttgaa agagaagaag ttggaaagcc ttgtggatgc agaactcgaa | 1740 |
| ggaaagtacg tggaaacaga agtggagcag ctgatacaaa tggctctgct ctgcactcaa | 1800 |
| agttctgcaa tggaacgtcc aaagatgtca gaagtagtga aatgctgga aggagatggt | 1860 |
| ttagctgaga gatgggaaga atggcaaaag gaggagatgc aatacatga ttttaactat | 1920 |
| caagcctatc ctcatgctgg cactgactgg ctcatcccct attccaattc ccttatcgaa | 1980 |
| aacgattacc cctcgggtcc aagataacct tttagaaagg gtcttttctt gtgggttctt | 2040 |
| caacaagtat atatatagat tggtgaagtt ttaagatgca aaaaaaccc atgcactttt | 2100 |
| gaatatcaac tcctctataa gtagttttgt gtctcttgac gaataaagaa tatcattact | 2160 |
| ccacttgagc ataaagcaag atgtttacca accaataaag cttaacaata tttttccgt | 2219 |

<210> SEQ ID NO 27
<211> LENGTH: 620
<212> TYPE: PRT
<213> ORGANISM: Arabidopsis thaliana

<400> SEQUENCE: 27

Met Thr Ser Ser Lys Met Glu Gln Arg Ser Leu Leu Cys Phe Leu Tyr
1               5                   10                  15

```
Leu Leu Leu Leu Phe Asn Phe Thr Leu Arg Val Ala Gly Asn Ala Glu
            20                  25                  30

Gly Asp Ala Leu Thr Gln Leu Lys Asn Ser Leu Ser Ser Gly Asp Pro
        35                  40                  45

Ala Asn Asn Val Leu Gln Ser Trp Asp Ala Thr Leu Val Thr Pro Cys
50                  55                  60

Thr Trp Phe His Val Thr Cys Asn Pro Glu Asn Lys Val Thr Arg Val
65                  70                  75                  80

Asp Leu Gly Asn Ala Lys Leu Ser Gly Lys Leu Val Pro Glu Leu Gly
                85                  90                  95

Gln Leu Leu Asn Leu Gln Tyr Leu Glu Leu Tyr Ser Asn Asn Ile Thr
            100                 105                 110

Gly Glu Ile Pro Glu Glu Leu Gly Asp Leu Val Glu Leu Val Ser Leu
            115                 120                 125

Asp Leu Tyr Ala Asn Ser Ile Ser Gly Pro Ile Pro Ser Ser Leu Gly
130                 135                 140

Lys Leu Gly Lys Leu Arg Phe Leu Arg Leu Asn Asn Asn Ser Leu Ser
145                 150                 155                 160

Gly Glu Ile Pro Met Thr Leu Thr Ser Val Gln Leu Gln Val Leu Asp
                165                 170                 175

Ile Ser Asn Asn Arg Leu Ser Gly Asp Ile Pro Val Asn Gly Ser Phe
            180                 185                 190

Ser Leu Phe Thr Pro Ile Ser Phe Ala Asn Asn Ser Leu Thr Asp Leu
            195                 200                 205

Pro Glu Pro Pro Pro Thr Ser Thr Ser Pro Thr Pro Pro Pro Pro Ser
210                 215                 220

Gly Gly Gln Met Thr Ala Ala Ile Ala Gly Val Ala Ala Gly Ala
225                 230                 235                 240

Ala Leu Leu Phe Ala Val Pro Ala Ile Ala Phe Ala Trp Trp Leu Arg
            245                 250                 255

Arg Lys Pro Gln Asp His Phe Phe Asp Val Pro Ala Glu Glu Asp Pro
            260                 265                 270

Glu Val His Leu Gly Gln Leu Lys Arg Phe Thr Leu Arg Glu Leu Leu
            275                 280                 285

Val Ala Thr Asp Asn Phe Ser Asn Lys Asn Val Leu Gly Arg Gly Gly
            290                 295                 300

Phe Gly Lys Val Tyr Lys Gly Arg Leu Ala Asp Gly Asn Leu Val Ala
305                 310                 315                 320

Val Lys Arg Leu Lys Glu Glu Arg Thr Lys Gly Gly Glu Leu Gln Phe
                325                 330                 335

Gln Thr Glu Val Glu Met Ile Ser Met Ala Val His Arg Asn Leu Leu
            340                 345                 350

Arg Leu Arg Gly Phe Cys Met Thr Pro Thr Glu Arg Leu Leu Val Tyr
            355                 360                 365

Pro Tyr Met Ala Asn Gly Ser Val Ala Ser Cys Leu Arg Glu Arg Pro
370                 375                 380

Glu Gly Asn Pro Ala Leu Asp Trp Pro Lys Arg Lys His Ile Ala Leu
385                 390                 395                 400

Gly Ser Ala Arg Gly Leu Ala Tyr Leu His Asp His Cys Asp Gln Lys
                405                 410                 415

Ile Ile His Arg Asp Val Lys Ala Ala Asn Ile Leu Leu Asp Glu Glu
            420                 425                 430

Phe Glu Ala Val Val Gly Asp Phe Gly Leu Ala Lys Leu Met Asn Tyr
```

```
                    435               440                 445
Asn Asp Ser His Val Thr Thr Ala Val Arg Gly Thr Ile Gly His Ile
450                     455                 460

Ala Pro Glu Tyr Leu Ser Thr Gly Lys Ser Ser Glu Lys Thr Asp Val
465                     470                 475                 480

Phe Gly Tyr Gly Val Met Leu Leu Glu Leu Ile Thr Gly Gln Lys Ala
                    485                 490                 495

Phe Asp Leu Ala Arg Leu Ala Asn Asp Asp Ile Met Leu Leu Asp
                500                 505                 510

Trp Val Lys Glu Val Leu Lys Glu Lys Leu Glu Ser Leu Val Asp
            515                 520                 525

Ala Glu Leu Glu Gly Lys Tyr Val Glu Thr Glu Val Glu Gln Leu Ile
530                     535                 540

Gln Met Ala Leu Leu Cys Thr Gln Ser Ser Ala Met Glu Arg Pro Lys
545                 550                 555                     560

Met Ser Glu Val Val Arg Met Leu Glu Gly Asp Gly Leu Ala Glu Arg
                    565                 570                 575

Trp Glu Glu Trp Gln Lys Glu Glu Met Pro Ile His Asp Phe Asn Tyr
                580                 585                 590

Gln Ala Tyr Pro His Ala Gly Thr Asp Trp Leu Ile Pro Tyr Ser Asn
                595                 600                 605

Ser Leu Ile Glu Asn Asp Tyr Pro Ser Gly Pro Arg
    610                 615                 620

<210> SEQ ID NO 28
<211> LENGTH: 1985
<212> TYPE: DNA
<213> ORGANISM: Arabidopsis thaliana

<400> SEQUENCE: 28
ggaaaatgga acatggatca tcccgtggct ttatttggct gattctattt ctcgattttg     60
tttccagagt caccggaaaa acacaagttg atgctctcat tgctctaaga agcagtttat    120
catcaggtga ccatacaaac aatatactcc aaagctggaa tgccactcac gttactccat    180
gttcatggtt tcatgttact tgcaatactg aaaacagtgt tactcgtctt gacctgggga    240
gtgctaatct atctggagaa ctggtgccac agcttgctca gcttccaaat ttgcagtact    300
tggaactttt taacaataat attactgggg agatacctga ggagcttggc gacttgatgg    360
aactagtaag cttggacctt tttgcaaaca acataagcgg tcccatccct tcctctcttg    420
gcaaactagg aaaactccgc ttcttgcgtc tttataacaa cagcttatct ggagaaattc    480
caaggtcttt gactgctctg ccgctggatg ttcttgatat ctcaaacaat cggctcagtg    540
gagatattcc tgttaatggt tccttttcgc agttcacttc tatgagtttt gccaataata    600
aattaaggcc gcgacctgca tctccttcac catcaccttc aggaacgtct gcagcaatag    660
tagtgggagt tgctgcgggt gcagcacttc tatttgcgct tgcttggtgg ctgagaagaa    720
aactgcaggg tcactttctt gatgtacctg ctgaagaaga cccagaggtt tatttaggac    780
aatttaaaag gttctccttg cgtgaactgc tagttgctac agaaaatttt agcaaaagaa    840
atgtattggg caaaggacgt tttggtatat tgtataaagg acgtttagct gatgacactc    900
tagtggctgt gaaacggcta aatgaagaac gtaccaaggg tggggaactg cagttttcaaa   960
ccgaagttga tgatcagt atggccgttc ataggaactt gcttcggctt cgtggctttt    1020
gcatgactcc aactgaaaga ttacttgttt atccctacat ggctaatgga agtgttgctt   1080
cttgtttaag agagcgtcct gaaggcaatc cagcccttga ctggccaaaa agaaagcata   1140
```

-continued

```
ttgctctggg atcagcaagg gggctcgcat atttacacga tcattgcgac caaaagatca  1200
ttcacctgga tgtgaaagct gcaaatatac tgttagatga agagtttgaa gctgttgttg  1260
gagattttgg gctagcaaaa ttaatgaatt ataacgactc ccatgtgaca actgctgtac  1320
ggggtacgat tggccatata gcgcccgagt acctctcgac aggaaaatct tctgagaaga  1380
ctgatgtttt tgggtacggg gtcatgcttc tcgagctcat cactggacaa aaggctttcg  1440
atcttgctcg gcttgcaaat gatgatgata tcatgttact cgactgggtg aaagaggttt  1500
tgaaagagaa gaagttggaa agccttgtgg atgcagaact cgaaggaaag tacgtggaaa  1560
cagaagtgga gcagctgata caaatggctc tgctctgcac tcaaagttct gcaatggaac  1620
gtccaaagat gtcagaagta gtgagaatgc tggaaggaga tggtttagct gagagatggg  1680
aagaatggca aaaggaggag atgccaatac atgattttaa ctatcaagcc tatcctcatg  1740
ctggcactga ctggctcatc ccctattcca attcccttat cgaaaacgat tacccctcgg  1800
ggccaagata acctttaga aagggtcatt tcttgtgggt tcttcaacaa gtatatatat  1860
aggtagtgaa gttgtaagaa gcaaaacccc acattcacct ttgaatatca ctactctata  1920
atactaatca tatctactat actttctctc cacttccatt aagcaataaa aactattctt  1980
aaatc                                                              1985
```

<210> SEQ ID NO 29
<211> LENGTH: 601
<212> TYPE: PRT
<213> ORGANISM: Arabidopsis thaliana

<400> SEQUENCE: 29

```
Met Glu His Gly Ser Ser Arg Gly Phe Ile Trp Leu Ile Leu Phe Leu
1               5                   10                  15

Asp Phe Val Ser Arg Val Thr Gly Lys Thr Gln Val Asp Ala Leu Ile
            20                  25                  30

Ala Leu Arg Ser Ser Leu Ser Ser Gly Asp His Thr Asn Asn Ile Leu
        35                  40                  45

Gln Ser Trp Asn Ala Thr His Val Thr Pro Cys Ser Trp Phe His Val
    50                  55                  60

Thr Cys Asn Thr Glu Asn Ser Val Thr Arg Leu Asp Leu Gly Ser Ala
65                  70                  75                  80

Asn Leu Ser Gly Glu Leu Val Pro Gln Leu Ala Gln Leu Pro Asn Leu
                85                  90                  95

Gln Tyr Leu Glu Leu Phe Asn Asn Asn Ile Thr Gly Glu Ile Pro Glu
            100                 105                 110

Glu Leu Gly Asp Leu Met Glu Leu Val Ser Leu Asp Leu Phe Ala Asn
        115                 120                 125

Asn Ile Ser Gly Pro Ile Pro Ser Ser Leu Gly Lys Leu Gly Lys Leu
    130                 135                 140

Arg Phe Leu Arg Leu Tyr Asn Asn Ser Leu Ser Gly Glu Ile Pro Arg
145                 150                 155                 160

Ser Leu Thr Ala Leu Pro Leu Asp Val Leu Asp Ile Ser Asn Asn Arg
                165                 170                 175

Leu Ser Gly Asp Ile Pro Val Asn Gly Ser Phe Ser Gln Phe Thr Ser
            180                 185                 190

Met Ser Phe Ala Asn Asn Lys Leu Arg Pro Arg Pro Ala Ser Pro Ser
        195                 200                 205

Pro Ser Pro Ser Gly Thr Ser Ala Ala Ile Val Val Gly Val Ala Ala
    210                 215                 220
```

Gly Ala Ala Leu Leu Phe Ala Leu Ala Trp Trp Leu Arg Arg Lys Leu
225                 230                 235                 240

Gln Gly His Phe Leu Asp Val Pro Ala Glu Glu Asp Pro Glu Val Tyr
            245                 250                 255

Leu Gly Gln Phe Lys Arg Phe Ser Leu Arg Glu Leu Leu Val Ala Thr
        260                 265                 270

Glu Lys Phe Ser Lys Arg Asn Val Leu Gly Lys Gly Arg Phe Gly Ile
    275                 280                 285

Leu Tyr Lys Gly Arg Leu Ala Asp Asp Thr Leu Val Ala Val Lys Arg
290                 295                 300

Leu Asn Glu Glu Arg Thr Lys Gly Gly Glu Leu Gln Phe Gln Thr Glu
305                 310                 315                 320

Val Glu Met Ile Ser Met Ala Val His Arg Asn Leu Leu Arg Leu Arg
            325                 330                 335

Gly Phe Cys Met Thr Pro Thr Glu Arg Leu Leu Val Tyr Pro Tyr Met
        340                 345                 350

Ala Asn Gly Ser Val Ala Ser Cys Leu Arg Glu Arg Pro Glu Gly Asn
    355                 360                 365

Pro Ala Leu Asp Trp Pro Lys Arg Lys His Ile Ala Leu Gly Ser Ala
370                 375                 380

Arg Gly Leu Ala Tyr Leu His Asp His Cys Asp Gln Lys Ile Ile His
385                 390                 395                 400

Leu Asp Val Lys Ala Ala Asn Ile Leu Leu Asp Glu Glu Phe Glu Ala
            405                 410                 415

Val Val Gly Asp Phe Gly Leu Ala Lys Leu Met Asn Tyr Asn Asp Ser
        420                 425                 430

His Val Thr Thr Ala Val Arg Gly Thr Ile Gly His Ile Ala Pro Glu
    435                 440                 445

Tyr Leu Ser Thr Gly Lys Ser Ser Glu Lys Thr Asp Val Phe Gly Tyr
450                 455                 460

Gly Val Met Leu Leu Glu Leu Ile Thr Gly Gln Lys Ala Phe Asp Leu
465                 470                 475                 480

Ala Arg Leu Ala Asn Asp Asp Ile Met Leu Leu Asp Trp Val Lys
            485                 490                 495

Glu Val Leu Lys Glu Lys Lys Leu Glu Ser Leu Val Asp Ala Glu Leu
        500                 505                 510

Glu Gly Lys Tyr Val Glu Thr Glu Val Glu Gln Leu Ile Gln Met Ala
    515                 520                 525

Leu Leu Cys Thr Gln Ser Ser Ala Met Glu Arg Pro Lys Met Ser Glu
530                 535                 540

Val Val Arg Met Leu Glu Gly Asp Gly Leu Ala Glu Arg Trp Glu Glu
545                 550                 555                 560

Trp Gln Lys Glu Glu Met Pro Ile His Asp Phe Asn Tyr Gln Ala Tyr
            565                 570                 575

Pro His Ala Gly Thr Asp Trp Leu Ile Pro Tyr Ser Asn Ser Leu Ile
        580                 585                 590

Glu Asn Asp Tyr Pro Ser Gly Pro Arg
    595                 600

<210> SEQ ID NO 30
<211> LENGTH: 2207
<212> TYPE: DNA
<213> ORGANISM: Arabidopsis thaliana

<400> SEQUENCE: 30

```
tttcttaaa aacctccaaa caagaatcg aaaaaagaa tatttcttat acaaaagaaa      60
taaacctcaa actctgcacc ttagagatta atactctcaa gaaaacaag ttttgattcg    120
gacaaagatg ttgcaaggaa gaagagaagc aaaaagagt tatgctttgt tctcttcaac   180
tttcttcttc ttctttatct gttttctttc ttcttcttct gcagaactca cagacaaagg   240
tgttaacttt gaagttgttg ccttaatagg aatcaaaagc tcactgactg atcctcatgg   300
agttctaatg aattgggatg acacagcagt tgatccatgt agctggaaca tgatcacttg   360
ttctgatggt tttgtcataa ggctagaagc tccaagccaa aacttatcag gaactctttc   420
atcaagtatt ggaaatttaa caaatcttca aactgtgtta ttgcagaaca attacataac   480
aggaaacatc cctcatgaga ttgggaaatt gatgaaactc aaaacacttg atctctctac   540
caataacttc actggtcaaa tcccattcac tctttcttac tccaaaaatc ttcagtactt   600
caggagggtt aataataaca gcctgacagg aacaattcct agctcattgg caaacatgac   660
ccaactcact tttttggatt tgtcgtataa taacttgagt ggaccagttc caagatcact   720
tgccaaaaca ttcaatgtta tgggcaattc tcagatttgt ccaacaggaa ctgagaaaga   780
ctgtaatggg actcagccta agccaatgtc aatcaccttg aacagttctc aaaataaatc   840
atctgatgga ggaactaaaa accggaaaat cgcggtagtc ttcggtgtaa gcttgacatg   900
tgtttgcttg ttgatcattg gctttggttt tcttcttttgg tggagaagaa gacataacaa   960
acaagtatta ttctttgaca ttaatgagca aaacaaggaa gaaatgtgtc tagggaatct  1020
aaggaggttt aatttcaaag aacttcaatc cgcaactagt aacttcagca gcaagaatct  1080
ggtcggaaaa ggagggtttg gaaatgtgta taaggttgt cttcatgatg aagtatcat    1140
cgcggtgaag agattaaagg atataaacaa tggtggtgga gaggttcagt ttcagacaga  1200
gcttgaaatg ataagccttg ccgtccaccg gaatctcctc cgcttatacg gtttctgtac  1260
tacttcctct gaacggcttc tcgtttatcc ttacatgtcc aatggcagtg tcgcttctcg  1320
tctcaaagct aaaccggtat tggattgggg cacaagaaag cgaatagcat taggagcagg  1380
aagagggttg ctgtatttgc atgagcaatg tgatccaaag atcattcacc gtgatgtcaa  1440
agctgcgaac atacttcttg acgattactt tgaagctgtt gtcggagatt tcgggttggc  1500
taagcttttg gatcatgagg agtcgcatgt gacaaccgcc gtgagaggaa cagtgggtca  1560
cattgcacct gagtatctct caacaggaca atcttctgag aagacagatg tgttcggttt  1620
cgggattctt cttctcgaat tgattactgg attgagagct cttgaattcg gaaaagcagc  1680
aaaccaaaga ggagcgatac ttgattgggt aaagaaacta caacaagaga agaagctaga  1740
acagatagta gacaaggatt tgaagagcaa ctacgataga atagaagtgg aagaaatggt  1800
tcaagtggct ttgctttgta cacagtatct tcccattcac cgtcctaaga tgtctgaagt  1860
tgtgagaatg cttgaaggcg atggtcttgt tgagaaatgg aagcttctt ctcagagagc   1920
agaaaccaat agaagttaca gtaaacctaa cgagttttct tcctctgaac gttattcgga  1980
tcttacagat gattcctcgg tgctggttca agccatggag ttatcaggtc caagatgaca  2040
agagaaacta tatgaatggc tttgggttg taaaaaacat atataagatt gtgtattttg   2100
ttgtatgctg tgatcttgta caggtttgg tatcagaaag acatattctc atgctttatc   2160
ccatgattag gaggaggtgg aatcaccgcc tccatttcgt agaaacg                2207
```

<210> SEQ ID NO 31  
<211> LENGTH: 636  
<212> TYPE: PRT  
<213> ORGANISM: Arabidopsis thaliana

```
<400> SEQUENCE: 31

Met Leu Gln Gly Arg Arg Glu Ala Lys Lys Ser Tyr Ala Leu Phe Ser
  1               5                  10                  15

Ser Thr Phe Phe Phe Phe Phe Ile Cys Phe Leu Ser Ser Ser Ser Ala
             20                  25                  30

Glu Leu Thr Asp Lys Gly Val Asn Phe Glu Val Val Ala Leu Ile Gly
         35                  40                  45

Ile Lys Ser Ser Leu Thr Asp Pro His Gly Val Leu Met Asn Trp Asp
 50                  55                  60

Asp Thr Ala Val Asp Pro Cys Ser Trp Asn Met Ile Thr Cys Ser Asp
 65                  70                  75                  80

Gly Phe Val Ile Arg Leu Glu Ala Pro Ser Gln Asn Leu Ser Gly Thr
                 85                  90                  95

Leu Ser Ser Ser Ile Gly Asn Leu Thr Asn Leu Gln Thr Val Leu Leu
                100                 105                 110

Gln Asn Asn Tyr Ile Thr Gly Asn Ile Pro His Glu Ile Gly Lys Leu
            115                 120                 125

Met Lys Leu Lys Thr Leu Asp Leu Ser Thr Asn Asn Phe Thr Gly Gln
130                 135                 140

Ile Pro Phe Thr Leu Ser Tyr Ser Lys Asn Leu Gln Tyr Phe Arg Arg
145                 150                 155                 160

Val Asn Asn Asn Ser Leu Thr Gly Thr Ile Pro Ser Ser Leu Ala Asn
                165                 170                 175

Met Thr Gln Leu Thr Phe Leu Asp Leu Ser Tyr Asn Asn Leu Ser Gly
                180                 185                 190

Pro Val Pro Arg Ser Leu Ala Lys Thr Phe Asn Val Met Gly Asn Ser
                195                 200                 205

Gln Ile Cys Pro Thr Gly Thr Glu Lys Asp Cys Asn Gly Thr Gln Pro
            210                 215                 220

Lys Pro Met Ser Ile Thr Leu Asn Ser Ser Gln Asn Lys Ser Ser Asp
225                 230                 235                 240

Gly Gly Thr Lys Asn Arg Lys Ile Ala Val Val Phe Gly Val Ser Leu
                245                 250                 255

Thr Cys Val Cys Leu Leu Ile Ile Gly Phe Gly Phe Leu Leu Trp Trp
                260                 265                 270

Arg Arg Arg His Asn Lys Gln Val Leu Phe Phe Asp Ile Asn Glu Gln
                275                 280                 285

Asn Lys Glu Glu Met Cys Leu Gly Asn Leu Arg Arg Phe Asn Phe Lys
            290                 295                 300

Glu Leu Gln Ser Ala Thr Ser Asn Phe Ser Ser Lys Asn Leu Val Gly
305                 310                 315                 320

Lys Gly Gly Phe Gly Asn Val Tyr Lys Gly Cys Leu His Asp Gly Ser
                325                 330                 335

Ile Ile Ala Val Lys Arg Leu Lys Asp Ile Asn Asn Gly Gly Gly Glu
                340                 345                 350

Val Gln Phe Gln Thr Glu Leu Glu Met Ile Ser Leu Ala Val His Arg
                355                 360                 365

Asn Leu Leu Arg Leu Tyr Gly Phe Cys Thr Thr Ser Ser Glu Arg Leu
            370                 375                 380

Leu Val Tyr Pro Tyr Met Ser Asn Gly Ser Val Ala Ser Arg Leu Lys
385                 390                 395                 400

Ala Lys Pro Val Leu Asp Trp Gly Thr Arg Lys Arg Ile Ala Leu Gly
                405                 410                 415
```

Ala Gly Arg Gly Leu Leu Tyr Leu His Glu Gln Cys Asp Pro Lys Ile
        420                 425                 430

Ile His Arg Asp Val Lys Ala Ala Asn Ile Leu Leu Asp Asp Tyr Phe
            435                 440                 445

Glu Ala Val Val Gly Asp Phe Gly Leu Ala Lys Leu Leu Asp His Glu
        450                 455                 460

Glu Ser His Val Thr Thr Ala Val Arg Gly Thr Val Gly His Ile Ala
465                 470                 475                 480

Pro Glu Tyr Leu Ser Thr Gly Gln Ser Ser Glu Lys Thr Asp Val Phe
                485                 490                 495

Gly Phe Gly Ile Leu Leu Leu Glu Leu Ile Thr Gly Leu Arg Ala Leu
            500                 505                 510

Glu Phe Gly Lys Ala Ala Asn Gln Arg Gly Ala Ile Leu Asp Trp Val
        515                 520                 525

Lys Lys Leu Gln Gln Glu Lys Lys Leu Glu Gln Ile Val Asp Lys Asp
        530                 535                 540

Leu Lys Ser Asn Tyr Asp Arg Ile Glu Val Glu Glu Met Val Gln Val
545                 550                 555                 560

Ala Leu Leu Cys Thr Gln Tyr Leu Pro Ile His Arg Pro Lys Met Ser
                565                 570                 575

Glu Val Val Arg Met Leu Glu Gly Asp Gly Leu Val Glu Lys Trp Glu
            580                 585                 590

Ala Ser Ser Gln Arg Ala Glu Thr Asn Arg Ser Tyr Ser Lys Pro Asn
        595                 600                 605

Glu Phe Ser Ser Ser Glu Arg Tyr Ser Asp Leu Thr Asp Asp Ser Ser
        610                 615                 620

Val Leu Val Gln Ala Met Glu Leu Ser Gly Pro Arg
625                 630                 635

<210> SEQ ID NO 32
<211> LENGTH: 2579
<212> TYPE: DNA
<213> ORGANISM: Arabidopsis thaliana

<400> SEQUENCE: 32
aataattaaa attcgtcttc cttccttgct ctcggcgata acttggtttc tctcctctct    60
ctcatctctc tttgtttcga ccctttttta gtatatttcc aggaaatatc ttcttcctcc   120
tttcgttttc tctatctcag ttttctctct tctcagcatt aagtagtcaa cggtcagcga   180
tctcggcgtt ccttctaatc ggaaaagtct agcttcagtt tctttttttt ttgcttttt    240 ggtttccgcg attaatcgat tgggtatttt tgattttctc ttcaaattaa gtcaacgggt   300
ggatacgcgt tgagagggct tttctcgtat tctgcttcta atttcatcat cttggtatta   360
ccttgtgtgg gtggtagctt aatcgaagga ttcgagatcc cttttatcag gggttttaac   420
aatgatggat tttctctgat gagggatagt tctagggttt gttttttaatc tcttgaggat   480 aaaatggaac gaagattaat gatcccttgc ttcttttggt tgattctcgt tttggatttg   540
gttctcagag tctcgggcaa cgccgaaggt gatgctctaa gtgcactgaa aaacagttta   600
gccgacccta taaggtgct tcaaagttgg gatgctactc ttgttactcc atgtacatgg   660
tttcatgtta cttgcaatag cgacaatagt gttacacgtg ttgaccttgg aatgcaaat    720 ctatctggac agctcgtaat gcaacttggt cagcttccaa acttgcagta cttggagctt   780
tatagcaata acattactgg gacaatccca gaacagcttg gaaatctgac ggaattggtg   840
agcttggatc tttacttgaa caatttaagc gggcctattc catcaactct cggccgactt   900

| | |
|---|---|
| aagaaactcc gtttcttgcg tcttaataac aatagcttat ctggagaaat tccaaggtct | 960 |
| ttgactgctg tcctgacgct acaagttctg gatctctcaa acaatcctct caccggagat | 1020 |
| attcctgtta atggttcctt ttcacttttc actccaatca gttttgccaa caccaagttg | 1080 |
| actccccttc ctgcatctcc accgcctcct atctctccta caccgccatc acctgcaggg | 1140 |
| agtaatagaa ttactggagc gattgcggga ggagttgctg caggtgctgc acttctattt | 1200 |
| gctgttccgg ccattgcact agcttggtgg cgaaggaaaa agccgcagga ccacttcttt | 1260 |
| gatgtaccag ctgaagagga cccagaagtt catttaggac aactgaagag gttttcattg | 1320 |
| cgtgaactac aagttgcttc ggataatttt agcaacaaga acatattggg tagaggtggt | 1380 |
| tttggtaaag tttataaagg acggttagct gatggtactt tagtggccgt taaaaggcta | 1440 |
| aaagaggagc gcacccaagg tggcgaactg cagttccaga cagaggttga gatgattagt | 1500 |
| atggcggttc acagaaactt gcttcggctt cgtggatttt gcatgactcc aaccgaaaga | 1560 |
| ttgcttgttt atccctacat ggctaatgga agtgttgcct cctgtttaag agaacgtccc | 1620 |
| gagtcccagc caccacttga ttggccaaag agacagcgta ttgcgttggg atctgcaaga | 1680 |
| gggcttgcgt atttacatga tcattgcgac ccaaagatta ttcatcgaga tgtgaaagct | 1740 |
| gcaaatattt tgttggatga agagtttgaa gccgtggttg gggattttgg acttgcaaaa | 1800 |
| ctcatggact acaaagacac acatgtgaca accgcagtgc gtgggacaat ggtcatata | 1860 |
| gcccctgagt acctttccac tggaaaatca tcagagaaaa ccgatgtctt gggtatgga | 1920 |
| gtcatgcttc ttgagcttat cactggacaa agggcttttg atcttgctcg cctcgcgaat | 1980 |
| gatgatgatg tcatgttact agactgggtg aaagggttgt aaaagagaa gaaattggaa | 2040 |
| gcactagtag atgttgatct tcagggtaat tacaaagacg aagaagtgga gcagctaatc | 2100 |
| caagtggctt tactctgcac tcagagttca ccaatggaaa gacccaaaat gtctgaagtt | 2160 |
| gtaagaatgc ttgaaggaga tggtttagct gagagatggg aagagtggca aaaggaggaa | 2220 |
| atgttcagac aagatttcaa ctacccaacc caccatccag ccgtgtctgg ctggatcatt | 2280 |
| ggcgattcca cttcccagat cgaaaacgaa tacccctcgg gtccaagata agattcgaaa | 2340 |
| cacgaatgtt ttttctgtat tttgtttttc tctgtattta ttgagggttt tagcttctgc | 2400 |
| tgctccatat tattggttct taagtgaata catgaggatc agattgggtt tgtaagtgtt | 2460 |
| atatgatgaa aaaggatttg aatgttgttg aaagctaaaa cccaaacatg tcttaagctc | 2520 |
| accacttgag gattgttgcg cacttgattc acaaatatgt atcccatcaa ttattctttt | 2579 |

<210> SEQ ID NO 33
<211> LENGTH: 615
<212> TYPE: PRT
<213> ORGANISM: Arabidopsis thaliana

<400> SEQUENCE: 33

Met Glu Arg Arg Leu Met Ile Pro Cys Phe Phe Trp Leu Ile Leu Val
1               5                   10                  15

Leu Asp Leu Val Leu Arg Val Ser Gly Asn Ala Glu Gly Asp Ala Leu
            20                  25                  30

Ser Ala Leu Lys Asn Ser Leu Ala Asp Pro Asn Lys Val Leu Gln Ser
        35                  40                  45

Trp Asp Ala Thr Leu Val Thr Pro Cys Thr Trp Phe His Val Thr Cys
    50                  55                  60

Asn Ser Asp Asn Ser Val Thr Arg Val Asp Leu Gly Asn Ala Asn Leu
65                  70                  75                  80

-continued

```
Ser Gly Gln Leu Val Met Gln Leu Gly Gln Leu Pro Asn Leu Gln Tyr
                85                  90                  95
Leu Glu Leu Tyr Ser Asn Asn Ile Thr Gly Thr Ile Pro Glu Gln Leu
            100                 105                 110
Gly Asn Leu Thr Glu Leu Val Ser Leu Asp Leu Tyr Leu Asn Asn Leu
        115                 120                 125
Ser Gly Pro Ile Pro Ser Thr Leu Gly Arg Leu Lys Lys Leu Arg Phe
    130                 135                 140
Leu Arg Leu Asn Asn Asn Ser Leu Ser Gly Glu Ile Pro Arg Ser Leu
145                 150                 155                 160
Thr Ala Val Leu Thr Leu Gln Val Leu Asp Leu Ser Asn Asn Pro Leu
                165                 170                 175
Thr Gly Asp Ile Pro Val Asn Gly Ser Phe Ser Leu Phe Thr Pro Ile
            180                 185                 190
Ser Phe Ala Asn Thr Lys Leu Thr Pro Leu Pro Ala Ser Pro Pro Pro
        195                 200                 205
Pro Ile Ser Pro Thr Pro Pro Ser Pro Ala Gly Ser Asn Arg Ile Thr
    210                 215                 220
Gly Ala Ile Ala Gly Gly Val Ala Ala Gly Ala Ala Leu Leu Phe Ala
225                 230                 235                 240
Val Pro Ala Ile Ala Leu Ala Trp Trp Arg Arg Lys Lys Pro Gln Asp
                245                 250                 255
His Phe Phe Asp Val Pro Ala Glu Glu Asp Pro Glu Val His Leu Gly
            260                 265                 270
Gln Leu Lys Arg Phe Ser Leu Arg Glu Leu Gln Val Ala Ser Asp Asn
        275                 280                 285
Phe Ser Asn Lys Asn Ile Leu Gly Arg Gly Gly Phe Gly Lys Val Tyr
    290                 295                 300
Lys Gly Arg Leu Ala Asp Gly Thr Leu Val Ala Val Lys Arg Leu Lys
305                 310                 315                 320
Glu Glu Arg Thr Gln Gly Gly Glu Leu Gln Phe Gln Thr Glu Val Glu
                325                 330                 335
Met Ile Ser Met Ala Val His Arg Asn Leu Leu Arg Leu Arg Gly Phe
            340                 345                 350
Cys Met Thr Pro Thr Glu Arg Leu Leu Val Tyr Pro Tyr Met Ala Asn
        355                 360                 365
Gly Ser Val Ala Ser Cys Leu Arg Glu Arg Pro Glu Ser Gln Pro Pro
    370                 375                 380
Leu Asp Trp Pro Lys Arg Gln Arg Ile Ala Leu Gly Ser Ala Arg Gly
385                 390                 395                 400
Leu Ala Tyr Leu His Asp His Cys Asp Pro Lys Ile Ile His Arg Asp
                405                 410                 415
Val Lys Ala Ala Asn Ile Leu Leu Asp Glu Glu Phe Glu Ala Val Val
            420                 425                 430
Gly Asp Phe Gly Leu Ala Lys Leu Met Asp Tyr Lys Asp Thr His Val
        435                 440                 445
Thr Thr Ala Val Arg Gly Thr Ile Gly His Ile Ala Pro Glu Tyr Leu
    450                 455                 460
Ser Thr Gly Lys Ser Ser Glu Lys Thr Asp Val Phe Gly Tyr Gly Val
465                 470                 475                 480
Met Leu Leu Glu Leu Ile Thr Gly Gln Arg Ala Phe Asp Leu Ala Arg
                485                 490                 495
Leu Ala Asn Asp Asp Asp Val Met Leu Leu Asp Trp Val Lys Gly Leu
            500                 505                 510
```

```
Leu Lys Glu Lys Lys Leu Glu Ala Leu Val Asp Val Asp Leu Gln Gly
        515                 520                 525

Asn Tyr Lys Asp Glu Glu Val Glu Gln Leu Ile Gln Val Ala Leu Leu
    530                 535                 540

Cys Thr Gln Ser Ser Pro Met Glu Arg Pro Lys Met Ser Glu Val Val
545                 550                 555                 560

Arg Met Leu Glu Gly Asp Gly Leu Ala Glu Arg Trp Glu Glu Trp Gln
            565                 570                 575

Lys Glu Glu Met Phe Arg Gln Asp Phe Asn Tyr Pro Thr His His Pro
            580                 585                 590

Ala Val Ser Gly Trp Ile Ile Gly Asp Ser Thr Ser Gln Ile Glu Asn
        595                 600                 605

Glu Tyr Pro Ser Gly Pro Arg
    610                 615

<210> SEQ ID NO 34
<211> LENGTH: 2206
<212> TYPE: DNA
<213> ORGANISM: Arabidopsis thaliana

<400> SEQUENCE: 34
gagagtgata attgcgaaat tgccaaaaaa cgcaaagtct accactagac aagaaaatcg      60
aagcttttca ctttctcttt tttctgtttt gttgtctttg gttctactct ccgcactgaa     120
tctttcgatc agcgataatt gtttccttct tttgggattt tctccttgga tggaaccagc     180
tcaattaatg agatgagatg agaatgttca gcttgcagaa gatggctatg gcttttactc     240
tcttgttttt tgcctgttta tgctcatttg tgtctccaga tgctcaaggg gatgcactgt     300
ttgcgttgag gatctcctta cgtgcattac cgaatcagct aagtgactgg aatcagaacc     360
aagttaatcc ttgcacttgg tcccaagtta tttgtgatga caaaaacttt gtcacttctc     420
ttacattgtc agatatgaac ttctcgggaa ccttgtcttc aagagtagga atcctagaaa     480
atctcaagac tcttacttta aagggaaatg gaattacggg tgaaatacca gaagactttg     540
gaaatctgac tagcttgact agtttggatt tggaggacaa tcagctaact ggtcgtatac     600
catccactat cggtaatctc aagaaacttc agttcttgac cttgagtagg aacaaactta     660
atgggactat tccggagtca ctcactggtc ttccaaacct gttaaacctg ctgcttgatt     720
ccaatagtct cagtggtcag attcctcaaa gtctgtttga gatcccaaaa tataatttca     780
cgtcaaacaa cttgaattgt ggcggtcgtc aacctcaccc ttgtgtatcc gcggttgccc     840
attcaggtga ttcaagcaag cctaaaactg gcattattgc tggagttgtt gctggagtta     900
cagttgttct ctttggaatc ttgttgtttc tgttctgcaa ggataggcat aaaggatata     960
gacgtgatgt gtttgtggat gttgcaggtg aagtggacag agaattgca tttggacagt    1020 tgaaaaggtt tgcatggaga gagctccagt tagcgacaga taacttcagc gaaagaatg     1080 tacttggtca aggaggcttt gggaaagttt acaaggagt gcttccggat aacaccaaag    1140
ttgctgtgaa gagattgacg gatttcgaaa gtcctggtgg agatgctgct ttccaaaggg    1200
aagtagagat gataagtgta gctgttcata ggaatctact ccgtcttatc gggttctgca    1260
ccacacaaac agaacgcctt ttggtttatc ccttcatgca gaatctaagt cttgcacatc    1320
gtctgagaga gatcaaagca ggcgacccgg ttctagattg ggagacgagg aaacggattg    1380
ccttaggagc agcgcgtggt tttgagtatc ttcatgaaca ttgcaatccg aagatcatac    1440
atcgtgatgt gaaagcagct aatgtgttac tagatgaaga ttttgaagca gtggttggtg    1500
```

-continued

```
attttggttt agccaagcta gtagatgtta gaaggactaa tgtgactact caagttcgag    1560
gaacaatggg tcacattgca ccagaatatt tatcaacagg gaaatcatca gagagaaccg    1620
atgttttcgg gtatggaatt atgcttcttg agcttgttac aggacaacgc gcaatagact    1680
tttcacgttt ggaggaagaa gatgatgtct tgttacttga ccacgtgaag aaactggaaa    1740
gagagaagag attaggagca atcgtagata agaatttgga tggagagtat ataaagaag     1800 aagtagagat gatgatacaa gtggctttgc tttgtacaca aggttcacca gaagaccgac    1860
cagtgatgtc tgaagttgtg aggatgttag aaggagaagg gcttgcggag agatgggaag    1920
agtggcaaaa cgtggaagtc acgagacgtc atgagtttga acggttgcag aggagatttg    1980
attggggtga agattctatg cataaccaag atgccattga attatctggt ggaagatgac    2040
caaaaacatc aaaccttgag tttactgtaa agttgccaac ttcactttt tgttttgttc     2100 ttcggtgaag aagtaaaatc agttgtataa atcttgtttt tgtttcatga tgtatctttt    2160
gactttaata aattctgtga atgaaaagaa ctatgatgtt ttgttg                   2206
```

<210> SEQ ID NO 35
<211> LENGTH: 613
<212> TYPE: PRT
<213> ORGANISM: Arabidopsis thaliana

<400> SEQUENCE: 35

```
Met Arg Met Phe Ser Leu Gln Lys Met Ala Met Ala Phe Thr Leu Leu
1               5                   10                  15

Phe Phe Ala Cys Leu Cys Ser Phe Val Ser Pro Asp Ala Gln Gly Asp
                20                  25                  30

Ala Leu Phe Ala Leu Arg Ile Ser Leu Arg Ala Leu Pro Asn Gln Leu
            35                  40                  45

Ser Asp Trp Asn Gln Asn Gln Val Asn Pro Cys Thr Trp Ser Gln Val
        50                  55                  60

Ile Cys Asp Asp Lys Asn Phe Val Thr Ser Leu Thr Leu Ser Asp Met
65                  70                  75                  80

Asn Phe Ser Gly Thr Leu Ser Ser Arg Val Gly Ile Leu Glu Asn Leu
                85                  90                  95

Lys Thr Leu Thr Leu Lys Gly Asn Gly Ile Thr Gly Glu Ile Pro Glu
                100                 105                 110

Asp Phe Gly Asn Leu Thr Ser Leu Thr Ser Leu Asp Leu Glu Asp Asn
            115                 120                 125

Gln Leu Thr Gly Arg Ile Pro Ser Thr Ile Gly Asn Leu Lys Lys Leu
        130                 135                 140

Gln Phe Leu Thr Leu Ser Arg Asn Lys Leu Asn Gly Thr Ile Pro Glu
145                 150                 155                 160

Ser Leu Thr Gly Leu Pro Asn Leu Leu Asn Leu Leu Asp Ser Asn
                165                 170                 175

Ser Leu Ser Gly Gln Ile Pro Gln Ser Leu Phe Glu Ile Pro Lys Tyr
            180                 185                 190

Asn Phe Thr Ser Asn Asn Leu Asn Cys Gly Gly Arg Gln Pro His Pro
        195                 200                 205

Cys Val Ser Ala Val Ala His Ser Gly Asp Ser Ser Lys Pro Lys Thr
    210                 215                 220

Gly Ile Ile Ala Gly Val Val Ala Gly Val Thr Val Val Leu Phe Gly
225                 230                 235                 240

Ile Leu Leu Phe Leu Phe Cys Lys Asp Arg His Lys Gly Tyr Arg Arg
                245                 250                 255
```

| | | | | | | | | | | | | | |
|---|---|---|---|---|---|---|---|---|---|---|---|---|---|
|Asp|Val|Phe|Val|Asp|Val|Ala|Gly|Glu|Val|Asp|Arg|Arg|Ile|Ala|Phe|
| | | |260| | | |265| | | |270| | | |
|Gly|Gln|Leu|Lys|Arg|Phe|Ala|Trp|Arg|Glu|Leu|Gln|Leu|Ala|Thr|Asp|
| | | |275| | | |280| | | |285| | | |
|Asn|Phe|Ser|Glu|Lys|Asn|Val|Leu|Gly|Gln|Gly|Gly|Phe|Gly|Lys|Val|
| | | |290| | | |295| | | |300| | | |
|Tyr|Lys|Gly|Val|Leu|Pro|Asp|Asn|Thr|Lys|Val|Ala|Val|Lys|Arg|Leu|
|305| | | |310| | | |315| | | |320| | | |
|Thr|Asp|Phe|Glu|Ser|Pro|Gly|Gly|Asp|Ala|Ala|Phe|Gln|Arg|Glu|Val|
| | | |325| | | |330| | | |335| | | |
|Glu|Met|Ile|Ser|Val|Ala|Val|His|Arg|Asn|Leu|Leu|Arg|Leu|Ile|Gly|
| | | |340| | | |345| | | |350| | | |
|Phe|Cys|Thr|Thr|Gln|Thr|Glu|Arg|Leu|Leu|Val|Tyr|Pro|Phe|Met|Gln|
| | | |355| | | |360| | | |365| | | |
|Asn|Leu|Ser|Leu|Ala|His|Arg|Leu|Arg|Glu|Ile|Lys|Ala|Gly|Asp|Pro|
| | | |370| | | |375| | | |380| | | |
|Val|Leu|Asp|Trp|Glu|Thr|Arg|Lys|Arg|Ile|Ala|Leu|Gly|Ala|Ala|Arg|
|385| | | |390| | | |395| | | |400| | | |
|Gly|Phe|Glu|Tyr|Leu|His|Glu|His|Cys|Asn|Pro|Lys|Ile|Ile|His|Arg|
| | | |405| | | |410| | | |415| | | |
|Asp|Val|Lys|Ala|Ala|Asn|Val|Leu|Leu|Asp|Glu|Asp|Phe|Glu|Ala|Val|
| | | |420| | | |425| | | |430| | | |
|Val|Gly|Asp|Phe|Gly|Leu|Ala|Lys|Leu|Val|Asp|Val|Arg|Arg|Thr|Asn|
| | | |435| | | |440| | | |445| | | |
|Val|Thr|Thr|Gln|Val|Arg|Gly|Thr|Met|Gly|His|Ile|Ala|Pro|Glu|Tyr|
| | | |450| | | |455| | | |460| | | |
|Leu|Ser|Thr|Gly|Lys|Ser|Ser|Glu|Arg|Thr|Asp|Val|Phe|Gly|Tyr|Gly|
|465| | | |470| | | |475| | | |480| | | |
|Ile|Met|Leu|Leu|Glu|Leu|Val|Thr|Gly|Gln|Arg|Ala|Ile|Asp|Phe|Ser|
| | | |485| | | |490| | | |495| | | |
|Arg|Leu|Glu|Glu|Glu|Asp|Asp|Val|Leu|Leu|Leu|Asp|His|Val|Lys|Lys|
| | | |500| | | |505| | | |510| | | |
|Leu|Glu|Arg|Glu|Lys|Arg|Leu|Gly|Ala|Ile|Val|Asp|Lys|Asn|Leu|Asp|
| | | |515| | | |520| | | |525| | | |
|Gly|Glu|Tyr|Ile|Lys|Glu|Glu|Val|Glu|Met|Met|Ile|Gln|Val|Ala|Leu|
| | | |530| | | |535| | | |540| | | |
|Leu|Cys|Thr|Gln|Gly|Ser|Pro|Glu|Asp|Arg|Pro|Val|Met|Ser|Glu|Val|
|545| | | |550| | | |555| | | |560| | | |
|Val|Arg|Met|Leu|Glu|Gly|Glu|Gly|Leu|Ala|Glu|Arg|Trp|Glu|Glu|Trp|
| | | |565| | | |570| | | |575| | | |
|Gln|Asn|Val|Glu|Val|Thr|Arg|Arg|His|Glu|Phe|Glu|Arg|Leu|Gln|Arg|
| | | |580| | | |585| | | |590| | | |
|Arg|Phe|Asp|Trp|Gly|Glu|Asp|Ser|Met|His|Asn|Gln|Asp|Ala|Ile|Glu|
| | | |595| | | |600| | | |605| | | |
|Leu|Ser|Gly|Gly|Arg| | | | | | | | | | | |
| | | |610| | | | | | | | | | | | |

<210> SEQ ID NO 36
<211> LENGTH: 2323
<212> TYPE: DNA
<213> ORGANISM: Arabidopsis thaliana

<400> SEQUENCE: 36

```
atagagattt ggttttttga ttcttccaat ctcactctct ctgtctttct ctctccatca      60
aataccaaat tatctggaag ctgagtacat cttgttttct gctcattcct ctgtttcaac     120
```

```
aatggagagt actattgtta tgatgatgat gataacaaga tctttctttt gcttcttggg    180 attttatgc cttctctgct cttctgttca cggattgctt tctcctaaag gtgttaactt    240
tgaagtgcaa gctttgatgg acataaaagc ttcattacat gatcctcatg gtgttcttga    300
taactgggat agagatgctg ttgatccttg tagttggaca atggtcactt gttcttctga    360
aaactttgtc attggcttag gcacaccaag tcagaattta tctggtacac tatctccaag    420
cattaccaac ttaacaaatc ttcggattgt gctgttgcag aacaacaaca taaaaggaaa    480
aattcctgct gagattggtc ggcttacgag gcttgagact cttgatcttt ctgataattt    540
cttccacggt gaaattcctt tttcagtagg ctatctacaa agcctgcaat atctgaggct    600
taacaacaat tctctctctg gagtgttttcc tctgtcacta tctaatatga ctcaacttgc    660
ctttcttgat ttatcataca acaatcttag tggtcctgtt ccaagatttg ctgcaaagac    720
gtttagcatc gttgggaacc cgctgatatg tccaacgggt accgaaccag actgcaatgg    780
aacaacattg atacctatgt ctatgaactt gaatcaaact ggagttcctt tatacgccgg    840
tggatcgagg aatcacaaaa tggcaatcgc tgttggatcc agcgttggga ctgtatcatt    900
aatcttcatt gctgttggtt tgtttctctg gtggagacaa agacataacc aaaacacatt    960
ctttgatgtt aaagatggga atcatcatga ggaagtttca cttggaaacc tgaggagatt   1020
tggtttcagg gagcttcaga ttgcgaccaa taacttcagc agtaagaact tattggggaa   1080
aggtggctat ggaaatgtat acaaaggaat acttggagat agtacagtgg ttgcagtgaa   1140
aaggcttaaa gatggaggag cattgggagg agagattcag tttcagacag aagttgaaat   1200
gatcagttta gctgttcatc gaaatctctt aagactctac ggtttctgca tcacacaaac   1260
tgagaagctt ctagtttatc cttatatgtc taatggaagc gttgcatctc gaatgaaagc   1320
aaaacctgtt cttgactgga gcataaggaa gaggatagcc ataggagctg caagagggct   1380
tgtgtatctc catgagcaat gtgatccgaa gattatccac cgcgatgtca aagcagcgaa   1440
tatacttctt gatgactact gtgaagctgt ggttggcgat tttggtttag ctaaactctt   1500
ggatcatcaa gattctcatg tgacaaccgc ggttagaggc acggtgggtc acattgctcc   1560
agagtatctc tcaactggtc aatcctctga gaaaacagat gttttggct tcgggattct   1620 tcttcttgag cttgtaaccg gacaaagagc ttttgagttt ggtaaagcgg ctaaccagaa   1680
aggtgtgatg cttgattggg ttaaaagat tcatcaagag aagaaacttg agctacttgt   1740
ggataaagag ttgttgaaga agaagagcta cgatgagatt gagttagacg aaatggtaag   1800
agtagctttg ttgtgcacac agtacctgcc aggacataga ccaaaaatgt ctgaagttgt   1860
tcgaatgctg gaaggagatg gacttgcaga gaaatgggaa gcttctcaaa gatcagacag   1920
tgtttcaaaa tgtagcaaca ggataaatga attgatgtca tcttcagaca gatactctga   1980
tcttaccgat gactctagtt tacttgtgca agcaatggag ctctctggtc ctagatgaaa   2040
tctatacatg aatctgaaga agaagaagaa catgcatctg tttcttgaat caagagggat   2100
tcttgttttt tgtataata gagaggtttt tggagggaa atgttgtgtc tctgtaactg   2160
tataggcttg ttgtgtaaga agttattact gcacttaggg ttaattcaaa gttctttaca   2220
taaaaaatga ttagttgcgt tgaatagagg gaacactttg ggagatttca tgtgtgaaat   2280
ttgggaattc atgtttgaga atgaaattta tcttattatt gga                    2323
```

<210> SEQ ID NO 37
<211> LENGTH: 638
<212> TYPE: PRT
<213> ORGANISM: Arabidopsis thaliana

<400> SEQUENCE: 37

```
Met Glu Ser Thr Ile Val Met Met Met Ile Thr Arg Ser Phe Phe
1               5                   10                  15

Cys Phe Leu Gly Phe Leu Cys Leu Leu Cys Ser Ser Val His Gly Leu
            20                  25                  30

Leu Ser Pro Lys Gly Val Asn Phe Glu Val Gln Ala Leu Met Asp Ile
            35                  40                  45

Lys Ala Ser Leu His Asp Pro His Gly Val Leu Asp Asn Trp Asp Arg
50                  55                  60

Asp Ala Val Asp Pro Cys Ser Trp Thr Met Val Thr Cys Ser Ser Glu
65                  70                  75                  80

Asn Phe Val Ile Gly Leu Gly Thr Pro Ser Gln Asn Leu Ser Gly Thr
                85                  90                  95

Leu Ser Pro Ser Ile Thr Asn Leu Thr Asn Leu Arg Ile Val Leu Leu
            100                 105                 110

Gln Asn Asn Asn Ile Lys Gly Lys Ile Pro Ala Glu Ile Gly Arg Leu
            115                 120                 125

Thr Arg Leu Glu Thr Leu Asp Leu Ser Asp Asn Phe Phe His Gly Glu
130                 135                 140

Ile Pro Phe Ser Val Gly Tyr Leu Gln Ser Leu Gln Tyr Leu Arg Leu
145                 150                 155                 160

Asn Asn Asn Ser Leu Ser Gly Val Phe Pro Leu Ser Leu Ser Asn Met
                165                 170                 175

Thr Gln Leu Ala Phe Leu Asp Leu Ser Tyr Asn Asn Leu Ser Gly Pro
            180                 185                 190

Val Pro Arg Phe Ala Ala Lys Thr Phe Ser Ile Val Gly Asn Pro Leu
            195                 200                 205

Ile Cys Pro Thr Gly Thr Glu Pro Asp Cys Asn Gly Thr Thr Leu Ile
            210                 215                 220

Pro Met Ser Met Asn Leu Asn Gln Thr Gly Val Pro Leu Tyr Ala Gly
225                 230                 235                 240

Gly Ser Arg Asn His Lys Met Ala Ile Ala Val Gly Ser Ser Val Gly
                245                 250                 255

Thr Val Ser Leu Ile Phe Ile Ala Val Gly Leu Phe Leu Trp Trp Arg
            260                 265                 270

Gln Arg His Asn Gln Asn Thr Phe Phe Asp Val Lys Asp Gly Asn His
            275                 280                 285

His Glu Val Ser Leu Gly Asn Leu Arg Arg Phe Gly Phe Arg Glu
            290                 295                 300

Leu Gln Ile Ala Thr Asn Asn Phe Ser Ser Lys Asn Leu Leu Gly Lys
305                 310                 315                 320

Gly Gly Tyr Gly Asn Val Tyr Lys Gly Ile Leu Gly Asp Ser Thr Val
                325                 330                 335

Val Ala Val Lys Arg Leu Lys Asp Gly Gly Ala Leu Gly Gly Glu Ile
            340                 345                 350

Gln Phe Gln Thr Glu Val Glu Met Ile Ser Leu Ala Val His Arg Asn
            355                 360                 365

Leu Leu Arg Leu Tyr Gly Phe Cys Ile Thr Gln Thr Glu Lys Leu Leu
370                 375                 380

Val Tyr Pro Tyr Met Ser Asn Gly Ser Val Ala Ser Arg Met Lys Ala
385                 390                 395                 400

Lys Pro Val Leu Asp Trp Ser Ile Arg Lys Arg Ile Ala Ile Gly Ala
                405                 410                 415
```

```
Ala Arg Gly Leu Val Tyr Leu His Glu Gln Cys Asp Pro Lys Ile Ile
            420                 425                 430

His Arg Asp Val Lys Ala Ala Asn Ile Leu Leu Asp Asp Tyr Cys Glu
            435                 440                 445

Ala Val Val Gly Asp Phe Gly Leu Ala Lys Leu Leu Asp His Gln Asp
            450                 455                 460

Ser His Val Thr Thr Ala Val Arg Gly Thr Val Gly His Ile Ala Pro
465                 470                 475                 480

Glu Tyr Leu Ser Thr Gly Gln Ser Ser Glu Lys Thr Asp Val Phe Gly
            485                 490                 495

Phe Gly Ile Leu Leu Leu Glu Leu Val Thr Gly Gln Arg Ala Phe Glu
            500                 505                 510

Phe Gly Lys Ala Ala Asn Gln Lys Gly Val Met Leu Asp Trp Val Lys
            515                 520                 525

Lys Ile His Gln Glu Lys Lys Leu Glu Leu Leu Val Asp Lys Glu Leu
            530                 535                 540

Leu Lys Lys Lys Ser Tyr Asp Glu Ile Glu Leu Asp Glu Met Val Arg
545                 550                 555                 560

Val Ala Leu Leu Cys Thr Gln Tyr Leu Pro Gly His Arg Pro Lys Met
                565                 570                 575

Ser Glu Val Val Arg Met Leu Gly Asp Gly Leu Ala Glu Lys Trp
            580                 585                 590

Glu Ala Ser Gln Arg Ser Asp Ser Val Ser Lys Cys Ser Asn Arg Ile
            595                 600                 605

Asn Glu Leu Met Ser Ser Ser Asp Arg Tyr Ser Asp Leu Thr Asp Asp
            610                 615                 620

Ser Ser Leu Leu Val Gln Ala Met Glu Leu Ser Gly Pro Arg
625                 630                 635

<210> SEQ ID NO 38
<211> LENGTH: 1845
<212> TYPE: DNA
<213> ORGANISM: Arabidopsis thaliana

<400> SEQUENCE: 38
atggagattt ctttgatgaa gtttctgttt ttaggaatct gggtttatta ttactctgtt      60
cttgactctg tttctgccat ggatagtctt ttatctccca agggtgttaa ctatgaagtg     120
gctgcgttaa tgtcagtgaa gaacaagatg aaagatgaga agaggttttt gtctggttgg     180
gatattaact ctgttgatcc ttgtacttgg aacatggttg gttgttcttc tgaaggtttt     240
gtggtttctc tagagatggc tagtaaagga ttatcaggga tactatctac tagtattggg     300
gaattaactc atcttcatac tttgttactt cagaataatc agttaactgg tccgattcct     360
tctgagttag gccaactctc tgagcttgaa acgcttgatt tatcggggaa tcggtttagt     420
ggtgaaatcc cagcttcttt agggttctta actcacttaa actacttgcg gcttagcagg     480 aatctttat ctgggcaagt ccctcacctc gtcgctggcc tctcaggtct ttctttcttg     540
gatctatctt tcaacaatct aagcggacca actccgaata tatcagcaaa agattacagg     600
attgtaggaa atgcatttct tgtggtcca gcttcccaag agctttgctc agatgctaca     660
cctgtgagaa atgcgacggg tttgtctgaa aaggacaata gcaaacatca cagcttagtg     720
ctctcttttg catttggcat tgttgttgcc tttatcatct ccctaatgtt tctcttcttc     780
tgggtgcttt ggcatcgatc acgtctctca agatcacacg tgcagcaaga ctacgaattt     840
gaaatcggcc atctgaaaag gttcagtttt cgcgaaatac aaaccgcaac aagcaatttt     900
```

-continued

```
agtccaaaga acattttggg acaaggaggg tttgggatgg tttataaagg gtatctccca    960
aatggaactg tggtggcagt taaaagattg aaagatccga tttatacagg agaagttcag   1020
tttcaaaccg aagtagagat gattggctta gctgttcacc gtaaccttt acgcctcttt   1080
ggattctgta tgaccccgga agagagaatg cttgtgtatc cgtacatgcc aaatggaagc   1140
gtagctgatc gtctgagaga caattatgga gaaaagccgt ctctagattg gaatcggagg   1200
ataagcattg cactcggcgc agctcgagga cttgtttact gcacgagca atgcaatcca   1260
aagattattc acagagacgt caaagctgca aatattctac ttgatgagag ctttgaagca   1320
atagttggcg attttggtct agcaaagctt ttagaccaga gagattcaca tgtcactacc   1380
gcagtccgag gaaccattgg acacatcgct cccgagtacc tttccactgg acagtcctca   1440
gagaaaaccg atgttttcgg attcggagta ctaatccttg aactcataac aggtcataag   1500
atgattgatc aaggcaatgg tcaagttcga aaaggaatga tattgagctg ggtaaggaca   1560
ttgaaagcag agaagagatt tgcagagatg gtggacagaa atttgaaggg agagtttgat   1620
gatttggtgt tggaggaagt agtggaattg gctttgcttt gtacacagcc acatccgaat   1680
ctaagaccga ggatgtctca agtgttgaag gtactagaag gtttagtgga acagtgtgaa   1740
ggagggtatg aagctagagc tccaagtgtc tctaggaact acagtaatgg tcatgaagag   1800
cagtcctta ttattgaagc cattgagctc tctggaccac gatga               1845
```

<210> SEQ ID NO 39
<211> LENGTH: 614
<212> TYPE: PRT
<213> ORGANISM: Arabidopsis thaliana

<400> SEQUENCE: 39

```
Met Glu Ile Ser Leu Met Lys Phe Leu Phe Leu Gly Ile Trp Val Tyr
 1               5                  10                  15

Tyr Tyr Ser Val Leu Asp Ser Val Ser Ala Met Asp Ser Leu Leu Ser
            20                  25                  30

Pro Lys Gly Val Asn Tyr Glu Val Ala Ala Leu Met Ser Val Lys Asn
        35                  40                  45

Lys Met Lys Asp Glu Lys Glu Val Leu Ser Gly Trp Asp Ile Asn Ser
    50                  55                  60

Val Asp Pro Cys Thr Trp Asn Met Val Gly Cys Ser Ser Glu Gly Phe
65                  70                  75                  80

Val Val Ser Leu Glu Met Ala Ser Lys Gly Leu Ser Gly Ile Leu Ser
                85                  90                  95

Thr Ser Ile Gly Glu Leu Thr His Leu His Thr Leu Leu Gln Asn
            100                 105                 110

Asn Gln Leu Thr Gly Pro Ile Pro Ser Glu Leu Gly Gln Leu Ser Glu
        115                 120                 125

Leu Glu Thr Leu Asp Leu Ser Gly Asn Arg Phe Ser Gly Glu Ile Pro
    130                 135                 140

Ala Ser Leu Gly Phe Leu Thr His Leu Asn Tyr Leu Arg Leu Ser Arg
145                 150                 155                 160

Asn Leu Leu Ser Gly Gln Val Pro His Leu Val Ala Gly Leu Ser Gly
                165                 170                 175

Leu Ser Phe Leu Asp Leu Ser Phe Asn Asn Leu Ser Gly Pro Thr Pro
            180                 185                 190

Asn Ile Ser Ala Lys Asp Tyr Arg Ile Val Gly Asn Ala Phe Leu Cys
        195                 200                 205
```

```
Gly Pro Ala Ser Gln Glu Leu Cys Ser Asp Ala Thr Pro Val Arg Asn
    210                 215                 220

Ala Thr Gly Leu Ser Glu Lys Asp Asn Ser Lys His His Ser Leu Val
225                 230                 235                 240

Leu Ser Phe Ala Phe Gly Ile Val Val Ala Phe Ile Ile Ser Leu Met
                245                 250                 255

Phe Leu Phe Phe Trp Val Leu Trp His Arg Ser Arg Leu Ser Arg Ser
                260                 265                 270

His Val Gln Gln Asp Tyr Glu Phe Glu Ile Gly His Leu Lys Arg Phe
            275                 280                 285

Ser Phe Arg Glu Ile Gln Thr Ala Thr Ser Asn Phe Ser Pro Lys Asn
    290                 295                 300

Ile Leu Gly Gln Gly Gly Phe Gly Met Val Tyr Lys Gly Tyr Leu Pro
305                 310                 315                 320

Asn Gly Thr Val Val Ala Val Lys Arg Leu Lys Asp Pro Ile Tyr Thr
                325                 330                 335

Gly Glu Val Gln Phe Gln Thr Glu Val Glu Met Ile Gly Leu Ala Val
                340                 345                 350

His Arg Asn Leu Leu Arg Leu Phe Gly Phe Cys Met Thr Pro Glu Glu
            355                 360                 365

Arg Met Leu Val Tyr Pro Tyr Met Pro Asn Gly Ser Val Ala Asp Arg
    370                 375                 380

Leu Arg Asp Asn Tyr Gly Glu Lys Pro Ser Leu Asp Trp Asn Arg Arg
385                 390                 395                 400

Ile Ser Ile Ala Leu Gly Ala Ala Arg Gly Leu Val Tyr Leu His Glu
                405                 410                 415

Gln Cys Asn Pro Lys Ile Ile His Arg Asp Val Lys Ala Ala Asn Ile
            420                 425                 430

Leu Leu Asp Glu Ser Phe Glu Ala Ile Val Gly Asp Phe Gly Leu Ala
    435                 440                 445

Lys Leu Leu Asp Gln Arg Asp Ser His Val Thr Thr Ala Val Arg Gly
450                 455                 460

Thr Ile Gly His Ile Ala Pro Glu Tyr Leu Ser Thr Gly Gln Ser Ser
465                 470                 475                 480

Glu Lys Thr Asp Val Phe Gly Phe Gly Val Leu Ile Leu Glu Leu Ile
                485                 490                 495

Thr Gly His Lys Met Ile Asp Gln Gly Asn Gly Gln Val Arg Lys Gly
            500                 505                 510

Met Ile Leu Ser Trp Val Arg Thr Leu Lys Ala Glu Lys Arg Phe Ala
    515                 520                 525

Glu Met Val Asp Arg Asp Leu Lys Gly Glu Phe Asp Asp Leu Val Leu
530                 535                 540

Glu Glu Val Val Glu Leu Ala Leu Leu Cys Thr Gln Pro His Pro Asn
545                 550                 555                 560

Leu Arg Pro Arg Met Ser Gln Val Leu Lys Val Leu Glu Gly Leu Val
                565                 570                 575

Glu Gln Cys Glu Gly Gly Tyr Glu Ala Arg Ala Pro Ser Val Ser Arg
            580                 585                 590

Asn Tyr Ser Asn Gly His Glu Glu Gln Ser Phe Ile Ile Glu Ala Ile
    595                 600                 605

Glu Leu Ser Gly Pro Arg
    610

<210> SEQ ID NO 40
```

<211> LENGTH: 2106
<212> TYPE: DNA
<213> ORGANISM: Arabidopsis thaliana

<400> SEQUENCE: 40

| | | | | | |
|---|---|---|---|---|---|
| catttctctc | ttcaacccca | tgttttcgtt | ctcttccgtt | tagagtgttt | tcagctcctc | 60 |
| tatggctcac | tcggggaacg | gtgaaagttt | ccatgatcct | cttcgaggat | tcattcaaag | 120 |
| aaattgcttt | agatggaaca | atcagaaatt | gatcttacaa | tgtttcatgg | ccttagcttt | 180 |
| tgtgggaatc | acttcgtcaa | caactcaacc | agatatcgaa | ggaggagctc | tgttgcagct | 240 |
| cagagattcg | cttaatgatt | cgagcaatcg | tctaaaatgg | acacgcgatt | ttgtgagccc | 300 |
| ttgctatagt | tggtcttatg | ttacctgcag | aggccagagt | gttgtggctc | taaatcttgc | 360 |
| ctcgagtgga | ttcacaggaa | cactctctcc | agctattaca | aaactgaagt | tcttggttac | 420 |
| cttagagtta | cagaacaata | gtttatctgg | tgccttacca | gattctcttg | ggaacatggt | 480 |
| taatctacag | actttaaacc | tatcagtgaa | tagtttcagc | ggatcgatac | cagcgagctg | 540 |
| gagtcagctc | tcgaatctaa | agcacttgga | tctctcatcc | aataatttaa | caggaagcat | 600 |
| cccaacacaa | ttcttctcaa | tcccaacatt | cgatttttca | ggaactcagc | ttatatgcgg | 660 |
| taaaagtttg | aatcagcctt | gttcttcaag | ttctcgtctt | ccagtcacat | cctccaagaa | 720 |
| aaagctgaga | gacattactt | tgactgcaag | ttgtgttgct | tctataatct | tattccttgg | 780 |
| agcaatggtt | atgtatcatc | accatcgcgt | ccgcagaacc | aaatacgaca | tcttttttga | 840 |
| tgtagctggg | gaagatgaca | ggaagatttc | ctttggacaa | ctaaaacgat | tctcttacg | 900 |
| tgaaatccag | ctcgcaacag | atagtttcaa | cgagagcaat | tgataggac | aaggaggatt | 960 |
| tggtaaagta | tacagaggtt | tgcttccaga | caaaacaaaa | gttgcagtga | aacgccttgc | 1020 |
| ggattacttc | agtcctggag | gagaagctgc | tttccaaaga | gagattcagc | tcataagcgt | 1080 |
| tgcggttcat | aaaaatctct | tacgccttat | tggcttctgc | acaacttcct | ctgagagaat | 1140 |
| ccttgtttat | ccatacatgg | aaaatcttag | tgttgcatat | cgactaagag | atttgaaagc | 1200 |
| gggagaggaa | ggattagact | ggccaacaag | gaagcgtgta | gcttttggtt | cagctcacgg | 1260 |
| tttagagtat | ctacacgaac | attgtaaccc | gaagatcata | caccgcgatc | tcaaggctgc | 1320 |
| aaacatactt | ttagacaaca | attttgagcc | agttcttgga | gatttcggtt | tagctaagct | 1380 |
| tgtggacaca | tctctgactc | atgtcacaac | tcaagtccga | ggcacaatgg | gtcacattgc | 1440 |
| gccagagtat | ctctgcacag | gaaaatcatc | tgaaaaaacc | gatgttttg | gttacggtat | 1500 |
| aacgcttctt | gagcttgtta | ctggtcagcg | cgcaatcgat | ttttcacgct | ggaagaaga | 1560 |
| ggaaaatatt | ctcttgcttg | atcatataaa | gaagttgctt | agagaacaga | gacttagaga | 1620 |
| cattgttgat | agcaatttga | ctacatatga | ctccaaagaa | gttgaaacaa | tcgttcaagt | 1680 |
| ggctcttctc | tgcacacaag | gctcaccaga | agatagacca | gcgatgtctg | aagtggtcaa | 1740 |
| aatgcttcaa | gggactggtg | gtttggctga | gaaatggact | gaatgggaac | aacttgaaga | 1800 |
| agttaggaac | aaagaagcat | tgttgcttcc | gactttaccg | gctacttggg | atgaagaaga | 1860 |
| aaccaccgtt | gatcaagaat | ctatccgatt | atcgacagca | agatgaagaa | gaaacagaga | 1920 |
| gagaaagata | tctatgaaaa | caaacttgca | ttacagaaga | taaacttaga | aagtatttta | 1980 |
| agctgctaat | tgtattgaac | caggtgggga | aaacgaagca | aacacacaac | gttgatttgt | 2040 |
| gtaatagatg | atatgatata | cataactagt | tgtgttttgt | atatatatga | atttggttat | 2100 |
| tttcgt | | | | | 2106 |

<210> SEQ ID NO 41

<211> LENGTH: 614
<212> TYPE: PRT
<213> ORGANISM: Arabidopsis thaliana

<400> SEQUENCE: 41

```
Met Ala His Ser Gly Asn Gly Glu Ser Phe His Asp Pro Leu Arg Gly
1               5                   10                  15

Phe Ile Gln Arg Asn Cys Phe Arg Trp Asn Asn Gln Lys Leu Ile Leu
            20                  25                  30

Gln Cys Phe Met Ala Leu Ala Phe Val Gly Ile Thr Ser Ser Thr Thr
        35                  40                  45

Gln Pro Asp Ile Glu Gly Gly Ala Leu Leu Gln Leu Arg Asp Ser Leu
    50                  55                  60

Asn Asp Ser Ser Asn Arg Leu Lys Trp Thr Arg Asp Phe Val Ser Pro
65                  70                  75                  80

Cys Tyr Ser Trp Ser Tyr Val Thr Cys Arg Gly Gln Ser Val Val Ala
                85                  90                  95

Leu Asn Leu Ala Ser Ser Gly Phe Thr Gly Thr Leu Ser Pro Ala Ile
            100                 105                 110

Thr Lys Leu Lys Phe Leu Val Thr Leu Glu Leu Gln Asn Asn Ser Leu
        115                 120                 125

Ser Gly Ala Leu Pro Asp Ser Leu Gly Asn Met Val Asn Leu Gln Thr
    130                 135                 140

Leu Asn Leu Ser Val Asn Ser Phe Ser Gly Ser Ile Pro Ala Ser Trp
145                 150                 155                 160

Ser Gln Leu Ser Asn Leu Lys His Leu Asp Leu Ser Ser Asn Asn Leu
                165                 170                 175

Thr Gly Ser Ile Pro Thr Gln Phe Phe Ser Ile Pro Thr Phe Asp Phe
            180                 185                 190

Ser Gly Thr Gln Leu Ile Cys Gly Lys Ser Leu Asn Gln Pro Cys Ser
        195                 200                 205

Ser Ser Ser Arg Leu Pro Val Thr Ser Ser Lys Lys Leu Arg Asp
    210                 215                 220

Ile Thr Leu Thr Ala Ser Cys Val Ala Ser Ile Ile Leu Phe Leu Gly
225                 230                 235                 240

Ala Met Val Met Tyr His His His Arg Val Arg Arg Thr Lys Tyr Asp
                245                 250                 255

Ile Phe Phe Asp Val Ala Gly Glu Asp Asp Arg Lys Ile Ser Phe Gly
            260                 265                 270

Gln Leu Lys Arg Phe Ser Leu Arg Glu Ile Gln Leu Ala Thr Asp Ser
        275                 280                 285

Phe Asn Glu Ser Asn Leu Ile Gly Gln Gly Gly Phe Gly Lys Val Tyr
    290                 295                 300

Arg Gly Leu Leu Pro Asp Lys Thr Lys Val Ala Val Lys Arg Leu Ala
305                 310                 315                 320

Asp Tyr Phe Ser Pro Gly Gly Glu Ala Ala Phe Gln Arg Glu Ile Gln
                325                 330                 335

Leu Ile Ser Val Ala Val His Lys Asn Leu Leu Arg Leu Ile Gly Phe
            340                 345                 350

Cys Thr Thr Ser Ser Glu Arg Ile Leu Val Tyr Pro Tyr Met Glu Asn
        355                 360                 365

Leu Ser Val Ala Tyr Arg Leu Arg Asp Leu Lys Ala Gly Glu Glu Gly
    370                 375                 380

Leu Asp Trp Pro Thr Arg Lys Arg Val Ala Phe Gly Ser Ala His Gly
385                 390                 395                 400
```

```
Leu Glu Tyr Leu His Glu His Cys Asn Pro Lys Ile Ile His Arg Asp
            405                 410                 415
Leu Lys Ala Ala Asn Ile Leu Leu Asp Asn Asn Phe Glu Pro Val Leu
        420                 425                 430
Gly Asp Phe Gly Leu Ala Lys Leu Val Asp Thr Ser Leu Thr His Val
            435                 440                 445
Thr Thr Gln Val Arg Gly Thr Met Gly His Ile Ala Pro Glu Tyr Leu
    450                 455                 460
Cys Thr Gly Lys Ser Ser Glu Lys Thr Asp Val Phe Gly Tyr Gly Ile
465                 470                 475                 480
Thr Leu Leu Glu Leu Val Thr Gly Gln Arg Ala Ile Asp Phe Ser Arg
                485                 490                 495
Leu Glu Glu Glu Asn Ile Leu Leu Asp His Ile Lys Lys Leu
            500                 505                 510
Leu Arg Glu Gln Arg Leu Arg Asp Ile Val Asp Ser Asn Leu Thr Thr
        515                 520                 525
Tyr Asp Ser Lys Glu Val Glu Thr Ile Val Gln Val Ala Leu Leu Cys
    530                 535                 540
Thr Gln Gly Ser Pro Glu Asp Arg Pro Ala Met Ser Glu Val Val Lys
545                 550                 555                 560
Met Leu Gln Gly Thr Gly Gly Leu Ala Glu Lys Trp Thr Glu Trp Glu
                565                 570                 575
Gln Leu Glu Glu Val Arg Asn Lys Glu Ala Leu Leu Leu Pro Thr Leu
            580                 585                 590
Pro Ala Thr Trp Asp Glu Glu Thr Thr Val Asp Gln Glu Ser Ile
        595                 600                 605
Arg Leu Ser Thr Ala Arg
    610

<210> SEQ ID NO 42
<211> LENGTH: 1854
<212> TYPE: DNA
<213> ORGANISM: Arabidopsis thaliana

<400> SEQUENCE: 42
atggctctgc ttattatcac tgccttagtt tttagtagtt tatggtcatc tgtgtcacca      60
gatgctcaag gggatgcatt atttgcgttg aggagctcgt acgtgcatc tcctgaacag     120 cttagtgatt ggaaccagaa tcaagtcgat ccttgtactt ggtctcaagt tatttgtgat     180
gacaagaaac atgttacttc tgtaaccttg tcttacatga acttctcctc gggaacactg     240
tcttcaggaa taggaatctt gacaactctc aagactctta cattgaaggg aaatggaata     300
atgggtggaa taccagaatc cattggaaat ctgtctagct tgaccagctt agatttggag     360
gataatcact taactgatcg cattccatcc actctcggta atctcaagaa tctacagttc     420
ttgaccttga gtaggaataa ccttaatggt tctatcccgg attcacttac aggtctatca     480
aaactgataa atattctgct cgactcaaat aatctcagtg gtgagattcc tcagagttta     540
ttcaaaatcc caaatacaa tttcacagca acaacttga gctgtggtgg cactttcccg     600
caaccttgtg taaccgagtc cagtccttca ggtgattcaa gcagtagaaa aactggaatc     660
atcgctggag ttgttagcgg aatagcggtt attctactag gattcttctt cttttttcttc     720 tgcaaggata acataaagg atataaacga gacgtatttg tggatgttgc aggaacgaac     780
tttaaaaaag gtttgatttc aggtgaagtg gacagaagga ttgcttttgg acagttgaga     840
agatttgcat ggagagagct tcagttggct acagatgagt tcagtgaaaa gaatgttctc     900
```

-continued

```
ggacaaggag gctttgggaa agtttacaaa ggattgcttt cggatggcac caaagtcgct    960
gtaaaaagat tgactgattt tgaacgtcca ggaggagatg aagctttcca gagagaagtt   1020
gagatgataa gtgtagctgt tcataggaat ctgcttcgcc ttatcggctt ttgtacaaca   1080
caaactgaac gactttggt gtatcctttc atgcagaatc taagtgttgc atattgctta   1140
agagagatta aacccgggga tccagttctg gattggttca ggaggaaaca gattgcgtta   1200
ggtgcagcac gaggactcga atatcttcat gaacattgca acccgaagat catacacaga   1260
gatgtgaaag ctgcaaatgt gttactagat gaagactttg aagcagtggt tggtgatttt   1320
ggtttagcca agttggtaga tgttagaagg actaatgtaa ccactcaggt ccgaggaaca   1380
atgggtcata ttgcaccaga atgtatatcc acagggaaat cgtcagagaa aaccgatgtt   1440
ttcgggtacg gaattatgct tctggagctt gtaactggac aaagagcaat tgatttctcg   1500
cggttagagg aagaagatga tgtcttattg ctagaccatg tgaagaaact ggaaagagag   1560
aagagattag aagcatagt agataagaag cttgatgagg attatataaa ggaagaagtt   1620
gaaatgatga tacaagtagc tctgctatgc acacaagcag caccggaaga acgaccagcg   1680
atgtcggaag tagtaagaat gctagaagga gaagggcttg cagagagatg ggaagagtgg   1740
cagaatcttg aagtgacgag acaagaagag tttcagaggt tgcagaggag atttgattgg   1800
ggtgaagatt ccattaataa tcaagatgct attgaattat ctggtggaag atag         1854
```

<210> SEQ ID NO 43
<211> LENGTH: 617
<212> TYPE: PRT
<213> ORGANISM: Arabidopsis thaliana
<400> SEQUENCE: 43

```
Met Ala Leu Leu Ile Ile Thr Ala Leu Val Phe Ser Ser Leu Trp Ser
1               5                   10                  15

Ser Val Ser Pro Asp Ala Gln Gly Asp Ala Leu Phe Ala Leu Arg Ser
            20                  25                  30

Ser Leu Arg Ala Ser Pro Glu Gln Leu Ser Asp Trp Asn Gln Asn Gln
        35                  40                  45

Val Asp Pro Cys Thr Trp Ser Gln Val Ile Cys Asp Asp Lys Lys His
    50                  55                  60

Val Thr Ser Val Thr Leu Ser Tyr Met Asn Phe Ser Ser Gly Thr Leu
65                  70                  75                  80

Ser Ser Gly Ile Gly Ile Leu Thr Thr Leu Lys Thr Leu Thr Leu Lys
                85                  90                  95

Gly Asn Gly Ile Met Gly Gly Ile Pro Glu Ser Ile Gly Asn Leu Ser
            100                 105                 110

Ser Leu Thr Ser Leu Asp Leu Glu Asp Asn His Leu Thr Asp Arg Ile
        115                 120                 125

Pro Ser Thr Leu Gly Asn Leu Lys Asn Leu Gln Phe Leu Thr Leu Ser
    130                 135                 140

Arg Asn Asn Leu Asn Gly Ser Ile Pro Asp Ser Leu Thr Gly Leu Ser
145                 150                 155                 160

Lys Leu Ile Asn Ile Leu Leu Asp Ser Asn Asn Leu Ser Gly Glu Ile
                165                 170                 175

Pro Gln Ser Leu Phe Lys Ile Pro Lys Tyr Asn Phe Thr Ala Asn Asn
            180                 185                 190

Leu Ser Cys Gly Gly Thr Phe Pro Gln Pro Cys Val Thr Glu Ser Ser
        195                 200                 205
```

```
Pro Ser Gly Asp Ser Ser Arg Lys Thr Gly Ile Ile Ala Gly Val
    210                 215                 220

Val Ser Gly Ile Ala Val Ile Leu Leu Gly Phe Phe Phe Phe Phe
225                 230                 235                 240

Cys Lys Asp Lys His Lys Gly Tyr Lys Arg Asp Val Phe Val Asp Val
                245                 250                 255

Ala Gly Thr Asn Phe Lys Lys Gly Leu Ile Ser Gly Glu Val Asp Arg
            260                 265                 270

Arg Ile Ala Phe Gly Gln Leu Arg Arg Phe Ala Trp Arg Glu Leu Gln
        275                 280                 285

Leu Ala Thr Asp Glu Phe Ser Glu Lys Asn Val Leu Gly Gln Gly Gly
        290                 295                 300

Phe Gly Lys Val Tyr Lys Gly Leu Leu Ser Asp Gly Thr Lys Val Ala
305                 310                 315                 320

Val Lys Arg Leu Thr Asp Phe Glu Arg Pro Gly Gly Asp Glu Ala Phe
                325                 330                 335

Gln Arg Glu Val Glu Met Ile Ser Val Ala Val His Arg Asn Leu Leu
                340                 345                 350

Arg Leu Ile Gly Phe Cys Thr Thr Gln Thr Glu Arg Leu Leu Val Tyr
            355                 360                 365

Pro Phe Met Gln Asn Leu Ser Val Ala Tyr Cys Leu Arg Glu Ile Lys
    370                 375                 380

Pro Gly Asp Pro Val Leu Asp Trp Phe Arg Arg Lys Gln Ile Ala Leu
385                 390                 395                 400

Gly Ala Ala Arg Gly Leu Glu Tyr Leu His Glu His Cys Asn Pro Lys
                405                 410                 415

Ile Ile His Arg Asp Val Lys Ala Ala Asn Val Leu Leu Asp Glu Asp
            420                 425                 430

Phe Glu Ala Val Val Gly Asp Phe Gly Leu Ala Lys Leu Val Asp Val
        435                 440                 445

Arg Arg Thr Asn Val Thr Thr Gln Val Arg Gly Thr Met Gly His Ile
    450                 455                 460

Ala Pro Glu Cys Ile Ser Thr Gly Lys Ser Ser Glu Lys Thr Asp Val
465                 470                 475                 480

Phe Gly Tyr Gly Ile Met Leu Leu Glu Leu Val Thr Gly Gln Arg Ala
                485                 490                 495

Ile Asp Phe Ser Arg Leu Glu Glu Glu Asp Val Leu Leu Leu Asp
            500                 505                 510

His Val Lys Lys Leu Glu Arg Glu Lys Arg Leu Glu Asp Ile Val Asp
        515                 520                 525

Lys Lys Leu Asp Glu Asp Tyr Ile Lys Glu Glu Val Glu Met Met Ile
    530                 535                 540

Gln Val Ala Leu Leu Cys Thr Gln Ala Ala Pro Glu Glu Arg Pro Ala
545                 550                 555                 560

Met Ser Glu Val Val Arg Met Leu Glu Gly Glu Gly Leu Ala Glu Arg
                565                 570                 575

Trp Glu Glu Trp Gln Asn Leu Glu Val Thr Arg Gln Glu Glu Phe Gln
            580                 585                 590

Arg Leu Gln Arg Arg Phe Asp Trp Gly Glu Asp Ser Ile Asn Asn Gln
        595                 600                 605

Asp Ala Ile Glu Leu Ser Gly Gly Arg
    610                 615

<210> SEQ ID NO 44
```

```
<211> LENGTH: 844
<212> TYPE: DNA
<213> ORGANISM: Arabidopsis thaliana

<400> SEQUENCE: 44
ggcgaaaacc atggtggcgc aaaacagtcg gcgggagctt ctagcagctt ccctgatcct      60
aactttagct ctaattcgtc taacggaagc aaactccgaa ggggacgctc ttcacgcgct     120
tcgccggagc ttatcagatc cagacaatgt tgttcagagt tgggatccaa ctcttgttaa     180
tccttgtact tggtttcatg tcacttgtaa tcaacaccat caagtcactc gtctggattt     240
ggggaattca aacttatctg gacatctagt acctgaactt gggaagcttg aacatttaca     300
atatcttgaa ctctacaaaa acgagattca aggaactata ccttctgagc ttggaaatct     360
gaagagtcta atcagtttgg atctgtacaa caacaatctc accgggaaaa tcccatcttc     420
tttgggaaaa ttgaagtcac ttgttttttt gcggcttaac gaaaaccgat tgaccggtcc     480
tattcctaga gaactcacag ttatttcaag ccttaaagtt gttgatgtct cagggaatga     540
tttgtgtgga acaattccag tagaaggacc ttttgaacac attcctatgc aaaactttga     600
gaacaacctg agattggagg gaccagaact actaggtctt gcgagctatg acaccaattg     660
cacttaaaaa gaagttgaag aacctataaa gaagaatgtt aggtgacctt gtaagaactc     720
tgtaccaagt gtttgtaaat ctatatagag ccttgtttca tgttatatat gaaagctttg     780
agagacagta acttgcaatg tattggtatt ggtagaaaaa gttgaaatga gaattgcttt     840
gtaa                                                                 844

<210> SEQ ID NO 45
<211> LENGTH: 218
<212> TYPE: PRT
<213> ORGANISM: Arabidopsis thaliana

<400> SEQUENCE: 45

Met Val Ala Gln Asn Ser Arg Arg Glu Leu Leu Ala Ala Ser Leu Ile
1               5                   10                  15

Leu Thr Leu Ala Leu Ile Arg Leu Thr Glu Ala Asn Ser Glu Gly Asp
            20                  25                  30

Ala Leu His Ala Leu Arg Arg Ser Leu Ser Asp Pro Asp Asn Val Val
        35                  40                  45

Gln Ser Trp Asp Pro Thr Leu Val Asn Pro Cys Thr Trp Phe His Val
    50                  55                  60

Thr Cys Asn Gln His His Gln Val Thr Arg Leu Asp Leu Gly Asn Ser
65                  70                  75                  80

Asn Leu Ser Gly His Leu Val Pro Glu Leu Gly Lys Leu Glu His Leu
                85                  90                  95

Gln Tyr Leu Glu Leu Tyr Lys Asn Glu Ile Gln Gly Thr Ile Pro Ser
            100                 105                 110

Glu Leu Gly Asn Leu Lys Ser Leu Ile Ser Leu Asp Leu Tyr Asn Asn
        115                 120                 125

Asn Leu Thr Gly Lys Ile Pro Ser Ser Leu Gly Lys Leu Lys Ser Leu
    130                 135                 140

Val Phe Leu Arg Leu Asn Glu Asn Arg Leu Thr Gly Pro Ile Pro Arg
145                 150                 155                 160

Glu Leu Thr Val Ile Ser Ser Leu Lys Val Val Asp Val Ser Gly Asn
                165                 170                 175

Asp Leu Cys Gly Thr Ile Pro Val Glu Gly Pro Phe Glu His Ile Pro
            180                 185                 190
```

Met Gln Asn Phe Glu Asn Asn Leu Arg Leu Glu Gly Pro Glu Leu Leu
        195                 200                 205

Gly Leu Ala Ser Tyr Asp Thr Asn Cys Thr
        210                 215

<210> SEQ ID NO 46
<211> LENGTH: 1154
<212> TYPE: DNA
<213> ORGANISM: Arabidopsis thaliana

<400> SEQUENCE: 46

| | | |
|---|---|---|
| accaatcgca taatcgattt cttccaactt caataaaggg gaaccaacgt aaccctaatt | 60 |
| ttgctttctc ctctttgttc agaaaatttt ccctttactc tcaaattcct tttcgatttc | 120 |
| cctctcttaa acctccgaaa gctcacatgg cgtctcgaaa ctatcggtgg gagctcttcg | 180 |
| cagcttcgtt aaccctaacc ttagctttga ttcacctggt cgaagcaaac tccgaaggag | 240 |
| atgctctcta cgctcttcgc cggagtttga cagatccaga ccatgtcctc cagagctggg | 300 |
| atccaactct tgttaatcct tgtacctggt tccatgtcac ctgtaaccaa gacaaccgcg | 360 |
| tcactcgtgt ggatttggga aattcaaacc tctctggaca tcttgcgcct gagcttggga | 420 |
| agcttgaaca tttacagtat ctagagctct acaaaaacaa catccaagga actataccct | 480 |
| tcgaacttgg aaatctgaag aatctcatca gcttggatct gtacaacaac aatcttacag | 540 |
| ggatagttcc cacttctttg ggaaaattga agtctctggt ctttttacgg cttaatgaca | 600 |
| accgattgac cggtccaatc cctagagcac tcacggcaat cccaagcctt aaagttgttg | 660 |
| acgtctcaag caatgatttg tgtggaacaa tcccaacaaa cggaccccttt gctcacattc | 720 |
| ctttacagaa ctttgagaac aacccgagat tggagggacc ggaattactc ggtcttgcaa | 780 |
| gctacgacac taactgcacc tgaaacaact ggcaaaacct gaaaatgaag aattgggggg | 840 |
| tgaccttgta agaacacttc accactttat caaatatcac atctattatg taataagtat | 900 |
| atatatgtag taaaaacaaa aaaaatgaag aatcgaatcg gtaatatcat ctggtctcaa | 960 |
| ttgagaactt cgaggtctgt atgtaaaatt tctaaatgcg attttcgctt actgtaatgt | 1020 |
| tcggttgtgg gattctgaga agtaaacattt gtattggtat ggtatcaagt tgttctgcct | 1080 |
| tgtctgcatt taacacttgt gttttagatc tgttatataa agccaaaaaa ggttttgtgt | 1140 |
| gatttggtac tatc | 1154 |

<210> SEQ ID NO 47
<211> LENGTH: 218
<212> TYPE: PRT
<213> ORGANISM: Arabidopsis thaliana

<400> SEQUENCE: 47

Met Ala Ser Arg Asn Tyr Arg Trp Glu Leu Phe Ala Ala Ser Leu Thr
1               5                  10                  15

Leu Thr Leu Ala Leu Ile His Leu Val Glu Ala Asn Ser Glu Gly Asp
            20                  25                  30

Ala Leu Tyr Ala Leu Arg Arg Ser Leu Thr Asp Pro Asp His Val Leu
        35                  40                  45

Gln Ser Trp Asp Pro Thr Leu Val Asn Pro Cys Thr Trp Phe His Val
    50                  55                  60

Thr Cys Asn Gln Asp Asn Arg Val Thr Arg Val Asp Leu Gly Asn Ser
65                  70                  75                  80

Asn Leu Ser Gly His Leu Ala Pro Glu Leu Gly Lys Leu Glu His Leu
                85                  90                  95

```
Gln Tyr Leu Glu Leu Tyr Lys Asn Asn Ile Gln Gly Thr Ile Pro Ser
                100                 105                 110

Glu Leu Gly Asn Leu Lys Asn Leu Ile Ser Leu Asp Leu Tyr Asn Asn
            115                 120                 125

Asn Leu Thr Gly Ile Val Pro Thr Ser Leu Gly Lys Leu Lys Ser Leu
        130                 135                 140

Val Phe Leu Arg Leu Asn Asp Asn Arg Leu Thr Gly Pro Ile Pro Arg
145                 150                 155                 160

Ala Leu Thr Ala Ile Pro Ser Leu Lys Val Val Asp Val Ser Ser Asn
                165                 170                 175

Asp Leu Cys Gly Thr Ile Pro Thr Asn Gly Pro Phe Ala His Ile Pro
            180                 185                 190

Leu Gln Asn Phe Glu Asn Asn Pro Arg Leu Glu Gly Pro Glu Leu Leu
        195                 200                 205

Gly Leu Ala Ser Tyr Asp Thr Asn Cys Thr
    210                 215
```

<210> SEQ ID NO 48
<211> LENGTH: 1722
<212> TYPE: DNA
<213> ORGANISM: Arabidopsis thaliana

<400> SEQUENCE: 48

| | |
|---|---:|
| atgaagattc aaattcatct cctttactcg ttcttgttcc tctgtttctc tactctcact | 60 |
| ctatcttctg agcccagaaa ccctgaagtt gaggcgttga taagtataag gaacaatttg | 120 |
| catgatcctc atggagcttt gaacaattgg gacgagtttt cagttgatcc ttgtagctgg | 180 |
| gctatgatca cttgctctcc cgacaaccte gtcattggac taggagcgcc gagccagtct | 240 |
| ctctcgggag gtttatctga gtctatcgga aatctcacaa atctccgaca agtgtcattg | 300 |
| caaaataaca catctccgg caaaattcca ccggagctcg gttttctacc caaattacaa | 360 |
| accttggatc tttccaacaa ccgattctcc ggtgacatcc ctgtttccat cgaccagcta | 420 |
| agcagccttc aatatctgga cttgtcttac aacaatctca gtggccctgt tcctaaattc | 480 |
| ccagcaagga ctttcaacgt tgctggtaat cctttgattg tagaagcaa cccacctgag | 540 |
| atttgttctg gatcaatcaa tgcaagtcca ctttctgttt ctttgagctc ttcatcagca | 600 |
| gataaacaag aggaagggct tcaaggactt ggaatctaa gaagcttcac attcagagaa | 660 |
| ctccatgttt atacagatgg tttcagttcc aagaacattc tcggcgctgg tggattcggt | 720 |
| aatgtgtaca gaggcaagct tggagatggg acaatggtgg cagtgaaacg gttgaaggat | 780 |
| attaatggaa cctcagggga ttcacagttt cgtatggagc tagagatgat tagcttagct | 840 |
| gttcataaga atctgcttcg gttaattggt tattgcgcaa cttctggtga aaggcttctt | 900 |
| gtttaccctt acatgcctaa tggaagcgtc gcctctaagc ttaaatctaa accggcattg | 960 |
| gactggaaca tgaggaagag gatagcaatt ggtgcagcga gaggtttgtt gtatctacat | 1020 |
| gagcaatgtg atcccaagat cattcataga gatgtaaagg cagctaatat tctcttagac | 1080 |
| gagtgctttg aagctgttgt tggtgacttt ggactcgcaa agctccttaa ccatgcggat | 1140 |
| tctcatgtca caactgcggt ccgtggtacg gttggccaca ttgcacctga atatctctcc | 1200 |
| actggtcagt cttctgagaa aaccgatgtg tttgggttcg gtatactatt gctcgagctc | 1260 |
| ataaccggac tgagagctct tgagtttggt aaaaccgtta gccagaaagg agctatgctt | 1320 |
| gaatgggtga ggaaattaca tgaagagatg aaagtagagg aactattgga tcgagaactc | 1380 |
| ggaactaact acgataagat tgaagttgga gagatgttgc aagtggcttt gctatgcaca | 1440 |

```
caatatctgc cagctcatcg tcctaaaatg tctgaagttg ttttgatgct tgaaggcgat    1500
ggattagccg agagatgggc tgcttcgcat aaccattcac atttctacca tgccaatatc    1560
tctttcaaga caatctcttc tctgtctact acttctgtct caaggcttga cgcacattgc    1620
aatgatccaa cttatcaaat gtttggatct tcggctttcg atgatgacga tgatcatcag    1680
cctttagatt cctttgccat ggaactatcc ggtccaagat aa                      1722
```

<210> SEQ ID NO 49
<211> LENGTH: 573
<212> TYPE: PRT
<213> ORGANISM: Arabidopsis thaliana

<400> SEQUENCE: 49

```
Met Lys Ile Gln Ile His Leu Leu Tyr Ser Phe Leu Phe Leu Cys Phe
1               5                   10                  15

Ser Thr Leu Thr Leu Ser Ser Glu Pro Arg Asn Pro Glu Val Glu Ala
            20                  25                  30

Leu Ile Ser Ile Arg Asn Asn Leu His Asp Pro His Gly Ala Leu Asn
        35                  40                  45

Asn Trp Asp Glu Phe Ser Val Asp Pro Cys Ser Trp Ala Met Ile Thr
    50                  55                  60

Cys Ser Pro Asp Asn Leu Val Ile Gly Leu Gly Ala Pro Ser Gln Ser
65                  70                  75                  80

Leu Ser Gly Gly Leu Ser Glu Ser Ile Gly Asn Leu Thr Asn Leu Arg
                85                  90                  95

Gln Val Ser Leu Gln Asn Asn Asn Ile Ser Gly Lys Ile Pro Pro Glu
            100                 105                 110

Leu Gly Phe Leu Pro Lys Leu Gln Thr Leu Asp Leu Ser Asn Asn Arg
        115                 120                 125

Phe Ser Gly Asp Ile Pro Val Ser Ile Asp Gln Leu Ser Ser Leu Gln
    130                 135                 140

Tyr Leu Asp Leu Ser Tyr Asn Asn Leu Ser Gly Pro Val Pro Lys Phe
145                 150                 155                 160

Pro Ala Arg Thr Phe Asn Val Ala Gly Asn Pro Leu Ile Cys Arg Ser
                165                 170                 175

Asn Pro Pro Glu Ile Cys Ser Gly Ser Ile Asn Ala Ser Pro Leu Ser
            180                 185                 190

Val Ser Leu Ser Ser Ser Ala Asp Lys Gln Glu Glu Gly Leu Gln
        195                 200                 205

Gly Leu Gly Asn Leu Arg Ser Phe Thr Phe Arg Glu Leu His Val Tyr
    210                 215                 220

Thr Asp Gly Phe Ser Ser Lys Asn Ile Leu Gly Ala Gly Gly Phe Gly
225                 230                 235                 240

Asn Val Tyr Arg Gly Lys Leu Gly Asp Gly Thr Met Val Ala Val Lys
                245                 250                 255

Arg Leu Lys Asp Ile Asn Gly Thr Ser Gly Asp Ser Gln Phe Arg Met
            260                 265                 270

Glu Leu Glu Met Ile Ser Leu Ala Val His Lys Asn Leu Leu Arg Leu
        275                 280                 285

Ile Gly Tyr Cys Ala Thr Ser Gly Glu Arg Leu Leu Val Tyr Pro Tyr
    290                 295                 300

Met Pro Asn Gly Ser Val Ala Ser Lys Leu Lys Ser Lys Pro Ala Leu
305                 310                 315                 320

Asp Trp Asn Met Arg Lys Arg Ile Ala Ile Gly Ala Ala Arg Gly Leu
                325                 330                 335
```

```
Leu Tyr Leu His Glu Gln Cys Asp Pro Lys Ile Ile His Arg Asp Val
            340                 345                 350
Lys Ala Ala Asn Ile Leu Leu Asp Glu Cys Phe Glu Ala Val Val Gly
            355                 360                 365
Asp Phe Gly Leu Ala Lys Leu Leu Asn His Ala Asp Ser His Val Thr
            370                 375                 380
Thr Ala Val Arg Gly Thr Val Gly His Ile Ala Pro Glu Tyr Leu Ser
385                 390                 395                 400
Thr Gly Gln Ser Ser Glu Lys Thr Asp Val Phe Gly Phe Gly Ile Leu
            405                 410                 415
Leu Leu Glu Leu Ile Thr Gly Leu Arg Ala Leu Glu Phe Gly Lys Thr
            420                 425                 430
Val Ser Gln Lys Gly Ala Met Leu Glu Trp Val Arg Lys Leu His Glu
            435                 440                 445
Glu Met Lys Val Glu Glu Leu Leu Asp Arg Glu Leu Gly Thr Asn Tyr
            450                 455                 460
Asp Lys Ile Glu Val Gly Glu Met Leu Gln Val Ala Leu Leu Cys Thr
465                 470                 475                 480
Gln Tyr Leu Pro Ala His Arg Pro Lys Met Ser Glu Val Val Leu Met
            485                 490                 495
Leu Glu Gly Asp Gly Leu Ala Glu Arg Trp Ala Ala Ser His Asn His
            500                 505                 510
Ser His Phe Tyr His Ala Asn Ile Ser Phe Lys Thr Ile Ser Ser Leu
            515                 520                 525
Ser Thr Thr Ser Val Ser Arg Leu Asp Ala His Cys Asn Asp Pro Thr
            530                 535                 540
Tyr Gln Met Phe Gly Ser Ser Ala Phe Asp Asp Asp His Gln
545                 550                 555                 560
Pro Leu Asp Ser Phe Ala Met Glu Leu Ser Gly Pro Arg
            565                 570

<210> SEQ ID NO 50
<211> LENGTH: 1301
<212> TYPE: DNA
<213> ORGANISM: Oryza sativa

<400> SEQUENCE: 50
tctcttctga agctgaagcc ctgcgaaata ggcctttaaa cgctttaagg ttactggatg      60
atcatatcgg cgtaagaccg gtttaaacat ggtttcgctt tgtgaatcca atgtgagtca     120
cgacgtgaca catggcacgt ccttggagct ttagacatat cgaatctgag cactggagtg     180
gccgagtggg tgagcggcca aatccgtttt agacagatcg cactgacacg atgttgatca     240
ttgatactaa taccatttta tcaagcagta gtgttgaaaa aaaaacttat gttctcttca     300
actgtgagat ttcatcccgt ttcaagatga acaagccatg catgtgagat gtgaacagaa     360
ggcagaagac agtggaaaga caggacaaat aagtgaagag ggatcaaatc aatgggcctg     420
acggtttctg aaagttgaca tggaaatcgc cggtgatcac cggtttatac gttatttaaa     480
tctgcgattt ccactttcgt ttgctttcgg ggttccaatt tgagtcacgc acatattctt     540
catcgtgctt tggatctcag caccgtagta acttttggac aaattgcatt cgccgacact     600
aataacatgt tctttttatg ctgctttaca tatactgctt atccacaccc aatcccatgt     660
tcatatatta tgagatggag ggagtaaact ttgttaacag caacatttttt tatattaaag     720
catcaactaa ttaaagcaca agatacgcat gttatctcaa taaatcttcc agtgcatgta     780
```

```
taaagaagat gtcgccgcta acttagataa tttttgtgac ttttatcctg gccggcataa      840
ttaattcttc cggaaattaa aagctagttt ttccatattc atcagtacag acaagacagc      900
atagtaagcg aagcatacct gacgtgttag ctcattgtaa ctcgatctgg aacactcgat      960
gctagataca gacagacact cctcgtgatg aacgttagca tttagcaaca tacggtgata     1020
aagcagctgg ggatcgatcc atccatccat cgtctttaca cgtacttacc ttgctaaccg     1080
cactgtcgac tcttgcatgt ttgcatgtaa tccaaatgga ccccacgtgg aacatgctca     1140
cagtgctttg cagctgcttt ccaaaatgct ttctttcact tcttccattc ctctgtccac     1200
aaaaaaagta gtgtgttctt gagcctatat aagagagggt cacacgctcc agtcgactca     1260
ccatcgatcc atctgacggt tagttccaag ggaaagaaga a                         1301
```